US012643871B2

(12) United States Patent
Lian et al.

(10) Patent No.: US 12,643,871 B2
(45) Date of Patent: *Jun. 2, 2026

(54) ARYL FORMAMIDE COMPOUND CONTAINING CHIRAL SULFUR OXIDE OR SALT THEREOF, PREPARATION METHOD, HERBICIDAL COMPOSITION AND USE THEREOF

(71) Applicant: Qingdao Kingagroot Chemical Compound Co., Ltd., Qingdao (CN)

(72) Inventors: Lei Lian, Qingdao (CN); Rongbao Hua, Qingdao (CN); Xuegang Peng, Qingdao (CN); De Zhao, Qingdao (CN); Qi Cui, Qingdao (CN)

(73) Assignee: Qingdao Kingagroot Chemical Compound Co., Ltd., Qingdao (CN)

( * ) Notice: Subject to any disclaimer, the term of this patent is extended or adjusted under 35 U.S.C. 154(b) by 804 days.

This patent is subject to a terminal disclaimer.

(21) Appl. No.: 17/637,184

(22) PCT Filed: Oct. 22, 2020

(86) PCT No.: PCT/CN2020/122622

§ 371 (c)(1),
(2) Date: Feb. 22, 2022

(87) PCT Pub. No.: WO2021/078174

PCT Pub. Date: Apr. 29, 2021

(65) Prior Publication Data

US 2022/0289696 A1 Sep. 15, 2022

(30) Foreign Application Priority Data

Oct. 23, 2019 (CN) ........................ 201911013581.1
May 11, 2020 (CN) ........................ 202010391788.9
May 29, 2020 (CN) ........................ 202010472859.8

(51) Int. Cl.
*C07D 271/113* (2006.01)
*A01N 43/82* (2006.01)

(52) U.S. Cl.
CPC .......... *C07D 271/113* (2013.01); *A01N 43/82* (2013.01)

(58) Field of Classification Search
CPC .................................................. C07D 271/113
See application file for complete search history.

(56) References Cited

U.S. PATENT DOCUMENTS 5,013,659 A 5/1991 Bedbrook et al.
5,637,739 A 6/1997 Jacobsen et al.
(Continued)

FOREIGN PATENT DOCUMENTS

CN 102639517 A 8/2012
CN 103282354 A 9/2013
(Continued)

OTHER PUBLICATIONS

Faruk, M.S.A. et al., Effect of herbicide Prechlor on the performance of T. aman rice, 2013, J. Bangladesh Agril. Univ., vol. 11, 257-264 (Year: 2013).*
(Continued)

*Primary Examiner* — Bethany P Barham
*Assistant Examiner* — Paul Hoerner
(74) *Attorney, Agent, or Firm* — Finnegan, Henderson, Farabow, Garrett & Dunner LLP

(57) ABSTRACT

The invention belongs to the technical field of agricultural chemicals, and particularly relates to an aryl formamide compound containing chiral sulfur oxide or salt thereof, a preparation method, a herbicidal composition and a use thereof. The aryl formamide compound containing chiral sulfur oxide or salt thereof has the following structural formula:

I

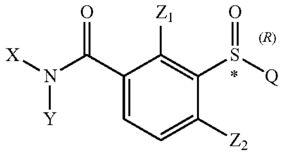

$Z_1$, and $Z_2$ each independently represent nitro, halogen, or cyano, etc.; X represents unsubstituted or substituted

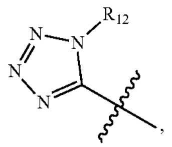

unsubstituted or substituted

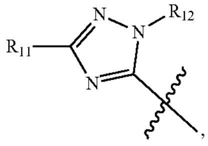

unsubstituted or substituted

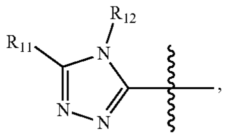

, unsubstituted or substituted

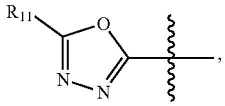

, unsubstituted or substituted

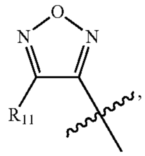

, unsubstituted or substituted

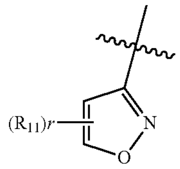

, or unsubstituted or substituted

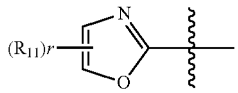

;

Q represents halogen, cyano, cyanoalkyl, or nitro, etc.; Y represents hydrogen, etc.; wherein the compound has advantages of excellent herbicidal activity, higher crop safety, and especially good selectivity for key crops such as wheat, rice, corn.

14 Claims, No Drawings

(56) References Cited

U.S. PATENT DOCUMENTS

| | | | | |
|---|---|---|---|---|
| 8,481,749 | B2 * | 7/2013 | Braun .................. | C07D 413/12<br>504/106 |
| 9,101,141 | B2 * | 8/2015 | Kohn ................... | C07D 271/07 |
| 2013/0316904 | A1 | 11/2013 | Dietrich et al. | |
| 2018/0105513 | A1 * | 4/2018 | Lian ..................... | C07D 405/14 |

FOREIGN PATENT DOCUMENTS

| | | | |
|---|---|---|---|
| CN | 103596946 | A | 2/2014 |
| CN | 103987701 | A | 8/2014 |
| CN | 104125948 | A | 10/2014 |
| CN | 104854104 | A | 8/2015 |
| CN | 105073719 | A | 11/2015 |
| CN | 106470979 | A | 3/2017 |
| CN | 107709317 | A | 2/2018 |
| CN | 108290846 | A | 7/2018 |
| CN | 111253333 | A | 6/2020 |
| EP | 0131624 | B1 | 1/1985 |
| EP | 0221044 | A1 | 5/1987 |
| EP | 0242246 | A | 10/1987 |
| EP | 0193259 | A | 12/1991 |
| EP | 0142924 | A2 | 4/1992 |
| EP | 0242236 | A | 8/1996 |
| EP | 0257993 | A2 | 11/1996 |
| JP | H06509981 | A | 11/1994 |
| JP | 2013505901 | A | 2/2013 |
| JP | 2013536817 | A | 9/2013 |
| JP | 2014510088 | A | 4/2014 |
| JP | 2014510089 | A | 4/2014 |
| JP | 2015505849 | A | 2/2015 |
| JP | 2016506385 | A | 3/2016 |
| JP | 2016537311 | A | 12/2016 |
| JP | 2017514789 | A | 6/2017 |
| JP | 2017523235 | A | 8/2017 |
| JP | 2018521054 | A | 8/2018 |
| JP | 2018531236 | A | 10/2018 |
| JP | 2021530934 | A | 11/2021 |
| WO | WO9113972 | A1 | 9/1991 |
| WO | WO 9119806 | A1 | 12/1991 |
| WO | WO 9200377 | A1 | 1/1992 |
| WO | WO 9211376 | A1 | 7/1992 |
| WO | WO 9214827 | A1 | 9/1992 |
| WO | WO 2012028579 | A1 | 3/2012 |
| WO | WO 2012130685 | A1 | 10/2012 |
| WO | WO 2014086746 | A1 | 6/2014 |
| WO | WO 2015/049225 | A1 | 4/2015 |
| WO | WO 2015/135946 | A1 | 9/2015 |
| WO | WO 2016/001073 | A1 | 1/2016 |
| WO | WO 2016128470 | A1 | 8/2016 |
| WO | WO 2016146561 | A1 | 9/2016 |
| WO | WO 2017144402 | A1 | 8/2017 |
| WO | WO 2018/202535 | A1 | 11/2018 |

OTHER PUBLICATIONS

H. Yamanaka et al., Prefabrication of optical actives, Physiological activity of optical active body, and Utilization of optical actives, *Separation of optical isomers, Quarterly Review of Chemistry* No. 6, Published by Maji Yoshida, Japan (1989).

N. Kurihara et al., Chirality in synthetic agrochemicals: bioactivity and safety consideration of IUPAC Reports on Pesticides (37), *Pure & Applied Chemistry*., vol. 69, No. 6, pp. 1335-1348 (1997).

Encyclopedia of Chinese Agriculture—Pesticide Volume, China Agriculture Press, Bibliography data and pp. 248-249 (1993).

2008-2009 Report on advances in chemistry, Science and technology of China press, Cover page and pp. 107-108 (2009).

Extended European Search Report of counterpart European Application No. 20878440.5 dated Oct. 17, 2023.

P. Christou, Transformation Technology, *Trends in Plant Science*, 1:423-431 (1996).

H. Braun et al., The General Mitochondrial Processing Peptidase from Potato Is an Integral Part of Cytochrome C Reductase of The Respiratory Chain, *Embo J.* 11:3219-3227 (1992).

F. Wolter et al., Rbcs Genes in Solanum Tuberosum: Conservation of Transit Peptide and Exon Shuffling During Evolution, *Proc. Natl. Acad. Sci. USA*, 85:846-850 (1988).

U. Sonnewald et al., Transgenic Tobacco Plants Expressing Yeast-Derived Invertase in Either the Cytosol, Vacuole or Apoplast: A Powerful Tool for Studying Sucrose Metabolism and Sink/Source Interactions, *Plant J.* 1:95-106 (1991).

International Search Report and Written Opinion of International Application No. PCT/CN2020/122622, mailed Dec. 30, 2020.

(56) References Cited

OTHER PUBLICATIONS

M. Couderchet et al., Biological Activity of Two Stereoisomers of the N-Thienyl Chloroacetamide Herbicide Dimethenamid, *Pesticide Science*, 50(3), pp. 221-227 (1997).
B. Chankvetadze, Liquid chromatographic separation of enantiomers, *Liquid Chromatography*, Second Edition, pp. 69-86 (2017).
W. Xu, Medicinal Chemistry, People's Medical Publishing House, bibliographic p. and pp. 283-284, Jul. 1, 2007.

* cited by examiner

ARYL FORMAMIDE COMPOUND CONTAINING CHIRAL SULFUR OXIDE OR SALT THEREOF, PREPARATION METHOD, HERBICIDAL COMPOSITION AND USE THEREOF

CROSS-REFERENCE TO RELATED APPLICATION

This application is a national stage filing under 35 U.S.C. § 371 of International Application No. PCT/CN2020/122622, filed Oct. 22, 2020, which claims the priority and benefits of Chinese Patent Application Nos. 201911013581.1, filed Oct. 23, 2019, 202010391788.9, filed May 11, 2020, and 202010472859.8, filed May 29, 2020, all of which are incorporated herein by reference.

TECHNICAL FIELD

The invention belongs to the technical field of agricultural chemicals, and particularly relates to an aryl formamide compound containing chiral sulfur oxide or salt thereof, a preparation method, a herbicidal composition and use thereof.

BACKGROUND ART

The prevention and control of weeds is a crucial step in the realization of high-efficiency agricultural processes. On the market, there are a wide variety of herbicides, for example, WO2014086746A1, WO2016146561A1, WO2017144402A1, WO2012028579A1, etc., disclose certain arylcarboxamides and their use as herbicides. However, due to the continuous expansion of the market, the resistance of weeds, the service life of chemicals and the economical efficiency of chemicals, as well as the increasing emphasis on the environment, especially the serious occurrence of resistance to mainstream weed herbicides (e.g., herbicides with the inhibition mechanism of ALS such as Penoxsulam, Bispyribac-sodium, and Nicosulfuron, herbicides with ACCe-based inhibition mechanism such as Cyhalofop-butyl, Clethodim, and Quizalofop-p-ethyl, as well as Glyphosate and the like) in the market, crops such as wheat, corn, rice, cotton and soybean encounter a serious challenge and lack effective chemicals to control weeds with resistance. This requires scientists to continuously research and develop new high-efficiency, safe, economic herbicides with different action modes.

In addition, many chiral herbicides have been developed in the market, such as aryloxyphenoxypropionic acid herbicides including Quizalofop-p-ethyl, Fluazifop-p-butyl, Cyhalofop-butyl, Metamifop, and Fenoxaprop-p-ethyl, aryloxypropionic acid herbicides including MCPA propionic acid and 2,4-D propionic acid, chloroamide herbicides including S-metolachlor, and the development of these chiral herbicides has greatly reduced the use of ineffective isomers, and provided better protection to environmental safety. However, there is not a sulfur-containing chiral herbicide that has been commercialized. The present application surprisingly finds an arylcarboxamide compound, a sulfur-containing chiral herbicide, which will has great commercial values.

CONTENTS OF THE INVENTION

The present invention provides an aryl formamide compound containing chiral sulfur oxide or salt thereof, a preparation method, a herbicidal composition and a use thereof, wherein the compound has advantages of excellent herbicidal activity, higher crop safety, and especially good selectivity for key crops such as wheat, rice, corn.

The technical solution adopted by the present invention is as follows:

The present invention provides an aryl formamide compound containing chiral sulfur oxide or salt thereof, which has the following structural formula:

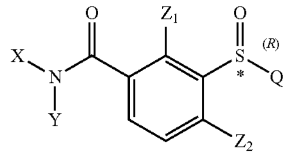

I $Z_1$, and $Z_2$ each independently represent nitro, halogen, cyano, formyl, thiocyano, sulfhydryl, a halogen-containing or not containing group selected from alkyl, alkenyl, alkynyl, cycloalkyl, cycloalkenyl, cycloalkylalkyl, and cycloalkenylalkyl, $OR^1$, $COOR^1$, $OCOR^1$, $OCOOR^1$, $NR^3SO_2R^2$, $OSO_2R^2$, $S(O)_mR^2$, $NR^3COR^1$, $NR^3COOR^1$, $C(O)NR^3OR^1$, $SO_2OR^1$, $C(O)NR^4R^5$, $NR^3C(O)NR^4R^5$, $OC(O)NR^4R^5$, $SO_2NR^4R^5$, $C(S)R^1$, $C(S)OR^1$, $C(S)SR^2$, $C(O)SR^2$, $SC(O)R^1$, $SC(S)R^1$, $OC(S)R^1$, -alkyl-$C(S)R^1$, -alkyl-$C(S)OR^1$, -alkyl-$C(O)SR^1$, -alkyl-$C(S)SR^1$, -alkyl-$SC(O)R^1$, -alkyl-$OC(S)R^1$, -alkyl-$SC(S)R^1$, —O-alkyl-$NR^4R^5$, —S-alkyl-$NR^4R^5$, -alkyl-O-alkyl-$NR^4R^5$, -alkyl-S-alkyl-$NR^4R^5$, -alkyl-$(C{=}S)_n$—$NR^4R^5$, —NH-alkyl-$NR^4R^5$, -alkyl-$OR^1$, -alkly-$COR^1$, -alkyl-$CO_2R^1$, -alkyl-$OCOR^1$, -alkyl-$NR^3COR^1$, -alkyl-$SO_2OR^1$, -alkyl-$NR^3SO_2R^2$, -alkyl-$OSO_2R^2$, -alkyl-$S(O)_mR^2$, -alkyl-$CONR^4R^5$, -alkyl-$SO_2NR^4R^5$, $NR^4R^5$,

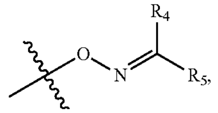

$P(O)(OR^6)_2$, $CH_2P(O)(OR^6)_2$, —$SO_2NR^4R^5$-alkyl-$S(O)_mR^2$, -alkyl-CN, aryl, heteroaryl, heterocyclyl, arylalkyl, heteroarylalkyl, or heterocyclylalkyl;

$R^1$, $R^3$, $R^4$, and $R^5$ each independently represent hydrogen, aryl, arylalkyl, heteroaryl, heteroarylalkyl, alkyl, halogenated alkyl, alkenyl, halogenated alkenyl, alkynyl, halogenated alkynyl, cycloalkyl, halogenated cycloalkyl, alkoxyalkyl, cycloalkylalkyl, wherein the last 10 groups as mentioned are each substituted by s groups selected from the group consisting of cyano, halogen, nitro, thiocyano, $OR^7$, $S(O)_mR^9$, $NR^7R^8$, $NR^8OR^7$, $COR^7$, $OCOR^7$, $SCOR^7$, $NR^8COR^7$, $CO_2R^7$, $COSR^7$, $CONR^7R^8$, and alkoxyalkoxycarbonyl;

$R^2$ independently represents aryl, arylalkyl, heteroaryl, heteroarylalkyl, alkyl, alkenyl, alkynyl, cycloalkyl, cycloalkylalkyl, wherein the last 5 groups as mentioned are each substituted by s groups selected from the group consisting of cyano, halogen, nitro, thiocyano, $OR^7$, $S(O)_mR^9$, $NR^7R^8$, $NR^8OR^7$, $COR^7$, $OCOR^7$, $SCOR^7$, $NR^8COR^7$, $CO_2R^7$, $COSR^7$, $CONR^7R^8$, and alkoxyalkoxycarbonyl;

$R^6$ independently represents methyl, or ethyl;

$R^7$, and $R^8$ each independently represent hydrogen, alkyl, alkenyl, or alkynyl;

$R^9$ independently represents alkyl, alkenyl, or alkynyl;

X represents

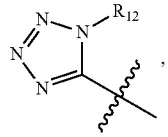
,
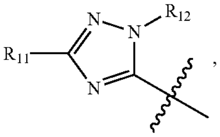
,
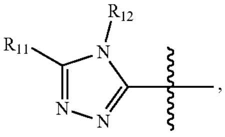
,
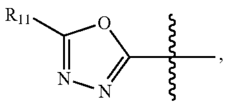
,
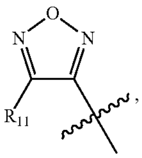
,
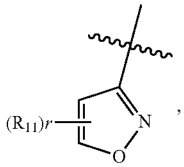
, or
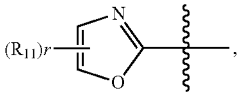
, each of which is unsubstituted or substituted;

$R_{11}$ independently represents hydrogen, halogen, cyano, nitro, alkyl unsubstituted or substituted by $R_{13}$, cycloalkyl unsubstituted or substituted by $R_{14}$, alkenyl, halogenated alkenyl, alkynyl, halogenated alkynyl, cycloalkenyl, $NH_2$, aminoacyl, carboxyl, alkoxyalkoxycarbonyl, $OR_{15}$, -alkyl-$OR_{15}$, $C(O)R_{16}$, -alkyl-$C(O)R_{16}$, $C(O)OR_{16}$, -alkyl-$C(O)OR_{16}$, $S(O)_mR_{16}$, -alkyl-$S(O)_mR_{16}$, $N(R_{16})_2$, $C(O)N(R_{16})_2$, $NHC(O)R_{17}$, heterocyclyl, heterocyclylalkyl, heterocyclyloxy, heterocyclylcarbonyl, aryl, arylalkyl, aryloxy, arylcarbonyl, heteroaryl, heteroarylalkyl, heteroaryloxy, heteroarylcarbonyl;

$R_{12}$ independently represents hydrogen, alkyl unsubstituted or substituted by $R_{18}$, cycloalkyl, halogenated cycloalkyl, alkenyl, halogenated alkenyl, alkynyl, halogenated alkynyl, cycloalkenyl, aryl; or, when M is

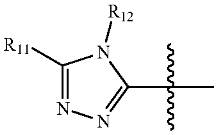
, $—(CH_2)_4—$ or —CH═CH—CH═CH— formed by $R_{11}$ and $R_{12}$, the nitrogen atom bound to $R_{12}$ and the carbon atom bound to $R_{11}$ together form a 6-membered ring;

$R_{15}$ independently represents alkyl which is unsubstituted or substituted with a substituent selected from $R_{21}$, cycloalkyl, halogenated cycloalkyl, alkenyl, halogenated alkenyl, alkynyl, halogenated alkynyl, cycloalkenyl, or phenyl;

$R_{16}$ independently represents alkyl, halogenated alkyl, cycloalkyl, alkenyl, halogenated alkenyl, alkynyl, halogenated alkynyl, or cycloalkenyl;

$R_{21}$ independently represents halogen, cyano, cycloalkyl, hydroxy, sulfhydryl, alkoxy, $C(O)R_{22}$, carboxyl, alkoxycarbonyl, alkoxyalkoxycarbonyl, $—S(O)_m$-alkyl, heteroaryl, heterocyclyl, or phenyl which is unsubstituted or substituted with one or more (for example 1, 2, 3, 4, or 5) groups independently selected from $R_{23}$;

$R_{17}$, and $R_{22}$ each independently represent hydrogen, alkyl, or $N(R_{24})R_{25}$;

$R_{23}$ independently represents halogen, cyano, nitro, alkyl, alkyl unsubstituted or substituted by $R_{31}$, cycloalkyl, halogenated cycloalkyl, alkenyl, halogenated alkenyl, alkynyl, halogenated alkynyl, cycloalkenyl, alkylcarbonyl, cycloalkylcarbonyl, halogenated alkylcarbonyl, halogenated cycloalkylcarbonyl, alkoxycarbonyl, halogenated alkoxycarbonyl, alkylaminocarbonyl, halogenated alkylaminocarbonyl, bis(alkyl)aminocarbonyl, $OR_{32}$, $S(O)_mR_{33}$, alkylaminosulfonyl, bis(alkyl)aminosulfonyl, $NH_2$, alkylamino, bisalkylamino, aryl, heteroaryl, heterocyclyl;

$R_{24}$ and $R_{25}$ each independently represent hydrogen, alkyl or phenyl; or, alkylidene chain formed by $R_{24}$ and $R_{25}$, and the nitrogen atom(s) bound to $R_{24}$ and $R_{25}$ together form a 3-7-membered ring, said alkylidene chain optionally contains one O, S, S(O), $S(O)_2$, NH or N-alkyl and optionally substituted by oxo or thio group;

$R_{13}$, $R_{14}$, $R_{18}$, and $R_{31}$ each independently represent halogen, cyano, nitro, carboxyl, alkoxycarbonyl, alkoxyalkoxycarbonyl, $S(O)_mR_{41}$, $OR_{42}$, alkyl, halogenated alkyl, alkenyl, halogenated alkenyl, alkynyl, halogenated alkynyl, aryl, heteroaryl, or heterocyclyl;

$R_{32}$ independently represents hydrogen, alkyl, halogenated alkyl, cycloalkyl, halogenated cycloalkyl, alkenyl, halogenated alkenyl, alkynyl, halogenated alkynyl, or cycloalkenyl;

$R_{33}$ independently represents alkyl, halogenated alkyl, cycloalkyl, alkenyl, halogenated alkenyl, alkynyl, halogenated alkynyl, or cycloalkenyl;

$R_{41}$, and $R_{42}$ each independently represent hydrogen, alkyl, halogenated alkyl, cycloalkyl, halogenated cycloalkyl, alkenyl, halogenated alkenyl, alkynyl, halogenated alkynyl, cycloalkenyl, phenyl, or benzyl;

Q represents halogen, cyano, cyanoalkyl, nitro, $N(R_{51})_2$, -alkyl-$N(R_{51})_2$, -alkyl-$N^+(R_{51})_3$, $CON(R_{51})_2$, -alkyl-$CON(R_{51})_2$, alkyl substituted by amino and carboxyl, $OR_{52}$, -alkyl-$OR_{52}$, $COR_{52}$, $COOR_{52}$, $COSR_{52}$, -alkyl-$COR_{52}$, -alkyl-$COOR_{52}$, -alkyl-$COSR_{52}$, -alkyl-$OCOR_{52}$, $Si(R_{52})_3$, -alkyl-O—$Si(R_{52})_3$, -alkyl-O—N═$C(R_{52})_2$, $S(O)_mR_{53}$, -alkyl-$S(O)_mR_{53}$, alkyl, halogenated alkyl; alkenyl or alkynyl group which is not substituted or substituted by at least one group (for example, one group, two groups, three groups, four groups, five groups) selected from halogen, cyano, cycloalkyl, alkylcarbonyl, alkoxycarbonyl, alkoxy, alkylsulfanyl, alkylsulfinyl, alkylsulfonyl or trialkylsilyl; unsubstituted or substituted cycloalkyl or cycloalkylalkyl; unsubstituted or substituted heterocyclyl, aryl, heteroaryl, heterocyclylalkyl, arylalkyl or heteroarylalkyl;

Y represents hydrogen, $OR_{54}$, $SR_{54}$, $COR_{54}$, $OCOR_{54}$, $COOR_{54}$, $CON(R_{55})_2$, $N(R_{55})_2$, $NR_{56}COOR_{54}$, $NR_{56}CON(R_{55})_2$, -alkyl-$R_{57}$, halogen-free or halogen-containing alkyl, halogen-free or halogen-containing alkenyl, halogen-free or halogen-containing alkynyl, halogen-free or halogen-containing cycloalkyl, unsubstituted or substituted arylalkyl, or unsubstituted or substituted heteroarylalkyl;

$R_{57}$ independently represents halogen-free or halogen-containing alkenyl, halogen-free or halogen-containing alkynyl, halogen-free or halogen-containing cycloalkyl, CN, $OR_{61}$, $OCOR_{61}$, $COOR_{61}$, $COR_{61}$, —O—(C═O)—O—$R_{61}$, $OSO_2R_{62}$, $SO_2OR_{61}$, $S(O)_mR_{62}$, $N(R_{63})_2$, $CON(R_{63})_2$, $SO_2N(R_{63})_2$, $NR_{64}COR_{61}$, $NR_{64}SO_2R_{62}$, or —O—(C═O)—$N(R_{63})_2$;

$R_{52}$, $R_{54}$, and $R_{61}$ each independently represent hydrogen, halogen-free or halogen-containing alkyl, halogen-free or halogen-containing alkenyl, halogen-free or halogen-containing alkynyl, halogen-free or halogen-containing cycloalkyl, halogen-free or halogen-containing cycloalkylalkyl, halogen-free or halogen-containing cycloalkenyl, halogen-free or halogen-containing alkoxyalkyl, unsubstituted or substituted heterocyclyl, unsubstituted or substituted heterocyclylalkyl, unsubstituted or substituted heterocyclyloxyalkyl, unsubstituted or substituted aryl, unsubstituted or substituted arylalkyl, unsubstituted or substituted aryloxyalkyl, unsubstituted or substituted heteroaryl, unsubstituted or substituted heteroarylalkyl, or unsubstituted or substituted heteroaryloxyalkyl;

$R_{53}$, and $R_{62}$ each independently represent halogen-free or halogen-containing alkyl, halogen-free or halogen-containing alkenyl, halogen-free or halogen-containing alkynyl, halogen-free or halogen-containing cycloalkyl, halogen-free or halogen-containing cycloalkylalkyl, halogen-free or halogen-containing cycloalkenyl, halogen-free or halogen-containing alkoxyalkyl, unsubstituted or substituted heterocyclyl, unsubstituted or substituted heterocyclylalkyl, unsubstituted or substituted aryl, unsubstituted or substituted arylalkyl, unsubstituted or substituted heteroaryl, or unsubstituted or substituted heteroarylalkyl;

$R_{51}$, $R_{55}$, $R_{56}$, $R_{63}$, and $R_{64}$ each independently represent hydrogen, nitro, alkoxyaminocarbonyl, trialkylsilyl, dialkylphosphonyl, $N(R_{71})_2$, $CON(R_{71})_2$, $OR_{71}$, $COR_{71}$, $CO_2R_{71}$, $COSR_{71}$, $OCOR_{71}$, $S(O)_mR_{72}$, alkyl, haloalkyl, alkenyl, haloalkenyl, alkynyl, haloalkynyl, cycloalkyl, cycloalkenyl, halocycloalkyl, alkoxyalkyl, cycloalkylalkyl, aryl, arylalkyl, aryloxy, aryloxyalkyl, arylalkyloxy, arylcarbonyl, arylsulfonyl, heteroaryl, heteroarylalkyl, heteroaryloxy, heteroaryloxyalkyl, heteroarylalkyloxy, heteroarylcarbonyl, heteroarylsulfonyl, heterocyclyl, heterocyclylalkyl, heterocyclyloxy, heterocyclyloxyalkyl, heterocyclylalkyloxy, heterocyclylcarbonyl, heterocyclylsulfonyl, -alkyl-$NR_{21}$-aryl, -alkyl-$NR_{21}$-heteroaryl, -alkyl-$NR_{21}$-heterocyclyl, wherein the last 35 groups as mentioned are each substituted by 0, 1, 2 or 3 groups selected from the group consisting of cyano, halogen, nitro, cyanothio, $OR_{71}$, $S(O)_mR_{72}$, $N(R_{71})_2$, $NR_{71}OR_{71}$, $COR_{71}$, $OCOR_{71}$, $SCOR_{72}$, $NR_{71}COR_{71}$, $NR_{71}SO_2R_{72}$, $CO_2R_{71}$, $COSR_{71}$, $CON(R_{71})_2$ and alkoxyalkoxycarbonyl;

$R_{71}$ independently represents hydrogen, alkyl, alkenyl, alkynyl, cycloalkyl, or cycloalkylalkyl;

$R_{72}$ independently represents alkyl, alkenyl, alkynyl, cycloalkyl, or cycloalkylalkyl;

r represents 0, 1 or 2;

m independently represents 0, 1 or 2;

n independently represents 0, or 1;

s independently represents 0, 1, 2 or 3.

Preferably, $Z_1$, and $Z_2$ each independently represent nitro, halogen, cyano, formyl, thiocyano, sulfhydryl, a halogen-containing or not containing group selected from C1-C8 alkyl, C2-C8 alkenyl, C2-C8 alkynyl, C3-C8 cycloalkyl, C3-C8 cycloalkenyl, C3-C8 cycloalkyl-C1-C6 alkyl, and C3-C8 cycloalkenyl-C1-C6 alkyl, $OR^1$, $COR^1$, $COOR^1$, $OCOR^1$, $OCOOR^1$, $NR^3SO_2R^2$, $OSO_2R^2$, $S(O)_mR^2$, $NR^3COR^1$, $NR^3COOR^1$, $C(O)NR^3OR^1$, $SO_2OR^1$, $C(O)NR^4R^5$, $NR^3C(O)NR^4R^5$, $OC(O)NR^4R^5$, $SO_2NR^4R^5$, $C(S)R^1$, $C(S)OR^1$, $C(S)SR^2$, $C(O)SR^2$, $SC(O)R^1$, $SC(S)R^1$, $OC(S)R^1$, —(C1-C6 alkyl)-$C(S)R^1$, —(C1-C6 alkyl)-$C(S)OR^1$, —(C1-C6 alkyl)-$C(O)SR^1$, —(C1-C6 alkyl)-$C(S)SR^1$, —(C1-C6 alkyl)-$SC(O)R^1$, —(C1-C6 alkyl)-$OC(S)R^1$, —(C1-C6 alkyl)-$SC(S)R^1$, —O—(C1-C6 alkyl)-$NR^4R^5$, —S—(C1-C6 alkyl)-$NR^4R^5$, —(C1-C6 alkyl)-O—(C1-C6 alkyl)-$NR^4R^5$, —(C1-C6 alkyl)-S—(C1-C6 alkyl)-$NR^4R^5$, —(C1-C6 alkyl)-$(C{=}S)_n$—$NR^4R^5$, —NH—(C1-C6 alkyl)-$NR^4R^5$, —(C1-C6 alkyl)-$OR^1$, —(C1-C6 alkyl)-$COR^1$, —(C1-C6 alkyl)-$CO_2R^1$, —(C1-C6 alkyl)-$OCOR^1$, —(C1-C6 alkyl)-$NR^3COR^1$, —(C1-C6 alkyl)-$SO_2OR^1$, —(C1-C6 alkyl)-$NR^3SO_2R^2$, —(C1-C6 alkyl)-$OSO_2R^2$, —(C1-C6 alkyl)-$S(O)_mR^2$, —(C1-C6 alkyl)-$CONR^4R^5$, —(C1-C6 alkyl)-$SO_2NR^4R^5$, $NR^4R^5$,

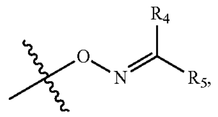

$P(O)(OR^6)_2$, $CH_2P(O)(OR^6)_2$, —$SO_2NR^4R^5$—(C1-C6 alkyl)-$S(O)_mR^2$, —(C1-C6 alkyl)-CN, aryl, heteroaryl, heterocyclyl, aryl-C1-C6 alkyl, heteroaryl-C1-C6 alkyl, or heterocyclyl-C1-C6 alkyl;

$R^1$, $R^3$, $R^4$, and $R^5$ each independently represent hydrogen, aryl, aryl-C1-C6 alkyl, heteroaryl, heteroaryl-C1-C6 alkyl, C1-C8 alkyl, halogenated C1-C8 alkyl, C2-C8 alkenyl, halogenated C2-C8 alkenyl, C2-C8 alkynyl, halogenated C2-C8 alkynyl, C3-C8 cycloalkyl, halogenated C3-C8 cycloalkyl, C1-C8 alkoxy-C1-C6 alkyl, C3-C8 cycloalkyl-C1-C6 alkyl, wherein the last 10 groups as mentioned are each substituted by s groups selected from the group consisting of cyano, halogen, nitro, thiocyano, $OR^7$, $S(O)_mR^9$, $NR^7R^8$, $NR^8OR^7$, $COR^7$, $OCOR^7$, $SCOR^7$, $NR^8COR^7$, $CO_2R^7$, $COSR^7$, $CONR^7R^8$, and C1-C8 alkoxy-C1-C6 alkoxycarbonyl;

$R_2$ independently represents aryl, aryl-C1-C6 alkyl, heteroaryl, heteroaryl-C1-C6 alkyl, C1-C8 alkyl, C2-C8 alkenyl, C2-C8 alkynyl, C3-C8 cycloalkyl, C3-C8 cycloalkyl-C1-C6 alkyl, wherein the last 5 groups as mentioned are each substituted by s groups selected from the group consisting of cyano, halogen, nitro, thiocyano, $OR^7$, $S(O)_mR^9$, $NR^7R^8$, $NR^8OR^7$, $COR^7$, $OCOR^7$, $SCOR^7$, $NR^8COR^7$, $CO_2R^7$, $COSR^7$, $CONR^7R^8$, and C1-C8 alkoxy-C1-C6 alkoxycarbonyl;

$R_6$ independently represents methyl, or ethyl;

$R^7$, and $R^8$ each independently represent hydrogen, C1-C8 alkyl, C2-C8 alkenyl, or C2-C8 alkynyl;

$R^9$ independently represents C1-C8 alkyl, C2-C8 alkenyl, or C2-C8 alkynyl;

X represents

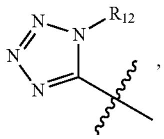 , 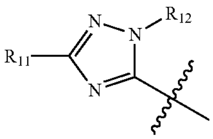 ,

-continued

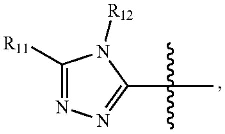, 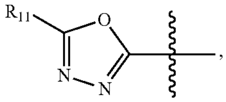,

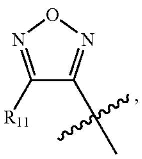, 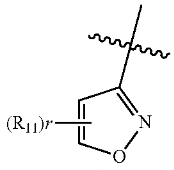, or

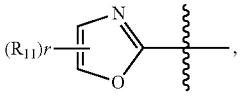, each of which is unsubstituted or substituted;

$R_{11}$ independently represents hydrogen, halogen, cyano, nitro, C1-C8 alkyl unsubstituted or substituted by $R_{13}$, C3-C8 cycloalkyl unsubstituted or substituted by $R_{14}$, C2-C8 alkenyl, halogenated C2-C8 alkenyl, C2-C8 alkynyl, halogenated C2-C8 alkynyl, C3-C8 cycloalkenyl, $NH_2$, aminoacyl, carboxyl, C1-C8 alkoxy-C1-C6 alkoxycarbonyl, $OR_{15}$, —(C1-$C_6$) alkyl-$OR_{15}$, C(O)$R_{16}$, —(C1-$C_6$) alkyl-C(O)$R_{16}$, C(O)O$R_{16}$, —(C1-$C_6$) alkyl-C(O)O$R_{16}$, $S(O)_mR_{16}$, —(C1-$C_6$) alkyl-$S(O)_m R_{16}$, $N(R_{16})_2$, C(O)$N(R_{16})_2$, NHC(O)$R_{17}$, heterocyclyl, heterocyclyl-C1-C6 alkyl, heterocyclyloxy, heterocyclylcarbonyl, aryl, aryl-C1-C6 alkyl, aryloxy, arylcarbonyl, heteroaryl, heteroaryl-C1-C6 alkyl, heteroaryloxy, heteroarylcarbonyl;

$R_{12}$ independently represents hydrogen, C1-C8 alkyl unsubstituted or substituted by $R_{18}$, C3-C8 cycloalkyl, halogenated C3-C8 cycloalkyl, C2-C8 alkenyl, halogenated C2-C8 alkenyl, C2-C8 alkynyl, halogenated C2-C8 alkynyl, C3-C8 cycloalkenyl, aryl; or, when M is

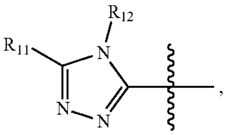,

—$(CH_2)_4$— or —CH═CH—CH═CH— formed by $R_{11}$ and $R_{12}$, the nitrogen atom bound to $R_{12}$ and the carbon atom bound to $R_{11}$ together form a 6-membered ring;

$R_{15}$ independently represents C1-C8 alkyl which is unsubstituted or substituted with a substituent selected from $R_{21}$, C3-C8 cycloalkyl, halogenated C3-C8 cycloalkyl, C2-C8 alkenyl, halogenated C2-C8 alkenyl, C2-C8 alkynyl, halogenated C2-C8 alkynyl, C3-C8 cycloalkenyl, or phenyl;

$R_{16}$ independently represents C1-C8 alkyl, halogenated C1-C8 alkyl, C3-C8cycloalkyl, C2-C8 alkenyl, halogenated C2-C8 alkenyl, C2-C8 alkynyl, halogenated C2-C8 alkynyl, or C3-C8 cycloalkenyl;

$R_{21}$ independently represents halogen, cyano, C3-C8 cycloalkyl, hydroxy, sulfhydryl, C1-C8 alkoxy, C(O)$R_{22}$, carboxyl, C1-C8 alkoxycarbonyl, C1-C8 alkoxy-C1-C6 alkoxycarbonyl, —$S(O)_m$-C1-C8 alkyl, heteroaryl, heterocyclyl, or phenyl which is unsubstituted or substituted with one or more (for example 1, 2, 3, 4, or 5) groups independently selected from $R_{23}$;

$R_{17}$, and $R_{22}$ each independently represent hydrogen, C1-C8 alkyl, or $N(R_{24})R_{25}$;

$R_{23}$ independently represents halogen, cyano, nitro, C1-C8 alkyl, C1-C8 alkyl unsubstituted or substituted by $R_{31}$, C3-C8 cycloalkyl, halogenated C3-C8 cycloalkyl, C2-C8 alkenyl, halogenated C2-C8 alkenyl, C2-C8 alkynyl, halogenated C2-C8 alkynyl, C3-C8 cycloalkenyl, C1-C8 alkylcarbonyl, C3-C8 cycloalkylcarbonyl, halogenated C1-C8 alkylcarbonyl, halogenated C3-C8 cycloalkylcarbonyl, C1-C8 alkoxycarbonyl, halogenated C1-C8 alkoxycarbonyl, C1-C8 alkylaminocarbonyl, halogenated C1-C8 alkylaminocarbonyl, bis(C1-C8 alkyl)aminocarbonyl, $OR_{32}$, $S(O)_mR_{33}$, C1-C8 alkylaminosulfonyl, bis(C1-C8 alkyl)aminosulfonyl, $NH_2$, C1-C8 alkylamino, bis(C1-C8 alkyl)amino, aryl, heteroaryl, heterocyclyl;

$R_{24}$ and $R_{25}$ each independently represent hydrogen, C1-C8 alkyl or phenyl; or, C2-C8 alkylidene chain formed by $R_{24}$ and $R_{25}$, and the nitrogen atom(s) bound to $R_{24}$ and $R_{25}$ together form a 3-7-membered ring, said C2-C8 alkylidene chain optionally contains one O, S, S(O), $S(O)_2$, NH or N-alkyl and optionally substituted by oxo or thio group;

$R_{13}$, $R_{14}$, $R_{18}$, and $R_{31}$ each independently represent halogen, cyano, nitro, carboxyl, C1-C8 alkoxycarbonyl, C1-C8 alkoxy-C1-C6 alkoxycarbonyl, $S(O)_mR_{41}$, $OR_{42}$, C1-C8 alkyl, halogenated C1-C8 alkyl, C2-C8 alkenyl, halogenated C2-C8 alkenyl, C2-C8 alkynyl, halogenated C2-C8 alkynyl, aryl, heteroaryl, or heterocyclyl;

$R_{32}$ independently represents hydrogen, C1-C8 alkyl, halogenated C1-C8 alkyl, C3-C8 cycloalkyl, halogenated C3-C8 cycloalkyl, C2-C8 alkenyl, halogenated C2-C8 alkenyl, C2-C8 alkynyl, halogenated C2-C8 alkynyl, or C3-C8 cycloalkenyl;

$R_{33}$ independently represents C1-C8 alkyl, halogenated C1-C8 alkyl, C3-C8 cycloalkyl, C2-C8 alkenyl, halogenated C2-C8 alkenyl, C2-C8 alkynyl, halogenated C2-C8 alkynyl, or C3-C8 cycloalkenyl;

$R_{41}$, and $R_{42}$ each independently represent hydrogen, C1-C8 alkyl, halogenated C1-C8 alkyl, C3-C8 cycloalkyl, halogenated C3-C8 cycloalkyl, C2-C8 alkenyl, halogenated C2-C8 alkenyl, C2-C8 alkynyl, halogenated C2-C8 alkynyl, C3-C8 cycloalkenyl, phenyl, or benzyl;

Q represents halogen, cyano, cyano-C1-C6 alkyl, nitro, $N(R_{51})_2$, —(C1-C6) alkyl-$N(R_{51})_2$, —(C1-C6) alkyl-$N^+(R_{51})_3$, CON$(R_{51})_2$, —(C1-C6) alkyl-CON$(R_{51})_2$, C1-C6 alkyl substituted by amino and carboxyl, $OR_{52}$, —(C1-C6) alkyl-$OR_{52}$, $COR_{52}$, $COOR_{52}$, $COSR_{52}$, —(C1-C6) alkyl-$COR_{52}$, —(C1-C6) alkyl-$COOR_{52}$, —(C1-C6) alkyl-$COSR_{52}$, —(C1-C6) alkyl-$OCOR_{52}$, $Si(R_{52})_3$, —(C1-C6) alkyl-O—$Si(R_{52})_3$, —(C1-C6) alkyl-O—N═$C(R_{52})_2$, $S(O)_mR_{53}$, —(C1-C6) alkyl-$S(O)_mR_{53}$, C1-C8 alkyl, halogenated C1-C8 alkyl; C2-C8 alkenyl or C2-C8 alkynyl group which is not substituted or substituted by at least one group (for example, one group, two groups, three groups, four groups, five groups) selected from halogen, cyano, C3-C8 cycloalkyl, C1-C8 alkylcarbonyl, C1-C8 alkoxycarbonyl, C1-C8 alkoxy, C1-C8 alkylsulfanyl, C1-C8 alkylsulfinyl, C1-C8 alkylsulfonyl or tri(C1-C8alkyl)silyl; C3-C8 cycloalkyl or C3-C8 cycloalkyl-C1-C6 alkyl, which is not substituted or substituted by at least one group (for example, one group, two groups, three groups, four groups, five groups) selected from C1-C8 alkyl, halogen or phenyl; heterocyclyl, aryl, heteroaryl, heterocyclyl-C1-C6 alkyl, aryl-C1-C6 alkyl or heteroaryl-C1-C6 alkyl, which is unsubstituted or substituted;

Y represents hydrogen, $OR_{54}$, $SR_{54}$, $COR_{54}$, $OCOR_{54}$, $COOR_{54}$, $CON(R_{55})_2$, $N(R_{55})_2$, $NR_{56}COOR_{54}$, $NR_{56}CON(R_{55})_2$, —(C1-C6 alkyl)-$R_{57}$, halogen-free or halogen-containing C1-C8 alkyl, halogen-free or halogen-containing C2-C8 alkenyl, halogen-free or halogen-containing C2-C8 alkynyl, halogen-free or halogen-containing C3-C8 cycloalkyl, unsubstituted or substituted aryl-C1-C6alkyl, or unsubstituted or substituted heteroaryl-C1-C6 alkyl;

$R_{57}$ independently represents halogen-free or halogen-containing C2-C8 alkenyl, halogen-free or halogen-containing C2-C8 alkynyl, halogen-free or halogen-containing C3-C8 cycloalkyl, CN, $OR_{61}$, $OCOR_{61}$, $COOR_{61}$, $COR_{61}$, —O—(C═O)—O—$R_{61}$, $OSO_2R_{62}$, $SO_2OR_{61}$, $S(O)_mR_{62}$, $N(R_{63})_2$, $CON(R_{63})_2$, $SO_2N(R_{63})_2$, $NR_{64}COR_{61}$, $NR_{64}SO_2R_{62}$, or —O—(C═O)—$N(R_{63})_2$;

$R_{52}$, $R_{54}$, and $R_{61}$ each independently represent hydrogen, halogen-free or halogen-containing C1-C8 alkyl, halogen-free or halogen-containing C2-C8 alkenyl, halogen-free or halogen-containing C2-C8 alkynyl, halogen-free or halogen-containing C3-C8 cycloalkyl, halogen-free or halogen-containing C3-C8 cycloalkyl-C1-C6 alkyl, halogen-free or halogen-containing C3-C8 cycloalkenyl, halogen-free or halogen-containing C1-C8 alkoxy-C1-C6 alkyl, unsubstituted or substituted heterocyclyl, unsubstituted or substituted heterocyclyl-C1-C6 alkyl, unsubstituted or substituted heterocyclyloxy-C1-C6 alkyl, unsubstituted or substituted aryl, unsubstituted or substituted aryl-C1-C6 alkyl, unsubstituted or substituted aryloxy-C1-C6 alkyl, unsubstituted or substituted heteroaryl, unsubstituted or substituted heteroaryl-C1-C6 alkyl, or unsubstituted or substituted heteroaryloxy-C1-C6 alkyl;

$R_{53}$, and $R_{62}$ each independently represent halogen-free or halogen-containing C1-C8 alkyl, halogen-free or halogen-containing C2-C8 alkenyl, halogen-free or halogen-containing C2-C8 alkynyl, halogen-free or halogen-containing C3-C8 cycloalkyl, halogen-free or halogen-containing C3-C8 cycloalkyl-C1-C6 alkyl, halogen-free or halogen-containing C3-C8 cycloalkenyl, halogen-free or halogen-containing C1-C8 alkoxy-C1-C6 alkyl, unsubstituted or substituted heterocyclyl, unsubstituted or substituted heterocyclyl-C1-C6 alkyl, unsubstituted or substituted aryl, unsubstituted or substituted aryl-C1-C6 alkyl, unsubstituted or substituted heteroaryl, or unsubstituted or substituted heteroaryl-C1-C6 alkyl;

$R_{51}$, $R_{55}$, $R_{56}$, $R_{63}$, and $R_{64}$ each independently represent hydrogen, nitro, C1-C8 alkoxyaminocarbonyl, tri(C1-C8alkyl)silyl, di(C1-C8alkyl)phosphonyl, $N(R_{71})_2$, $CON(R_{71})_2$, $OR_{71}$, $COR_{71}$, $CO_2R_{71}$, $COSR_{71}$, $OCOR_{71}$, $S(O)_mR_{72}$, C1-C8 alkyl, halogenated C1-C8 alkyl, C2-C8 alkenyl, halogenated C2-C8 alkenyl, C2-C8 alkynyl, halogenated C2-C8 alkynyl, C3-C8 cycloalkyl, C3-C8 cycloalkenyl, halogenated C3-C8 cycloalkyl, C1-C8 alkoxy-C1-C6 alkyl, C3-C8 cycloalkyl-C1-C6 alkyl, aryl, aryl-C1-C6 alkyl, aryloxy, aryloxy-C1-C6 alkyl, aryl-C1-C6 alkyloxy, arylcarbonyl, arylsulfonyl, heteroaryl, heteroaryl-C1-C6 alkyl, heteroaryloxy, heteroaryloxy-C1-C6 alkyl, heteroaryl-C1-C6 alkyloxy, heteroarylcarbonyl, heteroarylsulfonyl, heterocyclyl, heterocyclyl-C1-C6 alkyl, heterocyclyloxy, heterocyclyloxy-C1-C6 alkyl, heterocyclyl-C1-C6 alkyloxy, heterocyclylcarbonyl, heterocyclylsulfonyl, —(C1-C6 alkyl)-$NR_{21}$-aryl, —(C1-C6 alkyl)-$NR_{21}$-heteroaryl, or —(C1-C6 alkyl)-$NR_{21}$-heterocyclyl, wherein the last 35 groups as mentioned each are independently substituted by 0, 1, 2 or 3 groups selected from the group consisting of cyano, halogen, nitro, cyanothio, $OR_{71}$, $S(O)_mR_{72}$, $N(R_{71})_2$, $NR_{71}OR_{71}$, $COR_{71}$, $OCOR_{71}$, $SCOR_{72}$, $NR_{71}COR_{71}$, $NR_{71}SO_2R_{72}$, $CO_2R_{71}$, $COSR_{71}$, $CON(R_{71})_2$ and C1-C8 alkoxy-C1-C6 alkoxycarbonyl;

$R_{71}$ independently represents hydrogen, C1-C8 alkyl, C2-C8 alkenyl, C2-C8 alkynyl, C3-C8 cycloalkyl, or C3-C8 cycloalkyl-C1-C6 alkyl;

$R_{72}$ independently represents C1-C8 alkyl, C2-C8 alkenyl, C2-C8 alkynyl, C3-C8 cycloalkyl, or C3-C8 cycloalkyl-C1-C6 alkyl;

r represents 0, 1 or 2;

m independently represents 0, 1 or 2;

n independently represents 0, or 1;

s independently represents 0, 1, 2 or 3.

More preferably, $Z_1$, and $Z_2$ each independently represent nitro, halogen, cyano, formyl, thiocyano, sulfhydryl, a halogen-containing or not containing group selected from C1-C6 alkyl, C2-C6 alkenyl, C2-C6 alkynyl, C3-C6 cycloalkyl, C3-C6 cycloalkenyl, C3-C6 cycloalkyl-C1-C3 alkyl, and C3-C6 cycloalkenyl-C1-C3 alkyl, $OR^1$, $COR^1$, $COOR^1$, $OCOR^1$, $OCOOR^1$, $NR^3SO_2R^2$, $OSO_2R^2$, $S(O)_mR^2$, $NR^3COR^1$, $NR^3COOR^1$, $C(O)NR^3OR^1$, $SO_2OR^1$, $C(O)NR^4R^5$, $NR^3C(O)NR^4R^5$, $OC(O)NR^4R^5$, $SO_2NR^4R^5$, $C(S)R^1$, $C(S)OR^1$, $C(S)SR^2$, $C(O)SR^2$, $SC(O)R^1$, $SC(S)R^1$, $OC(S)R^1$, —(C1-C3 alkyl)-$C(S)R^1$, —(C1-C3 alkyl)-$C(S)OR^1$, —(C1-C3 alkyl)-$C(O)SR^1$, —(C1-C3 alkyl)-$C(S)SR^1$, —(C1-C3 alkyl)-$SC(O)R^1$, —(C1-C3 alkyl)-$OC(S)R^1$, —(C1-C3 alkyl)-$SC(S)R^1$, —O—(C1-C3 alkyl)-$NR^4R^5$, —S—(C1-C3 alkyl)-$NR^4R^5$, —(C1-C3 alkyl)-O—(C1-C3 alkyl)-$NR^4R^5$, —(C1-C3 alkyl)-S—(C1-C3 alkyl)-$NR^4R^5$, —(C1-C3 alkyl)-$(C{=}S)_n$—$NR^4R^5$, —NH—(C1-C3 alkyl)-$NR^4R^5$, —(C1-C3 alkyl)-$OR^1$, —(C1-C3 alkyl)-$COR^1$, —(C1-C3 alkyl)-$CO_2R^1$, —(C1-C3 alkyl)-$OCOR^1$, —(C1-C3 alkyl)-$NR^3COR^1$, —(C1-C3 alkyl)-$SO_2OR^1$, —(C1-C3 alkyl)-$NR^3SO_2R^2$, —(C1-C3 alkyl)-$OSO_2R^2$, —(C1-C3 alkyl)-$S(O)_mR^2$, —(C1-C3 alkyl)-$CONR^4R^5$, —(C1-C3 alkyl)-$SO_2NR^4R^5$, $NR^4R^5$,

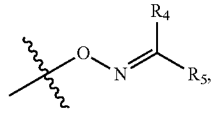

$P(O)(OR^6)_2$, $CH_2P(O)(OR^6)_2$, —$SO_2NR^4R^5$—(C1-C3 alkyl)-$S(O)_mR^2$, —(C1-C3 alkyl)-CN, aryl, heteroaryl, heterocyclyl, aryl-C1-C3 alkyl, heteroaryl-C1-C3 alkyl, or heterocyclyl-C1-C3 alkyl;

$R^1$, $R^3$, $R^4$, and $R^5$ each independently represent hydrogen, aryl, aryl-C1-C3 alkyl, heteroaryl, heteroaryl-C1-C3 alkyl, C1-C6 alkyl, halogenated C1-C6 alkyl, C2-C6 alkenyl, halogenated C2-C6 alkenyl, C2-C6 alkynyl, halogenated C2-C6 alkynyl, C3-C6 cycloalkyl, halogenated C3-C6 cycloalkyl, C1-C6 alkoxy-C1-C3 alkyl, C3-C6 cycloalkyl-C1-C3 alkyl, wherein the last 10 groups as mentioned are each substituted by s groups selected from the group consisting of cyano, halogen, nitro, thiocyano, $OR^7$, $S(O)_mR^9$, $NR^7R^8$, $NR^8OR^7$, $COR^7$, $OCOR^7$, $SCOR^7$, $NR^BCOR^7$, $CO_2R^7$, $COSR^7$, $CONR^7R^8$, and C1-C6 alkoxy-C1-C3 alkoxycarbonyl;

$R^2$ independently represents aryl, aryl-C1-C3 alkyl, heteroaryl, heteroaryl-C1-C3 alkyl, C1-C6 alkyl, C2-C6 alkenyl, C2-C6 alkynyl, C3-C6 cycloalkyl, C3-C6 cycloalkyl-C1-C3 alkyl, wherein the last 5 groups as mentioned are each substituted by s groups selected from the group consisting of cyano, halogen, nitro, thiocyano, $OR^7$, $S(O)_mR^9$, $NR^7R^8$, $NROR^7$, $COR^7$, $OCOR^7$, $SCOR^7$, $NR^8COR^7$, $CO_2R^7$, $COSR^7$, $CONR^7R^8$, and C1-C6 alkoxy-C1-C3 alkoxycarbonyl;

$R^6$ independently represents methyl, or ethyl;

$R^7$, and $R^8$ each independently represent hydrogen, C1-C6 alkyl, C2-C6 alkenyl, or C2-C6 alkynyl;

$R^9$ independently represents C1-C6 alkyl, C2-C6 alkenyl, or C2-C6 alkynyl;

X represents

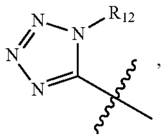,
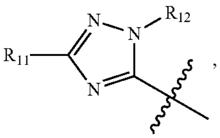,
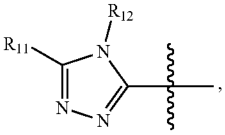,
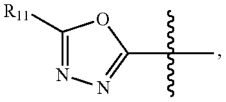,
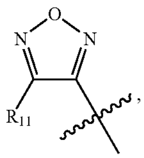,
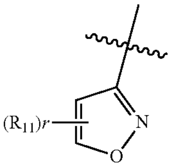, or
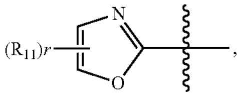, each of which is unsubstituted or substituted;

$R_{11}$ independently represents hydrogen, halogen, cyano, nitro, C1-C6 alkyl unsubstituted or substituted by $R^{13}$, C3-C6 cycloalkyl unsubstituted or substituted by $R^{14}$, C2-C6 alkenyl, halogenated C2-C6 alkenyl, C2-C6 alkynyl, halogenated C2-C6 alkynyl, C3-C6 cycloalkenyl, $NH_2$, aminoacyl, carboxyl, C1-C6 alkoxy-C1-C3 alkoxycarbonyl, $OR_{15}$, —(C1-C3) alkyl-$OR_{15}$, C(O)$R_{16}$, —(C1-C3) alkyl-C(O)$R_{16}$, C(O)$OR_{16}$, —(C1-C3) alkyl-C(O)$OR_{16}$, $S(O)_mR_{16}$, —(C1-C3) alkyl-$S(O)_m R_{16}$, $N(R_{16})_2$, C(O)$N(R_{16})_2$, NHC(O)$R_{17}$, heterocyclyl, heterocyclyl-C1-C3 alkyl, heterocyclyloxy, heterocyclylcarbonyl, aryl, aryl-C1-C3 alkyl, aryloxy, arylcarbonyl, heteroaryl, heteroaryl-C1-C3 alkyl, heteroaryloxy, heteroarylcarbonyl;

$R_{12}$ independently represents hydrogen, C1-C6 alkyl unsubstituted or substituted by $R_{18}$, C3-C6 cycloalkyl, halogenated C3-C6 cycloalkyl, C2-C6 alkenyl, halogenated C2-C6 alkenyl, C2-C6 alkynyl, halogenated C2-C6 alkynyl, C3-C6 cycloalkenyl, aryl; or, when M is

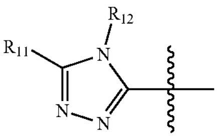, $-(CH_2)_4-$ or —CH═CH—CH═CH— formed by $R_{11}$ and $R_{12}$, the nitrogen atom bound to $R_{12}$ and the carbon atom bound to Rn together form a 6-membered ring;

$R_{15}$ independently represents C1-C6 alkyl which is unsubstituted or substituted with a substituent selected from $R_{21}$, C3-C6 cycloalkyl, halogenated C3-C6 cycloalkyl, C2-C6 alkenyl, halogenated C2-C6 alkenyl, C2-C6 alkynyl, halogenated C2-C6 alkynyl, C3-C6 cycloalkenyl, or phenyl;

$R_{16}$ independently represents C1-C6 alkyl, halogenated C1-C6 alkyl, C3-C6cycloalkyl, C2-C6 alkenyl, halogenated C2-C6 alkenyl, C2-C6 alkynyl, halogenated C2-C6 alkynyl, or C3-C6 cycloalkenyl;

$R_{21}$ independently represents halogen, cyano, C3-C6 cycloalkyl, hydroxy, sulfhydryl, C1-C6 alkoxy, C(O)$R_{22}$, carboxyl, C1-C6 alkoxycarbonyl, C1-C6 alkoxy-C1-C3 alkoxycarbonyl, $-S(O)_m$-C1-C6 alkyl, heteroaryl, heterocyclyl, or phenyl which is unsubstituted or substituted with one or more (for example 1, 2, 3, 4, or 5) groups independently selected from $R_{23}$;

$R_{17}$, and $R_{22}$ each independently represent hydrogen, C1-C6 alkyl, or $N(R_{24})R_{25}$;

$R_{23}$ independently represents halogen, cyano, nitro, C1-C6 alkyl, C1-C6 alkyl unsubstituted or substituted by $R_{31}$, C3-C6 cycloalkyl, halogenated C3-C6 cycloalkyl, C2-C6 alkenyl, halogenated C2-C6 alkenyl, C2-C6 alkynyl, halogenated C2-C6 alkynyl, C3-C6 cycloalkenyl, C1-C6 alkylcarbonyl, C3-C6 cycloalkylcarbonyl, halogenated C1-C6 alkylcarbonyl, halogenated C3-C6 cycloalkylcarbonyl, C1-C6 alkoxycarbonyl, halogenated C1-C6 alkoxycarbonyl, C1-C6 alkylaminocarbonyl, halogenated C1-C6 alkylaminocarbonyl, bis(C1-C6 alkyl)aminocarbonyl, $OR_{32}$, $S(O)_mR_{33}$, C1-C6 alkylaminosulfonyl, bis(C1-C6 alkyl)aminosulfonyl, $NH_2$, C1-C6 alkylamino, bis(C1-C6 alkyl)amino, aryl, heteroaryl, heterocyclyl;

$R_{24}$ and $R_{25}$ each independently represent hydrogen, C1-C6 alkyl or phenyl; or, C2-C6 alkylidene chain formed by $R_{24}$ and $R_{25}$, and the nitrogen atom(s) bound to $R_{24}$ and $R_{25}$ together form a 3-7-membered ring, said C2-C6 alkylidene chain optionally contains one O, S, S(O), $S(O)_2$, NH or N-alkyl and optionally substituted by oxo or thio group;

$R_{13}$, $R_{14}$, $R_{18}$, and $R_{31}$ each independently represent halogen, cyano, nitro, carboxyl, C1-C6 alkoxycarbonyl, C1-C6 alkoxy-C1-C3 alkoxycarbonyl, $S(O)_mR_{41}$, $OR_{42}$, C1-C6 alkyl, halogenated C1-C6 alkyl, C2-C6 alkenyl, halogenated C2-C6 alkenyl, C2-C6 alkynyl, halogenated C2-C6 alkynyl, aryl, heteroaryl, or heterocyclyl;

$R_{32}$ independently represents hydrogen, C1-C6 alkyl, halogenated C1-C6 alkyl, C3-C6 cycloalkyl, halogenated C3-C6 cycloalkyl, C2-C6 alkenyl, halogenated C2-C6 alkenyl, C2-C6 alkynyl, halogenated C2-C6 alkynyl, or C3-C6 cycloalkenyl;

$R_{33}$ independently represents C1-C6 alkyl, halogenated C1-C6 alkyl, C3-C6 cycloalkyl, C2-C6 alkenyl, halogenated C2-C6 alkenyl, C2-C6 alkynyl, halogenated C2-C6 alkynyl, or C3-C6 cycloalkenyl;

$R_{41}$, and $R_{42}$ each independently represent hydrogen, C1-C6 alkyl, halogenated C1-C6 alkyl, C3-C6 cycloalkyl, halogenated C3-C6 cycloalkyl, C2-C6 alkenyl, halogenated C2-C6 alkenyl, C2-C6 alkynyl, halogenated C2-C6 alkynyl, C3-C6 cycloalkenyl, phenyl, or benzyl;

Q represents halogen, cyano, cyano C1-C3 alkyl, nitro, $N(R_{51})_2$, —(C1-C3) alkyl-$N(R_{51})_2$, —(C1-C3) alkyl-$N^+(R_{51})_3$, $CON(R_{51})_2$, —(C1-C3) alkyl-$CON(R_{51})_2$, C1-C3 alkyl substituted by amino and carboxyl, $OR_{52}$, —(C1-C3) alkyl-$OR_{52}$, $COR_{52}$, $COOR_{52}$, $COSR_{52}$, —(C1-C3) alkyl-$COR_{52}$, —(C1-C3) alkyl-$COOR_{52}$, —(C1-C3) alkyl-$COSR_{52}$, —(C1-C3) alkyl-$OCOR_{52}$, $Si(R_{52})_3$, —(C1-C3) alkyl-O—$Si(R_{52})_3$, —(C1-C3) alkyl-O—N═$C(R_2)_2$, $S(O)_mR_{53}$, —(C1-C3) alkyl-$S(O)_mR_{53}$, C1-C8 alkyl, halogenated C1-C6 alkyl; C2-C6 alkenyl or C2-C6 alkynyl group which is not substituted or substituted by at least one group (for example, one group, two groups, three groups, four groups, five groups) selected from halogen, cyano, C3-C6 cycloalkyl, C1-C6 alkylcarbonyl, C1-C6 alkoxycarbonyl, C1-C6 alkoxy, C1-C6 alkylsulfanyl, C1-C6 alkylsulfinyl, C1-C6 alkylsulfonyl or tri(C1-C6 alkyl)silyl; C3-C6 cycloalkyl or C3-C6 cycloalkyl-C1-C6 alkyl, which is not substituted or substituted by at least one group (for example, one group, two groups, three groups, four groups, five groups) selected from C1-C6 alkyl, halogen or phenyl; heterocyclyl, aryl, heteroaryl, heterocyclyl-C1-C3 alkyl, aryl-C1-C3 alkyl or heteroaryl-C1-C3 alkyl, which is unsubstituted or substituted;

Y represents hydrogen, $OR_{54}$, $SR_{54}$, $COR_{54}$, $OCOR_{54}$, $COOR_{54}$, $CON(R_{55})_2$, $N(R_{55})_2$, $NR_{56}COOR_{54}$, $NR_{56}CON(R_{55})_2$, —(C1-C3alkyl)-$R_{57}$, halogen-free or halogen-containing C1-C6 alkyl, halogen-free or halogen-containing C2-C6 alkenyl, halogen-free or halogen-containing C2-C6 alkynyl, halogen-free or halogen-containing C3-C6 cycloalkyl, unsubstituted or substituted aryl-C1-C3 alkyl, or unsubstituted or substituted heteroaryl-C1-C3 alkyl;

$R_{57}$ independently represents halogen-free or halogen-containing C2-C6 alkenyl, halogen-free or halogen-containing C2-C6 alkynyl, halogen-free or halogen-containing C3-C6 cycloalkyl, CN, $OR_{61}$, $OCOR_{61}$, $COOR_{61}$, $COR_{61}$, —O—(C═O)—O—$R_{61}$, $OSO_2R_{62}$, $SO_2OR^{61}$, $S(O)_mR_{62}$, $N(R_{63})_2$, $CON(R_{63})_2$, $SO_2N(R_{63})_2$, $NR_{64}COR_{61}$, $NR_{64}SO_2R_{62}$, or —O—(C═O)—$N(R_{63})_2$;

$R_{52}$, $R_{54}$, and $R_{61}$ each independently represent hydrogen, halogen-free or halogen-containing C1-C6 alkyl, halogen-free or halogen-containing C2-C6 alkenyl, halogen-free or halogen-containing C2-C6 alkynyl, halogen-free or halogen-containing C3-C8 cycloalkyl, halogen-free or halogen-containing C3-C6 cycloalkyl-C1-C3 alkyl, halogen-free or halogen-containing C3-C6 cycloalkenyl, halogen-free or halogen-containing C1-C6 alkoxy-C1-C3 alkyl, unsubstituted or substituted heterocyclyl, unsubstituted or substituted heterocyclyl-C1-C3 alkyl, unsubstituted or substituted heterocyclyloxy-C1-C3 alkyl, unsubstituted or substituted aryl, unsubstituted or substituted aryl-C1-C3 alkyl, unsubstituted or substituted aryloxy-C1-C3 alkyl, unsubstituted or substituted heteroaryl, unsubstituted or substituted heteroaryl-C1-C3 alkyl, or unsubstituted or substituted heteroaryloxy-C1-C3 alkyl;

$R_{53}$, and $R_{62}$ each independently represent halogen-free or halogen-containing C1-C6 alkyl, halogen-free or halogen-containing C2-C6 alkenyl, halogen-free or halogen-containing C2-C6 alkynyl, halogen-free or halogen-containing C3-C6 cycloalkyl, halogen-free or halogen-containing C3-C6 cycloalkyl-C1-C3 alkyl, halogen-free or halogen-containing C3-C6 cycloalkenyl, halogen-free or halogen-containing C1-C6 alkoxy-C1-C3 alkyl, unsubstituted or substituted heterocyclyl, unsubstituted or substituted heterocyclyl-C1-C3 alkyl, unsubstituted or substituted aryl, unsubstituted or substituted aryl-C1-C3 alkyl, unsubstituted or substituted heteroaryl, or unsubstituted or substituted heteroaryl-C1-C3 alkyl;

$R_{51}$, $R_{55}$, $R_{56}$, $R_{63}$, and $R_{64}$ each independently represent hydrogen, nitro, C1-C6 alkoxyaminocarbonyl, tri(C1-C6alkyl)silyl, di(C1-C6alkyl)phosphonyl, $N(R_{71})_2$, $CON(R_{71})_2$, $OR_{71}$, $COR_{71}$, $CO_2R_{71}$, $COSR_{71}$, $OCOR_{71}$, $S(O)_mR_{72}$, C1-C6 alkyl, halogenated C1-C6 alkyl, C2-C6 alkenyl, halogenated C2-C6 alkenyl, C2-C6 alkynyl, halogenated C2-C6 alkynyl, C3-C6 cycloalkyl, C3-C6 cycloalkenyl, halogenated C3-C6 cycloalkyl, C1-C6 alkoxy-C1-C3 alkyl, C3-C6 cycloalkyl-C1-C3 alkyl, aryl, aryl-C1-C3 alkyl, aryloxy, aryloxy-C1-C3 alkyl, aryl-C1-C3 alkyloxy, arylcarbonyl, arylsulfonyl, heteroaryl, heteroaryl-C1-C3 alkyl, heteroaryloxy, heteroaryloxy-C1-C3 alkyl, heteroaryl-C1-C3 alkyloxy, heteroarylcarbonyl, heteroarylsulfonyl, heterocyclyl, heterocyclyl-C1-C3 alkyl, heterocyclyloxy, heterocyclyloxy-C1-C3 alkyl, heterocyclyl-C1-C3 alkyloxy, heterocyclylcarbonyl, heterocyclylsulfonyl, —(C1-C3 alkyl)-$NR_{21}$-aryl, —(C1-C3 alkyl)-$NR_{21}$-heteroaryl, or —(C1-C3 alkyl)-$NR_{21}$-heterocyclyl, wherein the last 35 groups as mentioned each are independently substituted by 0, 1, 2 or 3 groups selected from the group consisting of cyano, halogen, nitro, cyanothio, $OR_{71}$, $S(O)_mR_{72}$, $N(R_{71})_2$, $NR_{71}OR_{71}$, $COR_{71}$, $OCOR_{71}$, $SCOR_{72}$, $NR_{71}COR_{71}$, $NR_{71}SO_2R_{72}$, $CO_2R_{71}$, $COSR_{71}$, $CON(R_{71})_2$ and C1-C6 alkoxy-C1-C3 alkoxycarbonyl;

$R_{71}$ independently represents hydrogen, C1-C6 alkyl, C2-C6 alkenyl, C2-C6 alkynyl, C3-C6 cycloalkyl, or C3-C6 cycloalkyl-C1-C3 alkyl;

$R_{72}$ independently represents C1-C6 alkyl, C2-C6 alkenyl, C2-C6 alkynyl, C3-C6 cycloalkyl, or C3-C6 cycloalkyl-C1-C3 alkyl;

r represents 0, 1 or 2;

m independently represents 0, 1 or 2;

n independently represents 0, or 1;

s independently represents 0, 1, 2 or 3.

Further preferably, $Z_1$ represents halogen (for example, fluorine, or chlorine), cyano, C1-C6 alkyl(for example, methyl), C1-C6 alkoxy(for example, methoxy), C1-C6 alkoxy-C1-C6 alkoxy, C1-C6 alkoxy-C1-C6alkylsulfanyl, or C1-C6alkylsulfanyl(for example, methylsulfanyl);

$Z_2$ represents halogen, C1-C6 alkyl, halogenated C1-C6 alkyl(for example, trifluoromethyl, or difluoromethyl), or C1-C6 alkylsulfonyl(for example, methylsulfonyl);

X independently represents

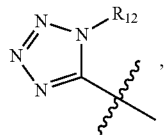
,
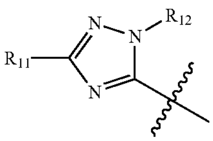
,

-continued

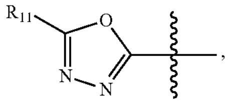, or 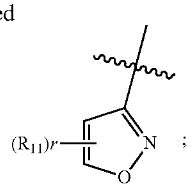 ;

$R_{11}$ independently represents hydrogen, C1-C6 alkyl, or C3-C6 cycloalkyl;

$R_{12}$ independently represents hydrogen, C1-C6 alkyl, or C1-C6 alkoxy-C1-C3 alkyl;

Q independently represents cyano, cyano C1-C3 alkyl, —(C1-C3 alkyl)-N($R_{51}$)$_2$, CON($R_{51}$)$_2$, —(C1-C3 alkyl)-CON($R_{51}$)$_2$, —(C1-C3 alkyl)-$OR_{52}$, $COR_{52}$, —(C1-C3 alkyl)-$COR_{52}$, —(C1-C3 alkyl)-$COOR_{52}$, —(C1-C3 alkyl)-$COSR_{52}$, —(C1-C3 alkyl)-$OCOR_{52}$, Si($R_{52}$)$_3$, —(C1-C3 alkyl)-O—Si($R_{52}$)$_3$, —(C1-C3 alkyl)-O—N═C($R_{52}$)$_2$, —(C1-C3 alkyl)-S(O)$_m$—(C1-C6 alkyl), C1-C8 alkyl, halogenated C1-C6 alkyl, C2-C6 alkenyl, C2-C6 alkynyl, halogenated C2-C6 alkenyl, C3-C6 cycloalkyl-C1-C3 alkyl, unsubstituted or substituted heterocyclyl, unsubstituted or substituted heterocyclyl C1-C3 alkyl, unsubstituted or substituted heteroaryl-C1-C3 alkyl, or unsubstituted or substituted phenyl-C1-C3 alkyl;

$R_{51}$ independently represents hydrogen, or C1-C6 alkyl;

$R_{52}$ independently represents hydrogen, C1-C6 alkyl, halogenated C1-C6 alkyl, phenyl-C1-C3 alkyl, or heteroaryl;

Y independently represents hydrogen, C2-C6 alkynyl, C1-C6 alkylcarbonyl, heteroarylcarbonyl, C1-C6 alkoxycarbonyl, or —(C1-C3 alkyl)-O—(C═O)—O—(C1-C6 alkyl);

r represents 0, 1, or 2;

m represents 0, 1, or 2;

wherein, the "heterocyclyl" refers to

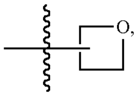, the "heteroaryl" refers to

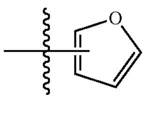 or 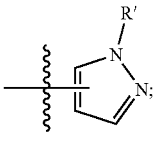;

the above-mentioned groups are unsubstituted or substituted by at least one group (for example, one group, two groups, three groups, four groups, five groups) selected from C1-C6 alkyl; R' represents C1-C6 alkyl.

In another preferred embodiment of the present invention, $Z_1$ represents halogen, C1-C6 alkoxy, or C1-C6 alkylsulfanyl;

$Z_2$ represents C1-C6 alkyl, halogenated C1-C6 alkyl, or C1-C6 alkylsulfonyl;

X independently represents

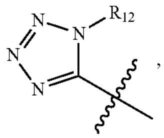, 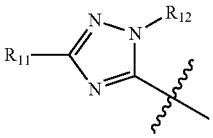,

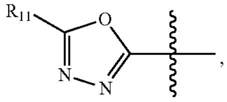, 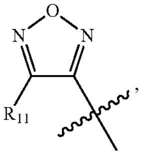, or

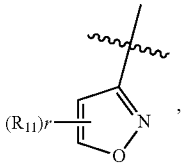, each of which is unsubstituted or substituted;

$R_{11}$ independently represents hydrogen, halogen, cyano, $NH_2$, C1-C6 alkyl which is unsubstituted or substituted with a substituent selected from $R_{13}$, C3-C6 cycloalkyl which is unsubstituted or substituted with a substituent selected from $R_{14}$, C2-C6 alkenyl, C2-C6 alkynyl, C1-C6 alkoxy, C1-C6 alkoxy C1-C3 alkyl, or C1-C6 alkylcarbonylamino;

$R_{12}$ independently represents C1-C6 alkyl, C3-C6 cycloalkyl, C1-C6 alkoxy-C1-C3 alkyl, phenyl, or benzyloxy-C1-C3 alkyl;

$R_{13}$, $R_{14}$ each independently represent halogen, cyano, C1-C6 alkyl, or phenyl;

Q independently represents cyano, cyano C1-C3 alkyl, N($R_{51}$)$_2$, —(C1-C3 alkyl)-N($R_{51}$)$_2$, —(C1-C3 alkyl)-N$^+$($R_{51}$)$_3$, CON($R_{51}$)$_2$, —(C1-C3 alkyl)-CON($R_{51}$)$_2$, $OR_{52}$, —(C1-C3 alkyl)-$OR_{52}$, $COR_{52}$, —(C1-C3 alkyl)-$COR_{52}$, —(C1-C3 alkyl)-$COOR_{52}$, —(C1-C3 alkyl)-$OCOR_{52}$, Si($R_{52}$)$_3$, —(C1-C3 alkyl)-O—Si($R_{52}$)$_3$, —(C1-C3 alkyl)-O—N═C($R_{52}$)$_2$, —(C1-C3 alkyl)-S(O)$_m$—(C1-C6 alkyl), C1-C6 alkyl, halogenated C1-C6 alkyl, C2-C6 alkenyl, C2-C6 alkynyl, halogenated C2-C6 alkenyl, halogenated C2-C6 alkynyl; C3-C6 cycloalkyl or C3-C6 cycloalkyl-C1-C3 alkyl, the said C3-C6 cycloalkyl or C3-C6 cycloalkyl-C1-C3 alkyl is unsubstituted or substituted by at least one group selected from C1-C6 alkyl, halogen and phenyl; heterocyclyl, phenyl, heteroaryl, heterocyclyl-C1-C3 alkyl, phenyl-C1-C3 alkyl or heteroaryl-C1-C3 alkyl, the said heterocyclyl, phenyl, heteroaryl, heterocyclyl-C1-C3 alkyl, phenyl-C1-C3 alkyl or heteroaryl-C1-C3 alkyl is unsubstituted or substituted;

$R_{51}$ independently represents hydrogen, C1-C6 alkyl, or halogenated C1-C6 alkyl;

$R_{52}$ independently represents hydrogen, halogen-free or halogen-containing C1-C6 alkyl, phenyl, phenyl-C1-C3 alkyl, or heteroaryl;

Y independently represents hydrogen, halogen-free or halogen-containing C1-C6 alkyl, C2-C6 alkenyl, C2-C6 alkynyl, cyano-C1-C3alkyl, C1-C6 alkylcarbonyl, benzyl, phenylcarbonyl, heterocyclylcarbonyl, heteroarylcarbonyl, C1-C6 alkyloxycarbonyl, or —(C1-C3alkyl)-O—(C═O)—O—(C1-C6alkyl);

r represents 2;

m represents 0, 1, or 2;

wherein, the "heterocyclyl" refers to

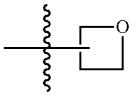
or
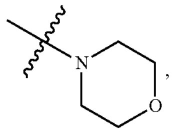
, the “heteroaryl” refers to

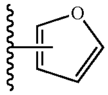
or
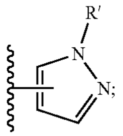
;

the above-mentioned groups are unsubstituted or substituted by at least one group selected from C1-C6 alkyl; R' represents C1-C6 alkyl.

The R configurational compound of the present invention has a stereochemical purity of 60-100% (R), preferably 70-100% (R), more preferably 80-100% (R), further preferably 90-100% (R), and further preferably 95-100% (R) based on the stereoisomer content with R and S configurations at the position (*). Where “stereochemical purity” refers to the percentage of the amount of the said stereoisomer in the total amount of stereoisomers having a chiral center.

In addition, the salt is a salt used in a common agricultural chemical, and for example, may be a metal salt, an amine salt, a sulfonium salt or a phosphonium salt. When these salts are used as herbicides for agriculture and horticulture, they are also included in the present invention. In the present invention, the salt of the compound is preferably in the form of its respective alkali metal salt, alkaline earth metal salt or ammonium salt (such as dimethyl ammonium salt, triethyl alcohol ammonium salt, isopropylamine salt, choline, etc.), preferably in the form of its respective alkali metal salt, more preferably in the form of its respective sodium salt or potassium salt, and most preferably in the form of its respective sodium salt.

The solvates of the compounds of the present invention are also encompassed in the invention.

Wherein, unless otherwise specified, the technical terms of the present invention used, whether used alone or used in compound word, the “heterocyclyl” includes, but is not limited to,

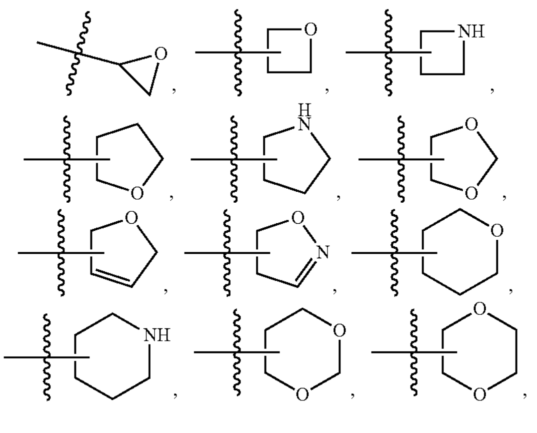

-continued

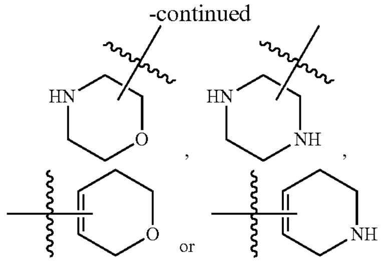

for example, which has 0, 1 or 2 oxo groups; the “aryl” of the present invention includes, but is not limited to, phenyl, naphthyl,

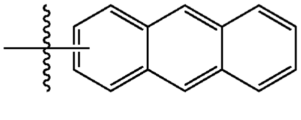
or
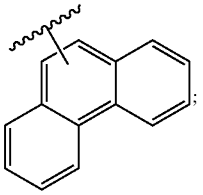
;

the “heteroaryl” is an aromatic cyclic group having, for example, 3 to 6 (for example, 3, 4, 5 or 6) ring atoms and which may also be fused with a benzo ring, and 1 to 4 (for example, 1, 2, 3 or 4) heteroatoms of the ring are selected from the group consisting of oxygen, nitrogen and sulfur, for example

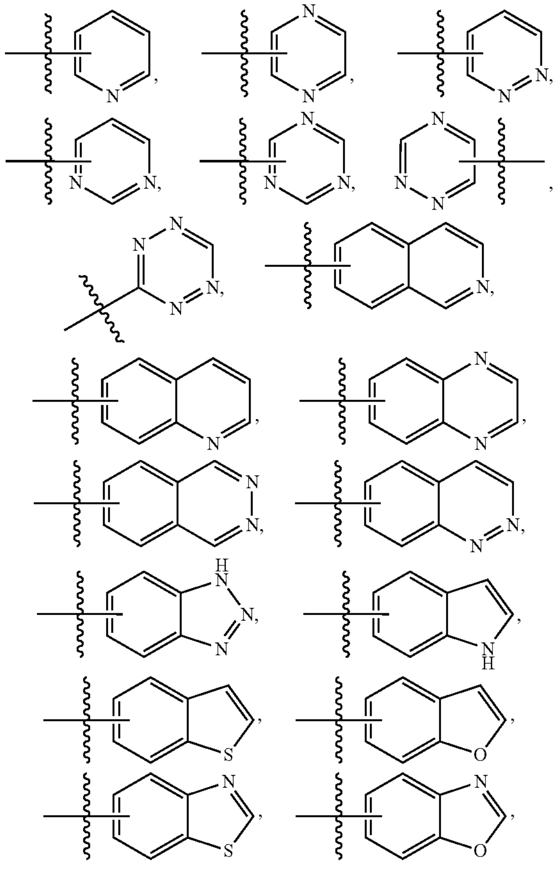

-continued

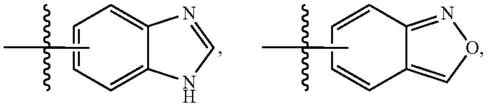

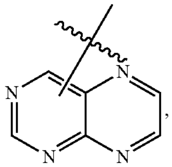

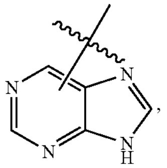

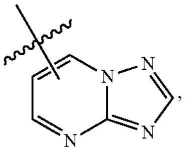

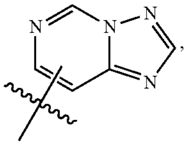

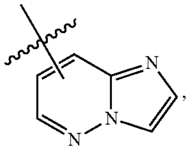

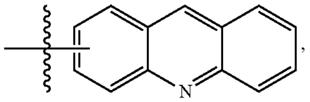

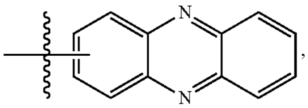

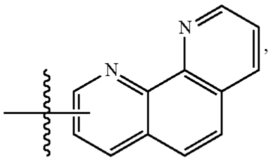

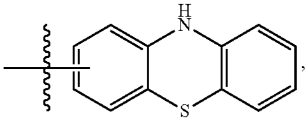

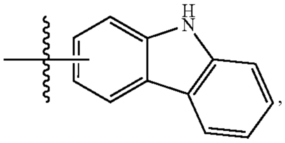

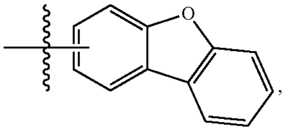

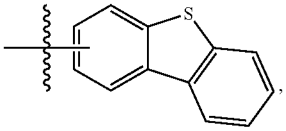

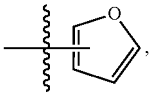

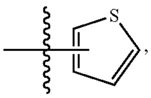

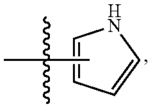

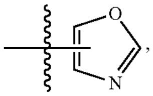

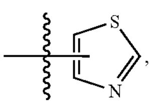

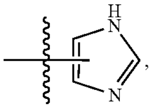

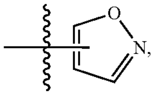

-continued

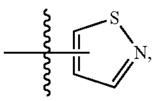

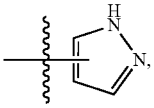

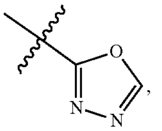

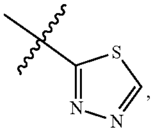

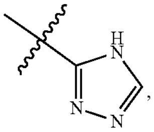

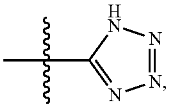

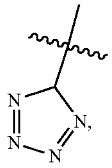

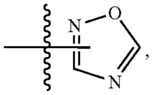

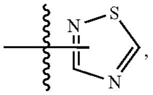

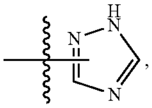

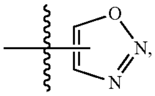

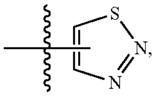

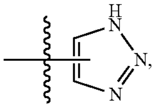

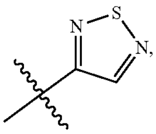

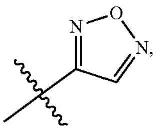

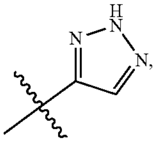

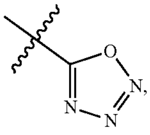

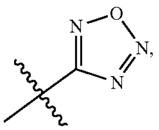

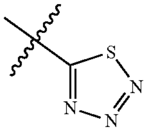

or

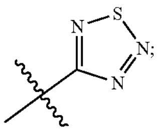

the above-mentioned groups are unsubstituted or substituted by at least one group (for example, one, two, three, four, five groups) selected from: halogen, nitro, amino, cyano, thiocyano, cyanoalkyl, sulfhydryl, hydroxy, hydroxyalkyl, carboxyl, formyl, trialkylsilyl, dialkylphosphonyl; heterocyclyl, heterocyclylalkyl, aryl, arylalkyl, heteroaryl or heteroarylalkyl, which is unsubstituted or substituted; alkyl, alkenyl, alkynyl, cycloalkyl, cycloalkenyl, cycloalkylalkyl, cycloalkyl substituted by alkyl, OR", SR", -alkyl-OR", —O— alkyl-OR", -alkyl-SR", COR", -alkyl-COR", —O—alkyl-COR", COOR", -alkyl-COOR", —O-alkyl-COOR", COSR", SOR", $SO_2R"$, —O—$SO_2R"$, -alkyl-$SO_2R"$, OCOR", -alkyl-OCOR" or SCOR" group, which is with or without halogen; amino, aminocarbonyl, aminocarbonylalkyl or aminosulfonyl group substituted by one or two groups selected from R", COR", $SO_2R"$ or OR", said R", COR", $SO_2R"$ or OR" is with or without halogen; or, two adjacent substitutable positions of the above-mentioned "heterocyclyl", "aryl", "heteroaryl" groups are linked with —$OCH_2CH_2$, —$OCH_2O$—, —$OCH_2CH_2O$— or —CH═CH—CH═CH— group to form a ring;

R" independently represents alkyl, alkenyl, alkynyl, cycloalkyl, cycloalkylalkyl, cycloalkenyl; heterocyclyl, heterocyclylalkyl, aryl, arylalkyl, heteroaryl or heteroarylalkyl which is unsubstituted or substituted.

Preferably, the above-mentioned groups are unsubstituted or substituted by at least one group (for example, one, two, three, four, five groups) selected from: halogen, nitro, amino, cyano, thiocyano, cyano C1-C6 alkyl, sulfhydryl, hydroxy, hydroxy C1-C6 alkyl, carboxyl, formyl, tri(C1-C6 alkyl)silyl, di(C1-C6 alkyl)phosphonyl; unsubstituted or substituted heterocyclyl, heterocyclyl-C1-C6 alkyl, aryl, aryl-C1-C6 alkyl, heteroaryl, heteroaryl-C1-C6 alkyl; C1-C6 alkyl, C2-C6 alkenyl, C2-C6 alkynyl, C3-C6 cycloalkyl, C3-C6 cycloalkenyl, C3-C6 cycloalkyl-C1-C6 alkyl, C3-C6 cycloalkyl substituted by C1-C6 alkyl, OR", SR", —C1-C6 alkyl-OR", —O—C1-C6 alkyl-OR", —C1-C6 alkyl-SR", COR", —C1-C6 alkyl-COR", —O—C1-C6 alkyl-COR", COOR", —C1-C6 alkyl-COOR", —O—C1-C6 alkyl-COOR", COSR", SOR", $SO_2R$", —O—$SO_2R$", —C1-C6 alkyl-$SO_2R$", OCOR", —C1-C6 alkyl-OCOR", SCOR", which is with or without halogen; amino, aminocarbonyl, aminocarbonyl-C1-C6 alkyl or aminosulfonyl group substituted by one or two groups selected from R", COR", $SO_2R$" or OR", said R", COR", $SO_2R$" or OR" is with or without halogen; or, two adjacent substitutable positions of the above-mentioned groups are linked with —$OCH_2CH_2$, —$OCH_2O$—, —$OCH_2CH_2O$— or —CH═CH—CH═CH— group to form a ring;

R" independently represents C1-C6 alkyl, C2-C6 alkenyl, C2-C6 alkynyl, C3-C6 cycloalkyl, C3-C6 cycloalkyl-C1-C6 alkyl, C3-C6 cycloalkenyl; heterocyclyl, heterocyclyl-C1-C6 alkyl, aryl, aryl-C1-C6 alkyl, heteroaryl, heteroaryl-C1-C6 alkyl, which is unsubstituted or substituted.

More preferably, the "heterocyclyl" refers to

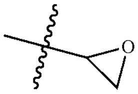,
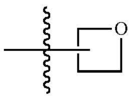,
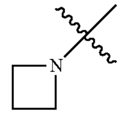,
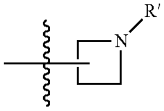,
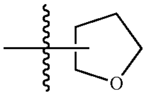,
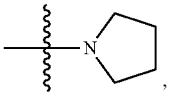,
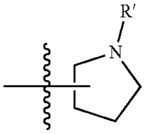,
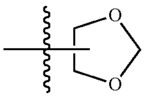,
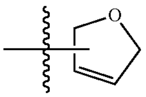,
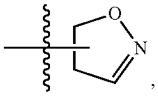,
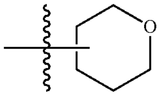,
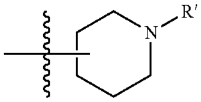,
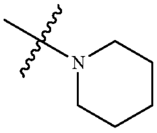,
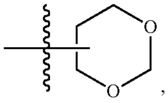,
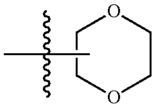,
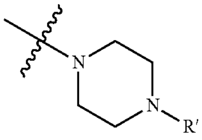,
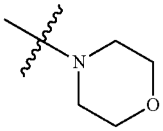,
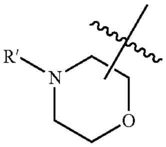,
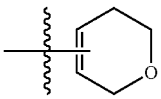, or -continued

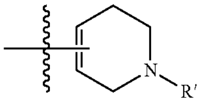

with 0, 1 or 2 oxo groups; the "aryl" refers to, for example, phenyl, naphthyl,

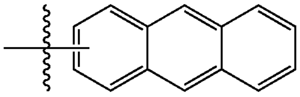 or 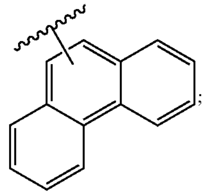;

the "heteroaryl" refers to, for example,

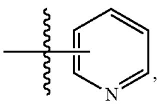,
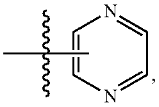,
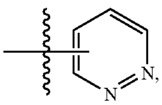,
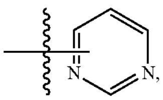,
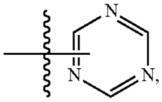,
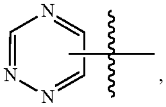,
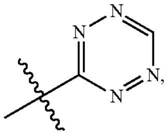
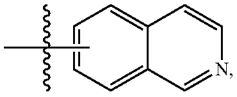,
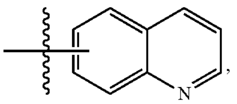,
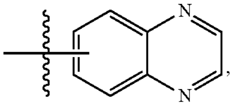,
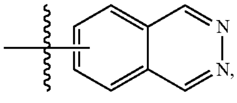,
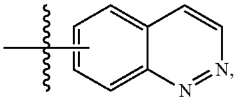,
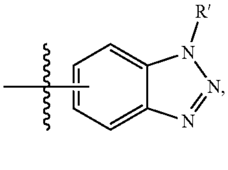,
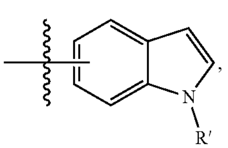,
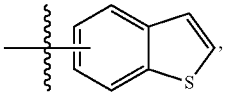,
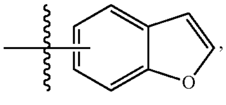,
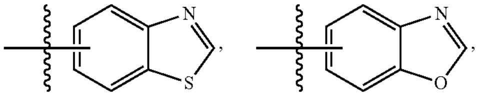
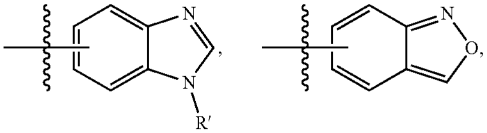

-continued

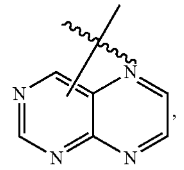
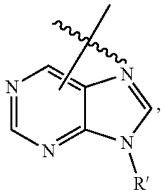
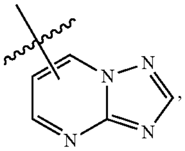
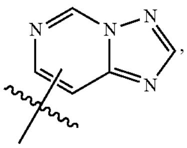
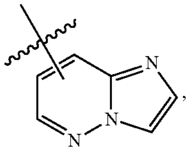
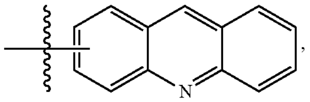
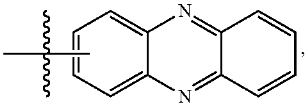
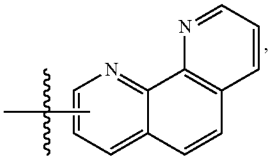
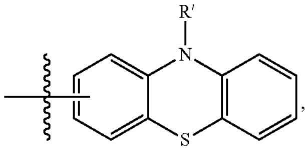
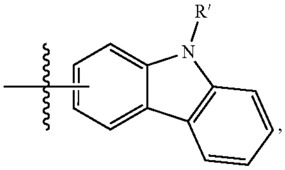
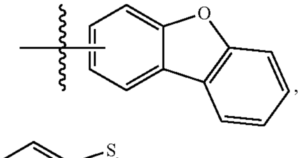
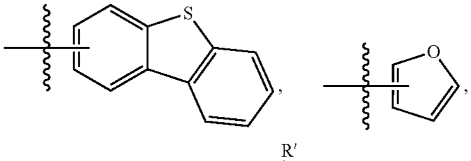
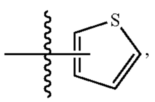
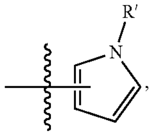
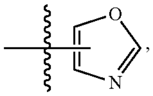
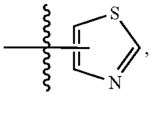
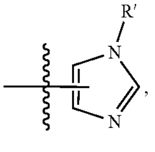
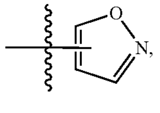

-continued

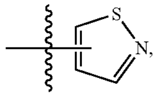
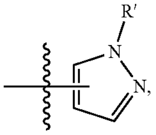
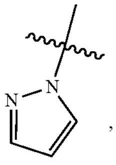
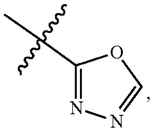
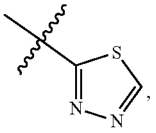
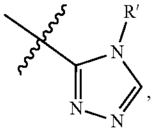
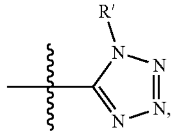
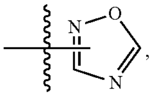
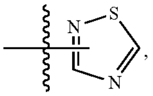
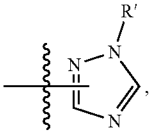
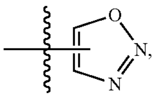
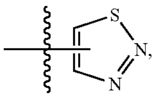
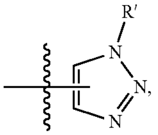
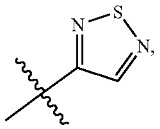
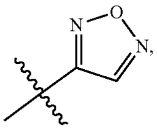
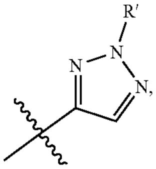
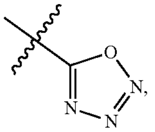
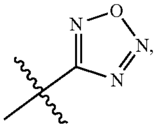
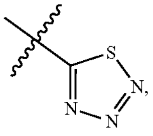
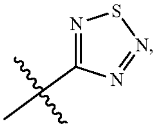
or
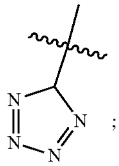
;

the above-mentioned groups are unsubstituted or substituted by at least one group (for example, one, two, three, four, five groups) selected from: halogen, nitro, amino, cyano, thiocyano, cyano C1-C6 alkyl, sulfhydryl, hydroxy, hydroxy C1-C6 alkyl, carboxyl, formyl;

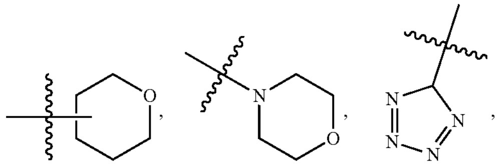

N, phenyl or benzyl group which is unsubstituted or substituted by at least one group (for example, one, two, three, four, five groups) selected from halogen, hydroxy, nitro, cyano, amino, carboxyl, C1-C6 alkyl with or without halogen, C2-C6 alkenyl with or without halogen, C2-C6 alkynyl with or without halogen, C3-C6 cycloalkyl with or without halogen, C1-C6 alkoxy with or without halogen, C1-C6 alkoxycarbonyl with or without halogen, C1-C6 alkylacyl with or without halogen, C1-C6 alkylacyloxy with or without halogen, C1-C6 alkylamino with or without halogen, or C1-C6 alkylsulfonyl with or without halogen; C1-C6 alkyl, C2-C6 alkenyl, C2-C6 alkynyl, C3-C6 cycloalkyl, C3-C6 cycloalkyl-C1-C6 alkyl, C3-C6 cycloalkyl substituted by C1-C6 alkyl, OR", SR", —(C1-C6) alkyl-OR", —O—(C1-C6) alkyl-OR", —(C1-C6) alkyl-SR", COR", —(C1-C6) alkyl-COR", —O—(C1-C6) alkyl-COR", COOR", —(C1-C6) alkyl-COOR", —O—(C1-C6) alkyl-COOR", COSR", SOR", $SO_2R$", —O—$SO_2R$", —(C1-C6) alkyl-$SO_2R$", OCOR", —(C1-C6) alkyl-OCOR" or SCOR" group which is with or without halogen; amino, aminocarbonyl or aminosulfonyl group substituted by one or two groups selected from R", COR", $SO_2R$" or OR", said R", COR", $SO_2R$" or OR" is with or without halogen; or, two adjacent substitutable positions of the above-mentioned “heterocyclyl”, “aryl”, “heteroaryl” groups are linked with —$OCH_2CH_2$, —$OCH_2O$—, —$OCH_2CH_2O$— or —CH═CH—CH═CH— group to form a ring;

R' independently represents hydrogen, nitro, hydroxy, amino; C1-C6 alkyl, C2-C6 alkenyl, C2-C6 alkynyl, C3-C6 cycloalkyl, C3-C6 cycloalkenyl, C3-C6 cycloalkyl-C1-C6 alkyl,

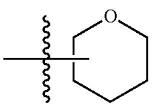,

C1-C6 alkoxy, C2-C6 alkenyloxy, C2-C6 alkynyloxy, C3-C6 cycloalkyloxy, C1-C6 alkoxy-C1-C6 alkyl, C1-C6 alkoxycarbonyl, C1-C6 alkylsulfanylcarbonyl, C1-C6 alkylsulfonyl, C1-C6 alkylsulfonyl-C1-C6 alkyl, C1-C6 alkylcarbonyl, C1-C6 alkylcarbonyl C1-C6 alkyl, C1-C6 alkylacyloxy, C1-C6 alkylamino, C1-C6 alkylaminocarbonyl, C1-C6 alkoxyaminocarbonyl, C1-C6 alkoxycarbonyl-C1-C6 alkyl, C1-C6 alkylaminocarbonyl-C1-C6 alkyl, tri(C1-C6 alkyl)silyl or di(C1-C6 alkyl)phosphonyl, which is with or without halogen; and phenyl or benzyl which is unsubstituted or substituted by at least one group (for example, one, two, three, four, five groups) selected from halogen, hydroxy, nitro, cyano, amino, carboxyl, C1-C6 alkyl with or without halogen, C2-C6 alkenyl with or without halogen, C2-C6 alkynyl with or without halogen, C3-C6 cycloalkyl with or without halogen, C1-C6 alkoxy with or without halogen, C1-C6 alkoxycarbonyl with or without halogen, C1-C6 alkylacyl with or without halogen, C1-C6 alkylacyloxy with or without halogen, C1-C6 alkylamino with or without halogen or C1-C6 alkylsulfonyl with or without halogen;

R" independently represents C1-C6 alkyl, C2-C6 alkenyl, C2-C6 alkynyl, C3-C6 cycloalkyl, C3-C6 cycloalkyl-C1-C6 alkyl, C3-C6 cycloalkenyl; and

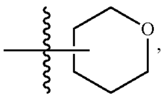, 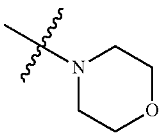, 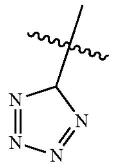, phenyl or benzyl which is unsubstituted or substituted by at least one group (for example, one, two, three, four, five groups) selected from halogen, hydroxy, nitro, cyano, amino, carboxyl, C1-C6 alkyl with or without halogen, C2-C6 alkenyl with or without halogen, C2-C6 alkynyl with or without halogen, C3-C6 cycloalkyl with or without halogen, C1-C6 alkoxy with or without halogen, C1-C6 alkoxycarbonyl with or without halogen, C1-C6 alkylacyl with or without halogen, C1-C6 alkylacyloxy with or without halogen, C1-C6 alkylamino with or without halogen, or C1-C6 alkylsulfonyl with or without halogen.

In the definition of the compound represented by the above Formula and all of the following structural formulas, the technical terms used, whether used alone or used in compound word, represent the following substituents: an alkyl having more than two carbon atoms may be linear or branched. For example, the alkyl in the compound word “-alkyl-$OR^1$” may be —$CH_2$—, —$CH_2CH_2$—, —CH($CH_3$)—, —C$(CH_3)_2$—, and the like. The alkyl is, for example, $C_1$ alkyl:methyl; $C_2$ alkyl:ethyl; $C_3$ alkyl:propyl such as n-propyl or isopropyl; $C_4$ alkyl:butyl such as n-butyl, isobutyl, tert-butyl or 2-butyl; $C_5$ alkyl:pentyl such as n-pentyl; $C_6$ alkyl:hexyl such as n-hexyl, isohexyl and 1,3-dimethylbutyl. Similarly, the alkenyl is, for example, allyl, 1-methylprop-2-en-1-yl, 2-methylprop-2-en-1-yl, but-2-en-1-yl, butyl-3-en-1-yl, 1-methylbut-3-en-1-yl and 1-methyl-but-2-en-1-yl. The alkynyl is, for example, propargyl, but-2-yn-1-yl, but-3-yn-1-yl, 1-methylbut-3-yn-1-yl. At least one (for example, 1, 2 or 3) multiple bonds may be placed at any position of each unsaturated group. The cycloalkyl is a carbocyclic saturated ring system having, for example, three to six carbon atoms, such as cyclopropyl, cyclobutyl, cyclopentyl or cyclohexyl. Similarly, the cycloalkenyl is monocycloalkenyl having, for example, three to six carbon ring members, such as cyclopropenyl, cyclobutenyl, cyclopentenyl, and cyclohexenyl, wherein double bond can be at any position. Halogen is fluorine, chlorine, bromine or iodine.

If a group is substituted by a group, which should be understood to mean that the group is substituted by one or more groups, which are same or different groups, selected from the mentioned groups. In addition, the same or different substitution characters contained in the same or different substituents are independently selected, and may be the same or different. This also applicable to a ring systems formed with different atoms and units. Meanwhile, the scope of the claims will exclude those compounds chemically unstable under standard conditions known to those skilled in the art.

In addition, unless specifically defined, the determinatives of the multiple parallel substituent (separated with “, “or” or”) of the present invention has limiting effect for each substituent, such as “alkyl, alkenyl, alkynyl, cycloalkyl, cycloalkenyl, cycloalkylalkyl or cycloalkenylalkyl, which is with or without halogen” means that“with or without halogen” has limiting effect on each group “alkyl”, “alkenyl”, “alkynyl”, “cycloalkyl”, “cycloalkenyl”, “cycloalkylalkyl”, “cycloalkenylalkyl”; “alkylamino” refers to the amino group which is monosubstituted or disubstituted by alkyl, other substituted amino groups are similarly defined; a group (including heterocyclic, aryl, heteroaryl, etc.) without being specified a linking site may be attached at any site, including a C or N site; if it is substituted, the substituent may be substituted at any site as long as it comply with the valence bond theory. For example, if the heteroaryl

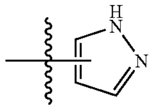

is substituted with one methyl, it can be N

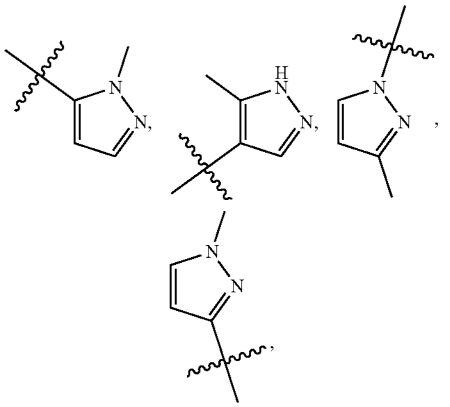

etc.

The enantiomers can be obtained from the mixtures obtained in the preparation by conventional separation methods, for example by chromatographic separation. The enantiomers may also be prepared selectively by using stereoselective reactions and using optically active starting materials and/or auxiliaries.

In certain embodiments, a method for preparing aryl formamide compound containing chiral sulfur oxide or salt thereof comprises the following step:

(1) the compound of formula I is obtained by liquid phase separation (such as chiral HPLC resolution) from a compound of formula I'

I'

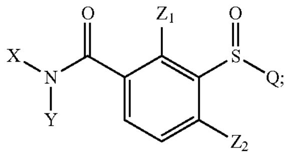

or, (2) the compound of formula I is prepared by using a compound of formula I"

I"

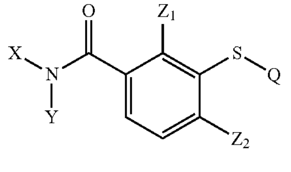

in the presence of peroxide (such as $H_2O_2$) and Jacobsen catalyst.

Preferably, the reaction (2) is carried out in the presence of a solvent; and the solvent is at least one of methanol, ethanol, isopropanol, acetonitrile, dichloroethane, DMF, DMSO, dioxane, dichloromethane or ethyl acetate.

The present invention also provides a herbicidal composition, comprising (i) the aryl formamide compound containing chiral sulfur oxide or salt thereof; preferably, further comprising (ii) one or more additional herbicides and/or safeners; more preferably, further comprising (iii) an agrochemically acceptable formulation auxiliary.

The present invention also provides a method for controlling a weed, comprising: applying at least one of the aryl formamide compounds containing chiral sulfur oxide or salts thereof or the herbicidal composition in an herbicidally effective amount on a plant or in a weed area.

The present invention also provides a use of at least one of the aryl formamide compounds containing chiral sulfur oxide or salts thereof or the herbicidal composition as above-described for controlling a weed, preferably, wherein the aryl formamide compound containing chiral sulfur oxide or salt thereof is used for preventing and/or controling a weed in a useful crop, wherein the useful crop is a transgenic crop or a crop treated by gene editing technique.

The compounds of the formula I according to the invention have an outstanding herbicidal activity against a broad spectrum of economically important monocotyledonous and dicotyledonous harmful plants. The active compounds also act efficiently on perennial weeds which produce shoots from rhizomes, root stocks or other perennial organs and which are difficult to control. In this context, it is generally immaterial whether the substances are applied pre-sowing, pre-emergence or post-emergence. Specifically, examples may be mentioned of some representatives of the monocotyledonous and dicotyledonous weed flora which can be controlled by the compounds according to the invention, without these being a restriction to certain species. Examples of weed species on which the active compounds act efficiently are, from amongst the monocotyledons, *Avena, Lolium, Alopecurus, Phalaris, Echinochloa, Digitaria, Setaria* and also *Cyperus* species from the annual sector and from amongst the perennial species *Agropyron, Cynodon, Imperata* and Sorghum, and also perennial *Cyperus* species.

In the case of the dicotyledonous weed species, the spectrum of action extends to species such as, for example, *Galium, Viola, Veronica, Lamium, Stellaria, Amaranthus, Sinapis, Ipomoea, Sida, Matricaria* and *Abutilon* from amongst the annuals, and *Convolvulus, Cirsium, Rumex* and *Artemisia* in the case of the perennial weeds. The active compounds according to the invention also effect outstanding control of harmful plants which occur under the specific conditions of rice growing such as, for example, *Echinochloa, Sagittaria, Alisma, Eleocharis, Scirpus* and *Cyperus*. If the compounds according to the invention are applied to the soil surface prior to germination, then the weed seedlings are either prevented completely from emerging, or the weeds grow until they have reached the cotyledon stage but then their growth stops, and, eventually, after three to four weeks have elapsed, they die completely. In particular, the compounds according to the invention exhibit excellent activity against *Apera* spica venti, *Chenopodium album, Lamium purpureum, Polygonum convulvulus, Stellaria media, Veronica* hederifolia, *Veronica persica, Viola* tricolor and against *Amaranthus, Galium* and *Kochia* species.

Although the compounds according to the invention have an excellent herbicidal activity against monocotyledonous and dicotyledonous weeds, crop plants of economically important crops such as, for example, wheat, barley, rye, rice, corn, sugarbeet, cotton and soya, are not damaged at all, or only to a negligible extent. In particular, they have excellent compatibility in cereals, such as wheat, barley and corn, in particular wheat. For these reasons, the present compounds are highly suitable for selectively controlling undesired plant growth in plantings for agricultural use or in plantings of ornamentals.

Owing to their herbicidal properties, these active compounds can also be employed for controlling harmful plants in crops of known or still to be developed genetically engineered plants. The transgenic plants generally have particularly advantageous properties, for example resistance to certain pesticides, in particular certain herbicides, resistance to plant diseases or causative organisms of plant diseases, such as certain insects or microorganisms such as fungi, bacteria or viruses. Other particular properties relate, for example, to the quantity, quality, storage-stability, composition and to specific ingredients of the harvested product. Thus, transgenic plants having an increased starch content or a modified quality of the starch or those having a different fatty acid composition of the harvested produce are known.

The use of the compounds of the formula I according to the invention or their salts in economically important transgenic crops of useful and ornamental plants, for example of cereal, such as wheat, barley, rye, oats, millet, rice, maniok and corn, or else in crops of sugarbeet, cotton, soya, rapeseed, potato, tomato, pea and other vegetable species is preferred. The compounds of the formula I can preferably be used as herbicides in crops of useful plants which are resistant or which have been made resistant by genetic engineering toward the phytotoxic effects of the herbicides.

Conventional ways for preparing novel plants which have modified properties compared to known plants comprise, for example, traditional breeding methods and the generation of mutants. Alternatively, novel plants having modified properties can be generated with the aid of genetic engineering methods (see, for example, EP-A 0 221 044, EP-A 0 131 624). For example, there have been described several cases of:

- genetically engineered changes in crop plants in order to modify the starch synthesized in the plants (for example WO 92/11376, WO 92/14827, WO 91/19806),
- transgenic crop plants which are resistant to certain herbicides of the glufosinate-(cf., for example, EP-A 0 242 236, EP-A 0 242 246) or glyphosate-type (WO 92/00377), or of the sulfonylurea-type (EP-A 0 257 993, U.S. Pat. No. 5,013,659A),
- transgenic crop plants, for example cotton, having the ability to produce *Bacillus thuringiensis* toxins (Bt toxins) which impart resistance to certain pests to the plants (EP-A 0 142 924, EP-A 0 193 259),
- transgenic crop plants having a modified fatty acid composition (WO 91/13972).

Numerous molecular biological techniques which allow the preparation of novel transgenic plants having modified properties are known in principle; see, for example, Sambrook et al., 1989, Molecular Cloning, A Laboratory Manual, 2nd ed. Cold Spring Harbor Laboratory Press, Cold Spring Harbor, N.Y; or Winnacker "Gene und Klone" [Genes and Clones], VCH Weinheim, 2nd edition 1996, or Christou, "Trends in Plant Science" 1 (1996) 423-431). In order to carry out such genetic engineering manipulations, it is possible to introduce nucleic acid molecules into plasmids which allow a mutagenesis or a change in the sequence to occur by recombination of DNA sequences. Using the abovementioned standard processes it is possible, for example, to exchange bases, to remove partial sequences or to add natural or synthetic sequences. To link the DNA fragments with each other, it is possible to attach adaptors or linkers to the fragments.

Plant cells having a reduced activity of a gene product can be prepared, for example, by expressing at least one appropriate antisense-RNA, a sense-RNA to achieve a cosuppression effect, or by expressing at least one appropriately constructed ribozyme which specifically cleaves transcripts of the above-mentioned gene product.

To this end it is possible to employ both DNA molecules which comprise the entire coding sequence of a gene product including any flanking sequences that may be present, and DNA molecules which comprise only parts of the coding sequence, it being necessary for these parts to be long enough to cause an antisense effect in the cells. It is also possible to use DNA sequences which have a high degree of homology to the coding sequences of a gene product but which are not entirely identical.

When expressing nucleic acid molecules in plants, the synthesized protein can be localized in any desired compartment of the plant cells. However, to achieve localization in a certain compartment, it is, for example, possible to link the coding region with DNA sequences which ensure localization in a certain compartment. Such sequences are known to the person skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated to whole plants using known techniques. The transgenic plants can in principle be plants of any desired plant species, i.e. both monocotyledonous and dicotyledonous plants. In this manner, it is possible to obtain transgenic plants which have modified properties by overexpression, suppression or inhibition of homologous (=natural) genes or gene sequences or by expression of heterologous (=foreign) genes or gene sequences.

When using the active compounds according to the invention in transgenic crops, in addition to the effects against harmful plants which can be observed in other crops, there are frequently effects which are specific for the application in the respective transgenic crop, for example a modified or specifically broadened spectrum of weeds which can be controlled, modified application rates which can be used for the application, preferably good combinability with the herbicides to which the transgenic crops are resistant, and an effect on the growth and the yield of the transgenic crop plants. The invention therefore also provides for the use of the compounds according to the invention as herbicides for controlling harmful plants in transgenic crop plants.

In addition, the substances according to the invention have outstanding growth-regulating properties in crop plants. They engage in the plant metabolism in a regulating manner and can this be employed for the targeted control of plant constituents and for facilitating harvesting, for example by provoking desiccation and stunted growth. Furthermore, they are also suitable for generally regulating and inhibiting undesirable vegetative growth, without destroying the plants in the process. Inhibition of vegetative growth plays an important role in many monocotyledon and dicotyledon crops because lodging can be reduced hereby, or prevented completely.

The compounds according to the invention can be applied in the customary formulations in the form of wettable powders, emulsifiable concentrates, sprayable solutions, dusts or granules. The invention therefore also provides herbicidal compositions comprising compounds of the formula I. The compounds of the formula I can be formulated in various ways depending on the prevailing biological and/or chemico-physical parameters. Examples of suitable formulation options are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil dispersions (OD), oil- or water-based dispersions, oil-miscible solutions, dusts (DP), capsule suspensions (CS), seed-dressing compositions, granules for broadcasting and soil application, granules in the form of microgranules, spray granules, coating granules and adsorption granules, water-dispersible granules (WG), water-soluble granules (SG), ULV formulations, microcapsules and waxes. These individual formulation types are known in principle and are described, for example, in Winnacker-Küchler, "Chemische Technologie" [Chemical Technology], Volume 7, C. Hauser Verlag Munich, 4th. Edition 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation auxiliaries, such as inert materials, surfactants, solvents and other additives, are likewise known and are described, for example, in Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y 1964; Schonfeldt, "Grenzflichenaktive Athylenoxidaddkte" [Surface-active ethylene oxide adducts], Wiss. Verlagagesell. Stuttgart 1976; Winnacker-Kiichler, "Chemische Technologie" [Chemical Technology], Volume 7, C. Hauser Verlag Munich, 4th Edition 1986.

Wettable powders are preparations which are uniformly dispersible in water and which contain, in addition to the active compound and as well as a diluent or inert substance, surfactants of ionic and/or nonionic type (wetting agents, dispersants), for example polyethoxylated alkyl phenols, polyethoxylated fatty alcohols, polyethoxylated fatty amines, fatty alcohol polyglycol ethersulfates, alkanesulfonates, alkylbenzenesulfonates, sodium ligninsulfonate, sodium 2,2'-dinaphthylmethane-6,6'-disulfonate, sodium dibutyinaphthalenesulfona-te or else sodium oleoylmethyltaurinate. To prepare the wettable powders, the herbicidally active compounds are finely ground, for example in customary apparatus such as hammer mills, fan mills and air-jet mills, and are mixed simultaneously or subsequently with the formulation auxiliaries.

Emulsifiable concentrates are prepared by dissolving the active compound in an organic solvent, for example butanol, cyclohexanone, dimethylformamide, xylene or else relatively high-boiling aromatic compounds or hydrocarbons or mixtures of the solvents, with the addition of one or more surfactants of ionic and/or nonionic type (emulsifiers). Examples of emulsifiers which can be used are calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters or polyoxyethylene sorbitan esters, for example polyoxyethylene sorbitan fatty acid esters.

Dusts are obtained by grinding the active compound with finely divided solid substances, for example talc, natural clays, such as kaolin, bentonite and pyrophyllite, or diatomaceous earth. Suspension concentrates can be water- or oil-based. They can be prepared, for example, by wet milling using commercially customary bead mills, with or without the addition of surfactants as already mentioned above, for example, in the case of the other formulation types.

Emulsions, for example oil-in-water emulsions (EW), can be prepared for example by means of stirrers, colloid mills and/or static mixers using aqueous organic solvents and, if desired, surfactants as already mentioned above, for example, in the case of the other formulation types.

Granules can be prepared either by spraying the active compound onto adsorptive, granulated inert material or by applying active-compound concentrates to the surface of carriers such as sand, kaolinites or granulated inert material, by means of adhesive binders, for example polyvinyl alcohol, sodium polyacrylate or else mineral oils. Suitable active compounds can also be granulated in the manner which is customary for the preparation of fertilizer granules, if desired as a mixture with fertilizers. Water-dispersible granules are generally prepared by the customary processes, such as spray-drying, fluidized-bed granulation, disk granulation, mixing using high-speed mixers, and extrusion without solid inert material.

For the preparation of disk, fluidized-bed, extruder and spray granules, see for example processes in "Spray-Drying Handbook" 3rd ed. 1979, G. Goodwin Ltd., London; J. E. Browning, "Agglomeration", Chemical and Engineering 1967, pages 147 ff.; "Perry's Chemical Engineer's Handbook", 5th Ed., McGraw-Hill, New York 1973, pp. 8-57. For further details on the formulation of crop protection products, see for example G. C. Klingman, "Weed Control as a Science", John Wiley and Sons Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations generally contain from 0.1 to 99% by weight, in particular from 0.1 to 95% by weight, of active compound of the formula I. In wettable powders the concentration of active compound is, for example, from about 10 to 99% by weight, the remainder to 100% by weight consisting of customary formulation constituents. In emulsifiable concentrates the concentration of active compound can be from about 1 to 90%, preferably from 5 to 80%, by weight. Formulations in the form of dusts contain from 1 to 30% by weight of active compound, preferably most commonly from 5 to 20% by weight of active compound, while sprayable solutions contain from about 0.05 to 80%, preferably from 2 to 50%, by weight of active compound. In the case of water-dispersible granules the content of active compound depends partly on whether the active compound is in liquid or solid form and on the granulation auxiliaries, fillers, etc. that are used. In water-dispersible granules the content of active compound, for example, is between 1 and 95% by weight, preferably between 10 and 80% by weight.

In addition, the formulations of active compound may comprise the tackifiers, wetting agents, dispersants, emulsifiers, penetrants, preservatives, antifreeze agents, solvents, fillers, carriers, colorants, antifoams, evaporation inhibitors and pH and viscosity regulators which are customary in each case.

Based on these formulations it is also possible to produce combinations with other pesticidally active substances, for example insecticides, acaricides, herbicides and fungicides, and also with safeners, fertilizers and/or growth regulators, for example in the form of a ready-mix or tank mix.

Suitable active compounds which can be combined with the active compounds according to the invention in mixed formulations or in a tank mix are, for example, known active compounds as described in for example World Herbicide New Product Technology Handbook, China Agricultural Science and Farming Techniques Press, 2010.9 and in the literature cited therein. For example the following active compounds may be mentioned as herbicides which can be combined with the compounds of the formula I (note: the compounds are either named by the "common name" in accordance with the International Organization for Standardization (ISO) or by the chemical names, if appropriate together with a customary code number): acetochlor, butachlor, alachlor, propisochlor, metolachlor, s-metolachlor, pretilachlor, propachlor, ethachlor, napropamide, R-left handed napropamide, propanil, mefenacet, diphenamid, diflufenican, ethaprochlor, beflubutamid, bromobutide, dimethenamid, dimethenamid-P, etobenzanid, flufenacet, thenylchlor, metazachlor, isoxaben, flamprop-M-methyl, flamprop-M-propyl, allidochlor, pethoxamid, chloranocryl, cyprazine, mefluidide, monalide, delachlor, prynachlor, terbuchlor, xylachlor, dimethachlor, cisanilide, trimexachlor, clomeprop, propyzamide, pentanochlor, carbetamide, benzoylprop-ethyl, cyprazole, butenachlor, tebutam, benzipram, mogrton, dichlofluanid, naproanilide, diethatyl-ethyl, naptalam, flufenacet, benzadox, chlorthiamid, chlorophthalimide, isocarbamide, picolinafen, atrazine, simazine, prometryn, cyanatryn, simetryn, ametryn, propazine, dipropetryn, SSH-108, terbutryn, terbuthylazine, triaziflam, cyprazine, proglinazine, trietazine, prometon, simetone, aziprotryne, desmetryn, dimethametryn, procyazine, mesoprazine, sebuthylazine, secbumeton, terbumeton, methoprotryne, cyanatryn, ipazine, chlorazine, atraton, pendimethalin, eglinazine, cyanuric acid, indaziflam, chlorsulfuron, metsulfuron-methyl, bensulfuron methyl, chlorimuron-ethyl, tribenuron-methyl, thifensulfuron-methyl, pyrazosulfuron-ethyl, mesosulfuron, iodosulfuron-methyl sodium, foramsulfuron, cinosulfuron, triasulfuron, sulfometuron methyl, nicosulfuron, ethametsulfuron-methyl, amidosulfuron, ethoxysulfuron, cyclosulfamuron, rimsulfuron, azimsulfuron, flazasulfuron, monosulfuron, monosulfuron-ester, flucarbazone-sodium, flupyrsulfuron-methyl, halosulfuron-methyl, oxasulfuron, imazosulfuron, primisulfuron, propoxycarbazone, prosulfuron, sulfosulfuron, trifloxysulfuron, triflusulfuron-methyl, tritosulfuron, sodium metsulfuron methyl, flucetosulfuron, HNPC—C, orthosulfamuron, propyrisulfuron, metazosulfuron, acifluorfen, fomesafen, lactofen, fluoroglycofen, oxyfluorfen, chlornitrofen, aclonifen, ethoxyfen-ethyl, bifenox, nitrofluorfen, chlomethoxyfen, fluorodifen, fluoronitrofen, furyloxyfen, nitrofen, TOPE, DMNP, PPG1013, AKH-7088, halosafen, chlortoluron, isoproturon, linuron, diuron, dymron, fluometuron, benzthiazuron, methabenzthiazuron, cumyluron, ethidimuron, isouron, tebuthiuron, buturon, chlorbromuron, methyldymron, phenobenzuron, SK-85, metobromuron, metoxuron, afesin, monuron, siduron, fenuron, fluothiuron, neburon, chloroxuron, noruron, isonoruron, 3-cyclooctyl-1, thiazfluron, tebuthiuron, difenoxuron, parafluron, methylamine tribunil, karbutilate, trimeturon, dimefuron, monisouron, anisuron, methiuron, chloreturon, tetrafluron, phenmedipham, phenmedipham-ethyl, desmedipham, asulam, terbucarb, barban, propham, chlorpropham, rowmate, swep, chlorbufam, carboxazole, chlorprocarb, fenasulam, BCPC, CPPC, carbasulam, butylate, benthiocarb, vemolate, molinate, triallate, dimepiperate, esprocarb, pyributicarb, cycloate, avadex, EPTC, ethiolate, orbencarb, pebulate, prosulfocarb, tiocarbazil, CDEC, dimexano, isopolinate, methiobencarb, 2,4-D butyl ester, MCPA-Na, 2,4-D isooctyl ester, MCPA isooctyl ester, 2,4-D sodium salt, 2,4-D dimethyla mine salt, MCPA-thioethyl, MCPA, 2,4-D propionic acid, high 2,4-D propionic acid salt, 2,4-D butyric acid, MCPA propionic acid, MCPA propionic acid salt, MCPA butyric acid, 2,4,5-D, 2,4,5-D propionic acid, 2,4,5-D butyric acid, MCPA amine salt, dicamba, erbon, chlorfenac, saison, TBA, chloramben, methoxy-TBA, diclofop-methyl, fluazifop-butyl, fluazifop-p-butyl, haloxyfop-methyl, haloxyfop-P, quizalofop-ethyl, quizalofop-p-ethyl, fenoxaprop-ethy, fenoxaprop-p-ethyl, propaquizafop, cyhalofop-butyl, metamifop, clodinafop-propargyl, fenthiaprop-ethyl, chloroazifop-propynyl, poppenate-methyl, trifopsime, isoxapyrifop, paraquat, diquat, oryzalin, ethalfluralin, isopropalin, nitralin, profluralin, prodinamine, benfluralin, fluchloraline, dinitramina, dipropalin, chlornidine, methalpropalin, dinoprop, glyphosate, anilofos, glufosinate ammonium, amiprophos-methyl, sulphosate, piperophos, bialaphos-sodium, bensulide, butamifos, phocarb, 2,4-DEP, H-9201, zytron, imazapyr, imazethapyr, imazaquin, imazamox, imazamox ammonium salt, imazapic, imazamethabenz-methyl, fluroxypyr, fluroxypyr isooctyl ester, clopyralid, picloram, trichlopyr, dithiopyr, haloxydine, 3,5,6-trichloro-2-pyridinol, thiazopyr, fluridone, aminopyralid, diflufenzopyr, triclopyr-butotyl, Cliodinate, sethoxydim, clethodim, cycloxydim, alloxydim, clefoxydim, butroxydim, tralkoxydim, tepraloxydim, buthidazole, metribuzin, hexazinone, metamitron, ethiozin, ametridione, amibuzin, bromoxynil, bromoxynil octanoate, ioxynil octanoate, ioxynil, dichlobenil, diphenatrile, pyraclonil, chloroxynil, iodobonil, flumetsulam, florasulam, penoxsulam, metosulam, cloransulam-methyl, diclosulam, pyroxsulam, benfuresate, bispyribac-sodium, pyribenzoxim, pyriftalid, pyriminobac-methyl, pyrithiobac-sodium, benzobicylon, mesotrione, sulcotrione, tembotrione, tefuryltrione, bicyclopyrone, ketodpiradox, isoxaflutole, clomazone, fenoxasulfone, methiozolin, fluazolate, pyraflufen-ethyl, pyrazolynate, difenzoquat, pyrazoxyfen, benzofenap, nipyraclofen, pyrasulfotole, topramezone, pyroxasulfone, cafenstrole, flupoxam, aminotriazole, amicarbazone, azafenidin, carfentrazone-ethyl, sulfentrazone, bencarbazone, benzfendizone, butafenacil, bromacil, isocil, lenacil, terbacil, flupropacil, cinidon-ethyl, flumiclorac-pentyl, flumioxazin, propyzamide, MK-129, flumezin, pentachlorophenol, dinoseb, dinoterb, dinoterb acetate, dinosam, DNOC, chloronitrophene, medinoterb acetate, dinofenate, oxadiargyl, oxadiazon, pentoxazone, Flufenacet, fluthiacet-methyl, fentrazamide, flufenpyr-ethyl, pyrazon, brompyrazon, metflurazon, kusakira, dimidazon, oxapyrazon, norflurazon, pyridafol, quinclorac, quinmerac, bentazone, pyridate, oxaziclomefone, benazolin, clomazone, cinmethylin, ZJ0702, pyribambenz-propyl, indanofan, sodium chlorate, dalapon, trichloroacetic acid, monochloroacetic acid, hexachloroacetone, flupropanate, cyperquat, bromofenoxim, epronaz, methazole, flurtamone, benfuresate, ethofumesate, tioclorim, chlorthal, fluorochloridone, tavron, acrolein, bentranil, tridiphane, chlorfenpropmethyl, thidiarizonaimin, phenisopham, busoxinone, methoxyphenone, saflufenacil, clacyfos, chloropon, alorac, diethamquat, etnipromid, iprymidam, ipfencarbazone, thiencarbazone-methyl, pyrimisulfan, chlorflurazole, tripropindan, sulglycapin, prosulfalin, cambendichlor, aminocyclopyrachlor, rodethanil, benoxacor, fenclorim, flurazole, fenchlorazole-ethyl, cloquintocet-mexyl, oxabetrinil, MG/91, cyometrinil, DKA-24, mefenpyr-diethyl, furilazole, fluxofenim, isoxadifen-ethyl, dichlormid, halauxifen-methyl, DOW florpyrauxifen, UBH-509, D489, LS 82-556, KPP-300, NC-324, NC-330, KH-218, DPX-N8189, SC-0744, DOWCO535, DK-8910, V-53482, PP-600, MBH-001, KIH-9201, ET-751, KIH-6127 and KIH-2023.

In the context of the present description, if an abbreviation of a generic name of active compound is used, it includes in each case all conventional derivatives thereof, such as esters and salts as well as isomers, in particular optical isomers, in particular one or more commercially available forms thereof. If the generic name denotes an ester or a salt, it also includes in each case all other conventional derivatives, such as other esters and salts, free acids and neutral compounds, as well as isomers, in particular optical isomers, in particular one or more commercially available forms thereof. The chemical name given to a compound means at least one compound encompassed by the generic name, and generally the preferred compound. In the case of sulfamide such as sulfonylurea, the salt thereof also includes a salt formed by exchanging a cation with a hydrogen atom in sulfonamide group. For example, 2,4-D or 2,4-D butyric acid derivatives include, but are not limited to, salts of 2,4-D or 2,4-D butyric acid, such as sodium salt, potassium salt, dimethylammonium salt, triethanol ammonium salt, isopropylamine salt, choline salt, etc., and esters of 2,4-D or 2,4-D butyric acid, such as methyl ester, ethyl ester, butyl ester, isooctyl ester, etc.; MCPA derivatives include, but are not limited to: MCPA sodium salt, potassium salt, dimethylammonium salt, isopropylamine salt, etc., and MCPA methyl ester, ethyl ester, isooctyl ester, ethyl thioester and the like.

For use, the formulations which are present in commercially available form are, if appropriate, diluted in the customary manner, for example using water in the case of wettable powders, emulsifiable concentrates, dispersions and water-dispersible granules. Products in the form of dusts, granules for soil application or broadcasting and sprayable solutions are usually not further diluted with other inert substances prior to use. The application rate of the compounds of the formula I required varies with the external conditions, such as temperature, humidity, the nature of the herbicide used and the like. It can vary within wide limits, for example between 0.001 and 1.0 kg/ha or more of active substance, but it is preferably between 0.005 and 750 g/ha, in particular between 0.005 and 500 g/ha.

Specific Mode for Carrying Out the Invention

The following embodiments are used to illustrate the present invention in detail and should not be taken as any limit to the present invention. The scope of the invention would be explained through the Claims.

In view of economics, variety and biological activity of a compound, we preferably synthesized several compounds, part of which are listed in the following Tables 1-2. The structure and information of a certain compound are shown in Tables 1-2. The compounds in Tables 1-2 are listed for further explication of the present invention, other than any limit therefor. The subject of the present invention should not be interpreted by those skilled in the art as being limited to the following compounds.

TABLE 1
Structures of compounds I
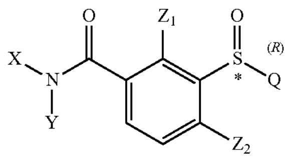
I
| Compound No. | X | Y | $Z_1$ | $Z_2$ | Q |
|---|---|---|---|---|---|
| 1 | 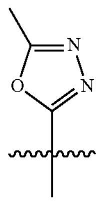 | H | F | $CF_3$ | Me |
| 2 | 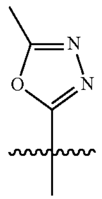 | H | F | $CF_3$ | Et |
| 3 | 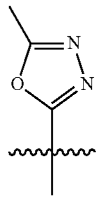 | H | F | $CF_3$ | 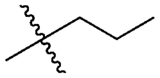 [SMILES: *CCC] |

TABLE 1-continued
Structures of compounds I
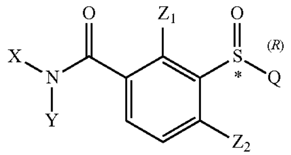
I
| Compound No. | X | Y | $Z_1$ | $Z_2$ | Q |
|---|---|---|---|---|---|
| 4 | 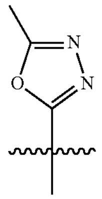 | H | F | $CF_3$ | 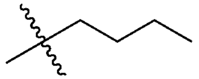 [SMILES: *CCCC] |
| 5 | 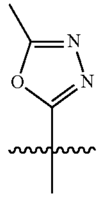 | H | F | $CF_3$ | 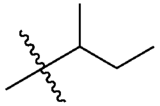 [SMILES: *C(C)CC] |
| 6 | 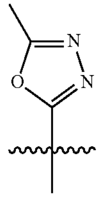 | H | F | $CF_3$ | 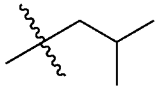 |

TABLE 1-continued
Structures of compounds I
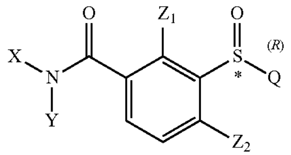
I
| Compound No. | X | Y | Z1 | Z2 | Q |
|---|---|---|---|---|---|
| 7 | 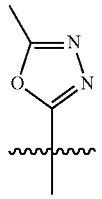 | H | F | $CF_3$ | 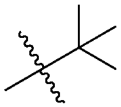 [SMILES: *C(C)(C)C] |
| 8 | 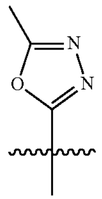 | H | F | $CF_3$ | 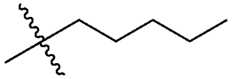 [SMILES: *CCCCC] |
| 9 | 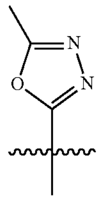 | H | F | $CF_3$ | 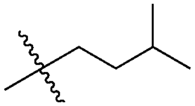 [SMILES: *CCC(C)C] |

TABLE 1-continued
Structures of compounds I
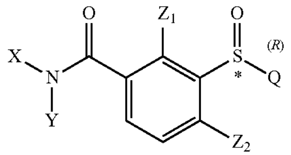
I
| Compound No. | X | Y | $Z_1$ | $Z_2$ | Q |
|---|---|---|---|---|---|
| 10 | 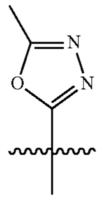 | H | F | $CF_3$ | 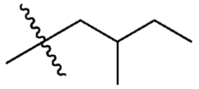 [SMILES: *CC(C)CC] |
| 11 | 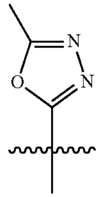 | H | F | $CF_3$ | 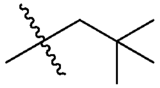 [SMILES: *CC(C)(C)C] |
| 12 | 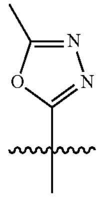 | H | F | $CF_3$ | 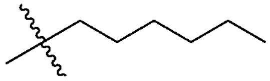 [SMILES: *CCCCCC] |

TABLE 1-continued
Structures of compounds I
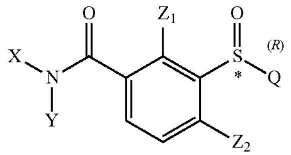
I
| Compound No. | X | Y | $Z_1$ | $Z_2$ | Q |
| --- | --- | --- | --- | --- | --- |
| 13 | 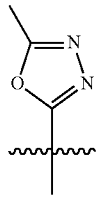 | H | F | $CF_3$ | 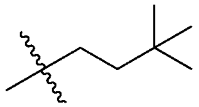 [SMILES: *CCC(C)(C)C] |
| 14 | 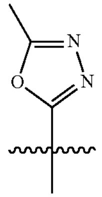 | H | F | $CF_3$ | 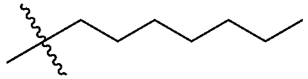 [SMILES: *CCCCCCC] |
| 15 | 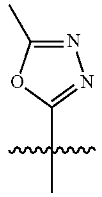 | H | F | $CF_3$ | 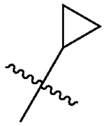 [SMILES: *C1CC1] |

TABLE 1-continued
Structures of compounds I
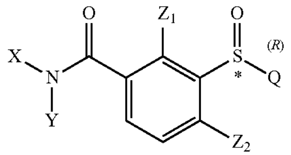
I
| Compound No. | X | Y | $Z_1$ | $Z_2$ | Q |
|---|---|---|---|---|---|
| 16 | 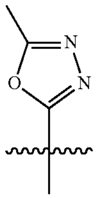 | H | F | $CF_3$ | 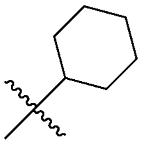 [SMILES: *C1CCCCC1] |
| 17 | 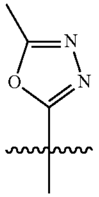 | H | F | $CF_3$ | 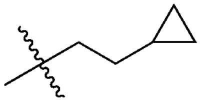 [SMILES: *CCC1CC1] |
| 18 | 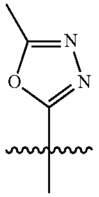 | H | F | $CF_3$ | 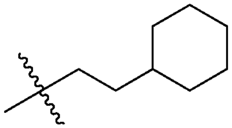 [SMILES: *CCC1CCCCC1] |

TABLE 1-continued
Structures of compounds I
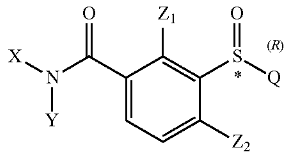
I
| Compound No. | X | Y | $Z_1$ | $Z_2$ | Q |
|---|---|---|---|---|---|
| 19 | 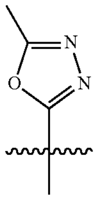 | H | F | $CF_3$ | 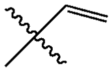 [SMILES: *C=C] |
| 20 | 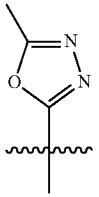 | H | F | $CF_3$ | 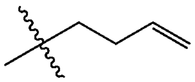 [SMILES: *CCC=C] |
| 21 | 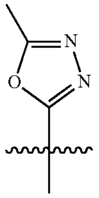 | H | F | $CF_3$ | 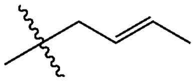 [SMILES: *C/C=C/C] |

TABLE 1-continued
Structures of compounds I
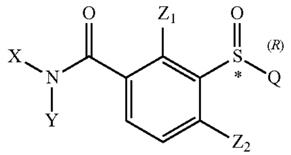
I
| Compound No. | X | Y | $Z_1$ | $Z_2$ | Q |
|---|---|---|---|---|---|
| 22 | 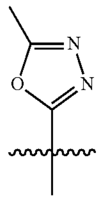 | H | F | $CF_3$ | 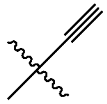 [SMILES: *C#C] |
| 23 | 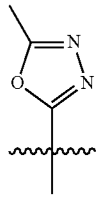 [SMILES: *c1nnc(C)o1] | H | F | $CF_3$ | 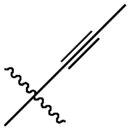 [SMILES: *C#CC] |
| 24 | 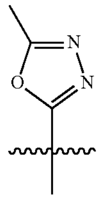 | H | F | $CF_3$ | 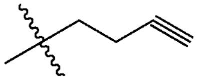 |

TABLE 1-continued
Structures of compounds I
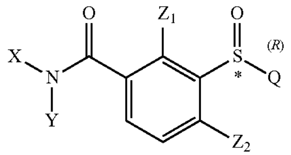
I
| Compound No. | X | Y | $Z_1$ | $Z_2$ | Q |
|---|---|---|---|---|---|
| 25 | 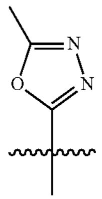 | H | F | $CF_3$ | 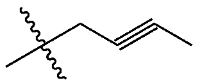 [SMILES: *CC#CC] |
| 26 | 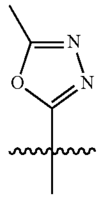 [SMILES: *c1nnc(C)o1] | H | F | $CF_3$ | 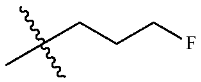 [SMILES: *CCCF] |
| 27 | 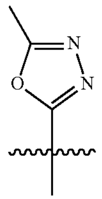 | H | F | $CF_3$ | 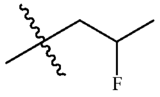 |

TABLE 1-continued
Structures of compounds I
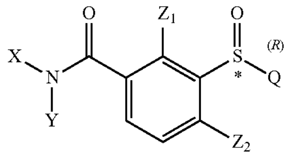
I
| Compound No. | X | Y | $Z_1$ | $Z_2$ | Q |
|---|---|---|---|---|---|
| 28 | 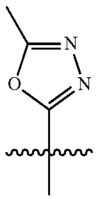 | H | F | $CF_3$ | 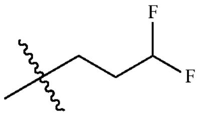 [SMILES: *CCC(F)F] |
| 29 | 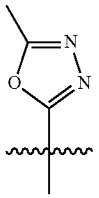 [SMILES: *c1nnc(C)o1] | H | F | $CF_3$ | 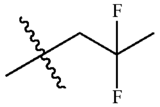 |
| 30 | 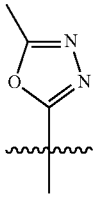 | H | F | $CF_3$ | 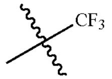 |

TABLE 1-continued
Structures of compounds I
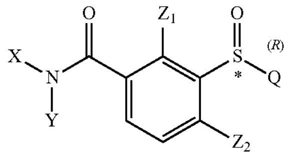
I
| Compound No. | X | Y | $Z_1$ | $Z_2$ | Q |
|---|---|---|---|---|---|
| 31 | 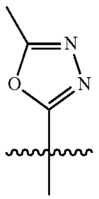 | H | F | $CF_3$ | 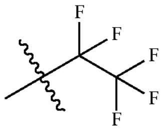 |
| 32 | 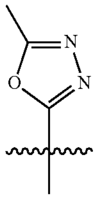 [SMILES: *c1nnc(C)o1] | H | F | $CF_3$ | 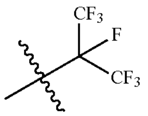 |
| 33 | 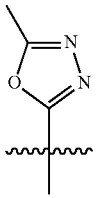 | H | F | $CF_3$ | 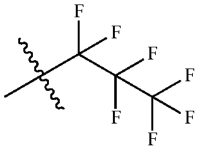 [SMILES: *C(F)(F)C(F)(F)C(F)(F)F] |

TABLE 1-continued
Structures of compounds I
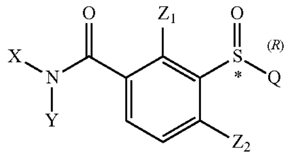
I
| Compound No. | X | Y | $Z_1$ | $Z_2$ | Q |
|---|---|---|---|---|---|
| 34 | 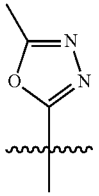 | H | F | $CF_3$ | 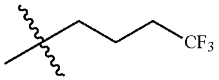 [SMILES: *CCCC(F)(F)F] |
| 35 | 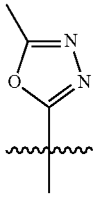 [SMILES: *c1nnc(C)o1] | H | F | $CF_3$ | 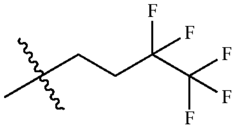 [SMILES: *CCC(F)(F)C(F)(F)F] |
| 36 | 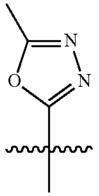 | H | F | $CF_3$ | 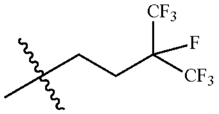 [SMILES: *CCC(F)(C(F)(F)F)C(F)(F)F] |

TABLE 1-continued
Structures of compounds I
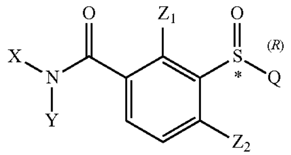
I
| Compound No. | X | Y | $Z_1$ | $Z_2$ | Q |
|---|---|---|---|---|---|
| 37 | 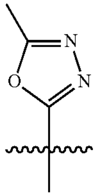 | H | F | $CF_3$ | 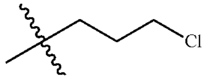 [SMILES: *CCCCl] |
| 38 | 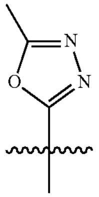 [SMILES: *c1nnc(C)o1] | H | F | $CF_3$ | 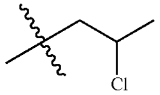 |
| 39 | 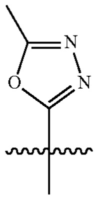 | H | F | $CF_3$ | 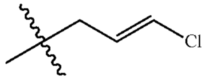 [SMILES: *C/C=C/Cl] |

TABLE 1-continued
Structures of compounds I
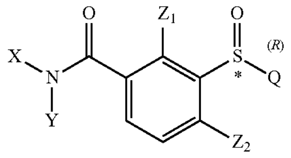
I
| Compound No. | X | Y | $Z_1$ | $Z_2$ | Q |
|---|---|---|---|---|---|
| 40 | 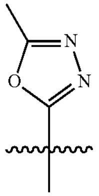 | H | F | $CF_3$ | 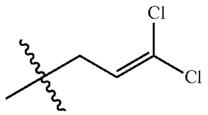 [SMILES: *CC=C(Cl)Cl] |
| 41 | 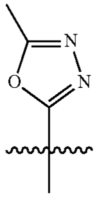 [SMILES: *c1nnc(C)o1] | H | F | $CF_3$ | 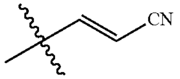 [SMILES: */C=C/C#N] |
| 42 | 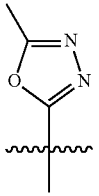 | H | F | $CF_3$ | 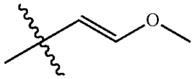 [SMILES: */C=C/OC] |

TABLE 1-continued
Structures of compounds I
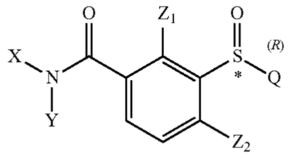
I
| Compound No. | X | Y | $Z_1$ | $Z_2$ | Q |
|---|---|---|---|---|---|
| 43 | 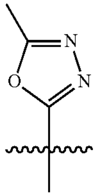 | H | F | $CF_3$ | 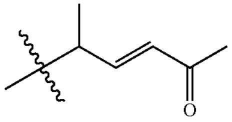 [SMILES: *C(C)/C=C/C(C)=O] |
| 44 | 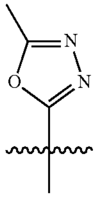 [SMILES: *c1nnc(C)o1] | H | F | $CF_3$ | 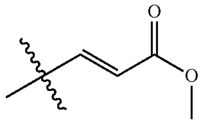 [SMILES: */C=C/C(=O)OC] |
| 45 | 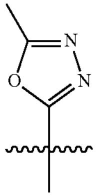 | H | F | $CF_3$ | 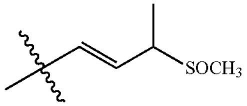 |

TABLE 1-continued
Structures of compounds I
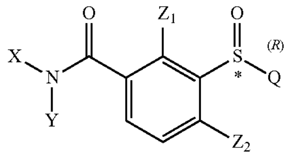
I
| Compound No. | X | Y | $Z_1$ | $Z_2$ | Q |
|---|---|---|---|---|---|
| 46 | 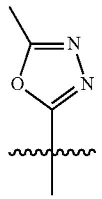 | H | F | $CF_3$ | 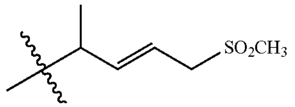 [SMILES: *C(C)/C=C/CS(C)(=O)=O] |
| 47 | 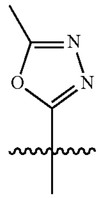 [SMILES: *c1nnc(C)o1] | H | F | $CF_3$ | 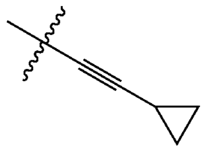 [SMILES: *C#CC1CC1] |
| 48 | 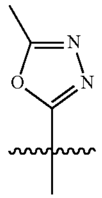 | H | F | $CF_3$ | 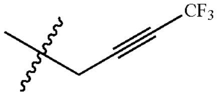 [SMILES: *CC#CC(F)(F)F] |

TABLE 1-continued
Structures of compounds I
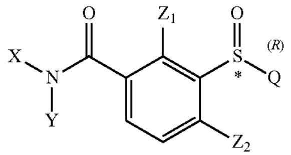
I
| Compound No. | X | Y | $Z_1$ | $Z_2$ | Q |
|---|---|---|---|---|---|
| 49 | 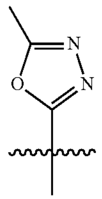 | H | F | $CF_3$ | 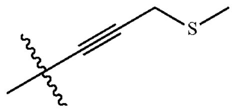 [SMILES: *C#CCSC] |
| 50 | 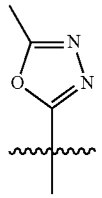 [SMILES: *c1nnc(C)o1] | H | F | $CF_3$ | 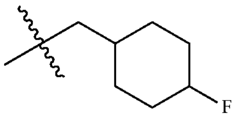 [SMILES: *CC1CCC(F)CC1] |
| 51 | 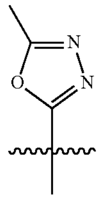 | H | F | $CF_3$ | 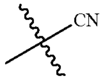 |

TABLE 1-continued
Structures of compounds I
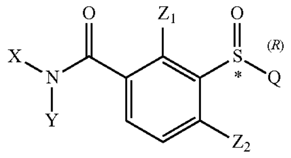
I
| Compound No. | X | Y | $Z_1$ | $Z_2$ | Q |
|---|---|---|---|---|---|
| 52 | 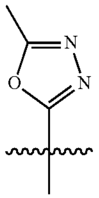 | H | F | $CF_3$ | 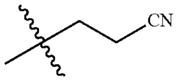 [SMILES: *CCC#N] |
| 53 | 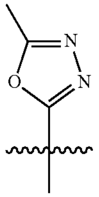 [SMILES: *c1nnc(C)o1] | H | F | $CF_3$ | 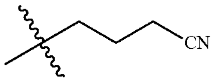 [SMILES: *CCCC#N] |
| 54 | 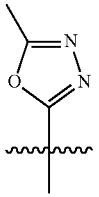 | H | F | $CF_3$ | 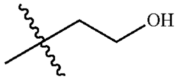 |

TABLE 1-continued
Structures of compounds I
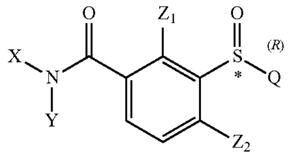
I
| Compound No. | X | Y | $Z_1$ | $Z_2$ | Q |
|---|---|---|---|---|---|
| 55 | 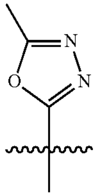 | H | F | $CF_3$ | 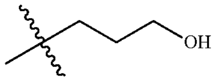 [SMILES: *CCCO] |
| 56 | 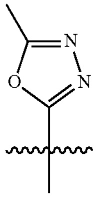 [SMILES: *c1nnc(C)o1] | H | F | $CF_3$ | 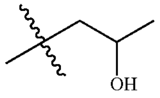 |
| 57 | 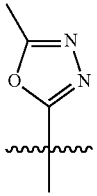 | H | F | $CF_3$ | 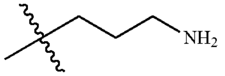 [SMILES: *CCCN] |

TABLE 1-continued
Structures of compounds I
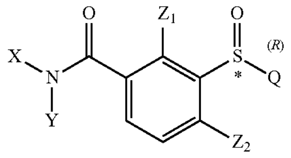
I
| Compound No. | X | Y | $Z_1$ | $Z_2$ | Q |
|---|---|---|---|---|---|
| 58 | 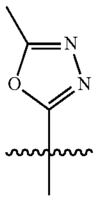 | H | F | $CF_3$ | 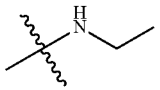 [SMILES: *NCC] |
| 59 | 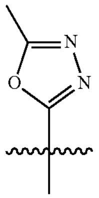 [SMILES: *c1nnc(C)o1] | H | F | $CF_3$ | 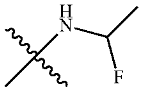 [SMILES: *NC(C)F] |
| 60 | 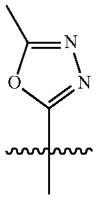 | H | F | $CF_3$ | 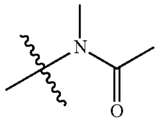 [SMILES: *N(C)C(C)=O] |

TABLE 1-continued
Structures of compounds I
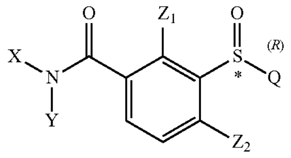
I
| Compound No. | X | Y | $Z_1$ | $Z_2$ | Q |
|---|---|---|---|---|---|
| 61 | 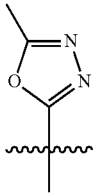 | H | F | $CF_3$ | 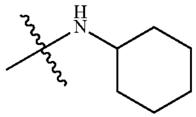 |
| 62 | 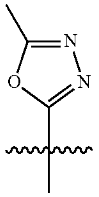 [SMILES: *c1nnc(C)o1] | H | F | $CF_3$ | 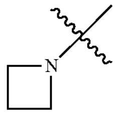 [SMILES: *N1CCC1] |
| 63 | 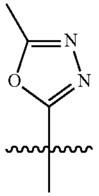 | H | F | $CF_3$ | 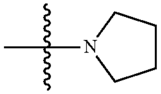 |

TABLE 1-continued
Structures of compounds I
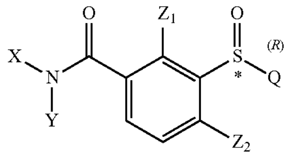
I
| Compound No. | X | Y | $Z_1$ | $Z_2$ | Q |
|---|---|---|---|---|---|
| 64 | 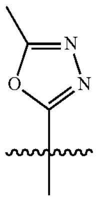 | H | F | $CF_3$ | 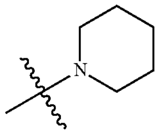 [SMILES: *N1CCCCC1] |
| 65 | 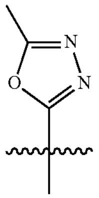 [SMILES: *c1nnc(C)o1] | H | F | $CF_3$ | 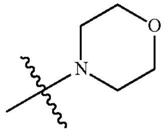 [SMILES: *N1CCOCC1] |
| 66 | 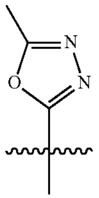 | H | F | $CF_3$ | 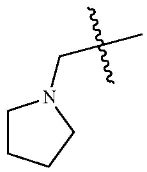 [SMILES: *CN1CCCC1] |

TABLE 1-continued
Structures of compounds I
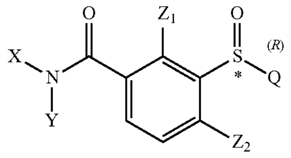
I
| Compound No. | X | Y | $Z_1$ | $Z_2$ | Q |
|---|---|---|---|---|---|
| 67 | 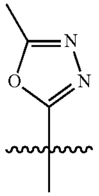 | H | F | $CF_3$ | 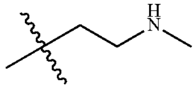 [SMILES: *CCNC] |
| 68 | 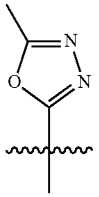 [SMILES: *c1nnc(C)o1] | H | F | $CF_3$ | 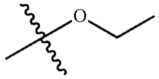 [SMILES: *OCC] |
| 69 | 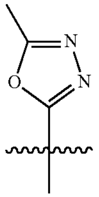 | H | F | $CF_3$ | 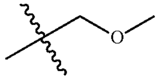 [SMILES: *COC] |

TABLE 1-continued
Structures of compounds I
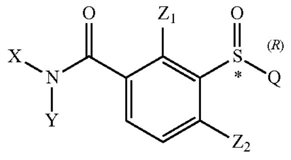
I
| Compound No. | X | Y | $Z_1$ | $Z_2$ | Q |
|---|---|---|---|---|---|
| 70 | 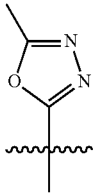 | H | F | $CF_3$ | 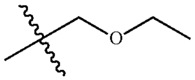 [SMILES: *COCC] |
| 71 | 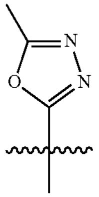 [SMILES: *c1nnc(C)o1] | H | F | $CF_3$ | 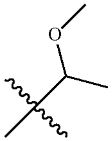 [SMILES: *C(C)OC] |
| 72 | 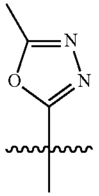 | H | F | $CF_3$ | 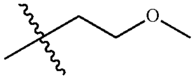 [SMILES: *CCOC] |

TABLE 1-continued
Structures of compounds I
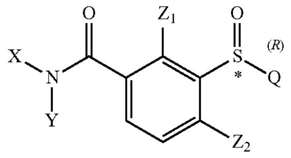
I
| Compound No. | X | Y | $Z_1$ | $Z_2$ | Q |
|---|---|---|---|---|---|
| 73 | 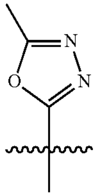 | H | F | $CF_3$ | 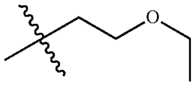 [SMILES: *CCOCC] |
| 74 | 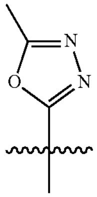 [SMILES: *c1nnc(C)o1] | H | F | $CF_3$ | 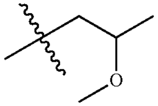 [SMILES: *CC(C)OC] |
| 75 | 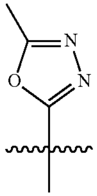 | H | F | $CF_3$ | 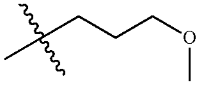 [SMILES: *CCCOC] |

TABLE 1-continued
Structures of compounds I
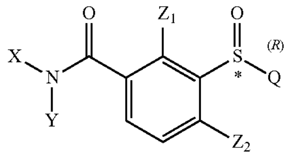
I
| Compound No. | X | Y | $Z_1$ | $Z_2$ | Q |
|---|---|---|---|---|---|
| 76 | 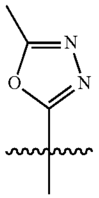 | H | F | $CF_3$ | 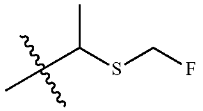 [SMILES: *C(C)SCF] |
| 77 | 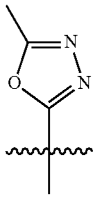 [SMILES: *c1nnc(C)o1] | H | F | $CF_3$ | 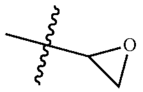 |
| 78 | 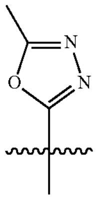 | H | F | $CF_3$ | 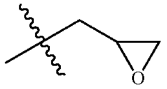 |

TABLE 1-continued
Structures of compounds I
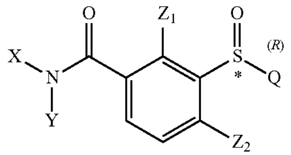
I
| Compound No. | X | Y | $Z_1$ | $Z_2$ | Q |
|---|---|---|---|---|---|
| 79 | 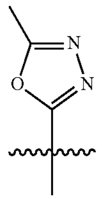 | H | F | $CF_3$ | 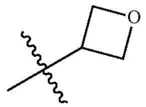 [SMILES: *C1COC1] |
| 80 | 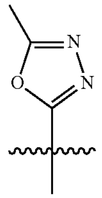 | H | F | $CF_3$ | 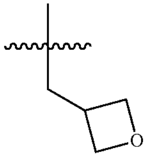 [SMILES: *CC1COC1] |
| 81 | 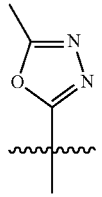 | H | F | $CF_3$ | 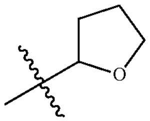 [SMILES: *C1CCCO1] |

TABLE 1-continued
Structures of compounds I
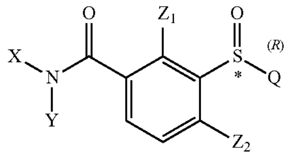
I
| Compound No. | X | Y | $Z_1$ | $Z_2$ | Q |
|---|---|---|---|---|---|
| 82 | 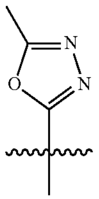 | H | F | $CF_3$ | 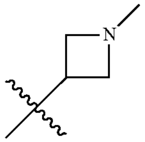 [SMILES: *C1CN(C)C1] |
| 83 | 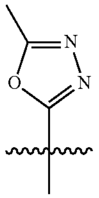 | H | F | $CF_3$ | 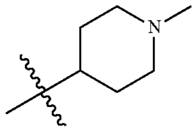 [SMILES: *C1CCN(C)CC1] |
| 84 | 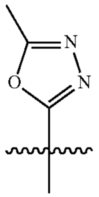 | H | F | $CF_3$ | 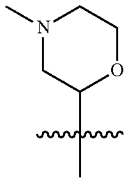 [SMILES: *C1CN(C)CCO1] |

TABLE 1-continued
Structures of compounds I
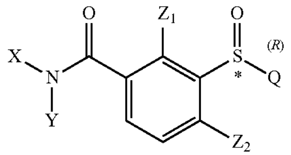
I
| Compound No. | X | Y | $Z_1$ | $Z_2$ | Q |
|---|---|---|---|---|---|
| 85 | 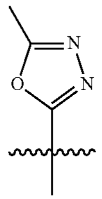 | H | F | $CF_3$ | 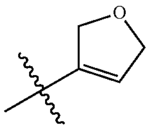 [SMILES: *C1=CCOC1] |
| 86 | 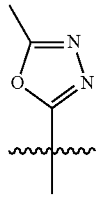 | H | F | $CF_3$ | 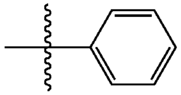 |
| 87 | 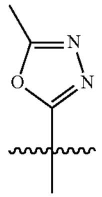 | H | F | $CF_3$ | 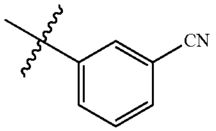 [SMILES: *c1cccc(C#N)c1] |

TABLE 1-continued
Structures of compounds I
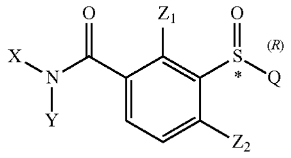
I
| Compound No. | X | Y | $Z_1$ | $Z_2$ | Q |
|---|---|---|---|---|---|
| 88 | 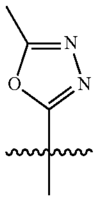 | H | F | $CF_3$ | 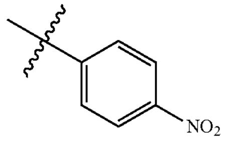 |
| 89 | 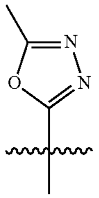 | H | F | $CF_3$ | 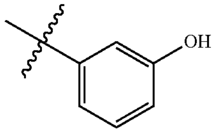 [SMILES: *c1cccc(O)c1] |
| 90 | 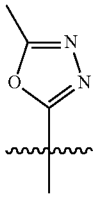 | H | F | $CF_3$ | 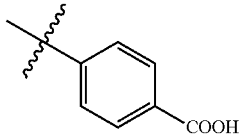 [SMILES: *c1ccc(C(=O)O)cc1] |

TABLE 1-continued
Structures of compounds I
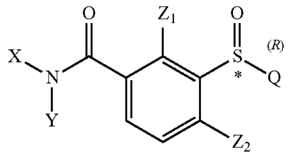
I
| Compound No. | X | Y | $Z_1$ | $Z_2$ | Q |
|---|---|---|---|---|---|
| 91 | 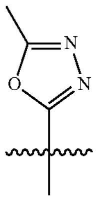 | H | F | $CF_3$ | 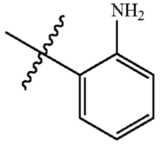 [SMILES: *c1ccccc1N] |
| 92 | 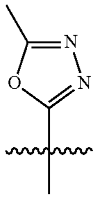 | H | F | $CF_3$ | 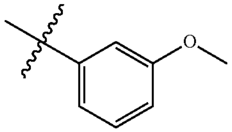 [SMILES: *c1cccc(OC)c1] |
| 93 | 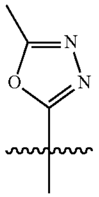 | H | F | $CF_3$ | 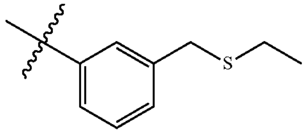 [SMILES: *c1cccc(CSCC)c1] |

TABLE 1-continued
Structures of compounds I
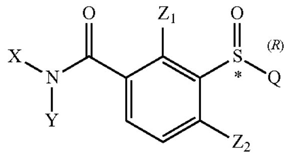
I
| Compound No. | X | Y | $Z_1$ | $Z_2$ | Q |
|---|---|---|---|---|---|
| 94 | 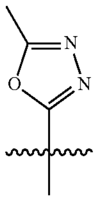 | H | F | $CF_3$ | 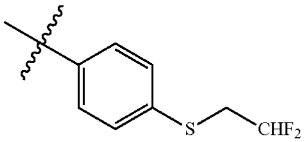 [SMILES: *c1ccc(SCC(F)F)cc1] |
| 95 | 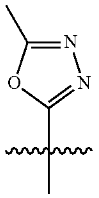 | H | F | $CF_3$ | 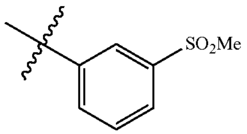 [SMILES: *c1cccc(S(C)(=O)=O)c1] |
| 96 | 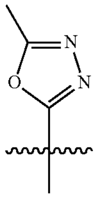 | H | F | $CF_3$ | 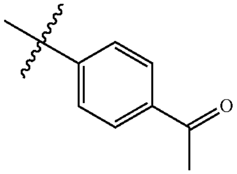 [SMILES: *c1ccc(C(C)=O)cc1] |

TABLE 1-continued
Structures of compounds I
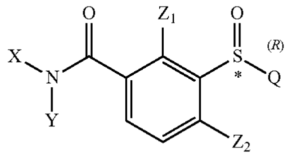
I
| Compound No. | X | Y | $Z_1$ | $Z_2$ | Q |
|---|---|---|---|---|---|
| 97 | 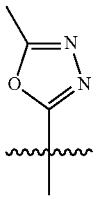 | H | F | $CF_3$ | 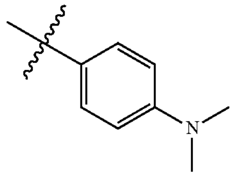 [SMILES: *c1ccc(N(C)C)cc1] |
| 98 | 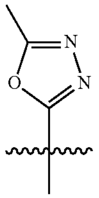 | H | F | $CF_3$ | 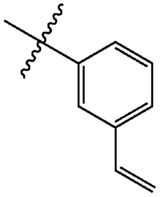 [SMILES: *c1cccc(C=C)c1] |
| 99 | 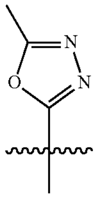 | H | F | $CF_3$ | 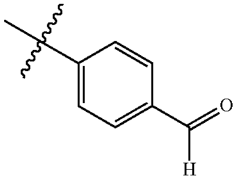 [SMILES: *c1ccc(C=O)cc1] |

TABLE 1-continued
Structures of compounds I
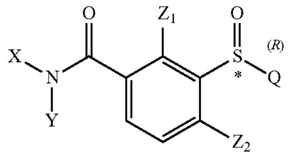
I
| Compound No. | X | Y | $Z_1$ | $Z_2$ | Q |
|---|---|---|---|---|---|
| 100 | 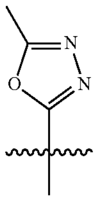 | H | F | $CF_3$ | 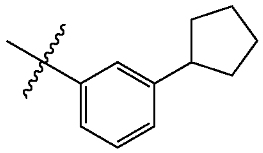 [SMILES: *c1cccc(C2CCCC2)c1] |
| 101 | 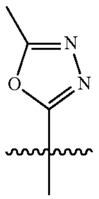 | H | F | $CF_3$ | 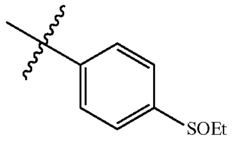 |
| 102 | 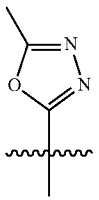 | H | F | $CF_3$ | 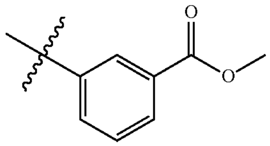 [SMILES: *c1cccc(C(=O)OC)c1] |

TABLE 1-continued
Structures of compounds I
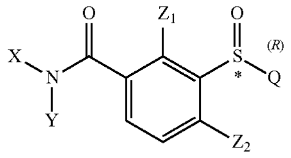
I
| Compound No. | X | Y | $Z_1$ | $Z_2$ | Q |
|---|---|---|---|---|---|
| 103 | 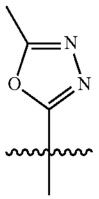 | H | F | $CF_3$ | 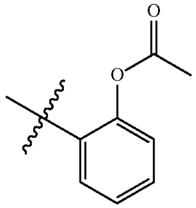 [SMILES: *c1ccccc1OC(C)=O] |
| 104 | 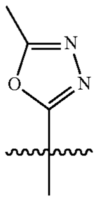 | H | F | $CF_3$ | 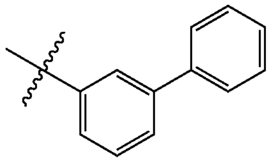 [SMILES: *c1cccc(-c2ccccc2)c1] |
| 105 | 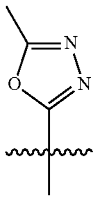 | H | F | $CF_3$ | 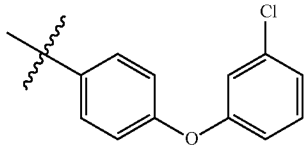 [SMILES: *c1ccc(Oc2cccc(Cl)c2)cc1] |

TABLE 1-continued
Structures of compounds I
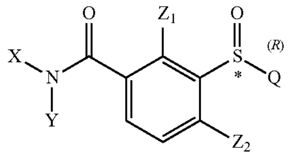
I
| Compound No. | X | Y | $Z_1$ | $Z_2$ | Q |
|---|---|---|---|---|---|
| 106 | 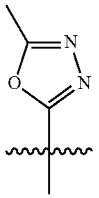 | H | F | $CF_3$ | 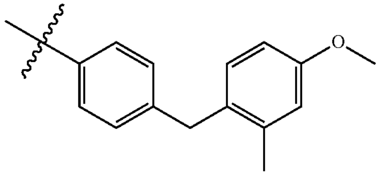 [SMILES: *c1ccc(Cc2ccc(OC)cc2C)cc1] |
| 107 | 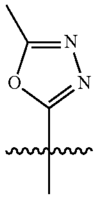 | H | F | $CF_3$ | 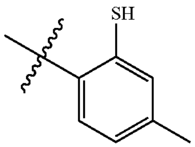 [SMILES: *c1ccc(C)cc1S] |
| 108 | 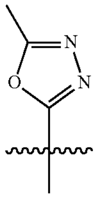 | H | F | $CF_3$ | 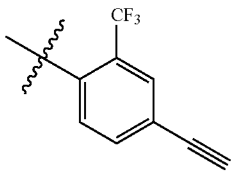 [SMILES: *c1ccc(C#C)cc1C(F)(F)F] |

TABLE 1-continued
Structures of compounds I
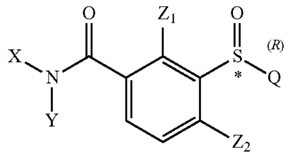
I
| Compound No. | X | Y | $Z_1$ | $Z_2$ | Q |
|---|---|---|---|---|---|
| 109 | 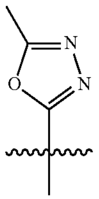 | H | F | $CF_3$ | 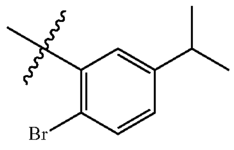 [SMILES: *c1cc(C(C)C)ccc1Br] |
| 110 | 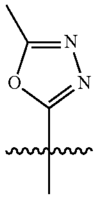 | H | F | $CF_3$ | 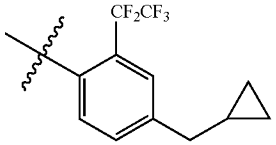 |
| 111 | 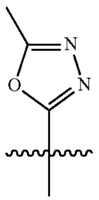 | H | F | $CF_3$ | 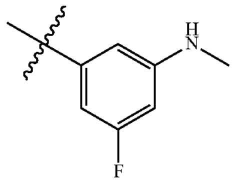 [SMILES: *c1cc(F)cc(NC)c1] |

TABLE 1-continued
Structures of compounds I
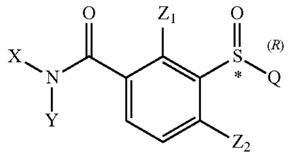
I
| Compound No. | X | Y | $Z_1$ | $Z_2$ | Q |
|---|---|---|---|---|---|
| 112 | 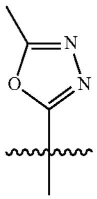 | H | F | $CF_3$ | 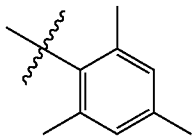 |
| 113 | 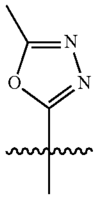 [SMILES: *c1nnc(C)o1] | H | F | $CF_3$ | 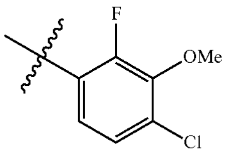 [SMILES: *c1ccc(Cl)c(OC)c1F] |
| 114 | 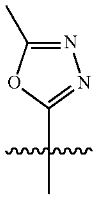 | H | F | $CF_3$ | 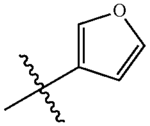 [SMILES: *c1ccoc1] |

TABLE 1-continued
Structures of compounds I
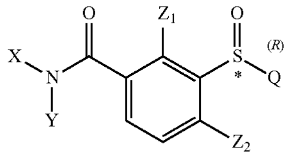
I
| Compound No. | X | Y | $Z_1$ | $Z_2$ | Q |
|---|---|---|---|---|---|
| 115 | 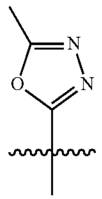 | H | F | $CF_3$ | 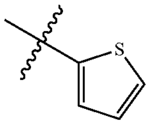 [SMILES: *c1cccs1] |
| 116 | 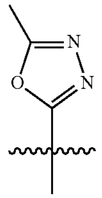 | H | F | $CF_3$ | 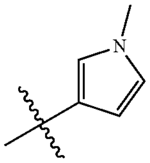 [SMILES: *c1ccn(C)c1] |
| 117 | 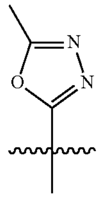 | H | F | $CF_3$ | 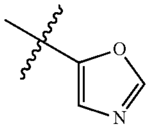 [SMILES: *c1cnco1] |

TABLE 1-continued
Structures of compounds I
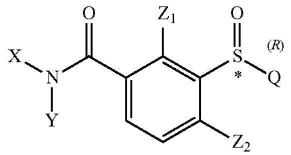
I
| Compound No. | X | Y | $Z_1$ | $Z_2$ | Q |
|---|---|---|---|---|---|
| 118 | 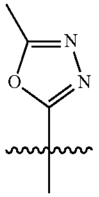 | H | F | $CF_3$ | 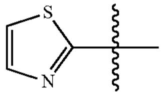 [SMILES: *c1nccs1] |
| 119 | 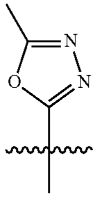 | H | F | $CF_3$ | 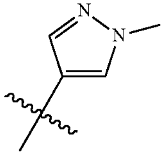 [SMILES: *c1cnn(C)c1] |
| 120 | 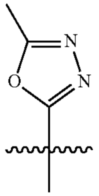 | H | F | $CF_3$ | 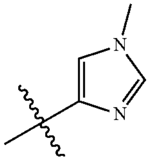 [SMILES: *c1cn(C)cn1] |

TABLE 1-continued
Structures of compounds I
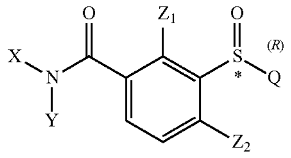
I
| Compound No. | X | Y | $Z_1$ | $Z_2$ | Q |
|---|---|---|---|---|---|
| 121 | 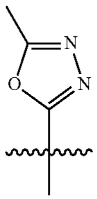 | H | F | $CF_3$ | 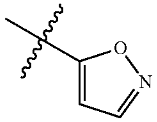 [SMILES: *c1ccno1] |
| 122 | 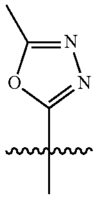 | H | F | $CF_3$ | 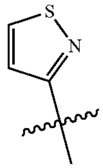 [SMILES: *c1ccsn1] |
| 123 | 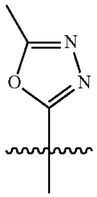 | H | F | $CF_3$ | 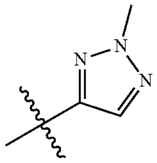 [SMILES: *c1cnn(C)n1] |

TABLE 1-continued
Structures of compounds I
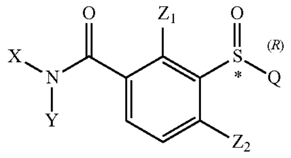
I
| Compound No. | X | Y | $Z_1$ | $Z_2$ | Q |
|---|---|---|---|---|---|
| 124 | 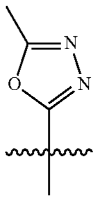 | H | F | $CF_3$ | 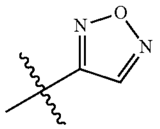 [SMILES: *c1cnon1] |
| 125 | 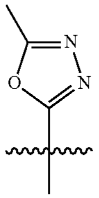 | H | F | $CF_3$ | 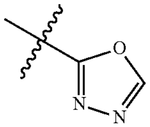 [SMILES: *c1nnco1] |
| 126 | 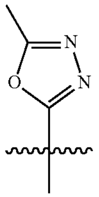 | H | F | $CF_3$ | 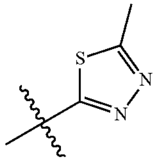 [SMILES: *c1nnc(C)s1] |

TABLE 1-continued
Structures of compounds I
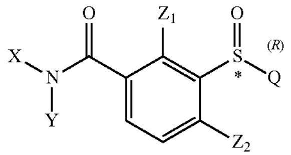
I
| Compound No. | X | Y | $Z_1$ | $Z_2$ | Q |
|---|---|---|---|---|---|
| 127 | 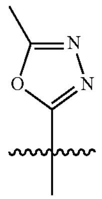 | H | F | $CF_3$ | 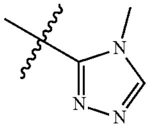 [SMILES: *c1nncn1C] |
| 128 | 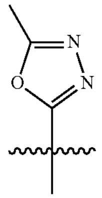 | H | F | $CF_3$ | 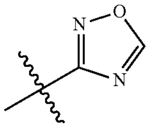 [SMILES: *c1ncon1] |
| 129 | 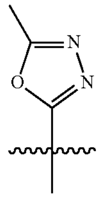 | H | F | $CF_3$ | 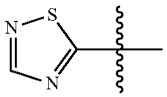 |

TABLE 1-continued
Structures of compounds I
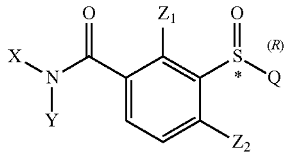
I
| Compound No. | X | Y | $Z_1$ | $Z_2$ | Q |
|---|---|---|---|---|---|
| 130 | 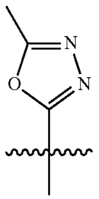 | H | F | $CF_3$ | 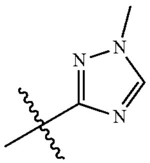 [SMILES: *c1ncn(C)n1] |
| 131 | 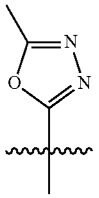 | H | F | $CF_3$ | 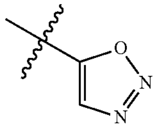 [SMILES: *c1cnno1] |
| 132 | 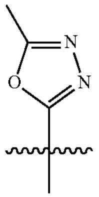 | H | F | $CF_3$ | 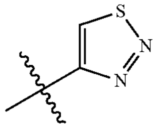 [SMILES: *c1csnn1] |

TABLE 1-continued
Structures of compounds I
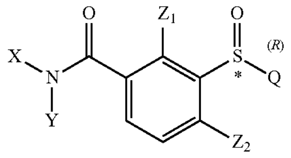
I
| Compound No. | X | Y | $Z_1$ | $Z_2$ | Q |
|---|---|---|---|---|---|
| 133 | 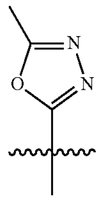 | H | F | $CF_3$ | 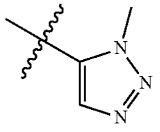 [SMILES: *c1cnnn1C] |
| 134 | 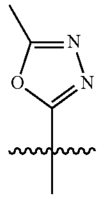 | H | F | $CF_3$ | 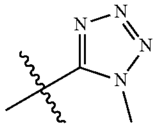 [SMILES: *c1nnnn1C] |
| 135 | 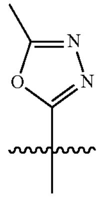 | H | F | $CF_3$ | 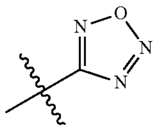 [SMILES: *c1nnon1] |

TABLE 1-continued
Structures of compounds I
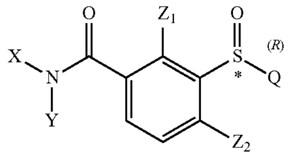
I
| Compound No. | X | Y | $Z_1$ | $Z_2$ | Q |
|---|---|---|---|---|---|
| 136 | 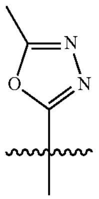 | H | F | $CF_3$ | 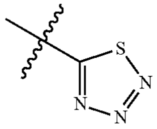 [SMILES: *c1nnns1] |
| 137 | 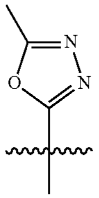 | H | F | $CF_3$ | 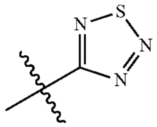 [SMILES: *c1nnsn1] |
| 138 | 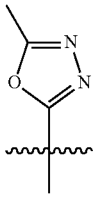 | H | F | $CF_3$ | 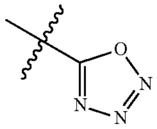 [SMILES: *c1nnno1] |

TABLE 1-continued
Structures of compounds I
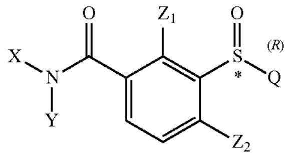
I
| Compound No. | X | Y | $Z_1$ | $Z_2$ | Q |
|---|---|---|---|---|---|
| 139 | 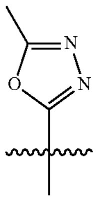 | H | F | $CF_3$ | 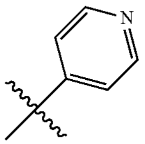 [SMILES: *c1ccncc1] |
| 140 | 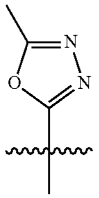 | H | F | $CF_3$ | 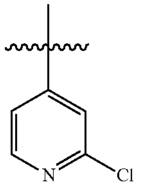 [SMILES: *c1ccnc(Cl)c1] |
| 141 | 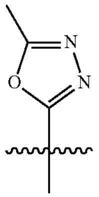 | H | F | $CF_3$ | 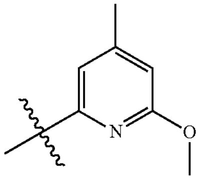 [SMILES: *c1cc(C)cc(OC)n1] |

TABLE 1-continued
Structures of compounds I
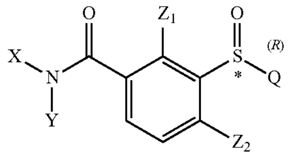
I
| Compound No. | X | Y | Z1 | Z2 | Q |
|---|---|---|---|---|---|
| 142 | 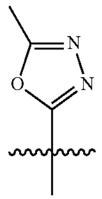 | H | F | $CF_3$ | 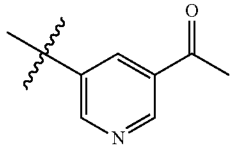 [SMILES: *c1cncc(C(C)=O)c1] |
| 143 | 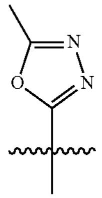 | H | F | $CF_3$ | 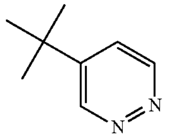 |
| 144 | 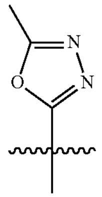 | H | F | $CF_3$ | 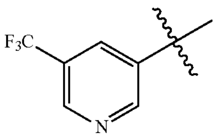 [SMILES: *c1cncc(C(F)(F)F)c1] |

TABLE 1-continued
Structures of compounds I
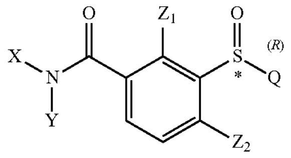
I
| Compound No. | X | Y | $Z_1$ | $Z_2$ | Q |
|---|---|---|---|---|---|
| 145 | 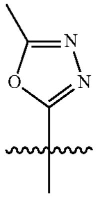 | H | F | $CF_3$ | 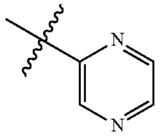 [SMILES: *c1cnccn1] |
| 146 | 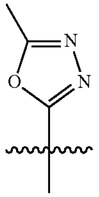 | H | F | $CF_3$ | 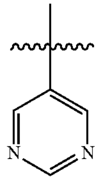 |
| 147 | 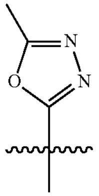 | H | F | $CF_3$ | 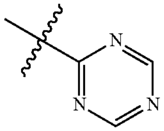 [SMILES: *c1ncncn1] |

TABLE 1-continued
Structures of compounds I
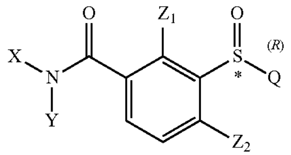
I
| Compound No. | X | Y | $Z_1$ | $Z_2$ | Q |
| --- | --- | --- | --- | --- | --- |
| 148 | 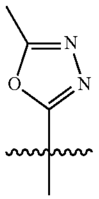 | H | F | $CF_3$ | 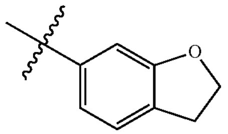 [SMILES: *c1ccc2c(c1)OCC2] |
| 149 | 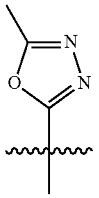 | H | F | $CF_3$ | 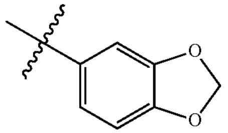 [SMILES: *c1ccc2c(c1)OCO2] |
| 150 | 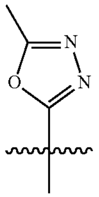 | H | F | $CF_3$ | 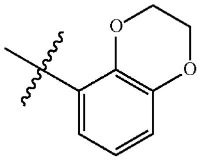 [SMILES: *c1cccc2c1OCCO2] |

TABLE 1-continued
Structures of compounds I
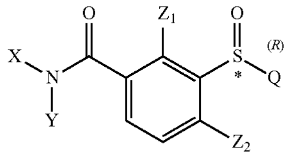
I
| Compound No. | X | Y | $Z_1$ | $Z_2$ | Q |
|---|---|---|---|---|---|
| 151 | 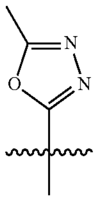 | H | F | $CF_3$ | 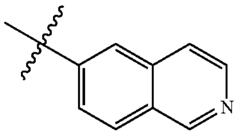 |
| 152 | 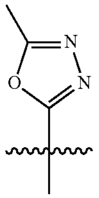 | H | F | $CF_3$ | 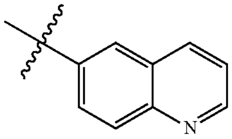 [SMILES: *c1ccc2ncccc2c1] |
| 153 | 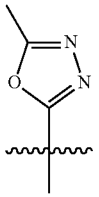 | H | F | $CF_3$ | 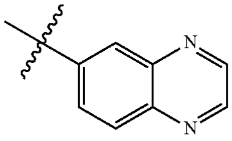 [SMILES: *c1ccc2nccnc2c1] |

TABLE 1-continued
Structures of compounds I
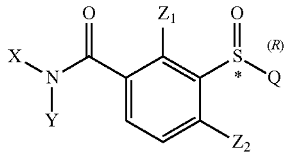
I
| Compound No. | X | Y | $Z_1$ | $Z_2$ | Q |
|---|---|---|---|---|---|
| 154 | 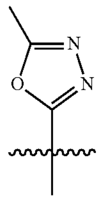 | H | F | $CF_3$ | 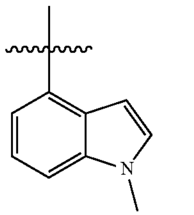 [SMILES: *c1cccc2c1ccn2C] |
| 155 | 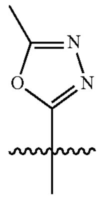 [SMILES: *c1nnc(C)o1] | H | F | $CF_3$ | 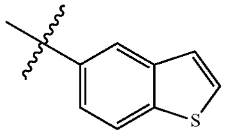 [SMILES: *c1ccc2sccc2c1] |
| 156 | 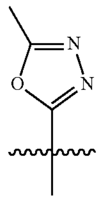 | H | F | $CF_3$ | 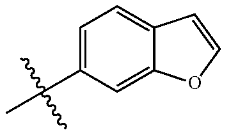 [SMILES: *c1ccc2ccoc2c1] |

TABLE 1-continued
Structures of compounds I
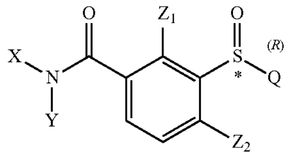
I
| Compound No. | X | Y | $Z_1$ | $Z_2$ | Q |
|---|---|---|---|---|---|
| 157 | 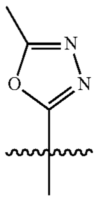 | H | F | $CF_3$ | 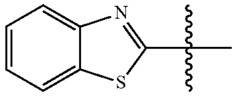 [SMILES: *c1nc2ccccc2s1] |
| 158 | 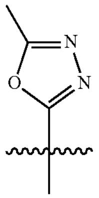 [SMILES: *c1nnc(C)o1] | H | F | $CF_3$ | 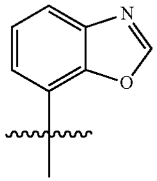 [SMILES: *c1cccc2ncoc12] |
| 159 | 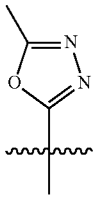 | H | F | $CF_3$ | 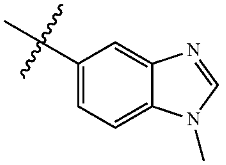 [SMILES: *c1ccc2c(c1)ncn2C] |

TABLE 1-continued
Structures of compounds I
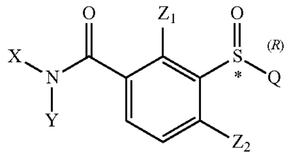
I
| Compound No. | X | Y | $Z_1$ | $Z_2$ | Q |
|---|---|---|---|---|---|
| 160 | 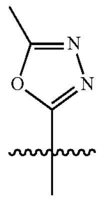 | H | F | $CF_3$ | 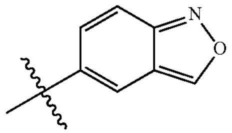 [SMILES: *c1ccc2nocc2c1] |
| 161 | 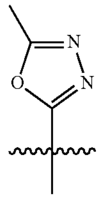 [SMILES: *c1nnc(C)o1] | H | F | $CF_3$ | 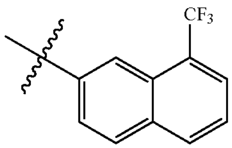 [SMILES: *c1ccc2cccc(C(F)(F)F)c2c1] |
| 162 | 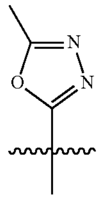 | H | F | $CF_3$ | 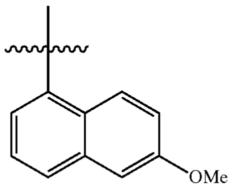 [SMILES: *c1cccc2cc(OC)ccc12] |

TABLE 1-continued
Structures of compounds I
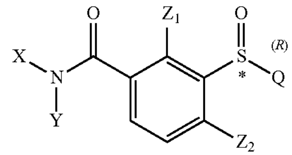
I
| Compound No. | X | Y | $Z_1$ | $Z_2$ | Q |
|---|---|---|---|---|---|
| 163 | 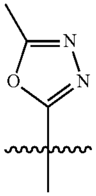 | H | F | $CF_3$ | 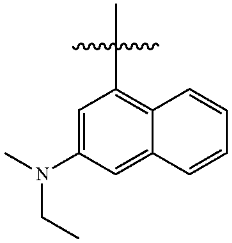 [SMILES: *c1cc(N(C)CC)cc2ccccc12] |
| 164 | 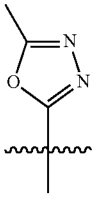 | H | F | $CF_3$ | 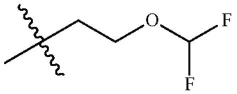 [SMILES: *CCOC(F)F] |
| 165 | 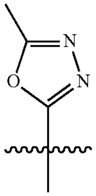 | H | F | $CF_3$ | 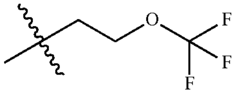 [SMILES: *CCOC(F)(F)F] |

TABLE 1-continued
Structures of compounds I
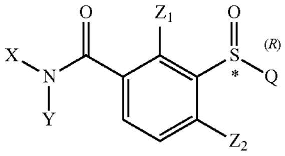
I
| Compound No. | X | Y | $Z_1$ | $Z_2$ | Q |
|---|---|---|---|---|---|
| 166 | 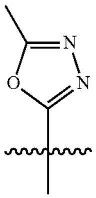 | H | F | $CF_3$ | 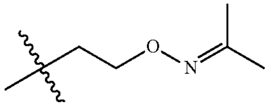 [SMILES: *CCON=C(C)C] |
| 167 | 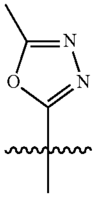 [SMILES: *c1nnc(C)o1] | H | F | $CF_3$ | 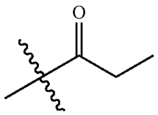 [SMILES: *C(=O)CC] |
| 168 | 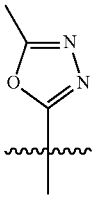 | H | F | $CF_3$ | 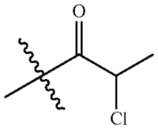 [SMILES: *C(=O)C(C)Cl] |

TABLE 1-continued
Structures of compounds I
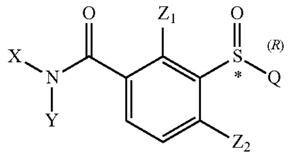
I
| Compound No. | X | Y | $Z_1$ | $Z_2$ | Q |
|---|---|---|---|---|---|
| 169 | 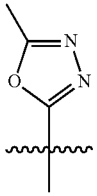 | H | F | $CF_3$ | 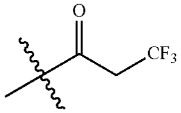 [SMILES: *C(=O)CC(F)(F)F] |
| 170 | 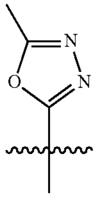 [SMILES: *c1nnc(C)o1] | H | F | $CF_3$ | 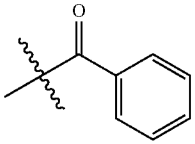 [SMILES: *C(=O)c1ccccc1] |
| 171 | 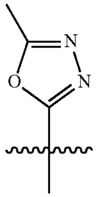 | H | F | $CF_3$ | 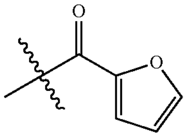 [SMILES: *C(=O)c1ccco1] |

TABLE 1-continued
Structures of compounds I
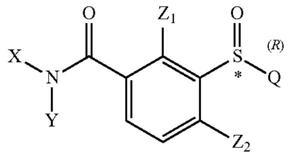
I
| Compound No. | X | Y | Z1 | Z2 | Q |
| --- | --- | --- | --- | --- | --- |
| 172 | 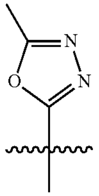 | H | F | $CF_3$ | 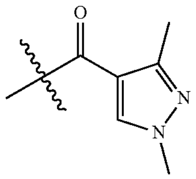 [SMILES: *C(=O)c1cn(C)nc1C] |
| 173 | 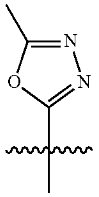 [SMILES: *c1nnc(C)o1] | H | F | $CF_3$ | 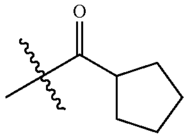 [SMILES: *C(=O)C1CCCC1] |
| 174 | 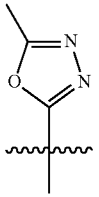 | H | F | $CF_3$ | 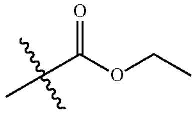 [SMILES: *C(=O)OCC] |

TABLE 1-continued
Structures of compounds I
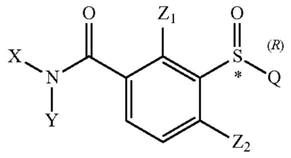
I
| Compound No. | X | Y | $Z_1$ | $Z_2$ | Q |
|---|---|---|---|---|---|
| 175 | 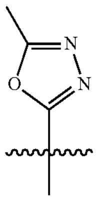 | H | F | $CF_3$ | 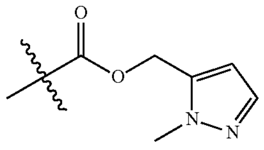 [SMILES: *C(=O)OCc1ccnn1C] |
| 176 | 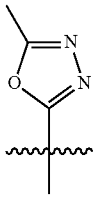 [SMILES: *c1nnc(C)o1] | H | F | $CF_3$ | 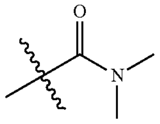 [SMILES: *C(=O)N(C)C] |
| 177 | 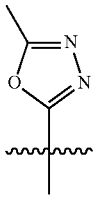 | H | F | $CF_3$ | 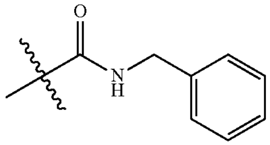 [SMILES: *C(=O)NCc1ccccc1] |

TABLE 1-continued
Structures of compounds I
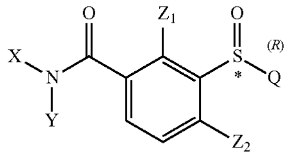
I
| Compound No. | X | Y | Z1 | Z2 | Q |
|---|---|---|---|---|---|
| 178 | 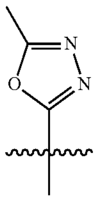 | H | F | $CF_3$ | 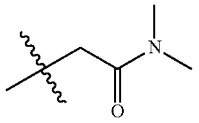 [SMILES: *CC(=O)N(C)C] |
| 179 | 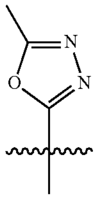 [SMILES: *c1nnc(C)o1] | H | F | $CF_3$ | 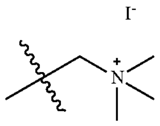 |
| 180 | 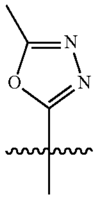 | H | F | $CF_3$ | 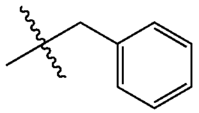 [SMILES: *Cc1ccccc1] |

TABLE 1-continued
Structures of compounds I
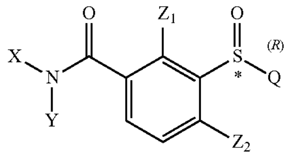
I
| Compound No. | X | Y | $Z_1$ | $Z_2$ | Q |
| --- | --- | --- | --- | --- | --- |
| 181 | 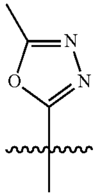 | H | F | $CF_3$ | 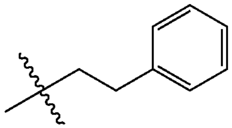 [SMILES: *CCc1ccccc1] |
| 182 | 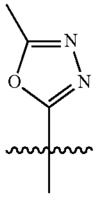 [SMILES: *c1nnc(C)o1] | H | F | $CF_3$ | 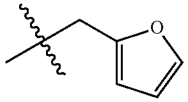 [SMILES: *Cc1ccco1] |
| 183 | 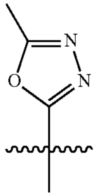 | H | F | $CF_3$ | 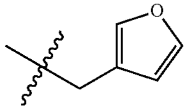 [SMILES: *Cc1ccoc1] |

TABLE 1-continued
Structures of compounds I
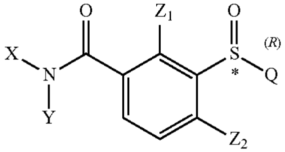
I
| Compound No. | X | Y | $Z_1$ | $Z_2$ | Q |
|---|---|---|---|---|---|
| 184 | 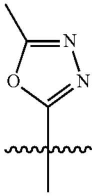 | H | F | $CF_3$ | 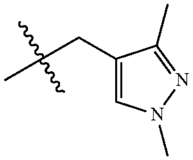 [SMILES: *Cc1cn(C)nc1C] |
| 185 | 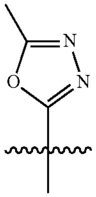 [SMILES: *c1nnc(C)o1] | H | F | $CF_3$ | 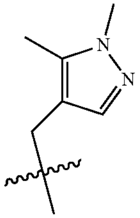 [SMILES: *Cc1cnn(C)c1C] |
| 186 | 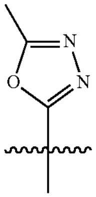 | H | F | $CF_3$ | 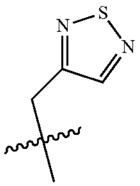 [SMILES: *Cc1cnsn1] |

TABLE 1-continued
Structures of compounds I
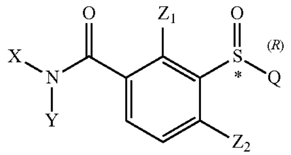
I
| Compound No. | X | Y | $Z_1$ | $Z_2$ | Q |
|---|---|---|---|---|---|
| 187 | 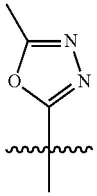 | H | F | $CF_3$ | 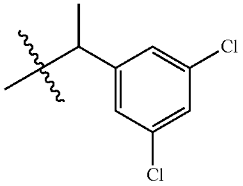 [SMILES: *C(C)c1cc(Cl)cc(Cl)c1] |
| 188 | 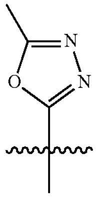 [SMILES: *c1nnc(C)o1] | H | F | $CF_3$ | 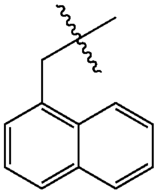 [SMILES: *Cc1cccc2ccccc12] |
| 189 | 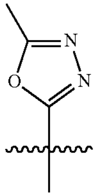 | H | F | $CF_3$ | 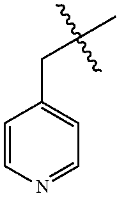 [SMILES: *Cc1ccncc1] |

TABLE 1-continued
Structures of compounds I
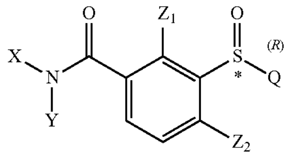
I
| Compound No. | X | Y | $Z_1$ | $Z_2$ | Q |
|---|---|---|---|---|---|
| 190 | 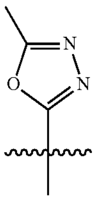 | H | F | $CF_3$ | 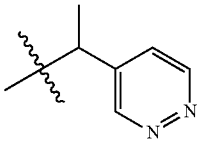 [SMILES: *C(C)c1ccnnc1] |
| 191 | 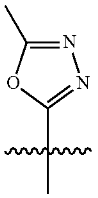 [SMILES: *c1nnc(C)o1] | H | F | $CF_3$ | 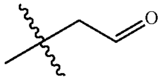 [SMILES: *CC=O] |
| 192 | 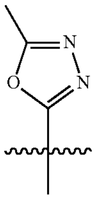 | H | F | $CF_3$ | 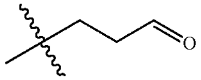 [SMILES: *CCC=O] |

TABLE 1-continued
Structures of compounds I
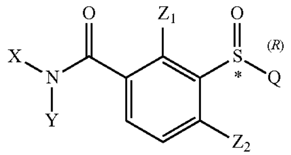
I
| Compound No. | X | Y | $Z_1$ | $Z_2$ | Q |
| --- | --- | --- | --- | --- | --- |
| 193 | 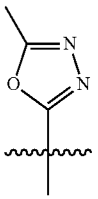 | H | F | $CF_3$ | 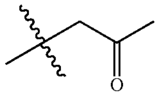 |
| 194 | 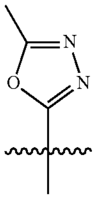 [SMILES: *c1nnc(C)o1] | H | F | $CF_3$ | 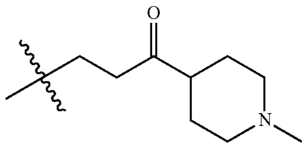 [SMILES: *CCC(=O)C1CCN(C)CC1] |
| 195 | 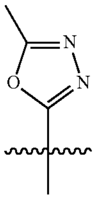 | H | F | $CF_3$ | 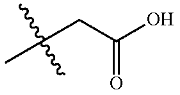 [SMILES: *CC(=O)O] |

TABLE 1-continued
Structures of compounds I
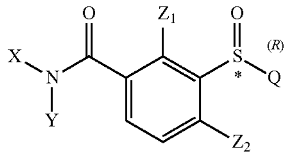
I
| Compound No. | X | Y | $Z_1$ | $Z_2$ | Q |
|---|---|---|---|---|---|
| 196 | 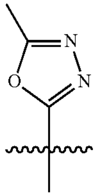 | H | F | $CF_3$ | 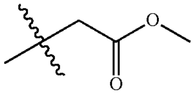 |
| 197 | 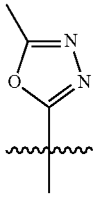 [SMILES: *c1nnc(C)o1] | H | F | $CF_3$ | 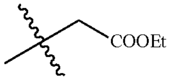 |
| 198 | 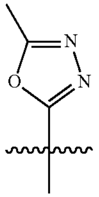 | H | F | $CF_3$ | 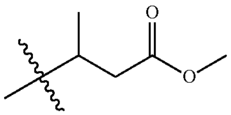 [SMILES: *C(C)CC(=O)OC] |

TABLE 1-continued
Structures of compounds I
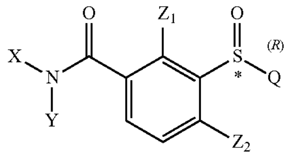
I
| Compound No. | X | Y | $Z_1$ | $Z_2$ | Q |
|---|---|---|---|---|---|
| 199 | 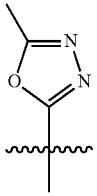 | H | F | $CF_3$ | 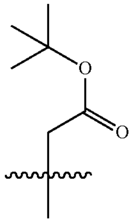 [SMILES: *CC(=O)OC(C)(C)C] |
| 200 | 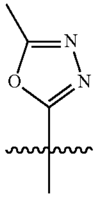 | H | F | $CF_3$ | 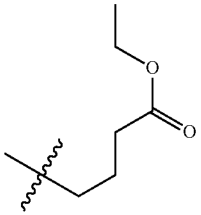 [SMILES: *CCCC(=O)OCC] |
| 201 | 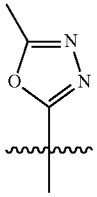 | H | F | $CF_3$ | 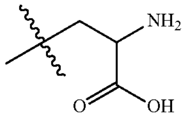 [SMILES: *CC(N)C(=O)O] |

TABLE 1-continued
Structures of compounds I
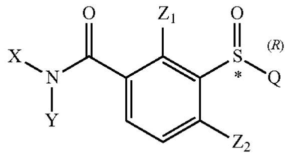
I
| Compound No. | X | Y | $Z_1$ | $Z_2$ | Q |
|---|---|---|---|---|---|
| 202 | 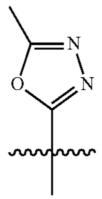 | H | F | $CF_3$ | 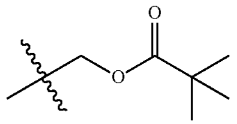 [SMILES: *COC(=O)C(C)(C)C] |
| 203 | 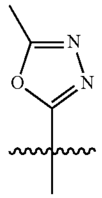 [SMILES: *c1nnc(C)o1] | H | F | $CF_3$ | 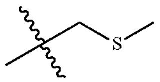 [SMILES: *CSC] |
| 204 | 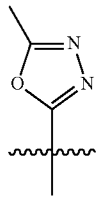 | H | F | $CF_3$ | 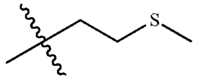 |

TABLE 1-continued
Structures of compounds I
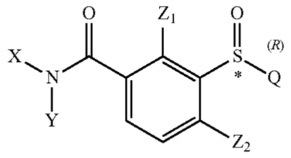
I
| Compound No. | X | Y | $Z_1$ | $Z_2$ | Q |
|---|---|---|---|---|---|
| 205 | 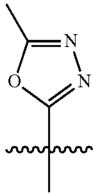 | H | F | $CF_3$ | 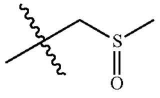 |
| 206 | 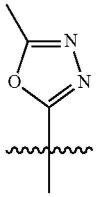 [SMILES: *c1nnc(C)o1] | H | F | $CF_3$ | 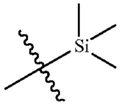 [SMILES: *[Si](C)(C)C] |
| 207 | 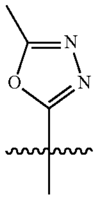 | H | F | $CF_3$ | 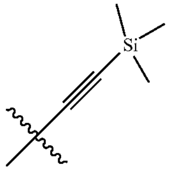 [SMILES: *C#C[Si](C)(C)C] |

TABLE 1-continued
Structures of compounds I
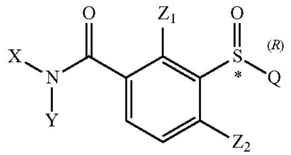
I
| Compound No. | X | Y | $Z_1$ | $Z_2$ | Q |
|---|---|---|---|---|---|
| 208 | 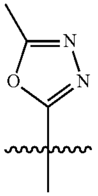 | H | F | $CF_3$ | 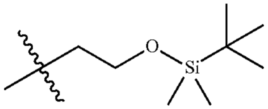 [SMILES: *CCO[Si](C)(C)C(C)(C)C] |
| 209 | 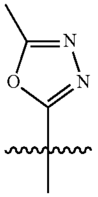 [SMILES: *c1nnc(C)o1] | H | F | $CF_3$ | 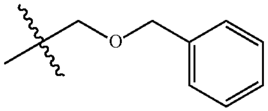 [SMILES: *COCc1ccccc1] |
| 210 | 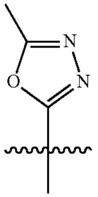 | Me | F | $CF_3$ | Et |

TABLE 1-continued
Structures of compounds I
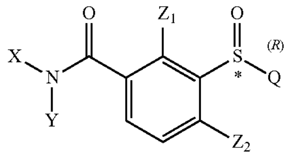
I
| Compound No. | X | Y | $Z_1$ | $Z_2$ | Q |
|---|---|---|---|---|---|
| 211 | 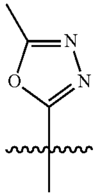 | Et | F | $CF_3$ | Et |
| 212 | 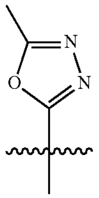 [SMILES: *c1nnc(C)o1] | 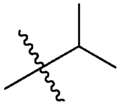 [SMILES: *C(C)C] | F | $CF_3$ | Et |
| 213 | 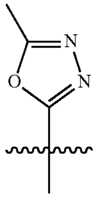 | 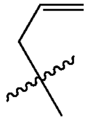 [SMILES: *CC=C] | F | $CF_3$ | Et |

TABLE 1-continued
Structures of compounds I
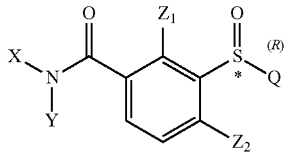
I
| Compound No. | X | Y | $Z_1$ | $Z_2$ | Q |
|---|---|---|---|---|---|
| 214 | 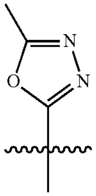 | 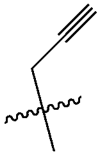 [SMILES: *CC#C] | F | $CF_3$ | Et |
| 215 | 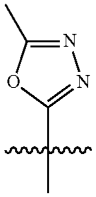 [SMILES: *c1nnc(C)o1] | 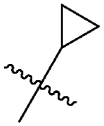 [SMILES: *C1CC1] | F | $CF_3$ | Et |
| 216 | 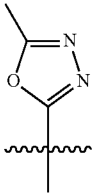 | 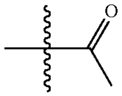 [SMILES: *C(C)=O] | F | $CF_3$ | Et |

TABLE 1-continued
Structures of compounds I
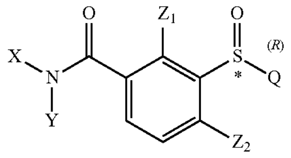
I
| Compound No. | X | Y | $Z_1$ | $Z_2$ | Q |
|---|---|---|---|---|---|
| 217 | 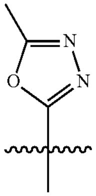 | 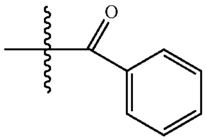 [SMILES: *C(=O)c1ccccc1] | F | $CF_3$ | Et |
| 218 | 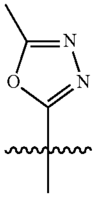 [SMILES: *c1nnc(C)o1] | 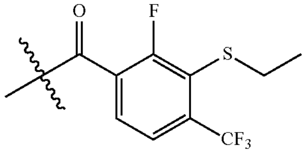 [SMILES: *C(=O)c1ccc(C(F)(F)F)c(SCC)c1F] | F | $CF_3$ | Et |
| 219 | 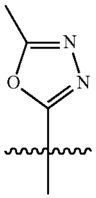 | 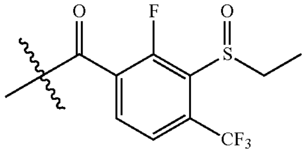 | F | $CF_3$ | Et |

TABLE 1-continued
Structures of compounds I
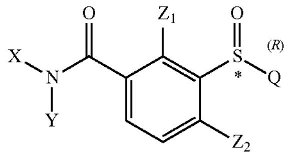
I
| Compound No. | X | Y | $Z_1$ | $Z_2$ | Q |
|---|---|---|---|---|---|
| 220 | 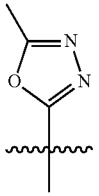 | 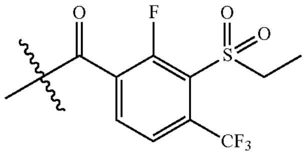 | F | $CF_3$ | Et |
| 221 | 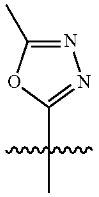 [SMILES: *c1nnc(C)o1] | 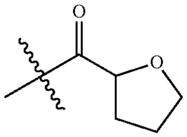 [SMILES: *C(=O)C1CCCO1] | F | $CF_3$ | Et |
| 222 | 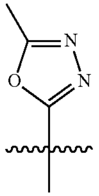 | 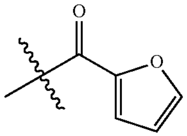 [SMILES: *C(=O)c1ccco1] | F | $CF_3$ | Et |

TABLE 1-continued
Structures of compounds I
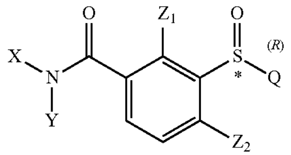
I
| Compound No. | X | Y | $Z_1$ | $Z_2$ | Q |
|---|---|---|---|---|---|
| 223 | 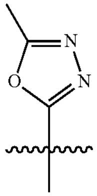 | 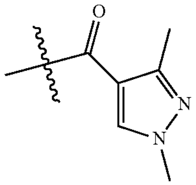 [SMILES: *C(=O)c1cn(C)nc1C] | F | $CF_3$ | Et |
| 224 | 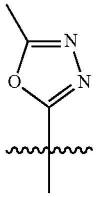 [SMILES: *c1nnc(C)o1] | 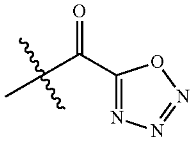 [SMILES: *C(=O)c1nnno1] | F | $CF_3$ | Et |
| 225 | 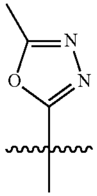 | 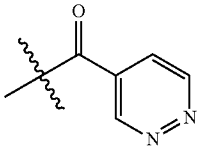 [SMILES: *C(=O)c1ccnnc1] | F | $CF_3$ | Et |

TABLE 1-continued
Structures of compounds I
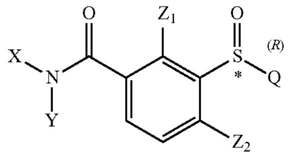
I
| Compound No. | X | Y | $Z_1$ | $Z_2$ | Q |
|---|---|---|---|---|---|
| 226 | 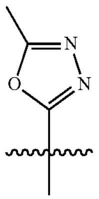 | 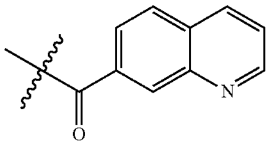 [SMILES: *C(=O)c1ccc2cccnc2c1] | F | $CF_3$ | Et |
| 227 | 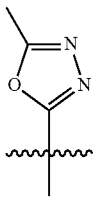 [SMILES: *c1nnc(C)o1] | 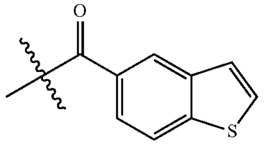 [SMILES: *C(=O)c1ccc2sccc2c1] | F | $CF_3$ | Et |
| 228 | 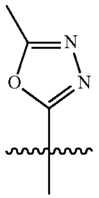 | 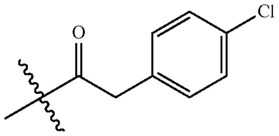 [SMILES: *C(=O)Cc1ccc(Cl)cc1] | F | $CF_3$ | Et |

TABLE 1-continued
Structures of compounds I
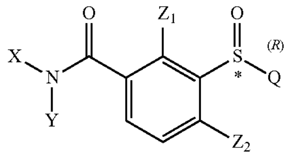
I
| Compound No. | X | Y | $Z_1$ | $Z_2$ | Q |
|---|---|---|---|---|---|
| 229 | 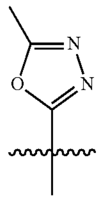 | 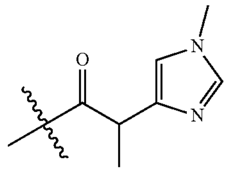 [SMILES: *C(=O)C(C)c1cn(C)cn1] | F | $CF_3$ | Et |
| 230 | 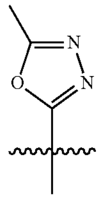 | 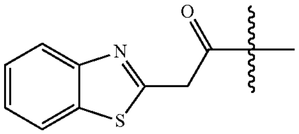 [SMILES: *C(=O)Cc1nc2ccccc2s1] | F | $CF_3$ | Et |
| 231 | 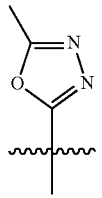 | 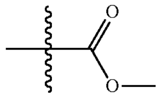 [SMILES: *C(=O)OC] | F | $CF_3$ | Et |

TABLE 1-continued
Structures of compounds I
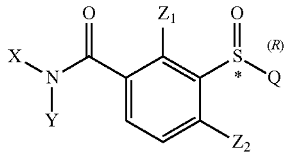
I
| Compound No. | X | Y | $Z_1$ | $Z_2$ | Q |
|---|---|---|---|---|---|
| 232 | 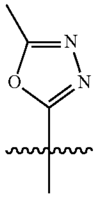 | 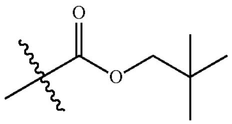 [SMILES: *C(=O)OCC(C)(C)C] | F | $CF_3$ | Et |
| 233 | 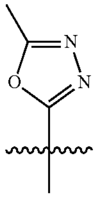 | 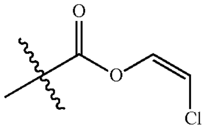 [SMILES: *C(=O)O/C=C\Cl] | F | $CF_3$ | Et |
| 234 | 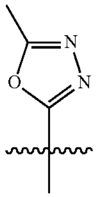 | 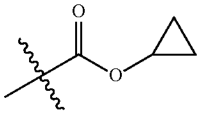 [SMILES: *C(=O)OC1CC1] | F | $CF_3$ | Et |

TABLE 1-continued
Structures of compounds I
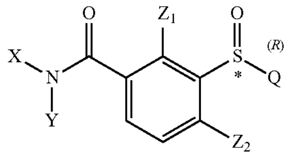
I
| Compound No. | X | Y | $Z_1$ | $Z_2$ | Q |
|---|---|---|---|---|---|
| 235 | 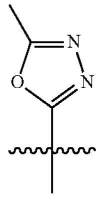 | 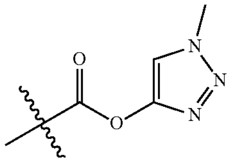 [SMILES: *C(=O)Oc1cn(C)nn1] | F | $CF_3$ | Et |
| 236 | 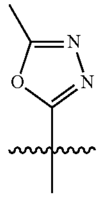 | 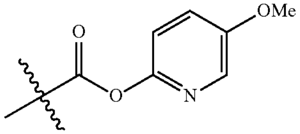 [SMILES: *C(=O)Oc1ccc(OC)cn1] | F | $CF_3$ | Et |
| 237 | 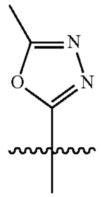 | 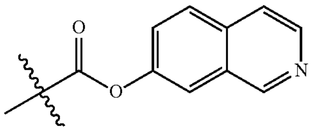 [SMILES: *C(=O)Oc1ccc2ccncc2c1] | F | $CF_3$ | Et |

TABLE 1-continued
Structures of compounds I
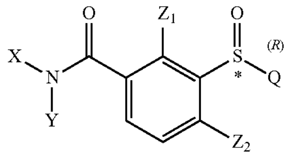
I
| Compound No. | X | Y | $Z_1$ | $Z_2$ | Q |
|---|---|---|---|---|---|
| 238 | 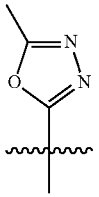 | 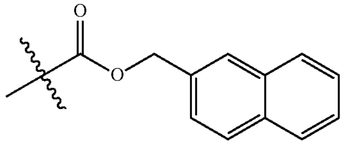 [SMILES: *C(=O)OCc1ccc2ccccc2c1] | F | $CF_3$ | Et |
| 239 | 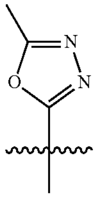 | 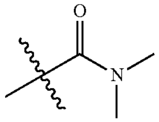 [SMILES: *C(=O)N(C)C] | F | $CF_3$ | Et |
| 240 | 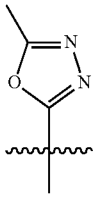 | 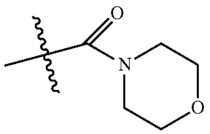 [SMILES: *C(=O)N1CCOCC1] | F | $CF_3$ | Et |

TABLE 1-continued
Structures of compounds I
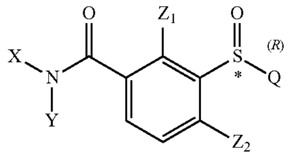
I
| Compound No. | X | Y | $Z_1$ | $Z_2$ | Q |
| --- | --- | --- | --- | --- | --- |
| 241 | 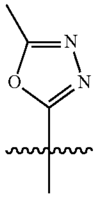 | 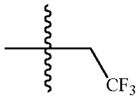 | F | $CF_3$ | Et |
| 242 | 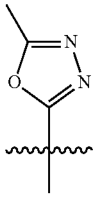 | 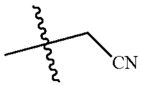 [SMILES: *CC#N] | F | $CF_3$ | Et |
| 243 | 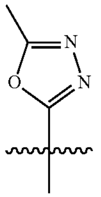 | 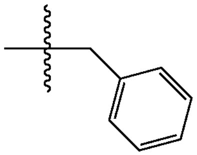 [SMILES: *Cc1ccccc1] | F | $CF_3$ | Et |

TABLE 1-continued
Structures of compounds I
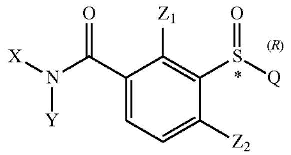
I
| Compound No. | X | Y | $Z_1$ | $Z_2$ | Q |
|---|---|---|---|---|---|
| 244 | 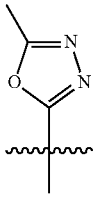 | 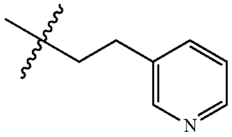 [SMILES: *CCc1cccnc1] | F | $CF_3$ | Et |
| 245 | 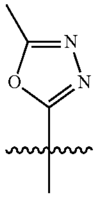 | 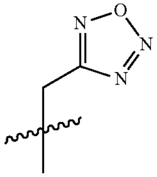 [SMILES: *Cc1nnon1] | F | $CF_3$ | Et |
| 246 | 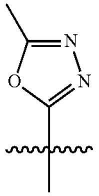 | 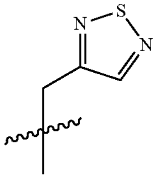 [SMILES: *Cc1cnsn1] | F | $CF_3$ | Et |

TABLE 1-continued
Structures of compounds I
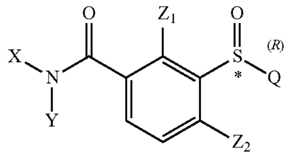
I
| Compound No. | X | Y | $Z_1$ | $Z_2$ | Q |
| --- | --- | --- | --- | --- | --- |
| 247 | 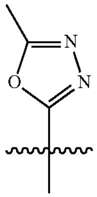 | 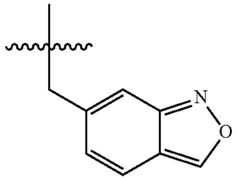 [SMILES: *Cc1ccc2conc2c1] | F | $CF_3$ | Et |
| 248 | 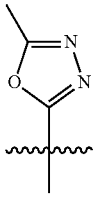 | 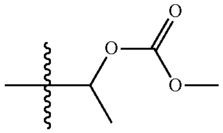 [SMILES: *C(C)OC(=O)OC] | F | $CF_3$ | Et |
| 249 | 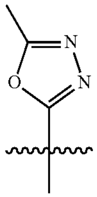 | Me | F | $CF_3$ | 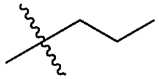 [SMILES: *CCC] |

TABLE 1-continued
Structures of compounds I
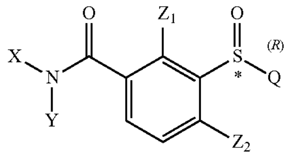
I
| Compound No. | X | Y | $Z_1$ | $Z_2$ | Q |
|---|---|---|---|---|---|
| 250 | 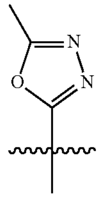 | 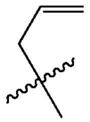 [SMILES: *CC=C] | F | $CF_3$ | 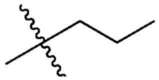 [SMILES: *CCC] |
| 251 | 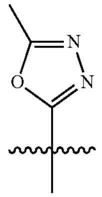 | 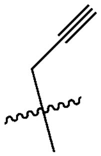 [SMILES: *CC#C] | F | $CF_3$ | 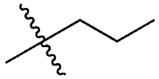 [SMILES: *CCC] |
| 252 | 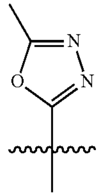 | 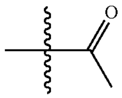 | F | $CF_3$ | 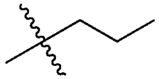 [SMILES: *CCC] |

TABLE 1-continued
Structures of compounds I
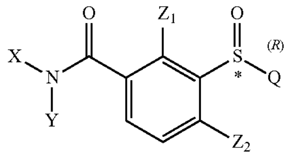
I
| Compound No. | X | Y | $Z_1$ | $Z_2$ | Q |
|---|---|---|---|---|---|
| 253 | 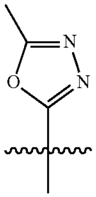 | 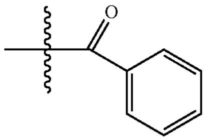 [SMILES: *C(=O)c1ccccc1] | F | $CF_3$ | 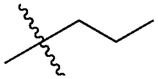 [SMILES: *CCC] |
| 254 | 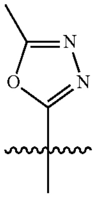 | 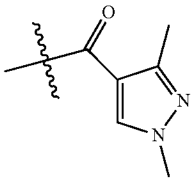 [SMILES: *C(=O)c1cn(C)nc1C] | F | $CF_3$ | 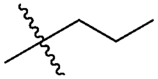 [SMILES: *CCC] |
| 255 | 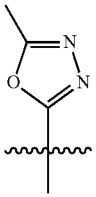 | 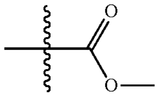 | F | $CF_3$ | 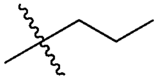 [SMILES: *CCC] |

TABLE 1-continued
Structures of compounds I
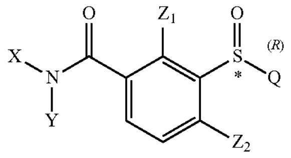
I
| Compound No. | X | Y | $Z_1$ | $Z_2$ | Q |
|---|---|---|---|---|---|
| 256 | 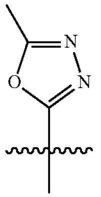 | 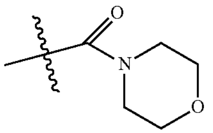 [SMILES: *C(=O)N1CCOCC1] | F | $CF_3$ | 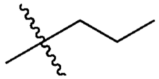 [SMILES: *CCC] |
| 257 | 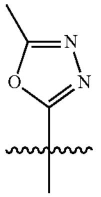 | 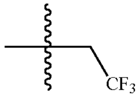 | F | $CF_3$ | 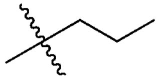 [SMILES: *CCC] |
| 258 | 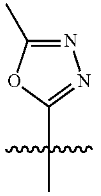 | 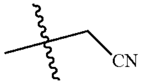 [SMILES: *CC#N] | F | $CF_3$ | 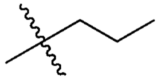 [SMILES: *CCC] |

TABLE 1-continued
Structures of compounds I
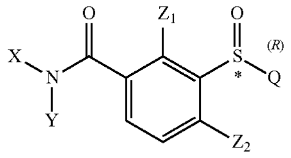
I
| Compound No. | X | Y | $Z_1$ | $Z_2$ | Q |
|---|---|---|---|---|---|
| 259 | 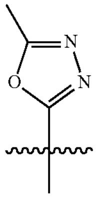 | 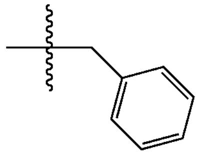 [SMILES: *Cc1ccccc1] | F | $CF_3$ | 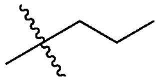 [SMILES: *CCC] |
| 260 | 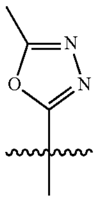 | 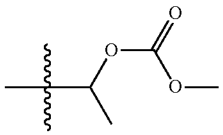 [SMILES: *C(C)OC(=O)OC] | F | $CF_3$ | 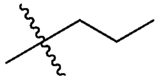 [SMILES: *CCC] |
| 261 | 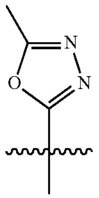 | 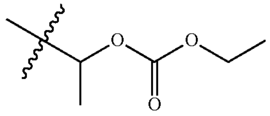 [SMILES: *C(C)OC(=O)OCC] | F | $CF_3$ | 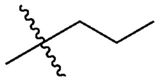 [SMILES: *CCC] |

TABLE 1-continued
Structures of compounds I
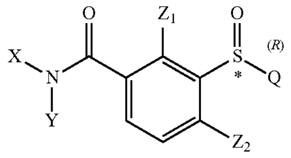
I
| Compound No. | X | Y | $Z_1$ | $Z_2$ | Q |
|---|---|---|---|---|---|
| 262 | 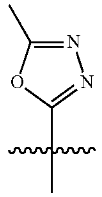 | 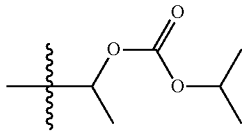 [SMILES: *C(C)OC(=O)OC(C)C] | F | $CF_3$ | 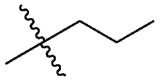 [SMILES: *CCC] |
| 263 | 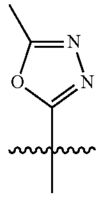 | 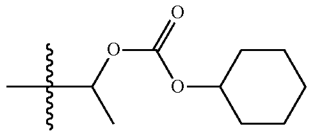 [SMILES: *C(C)OC(=O)OC1CCCCC1] | F | $CF_3$ | 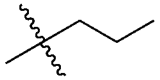 [SMILES: *CCC] |
| 264 | 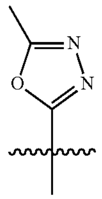 | 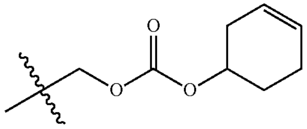 [SMILES: *COC(=O)OC1CC=CCC1] | F | $CF_3$ | 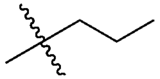 [SMILES: *CCC] |

TABLE 1-continued
Structures of compounds I
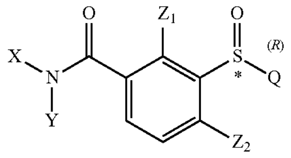
I
| Compound No. | X | Y | $Z_1$ | $Z_2$ | Q |
| --- | --- | --- | --- | --- | --- |
| 265 | 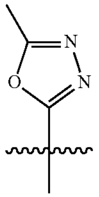 | 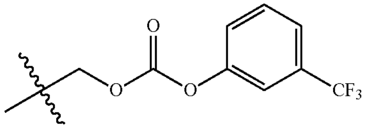 [SMILES: *COC(=O)Oc1cccc(C(F)(F)F)c1] | F | $CF_3$ | 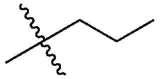 [SMILES: *CCC] |
| 266 | 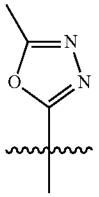 | 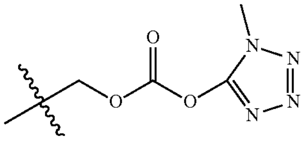 [SMILES: *COC(=O)Oc1nnnn1C] | F | $CF_3$ | 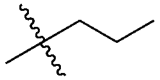 [SMILES: *CCC] |
| 267 | 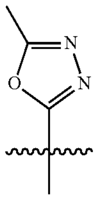 | 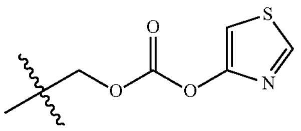 [SMILES: *COC(=O)Oc1cscn1] | F | $CF_3$ | 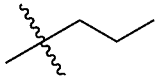 [SMILES: *CCC] |

TABLE 1-continued
Structures of compounds I
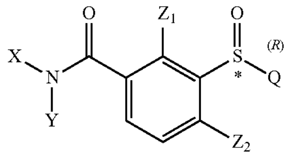
I
| Compound No. | X | Y | $Z_1$ | $Z_2$ | Q |
|---|---|---|---|---|---|
| 268 | 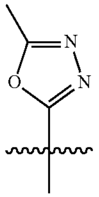 | 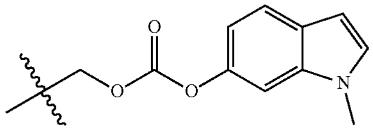 [SMILES: *COC(=O)Oc1ccc2ccn(C)c2c1] | F | $CF_3$ | 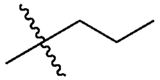 [SMILES: *CCC] |
| 269 | 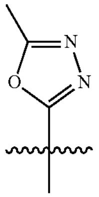 | 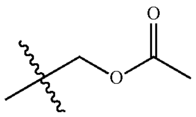 [SMILES: *COC(C)=O] | F | $CF_3$ | 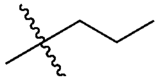 [SMILES: *CCC] |
| 270 | 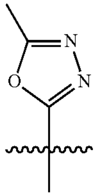 | 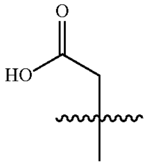 | F | $CF_3$ | 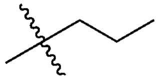 [SMILES: *CCC] |

TABLE 1-continued
Structures of compounds I
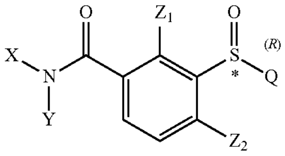
I
| Compound No. | X | Y | $Z_1$ | $Z_2$ | Q |
|---|---|---|---|---|---|
| 271 | 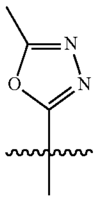 | 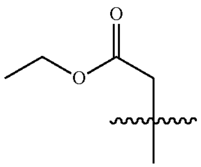 [SMILES: *CC(=O)OCC] | F | $CF_3$ | 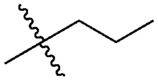 [SMILES: *CCC] |
| 272 | 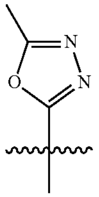 | 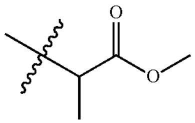 [SMILES: *C(C)C(=O)OC] | F | $CF_3$ | 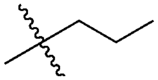 [SMILES: *CCC] |
| 273 | 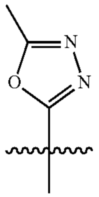 | 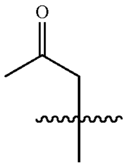 | F | $CF_3$ | 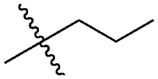 [SMILES: *CCC] |

TABLE 1-continued
Structures of compounds I
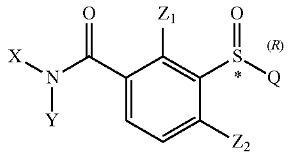
I
| Compound No. | X | Y | $Z_1$ | $Z_2$ | Q |
|---|---|---|---|---|---|
| 274 | 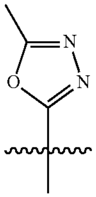 | 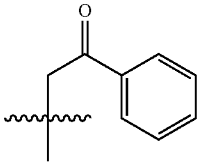 [SMILES: *CC(=O)c1ccccc1] | F | $CF_3$ | 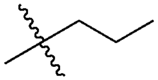 [SMILES: *CCC] |
| 275 | 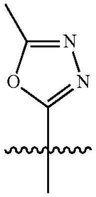 | 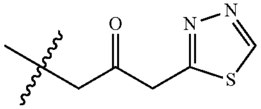 [SMILES: *CC(=O)Cc1nncs1] | F | $CF_3$ | 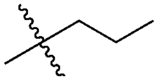 [SMILES: *CCC] |
| 276 | 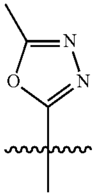 | 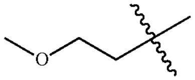 [SMILES: *CCOC] | F | $CF_3$ | 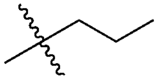 [SMILES: *CCC] |

TABLE 1-continued
Structures of compounds I
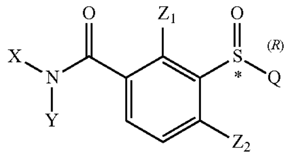
I
| Compound No. | X | Y | $Z_1$ | $Z_2$ | Q |
|---|---|---|---|---|---|
| 277 | 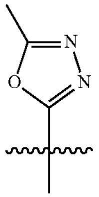 | 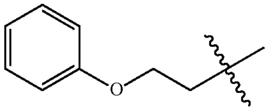 [SMILES: *CCOc1ccccc1] | F | $CF_3$ | 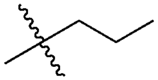 [SMILES: *CCC] |
| 278 | 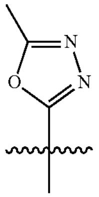 | 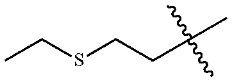 [SMILES: *CCSCC] | F | $CF_3$ | 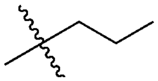 [SMILES: *CCC] |
| 279 | 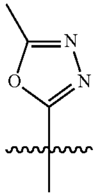 | 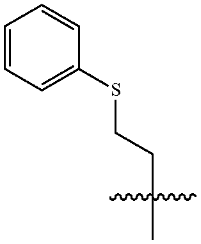 [SMILES: *CCSc1ccccc1] | F | $CF_3$ | 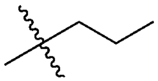 [SMILES: *CCC] |

TABLE 1-continued
Structures of compounds I
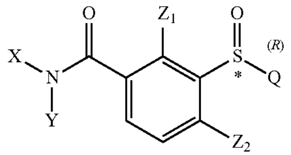
I
| Compound No. | X | Y | $Z_1$ | $Z_2$ | Q |
|---|---|---|---|---|---|
| 280 | 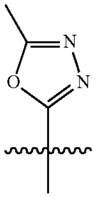 | 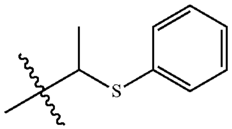 [SMILES: *C(C)Sc1ccccc1] | F | $CF_3$ | 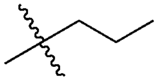 [SMILES: *CCC] |
| 281 | 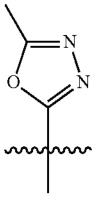 | 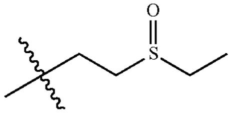 [SMILES: *CCS(=O)CC] | F | $CF_3$ | 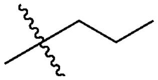 [SMILES: *CCC] |
| 282 | 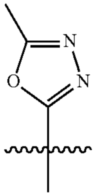 | 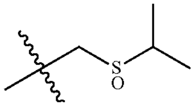 | F | $CF_3$ | 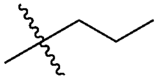 [SMILES: *CCC] |

TABLE 1-continued
Structures of compounds I
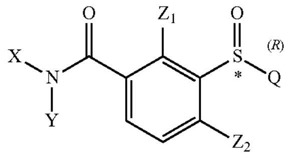
I
| Compound No. | X | Y | $Z_1$ | $Z_2$ | Q |
|---|---|---|---|---|---|
| 283 | 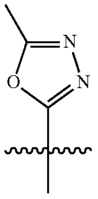 | 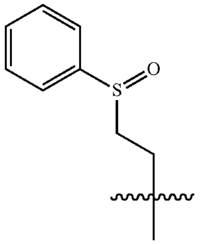 [SMILES: *CCS(=O)c1ccccc1] | F | $CF_3$ | 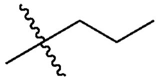 [SMILES: *CCC] |
| 284 | 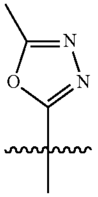 | 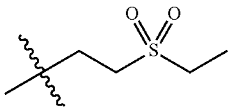 [SMILES: *CCS(=O)(=O)CC] | F | $CF_3$ | 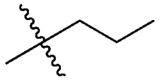 [SMILES: *CCC] |
| 285 | 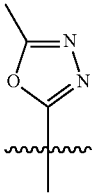 | 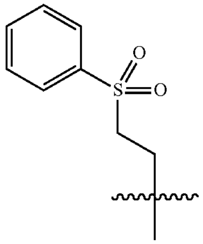 [SMILES: *CCS(=O)(=O)c1ccccc1] | F | $CF_3$ | 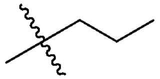 [SMILES: *CCC] |

TABLE 1-continued
Structures of compounds I
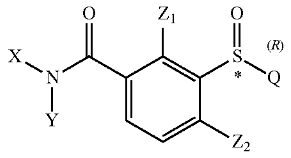
I
| Compound No. | X | Y | $Z_1$ | $Z_2$ | Q |
|---|---|---|---|---|---|
| 286 | 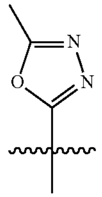 | 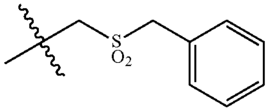 | F | $CF_3$ | 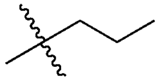 [SMILES: *CCC] |
| 287 | 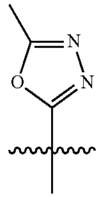 | 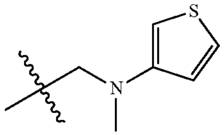 [SMILES: *CN(C)c1ccsc1] | F | $CF_3$ | 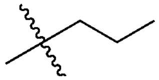 [SMILES: *CCC] |
| 288 | 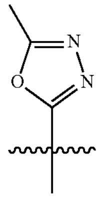 | 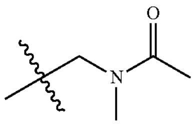 [SMILES: *CN(C)C(C)=O] | F | $CF_3$ | 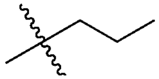 [SMILES: *CCC] |

TABLE 1-continued
Structures of compounds I
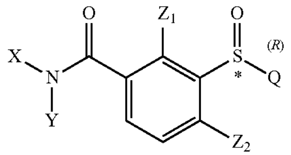
I
| Compound No. | X | Y | $Z_1$ | $Z_2$ | Q |
| --- | --- | --- | --- | --- | --- |
| 289 | 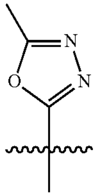 | 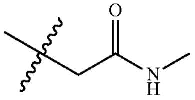 [SMILES: *CC(=O)NC] | F | $CF_3$ | 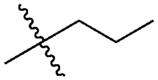 [SMILES: *CCC] |
| 290 | 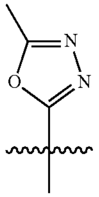 [SMILES: *c1nnc(C)o1] | 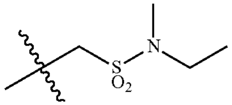 [SMILES: *CS(=O)(=O)N(C)CC] | F | $CF_3$ | 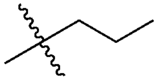 [SMILES: *CCC] |
| 291 | 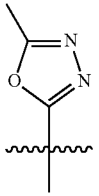 | 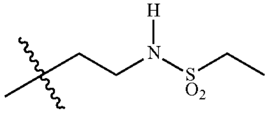 [SMILES: *CCNS(=O)(=O)CC] | F | $CF_3$ | 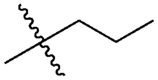 [SMILES: *CCC] |

TABLE 1-continued
Structures of compounds I
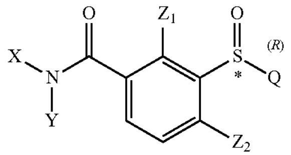
I
| Compound No. | X | Y | $Z_1$ | $Z_2$ | Q |
|---|---|---|---|---|---|
| 292 | 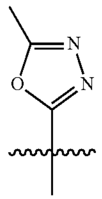 | 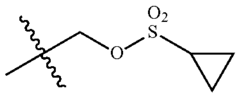 [SMILES: *COS(=O)(=O)C1CC1] | F | $CF_3$ | 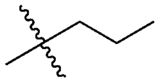 [SMILES: *CCC] |
| 293 | 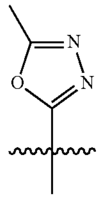 [SMILES: *c1nnc(C)o1] | 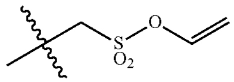 [SMILES: *CS(=O)(=O)OC=C] | F | $CF_3$ | 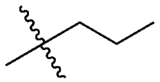 [SMILES: *CCC] |
| 294 | 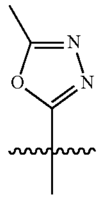 | 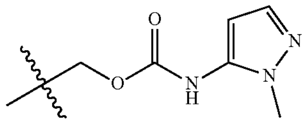 [SMILES: *COC(=O)Nc1ccnn1C] | F | $CF_3$ | 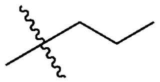 [SMILES: *CCC] |

TABLE 1-continued
Structures of compounds I
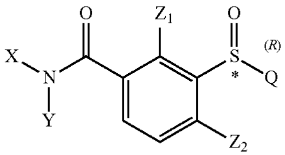
I
| Compound No. | X | Y | $Z_1$ | $Z_2$ | Q |
|---|---|---|---|---|---|
| 295 | 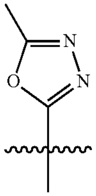 | OMe | F | $CF_3$ | 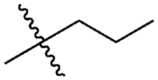 [SMILES: *CCC] |
| 296 | 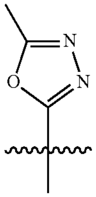 [SMILES: *c1nnc(C)o1] | 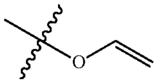 [SMILES: *OC=C] | F | $CF_3$ | 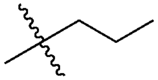 [SMILES: *CCC] |
| 297 | 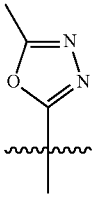 | 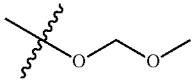 [SMILES: *OCOC] | F | $CF_3$ | 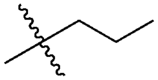 [SMILES: *CCC] |

TABLE 1-continued
Structures of compounds I
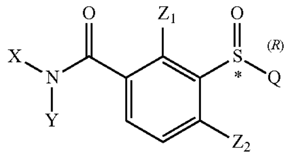
I
| Compound No. | X | Y | $Z_1$ | $Z_2$ | Q |
|---|---|---|---|---|---|
| 298 | 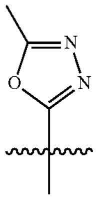 | 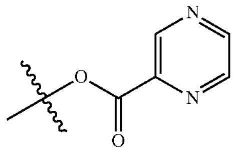 [SMILES: *OC(=O)c1cnccn1] | F | $CF_3$ | 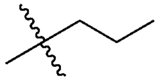 [SMILES: *CCC] |
| 299 | 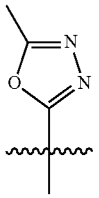 [SMILES: *c1nnc(C)o1] | 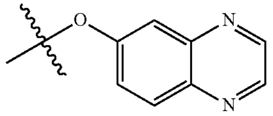 [SMILES: *Oc1ccc2nccnc2c1] | F | $CF_3$ | 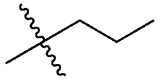 [SMILES: *CCC] |
| 300 | 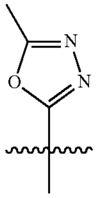 | 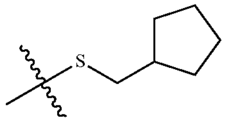 [SMILES: *SCC1CCCC1] | F | $CF_3$ | 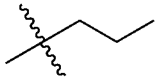 [SMILES: *CCC] |

TABLE 1-continued
Structures of compounds I
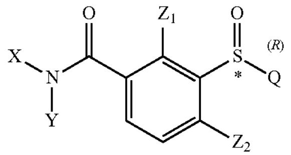
I
| Compound No. | X | Y | $Z_1$ | $Z_2$ | Q |
|---|---|---|---|---|---|
| 301 | 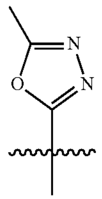 | 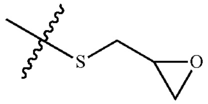 [SMILES: *SCC1CO1] | F | $CF_3$ | 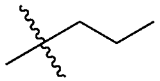 [SMILES: *CCC] |
| 302 | 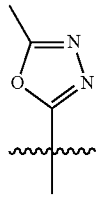 [SMILES: *c1nnc(C)o1] | 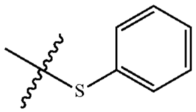 [SMILES: *Sc1ccccc1] | F | $CF_3$ | 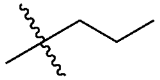 [SMILES: *CCC] |
| 303 | 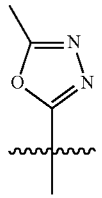 | 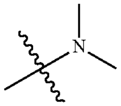 [SMILES: *N(C)C] | F | $CF_3$ | 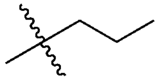 [SMILES: *CCC] |

TABLE 1-continued
Structures of compounds I
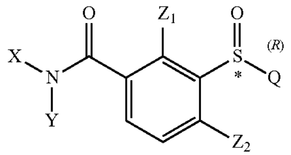
I
| Compound No. | X | Y | $Z_1$ | $Z_2$ | Q |
|---|---|---|---|---|---|
| 304 | 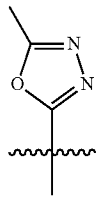 | 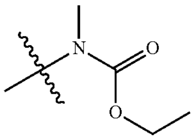 [SMILES: *N(C)C(=O)OCC] | F | $CF_3$ | 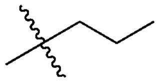 [SMILES: *CCC] |
| 305 | 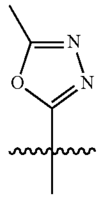 [SMILES: *c1nnc(C)o1] | 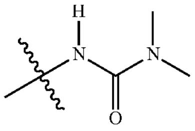 [SMILES: *NC(=O)N(C)C] | F | $CF_3$ | 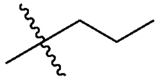 [SMILES: *CCC] |
| 306 | 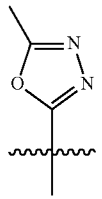 | H | OMe | $CF_3$ | Et |

TABLE 1-continued
Structures of compounds I
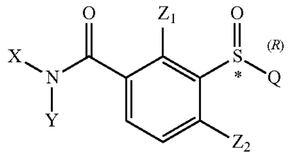
I
| Compound No. | X | Y | $Z_1$ | $Z_2$ | Q |
|---|---|---|---|---|---|
| 307 | 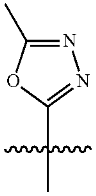 | H | OMe | $CF_3$ | 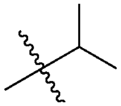 [SMILES: *C(C)C] |
| 308 | 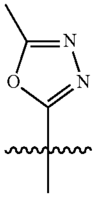 [SMILES: *c1nnc(C)o1] | H | OMe | $CF_3$ | 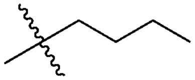 [SMILES: *CCCC] |
| 309 | 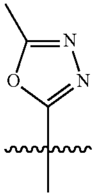 | H | OMe | $CF_3$ | 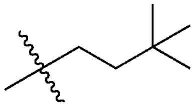 [SMILES: *CCC(C)(C)C] |

TABLE 1-continued
Structures of compounds I
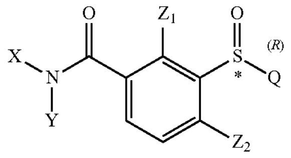
I
| Compound No. | X | Y | $Z_1$ | $Z_2$ | Q |
|---|---|---|---|---|---|
| 310 | 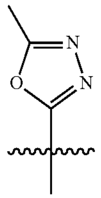 | H | OMe | $CF_3$ | 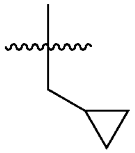 [SMILES: *CC1CC1] |
| 311 | 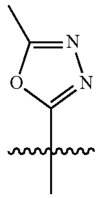 [SMILES: *c1nnc(C)o1] | H | OMe | $CF_3$ | 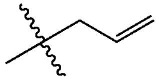 [SMILES: *CC=C] |
| 312 | 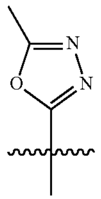 | H | OMe | $CF_3$ | 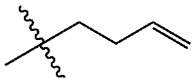 [SMILES: *CCC=C] |

TABLE 1-continued
Structures of compounds I
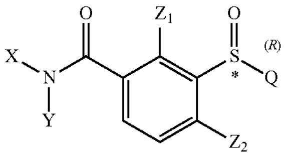
I
| Compound No. | X | Y | $Z_1$ | $Z_2$ | Q |
|---|---|---|---|---|---|
| 313 | 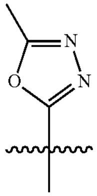 | H | OMe | $CF_3$ | 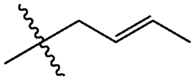 [SMILES: *C/C=C/C] |
| 314 | 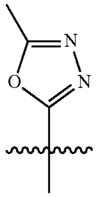 [SMILES: *c1nnc(C)o1] | H | OMe | $CF_3$ | 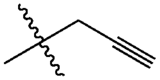 [SMILES: *CC#C] |
| 315 | 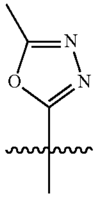 | H | OMe | $CF_3$ | 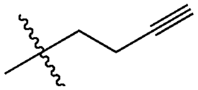 [SMILES: *CCC#C] |

TABLE 1-continued
Structures of compounds I
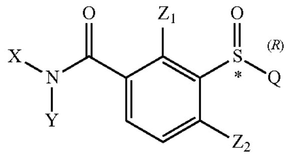
I
| Compound No. | X | Y | $Z_1$ | $Z_2$ | Q |
|---|---|---|---|---|---|
| 316 | 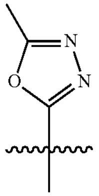 | H | OMe | $CF_3$ | 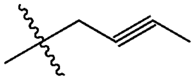 [SMILES: *CC#CC] |
| 317 | 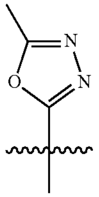 [SMILES: *c1nnc(C)o1] | H | OMe | $CF_3$ | 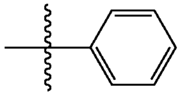 [SMILES: *c1ccccc1] |
| 318 | 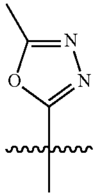 | H | OMe | $CF_3$ | 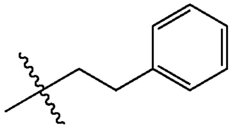 [SMILES: *CCc1ccccc1] |

TABLE 1-continued
Structures of compounds I
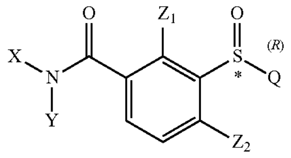
I
| Compound No. | X | Y | $Z_1$ | $Z_2$ | Q |
| --- | --- | --- | --- | --- | --- |
| 319 | 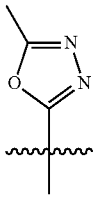 | H | OMe | $CF_3$ | 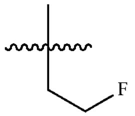 [SMILES: *CCF] |
| 320 | 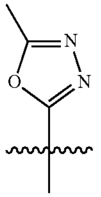 [SMILES: *c1nnc(C)o1] | H | OMe | $CF_3$ | 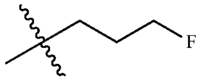 [SMILES: *CCCF] |
| 321 | 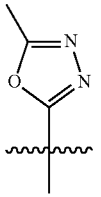 | H | OMe | $CF_3$ | 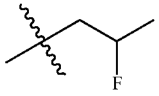 [SMILES: *CC(C)F] |

TABLE 1-continued
Structures of compounds I
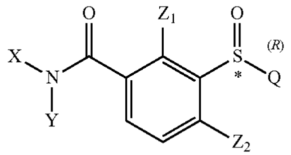
I
| Compound No. | X | Y | $Z_1$ | $Z_2$ | Q |
|---|---|---|---|---|---|
| 322 | 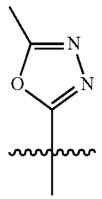 | H | OMe | $CF_3$ | 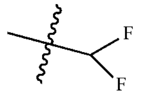 [SMILES: *C(F)F] |
| 323 | 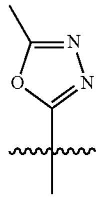 [SMILES: *c1nnc(C)o1] | H | OMe | $CF_3$ | 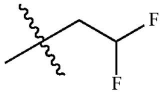 [SMILES: *CC(F)F] |
| 324 | 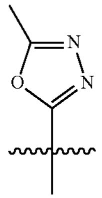 | H | OMe | $CF_3$ | 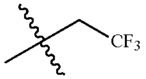 [SMILES: *CC(F)(F)F] |

TABLE 1-continued
Structures of compounds I
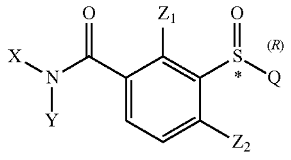
I
| Compound No. | X | Y | $Z_1$ | $Z_2$ | Q |
|---|---|---|---|---|---|
| 325 | 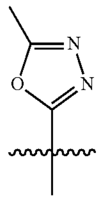 | H | OMe | $CF_3$ | 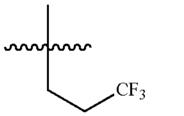 |
| 326 | 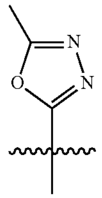 [SMILES: *c1nnc(C)o1] | H | OMe | $CF_3$ | 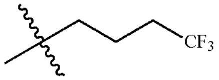 [SMILES: *CCCC(F)(F)F] |
| 327 | 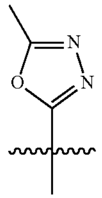 | H | OMe | $CF_3$ | 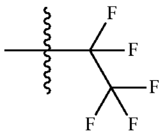 [SMILES: *C(F)(F)C(F)(F)F] |

TABLE 1-continued
Structures of compounds I
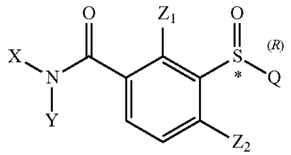
I
| Compound No. | X | Y | $Z_1$ | $Z_2$ | Q |
|---|---|---|---|---|---|
| 328 | 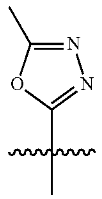 | H | OMe | $CF_3$ | 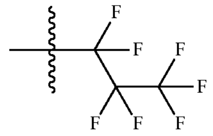 |
| 329 | 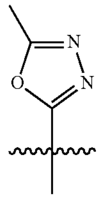 [SMILES: *c1nnc(C)o1] | H | OMe | $CF_3$ | 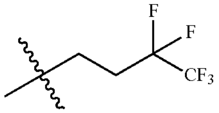 [SMILES: *CCC(F)(F)C(F)(F)F] |
| 330 | 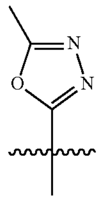 | H | OMe | $CF_3$ | 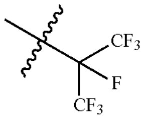 |

TABLE 1-continued
Structures of compounds I
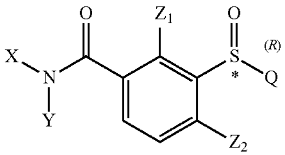
I
| Compound No. | X | Y | $Z_1$ | $Z_2$ | Q |
|---|---|---|---|---|---|
| 331 | 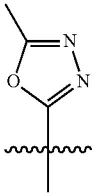 | H | OMe | $CF_3$ | 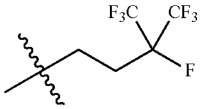 [SMILES: *CCC(F)(C(F)(F)F)C(F)(F)F] |
| 332 | 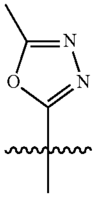 [SMILES: *c1nnc(C)o1] | H | OMe | $CF_3$ | 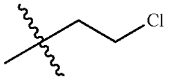 [SMILES: *CCCl] |
| 333 | 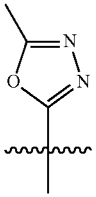 | H | OMe | $CF_3$ | 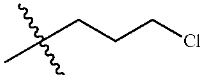 [SMILES: *CCCCl] |

TABLE 1-continued
Structures of compounds I
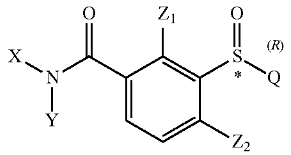
I
| Compound No. | X | Y | $Z_1$ | $Z_2$ | Q |
|---|---|---|---|---|---|
| 334 | 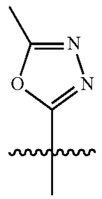 | H | OMe | $CF_3$ | 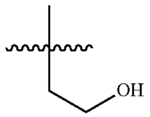 [SMILES: *CCO] |
| 335 | 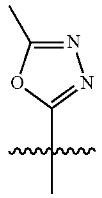 [SMILES: *c1nnc(C)o1] | H | OMe | $CF_3$ | 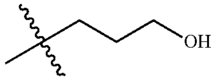 [SMILES: *CCCO] |
| 336 | 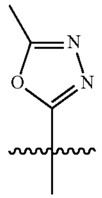 | H | OMe | $CF_3$ | 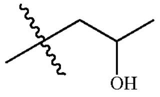 |

TABLE 1-continued
Structures of compounds I
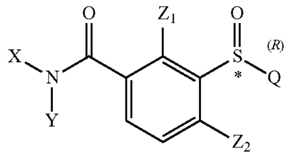
I
| Compound No. | X | Y | $Z_1$ | $Z_2$ | Q |
|---|---|---|---|---|---|
| 337 | 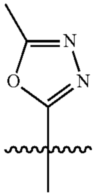 | H | OMe | $CF_3$ | 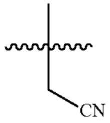 |
| 338 | 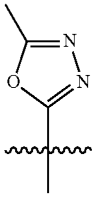 [SMILES: *c1nnc(C)o1] | H | OMe | $CF_3$ | 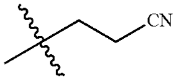 [SMILES: *CCC#N] |
| 339 | 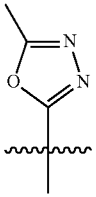 | H | OMe | $CF_3$ | 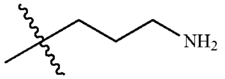 [SMILES: *CCCN] |

TABLE 1-continued
Structures of compounds I
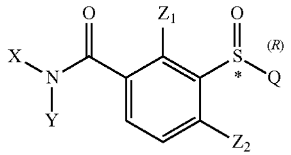
I
| Compound No. | X | Y | $Z_1$ | $Z_2$ | Q |
|---|---|---|---|---|---|
| 340 | 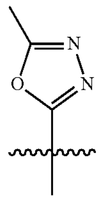 | H | OMe | $CF_3$ | 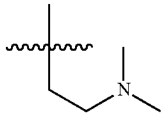 [SMILES: *CCN(C)C] |
| 341 | 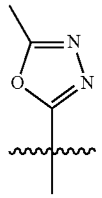 [SMILES: *c1nnc(C)o1] | H | OMe | $CF_3$ | 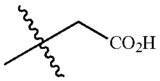 [SMILES: *CC(=O)O] |
| 342 | 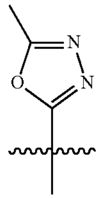 | H | OMe | $CF_3$ | 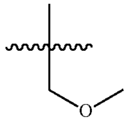 [SMILES: *COC] |

TABLE 1-continued
Structures of compounds I
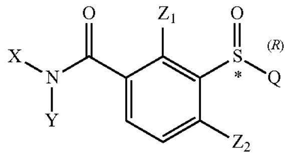
I
| Compound No. | X | Y | $Z_1$ | $Z_2$ | Q |
|---|---|---|---|---|---|
| 343 | 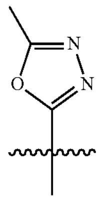 | H | OMe | $CF_3$ | 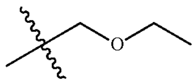 [SMILES: *COCC] |
| 344 | 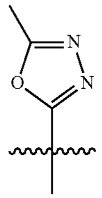 [SMILES: *c1nnc(C)o1] | H | OMe | $CF_3$ | 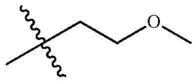 [SMILES: *CCOC] |
| 345 | 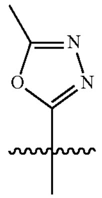 | H | OMe | $CF_3$ | 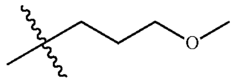 [SMILES: *CCCOC] |

TABLE 1-continued
Structures of compounds I
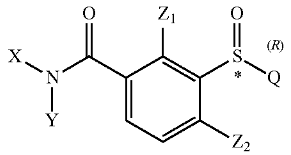
I
| Compound No. | X | Y | $Z_1$ | $Z_2$ | Q |
|---|---|---|---|---|---|
| 346 | 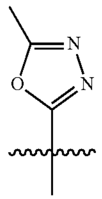 | H | OMe | $CF_3$ | 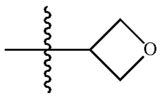 [SMILES: *C1COC1] |
| 347 | 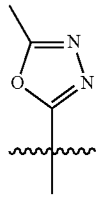 [SMILES: *c1nnc(C)o1] | H | OMe | $CF_3$ | 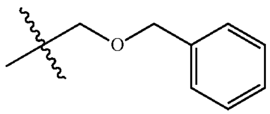 [SMILES: *COCc1ccccc1] |
| 348 | 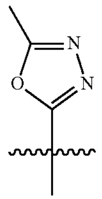 | H | OMe | $CF_3$ | 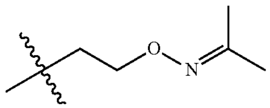 [SMILES: *CCON=C(C)C] |

TABLE 1-continued
Structures of compounds I
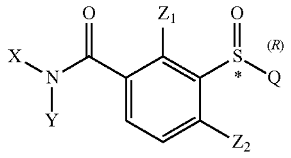
I
| Compound No. | X | Y | $Z_1$ | $Z_2$ | Q |
|---|---|---|---|---|---|
| 349 | 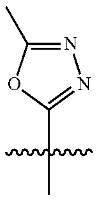 | H | OMe | $CF_3$ | 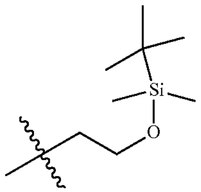 [SMILES: *CCO[Si](C)(C)C(C)(C)C] |
| 350 | 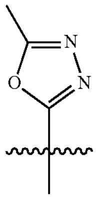 [SMILES: *c1nnc(C)o1] | H | OMe | $CF_3$ | 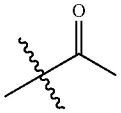 [SMILES: *C(C)=O] |
| 351 | 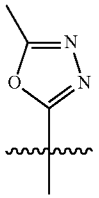 | H | OMe | $CF_3$ | 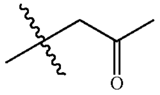 |

TABLE 1-continued
Structures of compounds I
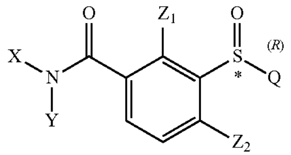
I
| Compound No. | X | Y | $Z_1$ | $Z_2$ | Q |
|---|---|---|---|---|---|
| 352 | 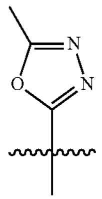 | H | OMe | $CF_3$ | 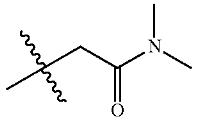 [SMILES: *CC(=O)N(C)C] |
| 353 | 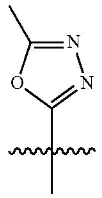 [SMILES: *c1nnc(C)o1] | H | OMe | $CF_3$ | 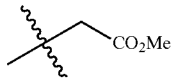 [SMILES: *CC(=O)OC] |
| 354 | 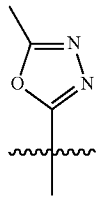 | H | OMe | $CF_3$ | 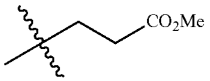 [SMILES: *CCC(=O)OC] |

TABLE 1-continued
Structures of compounds I
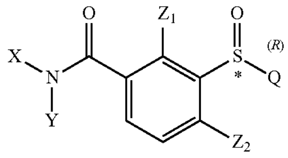
I
| Compound No. | X | Y | $Z_1$ | $Z_2$ | Q |
| --- | --- | --- | --- | --- | --- |
| 355 | 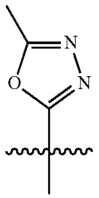 | H | OMe | $CF_3$ | 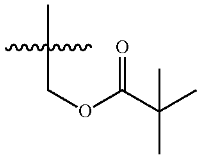 [SMILES: *COC(=O)C(C)(C)C] |
| 356 | 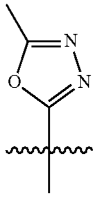 [SMILES: *c1nnc(C)o1] | H | OMe | $CF_3$ | 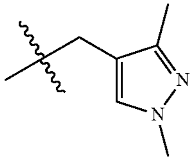 [SMILES: *Cc1cn(C)nc1C] |
| 357 | 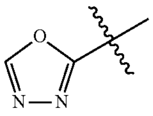 [SMILES: *c1nnco1] | H | F | $CF_3$ | 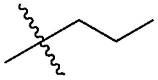 [SMILES: *CCC] |
| 358 | 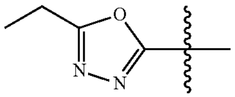 | H | F | $CF_3$ | 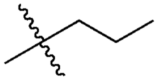 [SMILES: *CCC] |

TABLE 1-continued
Structures of compounds I
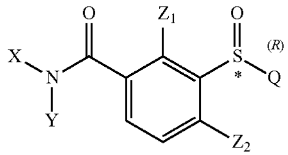
I
| Compound No. | X | Y | $Z_1$ | $Z_2$ | Q |
|---|---|---|---|---|---|
| 359 | 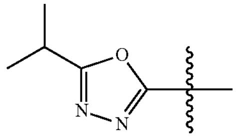 [SMILES: *c1nnc(C(C)C)o1] | H | F | $CF_3$ | 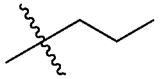 [SMILES: *CCC] |
| 360 | 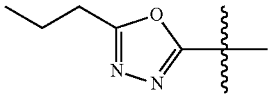 | H | F | $CF_3$ | 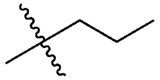 [SMILES: *CCC] |
| 361 | 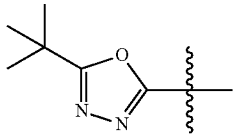 [SMILES: *c1nnc(C(C)(C)C)o1] | H | F | $CF_3$ | 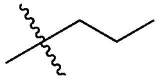 [SMILES: *CCC] |
| 362 | 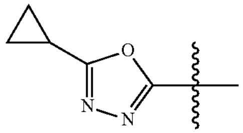 [SMILES: *c1nnc(C2CC2)o1] | H | F | $CF_3$ | 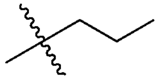 [SMILES: *CCC] |
| 363 | 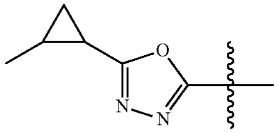 [SMILES: *c1nnc(C2CC2C)o1] | H | F | $CF_3$ | 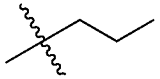 [SMILES: *CCC] |

TABLE 1-continued
Structures of compounds I
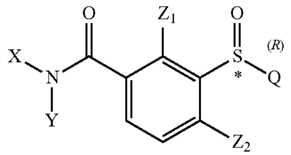
I
| Compound No. | X | Y | $Z_1$ | $Z_2$ | Q |
|---|---|---|---|---|---|
| 364 | 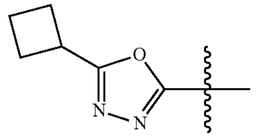 [SMILES: *c1nnc(C2CCC2)o1] | H | F | $CF_3$ | 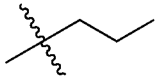 [SMILES: *CCC] |
| 365 | 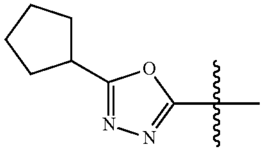 [SMILES: *c1nnc(C2CCCC2)o1] | H | F | $CF_3$ | 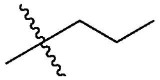 [SMILES: *CCC] |
| 366 | 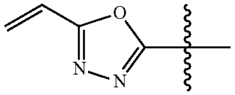 | H | F | $CF_3$ | 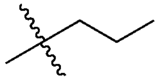 |
| 367 | 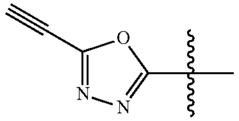 [SMILES: *c1nnc(C#C)o1] | H | F | $CF_3$ | 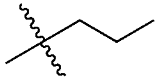 [SMILES: *CCC] |
| 368 | 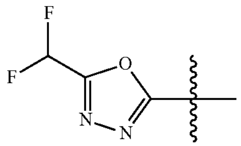 [SMILES: *c1nnc(C(F)F)o1] | H | F | $CF_3$ | 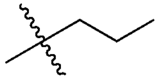 [SMILES: *CCC] |

TABLE 1-continued
Structures of compounds I
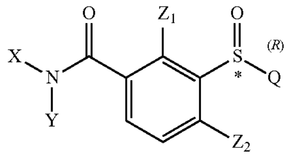
I
| Compound No. | X | Y | $Z_1$ | $Z_2$ | Q |
|---|---|---|---|---|---|
| 369 | 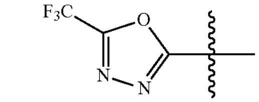 | H | F | $CF_3$ | 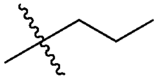 [SMILES: *CCC] |
| 370 | 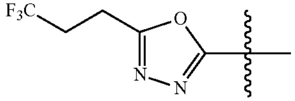 [SMILES: *c1nnc(CCC(F)(F)F)o1] | H | F | $CF_3$ | 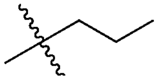 [SMILES: *CCC] |
| 371 | 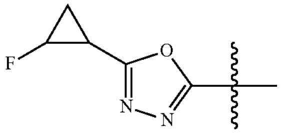 [SMILES: *c1nnc(C2CC2F)o1] | H | F | $CF_3$ | 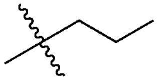 [SMILES: *CCC] |
| 372 | 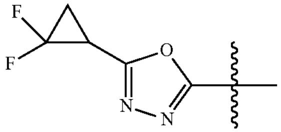 [SMILES: *c1nnc(C2CC2(F)F)o1] | H | F | $CF_3$ | 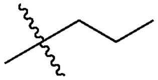 [SMILES: *CCC] |
| 373 | 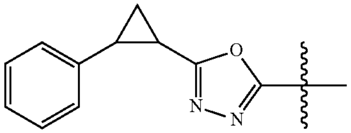 [SMILES: *c1nnc(C2CC2c2ccccc2)o1] | H | F | $CF_3$ | 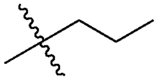 [SMILES: *CCC] |
| 374 | 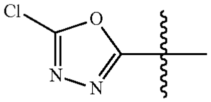 [SMILES: *c1nnc(Cl)o1] | H | F | $CF_3$ | 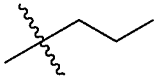 [SMILES: *CCC] |

TABLE 1-continued
Structures of compounds I
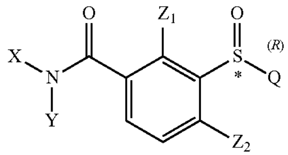
I
| Compound No. | X | Y | Z₁ | Z₂ | Q |
|---|---|---|---|---|---|
| 375 | 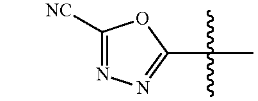 | H | F | $CF_3$ | 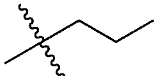 [SMILES: *CCC] |
| 376 | 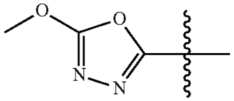 | H | F | $CF_3$ | 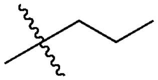 [SMILES: *CCC] |
| 377 | 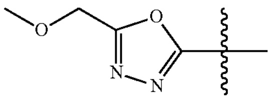 [SMILES: *c1nnc(COC)o1] | H | F | $CF_3$ | 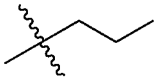 [SMILES: *CCC] |
| 378 | 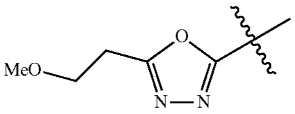 [SMILES: *c1nnc(CCOC)o1] | H | F | $CF_3$ | 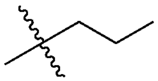 [SMILES: *CCC] |
| 379 | 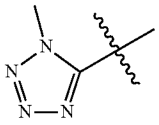 [SMILES: *c1nnnn1C] | H | F | $CF_3$ | 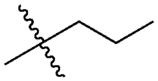 [SMILES: *CCC] |
| 380 | 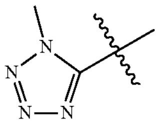 [SMILES: *c1nnnn1C] | H | F | $CF_3$ | 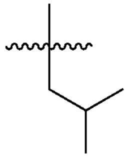 [SMILES: *CC(C)C] |

TABLE 1-continued
Structures of compounds I
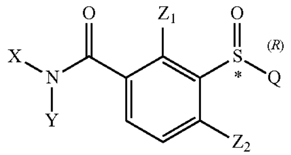
I
| Compound No. | X | Y | $Z_1$ | $Z_2$ | Q |
|---|---|---|---|---|---|
| 381 | 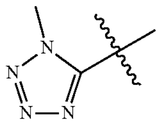 [SMILES: *c1nnnn1C] | H | F | $CF_3$ | 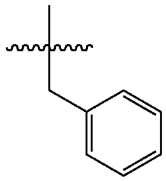 [SMILES: *Cc1ccccc1] |
| 382 | 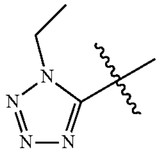 [SMILES: *c1nnnn1CC] | H | F | $CF_3$ | 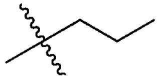 [SMILES: *CCC] |
| 383 | 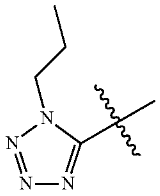 [SMILES: *c1nnnn1CCC] | H | F | $CF_3$ | 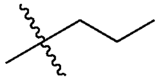 [SMILES: *CCC] |

TABLE 1-continued
Structures of compounds I
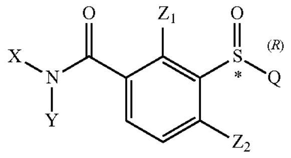
I
| Compound No. | X | Y | $Z_1$ | $Z_2$ | Q |
|---|---|---|---|---|---|
| 384 | 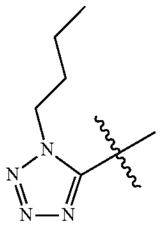 [SMILES: *c1nnnn1CCCC] | H | F | $CF_3$ | 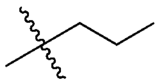 [SMILES: *CCC] |
| 385 | 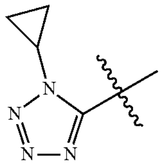 [SMILES: *c1nnnn1C1CC1] | H | F | $CF_3$ | 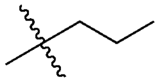 [SMILES: *CCC] |
| 386 | 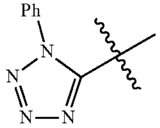 [SMILES: *c1nnnn1-c1ccccc1] | H | F | $CF_3$ | 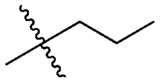 [SMILES: *CCC] |
| 387 | 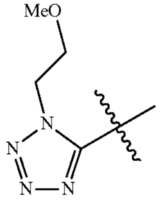 [SMILES: *c1nnnn1CCOC] | H | F | $CF_3$ | 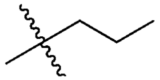 [SMILES: *CCC] |

TABLE 1-continued
Structures of compounds I
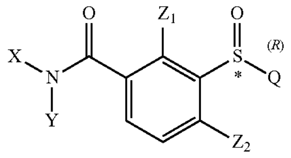
I
| Compound No. | X | Y | $Z_1$ | $Z_2$ | Q |
|---|---|---|---|---|---|
| 388 | 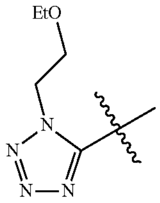 [SMILES: *c1nnnn1CCOCC] | H | F | $CF_3$ | 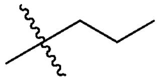 [SMILES: *CCC] |
| 389 | 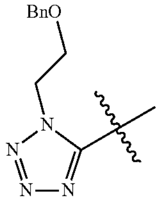 [SMILES: *c1nnnn1CCOCc1ccccc1] | H | F | $CF_3$ | 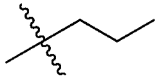 [SMILES: *CCC] |
| 390 | 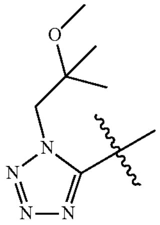 [SMILES: *c1nnnn1CC(C)(C)OC] | H | F | $CF_3$ | 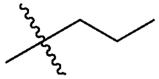 [SMILES: *CCC] |

TABLE 1-continued
Structures of compounds I
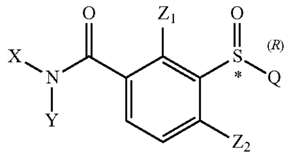
I
| Compound No. | X | Y | $Z_1$ | $Z_2$ | Q |
|---|---|---|---|---|---|
| 391 | 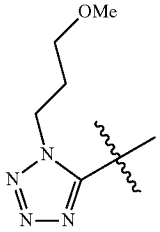 [SMILES: *c1nnnn1CCCOC] | H | F | $CF_3$ | 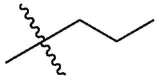 [SMILES: *CCC] |
| 392 | 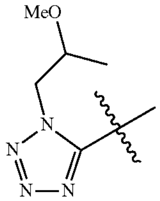 [SMILES: *c1nnnn1CC(C)OC] | H | F | $CF_3$ | 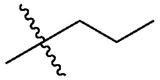 [SMILES: *CCC] |
| 393 | 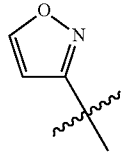 | H | F | $CF_3$ | 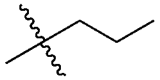 [SMILES: *CCC] |
| 394 | 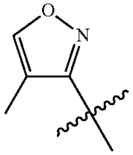 [SMILES: *c1nocc1C] | H | F | $CF_3$ | 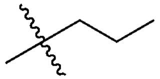 [SMILES: *CCC] |

TABLE 1-continued
Structures of compounds I
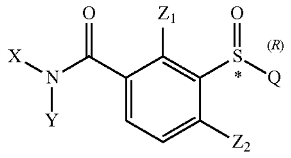
I
| Compound No. | X | Y | $Z_1$ | $Z_2$ | Q |
|---|---|---|---|---|---|
| 395 | 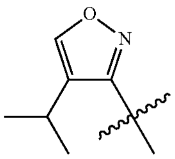 [SMILES: *c1nocc1C(C)C] | H | F | $CF_3$ | 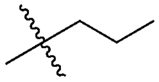 [SMILES: *CCC] |
| 396 | 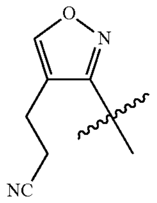 [SMILES: *c1nocc1CCC#N] | H | F | $CF_3$ | 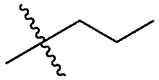 |
| 397 | 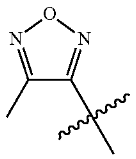 [SMILES: *c1nonc1C] | H | F | $CF_3$ | 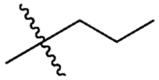 [SMILES: *CCC] |
| 398 | 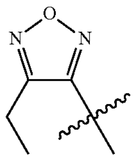 | H | F | $CF_3$ | 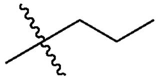 [SMILES: *CCC] |

TABLE 1-continued
Structures of compounds I
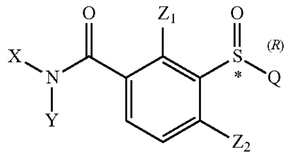
I
| Compound No. | X | Y | $Z_1$ | $Z_2$ | Q |
|---|---|---|---|---|---|
| 399 | 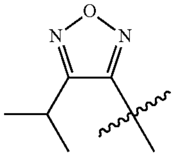 [SMILES: *c1nonc1C(C)C] | H | F | $CF_3$ | 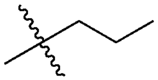 [SMILES: *CCC] |
| 400 | 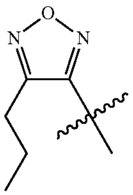 [SMILES: *c1nonc1CCC] | H | F | $CF_3$ | 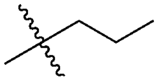 [SMILES: *CCC] |
| 401 | 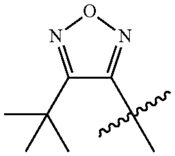 [SMILES: *c1nonc1C(C)(C)C] | H | F | $CF_3$ | 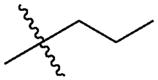 [SMILES: *CCC] |
| 402 | 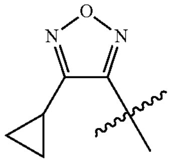 [SMILES: *c1nonc1C1CC1] | H | F | $CF_3$ | 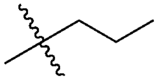 [SMILES: *CCC] |

TABLE 1-continued
Structures of compounds I
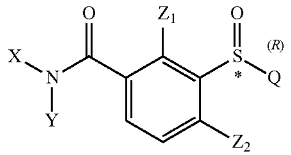
I
| Compound No. | X | Y | $Z_1$ | $Z_2$ | Q |
|---|---|---|---|---|---|
| 403 | 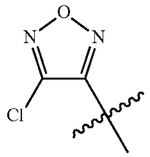 | H | F | $CF_3$ | 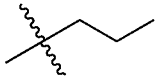 [SMILES: *CCC] |
| 404 | 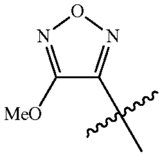 | H | F | $CF_3$ | 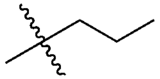 [SMILES: *CCC] |
| 405 | 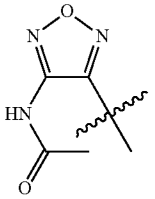 | H | F | $CF_3$ | 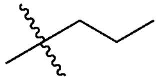 [SMILES: *CCC] |
| 406 | 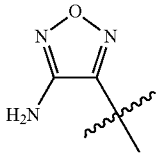 [SMILES: *c1nonc1N] | H | F | $CF_3$ | 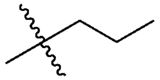 [SMILES: *CCC] |

TABLE 1-continued
Structures of compounds I
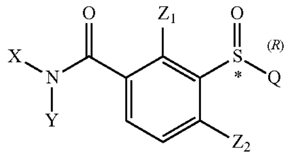
I
| Compound No. | X | Y | $Z_1$ | $Z_2$ | Q |
|---|---|---|---|---|---|
| 407 | 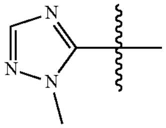 [SMILES: *c1ncnn1C] | H | F | $CF_3$ | 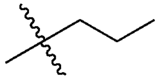 [SMILES: *CCC] |
| 408 | 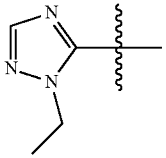 [SMILES: *c1ncnn1CC] | H | F | $CF_3$ | 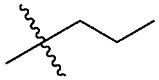 [SMILES: *CCC] |
| 409 | 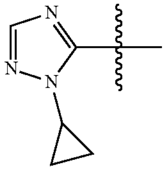 [SMILES: *c1ncnn1C1CC1] | H | F | $CF_3$ | 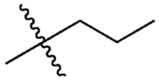 [SMILES: *CCC] |
| 410 | 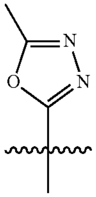 [SMILES: *c1nnc(C)o1] | Me | OMe | $CF_3$ | Et |

TABLE 1-continued
Structures of compounds I
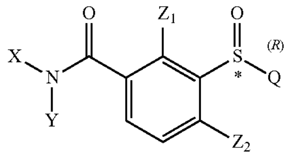
I
| Compound No. | X | Y | $Z_1$ | $Z_2$ | Q |
|---|---|---|---|---|---|
| 411 | 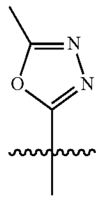 | 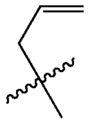 | OMe | $CF_3$ | Et |
| 412 | 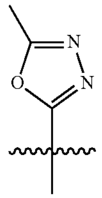 [SMILES: *c1nnc(C)o1] | 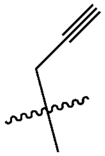 [SMILES: *CC#C] | OMe | $CF_3$ | Et |
| 413 | 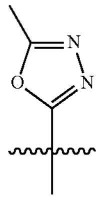 | 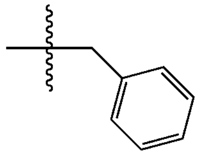 [SMILES: *Cc1ccccc1] | OMe | $CF_3$ | Et |

TABLE 1-continued
Structures of compounds I
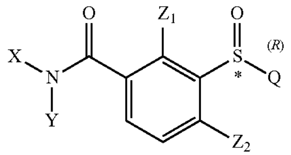
I
| Compound No. | X | Y | $Z_1$ | $Z_2$ | Q |
|---|---|---|---|---|---|
| 414 | 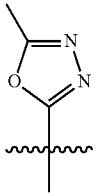 | 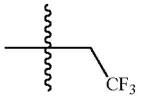 | OMe | $CF_3$ | Et |
| 415 | 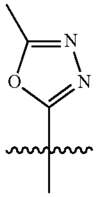 [SMILES: *c1nnc(C)o1] | 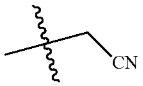 [SMILES: *CC#N] | OMe | $CF_3$ | Et |
| 416 | 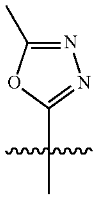 | 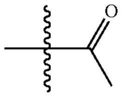 | OMe | $CF_3$ | Et |

TABLE 1-continued
Structures of compounds I
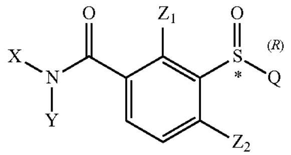
I
| Compound No. | X | Y | $Z_1$ | $Z_2$ | Q |
|---|---|---|---|---|---|
| 417 | 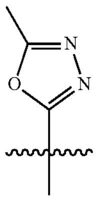 | 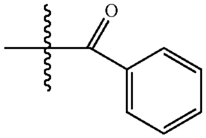 [SMILES: *C(=O)c1ccccc1] | OMe | $CF_3$ | Et |
| 418 | 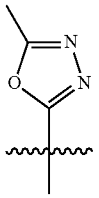 [SMILES: *c1nnc(C)o1] | 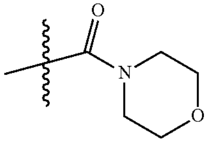 [SMILES: *C(=O)N1CCOCC1] | OMe | $CF_3$ | Et |
| 419 | 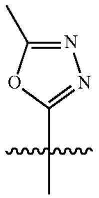 | 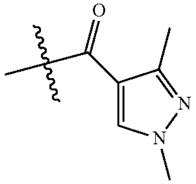 [SMILES: *C(=O)c1cn(C)nc1C] | OMe | $CF_3$ | Et |

TABLE 1-continued
Structures of compounds I
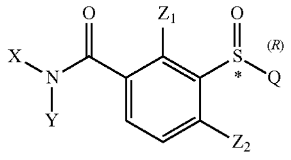
I
| Compound No. | X | Y | $Z_1$ | $Z_2$ | Q |
|---|---|---|---|---|---|
| 420 | 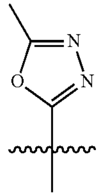 | 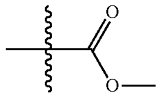 [SMILES: *C(=O)OC] | OMe | $CF_3$ | Et |
| 421 | 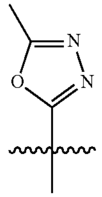 [SMILES: *c1nnc(C)o1] | 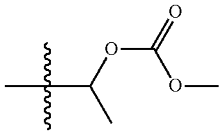 [SMILES: *C(C)OC(=O)OC] | OMe | $CF_3$ | Et |
| 422 | 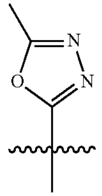 | 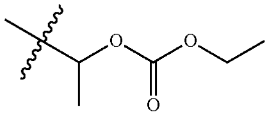 [SMILES: *C(C)OC(=O)OCC] | OMe | $CF_3$ | Et |
| 423 | 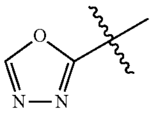 [SMILES: *c1nnco1] | H | OMe | $CF_3$ | Et |

TABLE 1-continued
Structures of compounds I
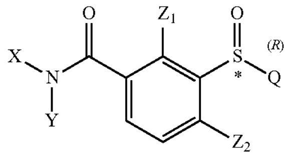
I
| Compound No. | X | Y | $Z_1$ | $Z_2$ | Q |
|---|---|---|---|---|---|
| 424 | 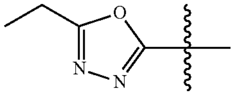 [SMILES: *c1nnc(CC)o1] | H | OMe | $CF_3$ | Et |
| 425 | 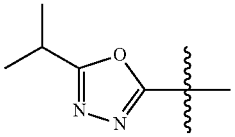 | H | OMe | $CF_3$ | Et |
| 426 | 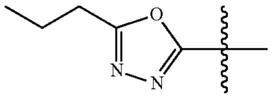 [SMILES: *c1nnc(CCC)o1] | H | OMe | $CF_3$ | Et |
| 427 | 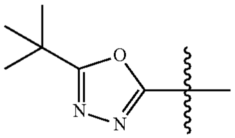 [SMILES: *c1nnc(C(C)(C)C)o1] | H | OMe | $CF_3$ | Et |
| 428 | 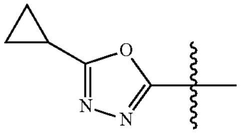 [SMILES: *c1nnc(C2CC2)o1] | H | OMe | $CF_3$ | Et |

TABLE 1-continued
Structures of compounds I
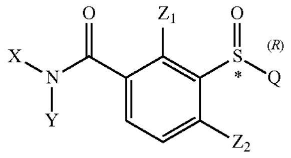
I
| Compound No. | X | Y | $Z_1$ | $Z_2$ | Q |
|---|---|---|---|---|---|
| 429 | 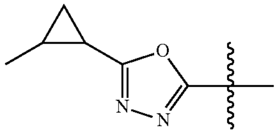 [SMILES: *c1nnc(C2CC2C)o1] | H | OMe | $CF_3$ | Et |
| 430 | 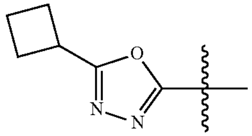 [SMILES: *c1nnc(C2CCC2)o1] | H | OMe | $CF_3$ | Et |
| 431 | 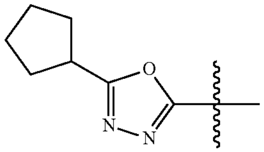 [SMILES: *c1nnc(C2CCCC2)o1] | H | OMe | $CF_3$ | Et |
| 432 | 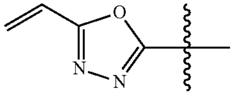 [SMILES: *c1nnc(C=C)o1] | H | OMe | $CF_3$ | Et |
| 433 | 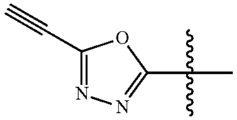 [SMILES: *c1nnc(C#C)o1] | H | OMe | $CF_3$ | Et |

TABLE 1-continued
Structures of compounds I
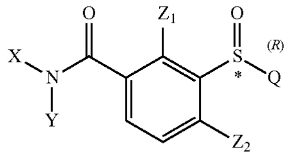
I
| Compound No. | X | Y | $Z_1$ | $Z_2$ | Q |
|---|---|---|---|---|---|
| 434 | 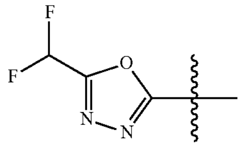 [SMILES: *c1nnc(C(F)F)o1] | H | OMe | $CF_3$ | Et |
| 435 | 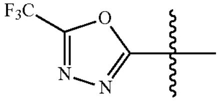 [SMILES: *c1nnc(C(F)(F)F)o1] | H | OMe | $CF_3$ | Et |
| 436 | 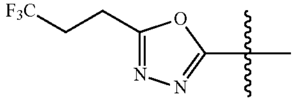 [SMILES: *c1nnc(CCC(F)(F)F)o1] | H | OMe | $CF_3$ | Et |
| 437 | 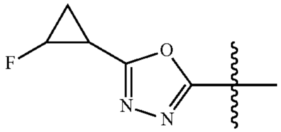 [SMILES: *c1nnc(C2CC2F)o1] | H | OMe | $CF_3$ | Et |
| 438 | 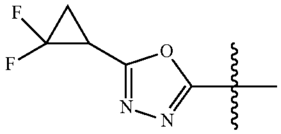 [SMILES: *c1nnc(C2CC2(F)F)o1] | H | OMe | $CF_3$ | Et |

TABLE 1-continued
Structures of compounds I
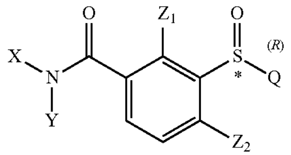
I
| Compound No. | X | Y | $Z_1$ | $Z_2$ | Q |
|---|---|---|---|---|---|
| 439 | 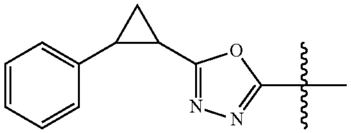 [SMILES: *c1nnc(C2CC2c2ccccc2)o1] | H | OMe | $CF_3$ | Et |
| 440 | 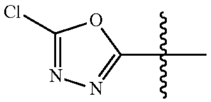 [SMILES: *c1nnc(Cl)o1] | H | OMe | $CF_3$ | Et |
| 441 | 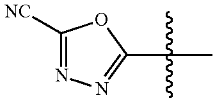 [SMILES: *c1nnc(C#N)o1] | H | OMe | $CF_3$ | Et |
| 442 | 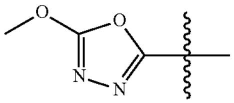 | H | OMe | $CF_3$ | Et |
| 443 | 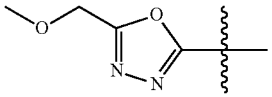 [SMILES: *c1nnc(COC)o1] | H | OMe | $CF_3$ | Et |
| 444 | 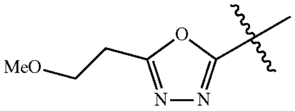 [SMILES: *c1nnc(CCOC)o1] | H | OMe | $CF_3$ | Et |

TABLE 1-continued
Structures of compounds I
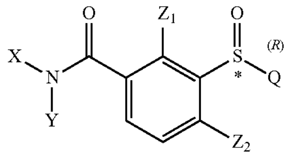
I
| Compound No. | X | Y | $Z_1$ | $Z_2$ | Q |
| --- | --- | --- | --- | --- | --- |
| 445 | 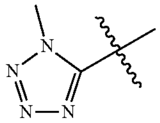 [SMILES: *c1nnnn1C] | H | OMe | $CF_3$ | Et |
| 446 | 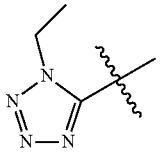 [SMILES: *c1nnnn1CC] | H | OMe | $CF_3$ | Et |
| 447 | 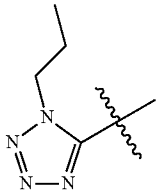 [SMILES: *c1nnnn1CCC] | H | OMe | $CF_3$ | Et |
| 448 | 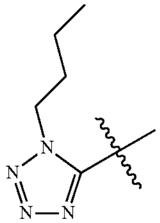 [SMILES: *c1nnnn1CCCC] | H | OMe | $CF_3$ | Et |

TABLE 1-continued
Structures of compounds I
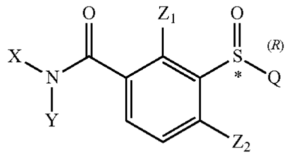
I
| Compound No. | X | Y | $Z_1$ | $Z_2$ | Q |
|---|---|---|---|---|---|
| 449 | 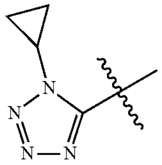 [SMILES: *c1nnnn1C1CC1] | H | OMe | $CF_3$ | Et |
| 450 | 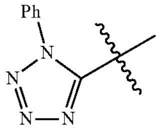 [SMILES: *c1nnnn1-c1ccccc1] | H | OMe | $CF_3$ | Et |
| 451 | 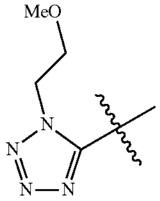 [SMILES: *c1nnnn1CCOC] | H | OMe | $CF_3$ | Et |
| 452 | 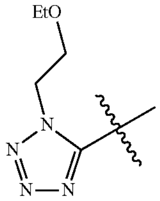 [SMILES: *c1nnnn1CCOCC] | H | OMe | $CF_3$ | Et |

TABLE 1-continued
Structures of compounds I
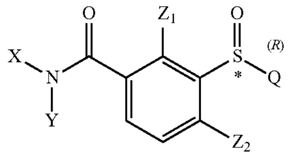
I
| Compound No. | X | Y | $Z_1$ | $Z_2$ | Q |
|---|---|---|---|---|---|
| 453 | 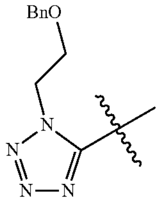 [SMILES: *c1nnnn1CCOCc1ccccc1] | H | OMe | $CF_3$ | Et |
| 454 | 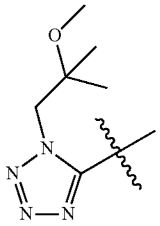 [SMILES: *c1nnnn1CC(C)(C)OC] | H | OMe | $CF_3$ | Et |
| 455 | 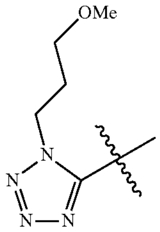 [SMILES: *c1nnnn1CCCOC] | H | OMe | $CF_3$ | Et |

TABLE 1-continued
Structures of compounds I
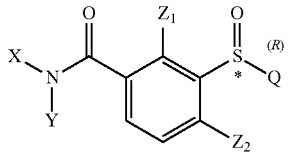
I
| Compound No. | X | Y | $Z_1$ | $Z_2$ | Q |
|---|---|---|---|---|---|
| 456 | 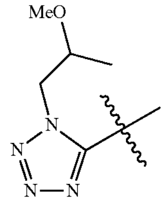 [SMILES: *c1nnnn1CC(C)OC] | H | OMe | $CF_3$ | Et |
| 457 | 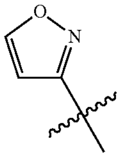 [SMILES: *c1ccon1] | H | OMe | $CF_3$ | Et |
| 458 | 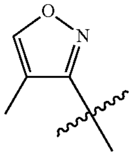 [SMILES: *c1nocc1C] | H | OMe | $CF_3$ | Et |
| 459 | 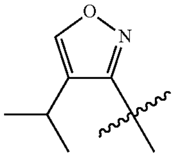 [SMILES: *c1nocc1C(C)C] | H | OMe | $CF_3$ | Et |

TABLE 1-continued
Structures of compounds I
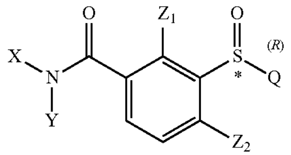
I
| Compound No. | X | Y | $Z_1$ | $Z_2$ | Q |
|---|---|---|---|---|---|
| 460 | 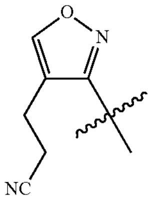 | H | OMe | $CF_3$ | Et |
| 461 | 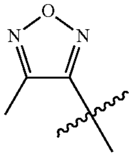 [SMILES: *c1nonc1C] | H | OMe | $CF_3$ | Et |
| 462 | 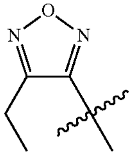 [SMILES: *c1nonc1CC] | H | OMe | $CF_3$ | Et |
| 463 | 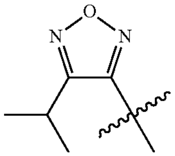 [SMILES: *c1nonc1C(C)C] | H | OMe | $CF_3$ | Et |

TABLE 1-continued
Structures of compounds I
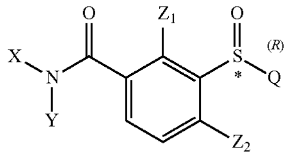
I
| Compound No. | X | Y | $Z_1$ | $Z_2$ | Q |
|---|---|---|---|---|---|
| 464 | 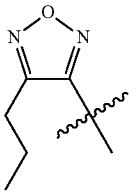 | H | OMe | $CF_3$ | Et |
| 465 | 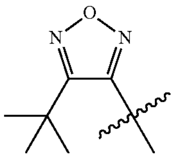 [SMILES: *c1nonc1C(C)(C)C] | H | OMe | $CF_3$ | Et |
| 466 | 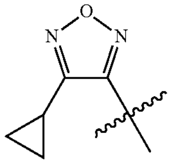 [SMILES: *c1nonc1C1CC1] | H | OMe | $CF_3$ | Et |
| 467 | 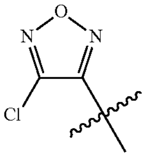 | H | OMe | $CF_3$ | Et |

TABLE 1-continued
Structures of compounds I
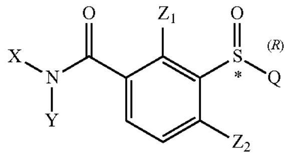
I
| Compound No. | X | Y | $Z_1$ | $Z_2$ | Q |
| --- | --- | --- | --- | --- | --- |
| 468 | 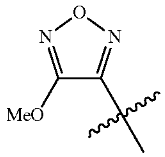 | H | OMe | $CF_3$ | Et |
| 469 | 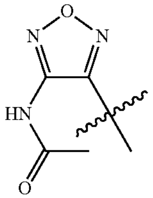 [SMILES: *c1nonc1NC(C)=O] | H | OMe | $CF_3$ | Et |
| 470 | 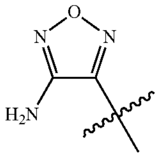 [SMILES: *c1nonc1N] | H | OMe | $CF_3$ | Et |
| 471 | 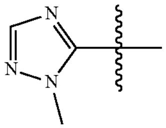 [SMILES: *c1ncnn1C] | H | OMe | $CF_3$ | Et |

TABLE 1-continued
Structures of compounds I
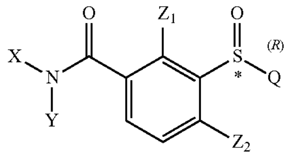
I
| Compound No. | X | Y | $Z_1$ | $Z_2$ | Q |
|---|---|---|---|---|---|
| 472 | 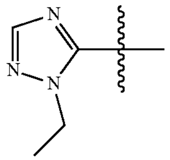 [SMILES: *c1ncnn1CC] | H | OMe | $CF_3$ | Et |
| 473 | 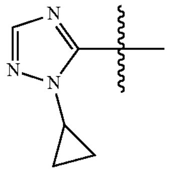 [SMILES: *c1ncnn1C1CC1] | H | OMe | $CF_3$ | Et |
| 474 | 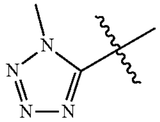 [SMILES: *c1nnnn1C] | H | Me | Me | Et |
| 475 | 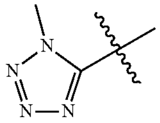 [SMILES: *c1nnnn1C] | H | Me | Me | 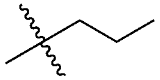 [SMILES: *CCC] |
| 476 | 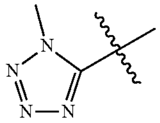 [SMILES: *c1nnnn1C] | H | Me | Me | 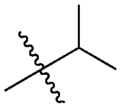 [SMILES: *C(C)C] |

TABLE 1-continued
Structures of compounds I
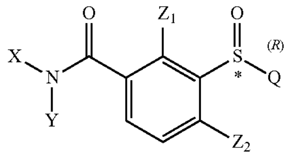
I
| Compound No. | X | Y | $Z_1$ | $Z_2$ | Q |
|---|---|---|---|---|---|
| 477 | 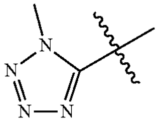 [SMILES: *c1nnnn1C] | H | Me | Me | 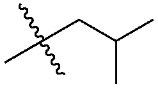 [SMILES: *CC(C)C] |
| 478 | 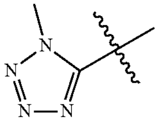 [SMILES: *c1nnnn1C] | H | Me | Me | 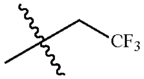 |
| 479 | 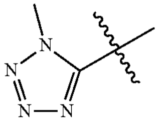 [SMILES: *c1nnnn1C] | H | Me | 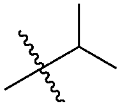 [SMILES: *C(C)C] | Me |
| 480 | 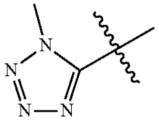 [SMILES: *c1nnnn1C] | H | Me | 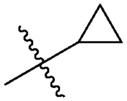 [SMILES: *C1CC1] | Me |
| 481 | 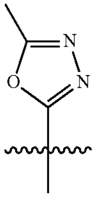 | H | Me | Me | Et |

TABLE 1-continued
Structures of compounds I
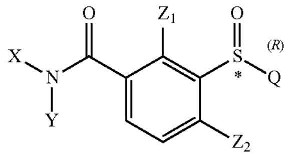
I
| Compound No. | X | Y | $Z_1$ | $Z_2$ | Q |
|---|---|---|---|---|---|
| 482 | 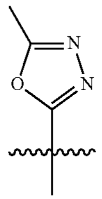 | H | Me | Me | 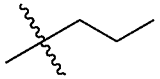 [SMILES: *CCC] |
| 483 | 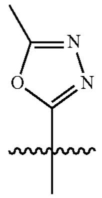 | H | Me | Me | 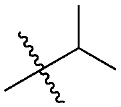 [SMILES: *C(C)C] |
| 484 | 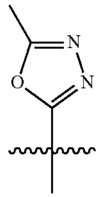 | H | Me | Me | 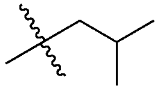 |

TABLE 1-continued
Structures of compounds I
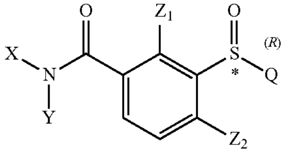
I
| Compound No. | X | Y | $Z_1$ | $Z_2$ | Q |
|---|---|---|---|---|---|
| 485 | 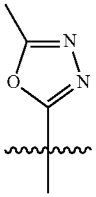 | H | Me | Me | 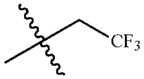 [SMILES: *CC(F)(F)F] |
| 486 | 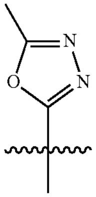 | H | Me | 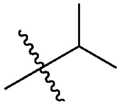 [SMILES: *C(C)C] | Me |
| 487 | 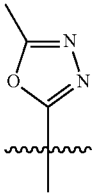 | H | Me | 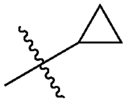 [SMILES: *C1CC1] | Me |

TABLE 1-continued
Structures of compounds I
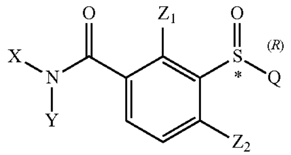
I
| Compound No. | X | Y | $Z_1$ | $Z_2$ | Q |
|---|---|---|---|---|---|
| 488 | 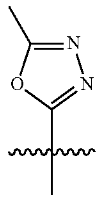 | H | F | CN | Me |
| 489 | 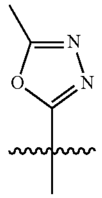 | H | Cl | CN | Me |
| 490 | 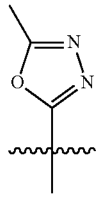 | H | Me | CN | Me |

TABLE 1-continued
Structures of compounds I
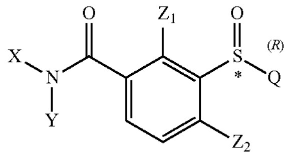
I
| Compound No. | X | Y | $Z_1$ | $Z_2$ | Q |
| --- | --- | --- | --- | --- | --- |
| 491 | 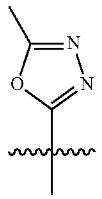 | H | Me | $SO_2Me$ | Me |
| 492 | 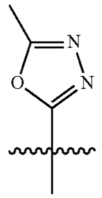 | H | Me | $SO_2Me$ | 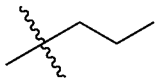 [SMILES: *CCC] |
| 493 | 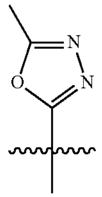 | H | Me | $SO_2Me$ | 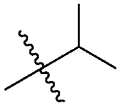 [SMILES: *C(C)C] |

TABLE 1-continued
Structures of compounds I
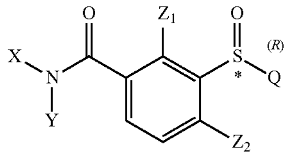
I
| Compound No. | X | Y | $Z_1$ | $Z_2$ | Q |
|---|---|---|---|---|---|
| 494 | 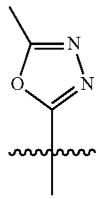 | H | Me | $SO_2Me$ | 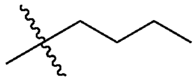 [SMILES: *CCCC] |
| 495 | 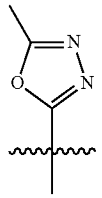 [SMILES: *c1nnc(C)o1] | H | Me | $SO_2Me$ | 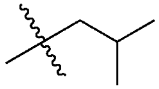 [SMILES: *CC(C)C] |
| 496 | 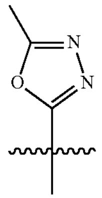 | H | Me | $SO_2Me$ | 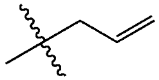 [SMILES: *CC=C] |

TABLE 1-continued
Structures of compounds I
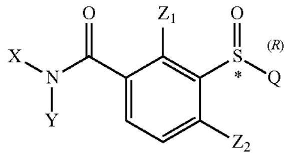
I
| Compound No. | X | Y | $Z_1$ | $Z_2$ | Q |
|---|---|---|---|---|---|
| 497 | 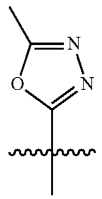 | H | Me | $SO_2Me$ | 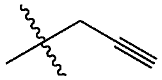 [SMILES: *CC#C] |
| 498 | 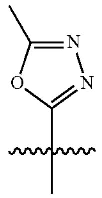 [SMILES: *c1nnc(C)o1] | H | Me | $SO_2Me$ | 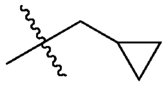 [SMILES: *CC1CC1] |
| 499 | 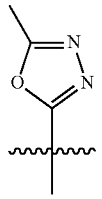 | H | Me | $SO_2Me$ | 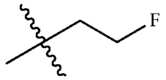 |

TABLE 1-continued
Structures of compounds I
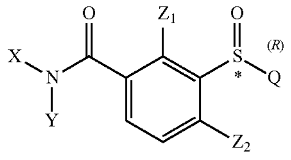
I
| Compound No. | X | Y | $Z_1$ | $Z_2$ | Q |
|---|---|---|---|---|---|
| 500 | 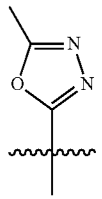 | H | M e | $SO_2Me$ | 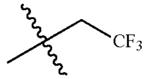 [SMILES: *CC(F)(F)F] |
| 501 | 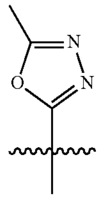 [SMILES: *c1nnc(C)o1] | H | Me | $SO_2Me$ | 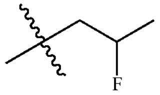 |
| 502 | 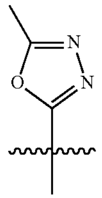 | H | Me | $SO_2Me$ | 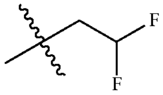 |

TABLE 1-continued
Structures of compounds I
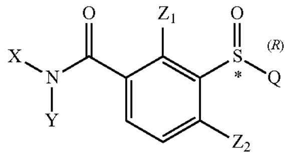
I
| Compound No. | X | Y | $Z_1$ | $Z_2$ | Q |
|---|---|---|---|---|---|
| 503 | 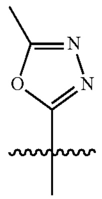 | H | Me | $SO_2Me$ | 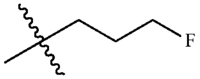 [SMILES: *CCCF] |
| 504 | 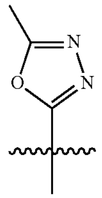 [SMILES: *c1nnc(C)o1] | H | Me | $SO_2Me$ | 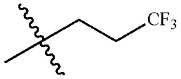 [SMILES: *CCC(F)(F)F] |
| 505 | 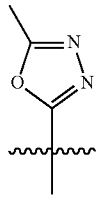 | H | Me | $SO_2Me$ | 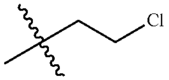 [SMILES: *CCCl] |

TABLE 1-continued
Structures of compounds I
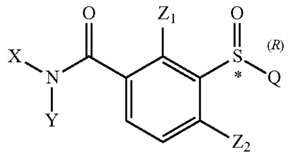
I
| Compound No. | X | Y | $Z_1$ | $Z_2$ | Q |
|---|---|---|---|---|---|
| 506 | 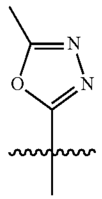 | H | Me | $SO_2Me$ | 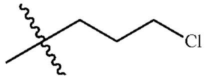 [SMILES: *CCCCl] |
| 507 | 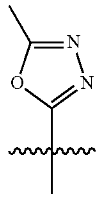 [SMILES: *c1nnc(C)o1] | H | Me | $SO_2Me$ | 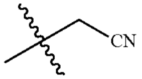 [SMILES: *CC#N] |
| 508 | 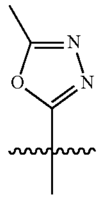 | H | Me | $SO_2Me$ | 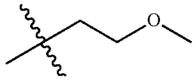 |

TABLE 1-continued
Structures of compounds I
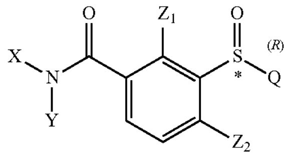
I
| Compound No. | X | Y | $Z_1$ | $Z_2$ | Q |
|---|---|---|---|---|---|
| 509 | 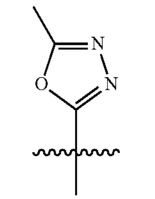 | H | Me | $SO_2Me$ | 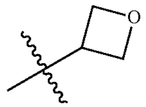 [SMILES: *C1COC1] |
| 510 | 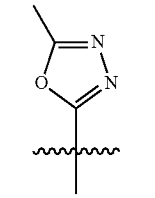 [SMILES: *c1nnc(C)o1] | H | Me | $SO_2Me$ | 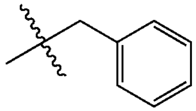 [SMILES: *Cc1ccccc1] |
| 511 | 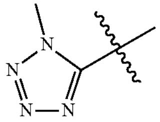 [SMILES: *c1nnnn1C] | H | Me | $SO_2Me$ | Me |
| 512 | 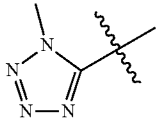 [SMILES: *c1nnnn1C] | H | Me | $SO_2Me$ | 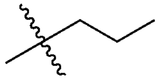 [SMILES: *CCC] |

TABLE 1-continued
Structures of compounds I
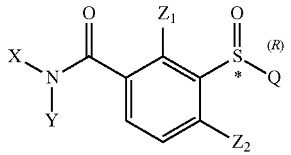
I
| Compound No. | X | Y | $Z_1$ | $Z_2$ | Q |
|---|---|---|---|---|---|
| 513 | 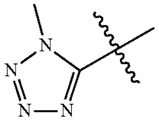 [SMILES: *c1nnnn1C] | H | Me | $SO_2Me$ | 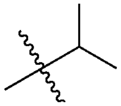 [SMILES: *C(C)C] |
| 514 | 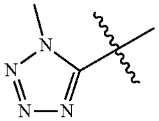 [SMILES: *c1nnnn1C] | H | Me | $SO_2Me$ | 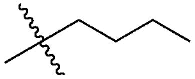 [SMILES: *CCCC] |
| 515 | 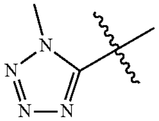 [SMILES: *c1nnnn1C] | H | Me | $SO_2Me$ | 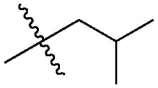 [SMILES: *CC(C)C] |
| 516 | 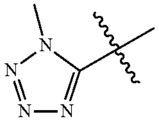 [SMILES: *c1nnnn1C] | H | Me | $SO_2Me$ | 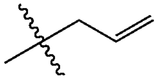 [SMILES: *CC=C] |
| 517 | 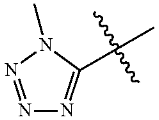 [SMILES: *c1nnnn1C] | H | Me | $SO_2Me$ | 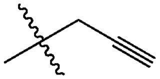 [SMILES: *CC#C] |

TABLE 1-continued
Structures of compounds I
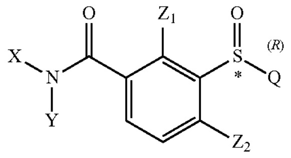
I
| Compound No. | X | Y | $Z_1$ | $Z_2$ | Q |
|---|---|---|---|---|---|
| 518 | 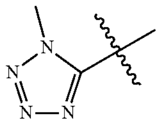 [SMILES: *c1nnnn1C] | H | Me | $SO_2Me$ | 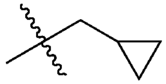 [SMILES: *CC1CC1] |
| 519 | 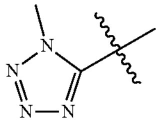 [SMILES: *c1nnnn1C] | H | Me | $SO_2Me$ | 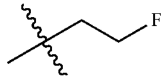 [SMILES: *CCF] |
| 520 | 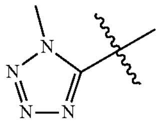 [SMILES: *c1nnnn1C] | H | Me | $SO_2Me$ | 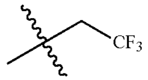 [SMILES: *CC(F)(F)F] |
| 521 | 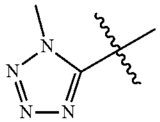 [SMILES: *c1nnnn1C] | H | Me | $SO_2Me$ | 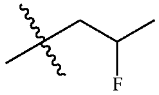 [SMILES: *CC(C)F] |
| 522 | 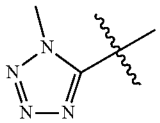 [SMILES: *c1nnnn1C] | H | Me | $SO_2Me$ | 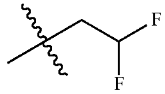 [SMILES: *CC(F)F] |

TABLE 1-continued
Structures of compounds I
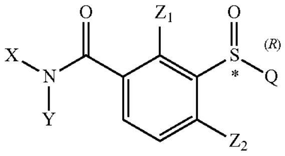
I
| Compound No. | X | Y | $Z_1$ | $Z_2$ | Q |
|---|---|---|---|---|---|
| 523 | 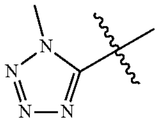 [SMILES: *c1nnnn1C] | H | Me | $SO_2Me$ | 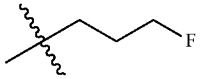 [SMILES: *CCCF] |
| 524 | 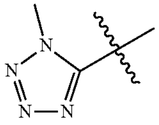 [SMILES: *c1nnnn1C] | H | Me | $SO_2Me$ | 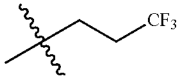 [SMILES: *CCC(F)(F)F] |
| 525 | 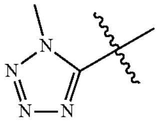 [SMILES: *c1nnnn1C] | H | Me | $SO_2Me$ | 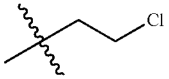 [SMILES: *CCCl] |
| 526 | 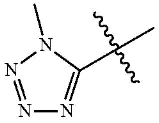 [SMILES: *c1nnnn1C] | H | Me | $SO_2Me$ | 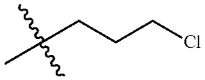 [SMILES: *CCCCl] |
| 527 | 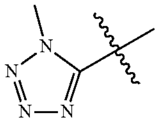 [SMILES: *c1nnnn1C] | H | Me | $SO_2Me$ | 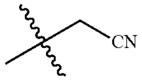 [SMILES: *CC#N] |

TABLE 1-continued
Structures of compounds I
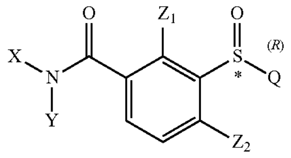
I
| Compound No. | X | Y | $Z_1$ | $Z_2$ | Q |
|---|---|---|---|---|---|
| 528 | 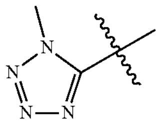 [SMILES: *c1nnnn1C] | H | Me | $SO_2Me$ | 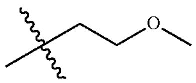 [SMILES: *CCOC] |
| 529 | 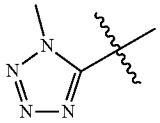 [SMILES: *c1nnnn1C] | H | Me | $SO_2Me$ | 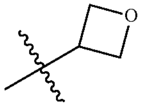 [SMILES: *C1COC1] |
| 530 | 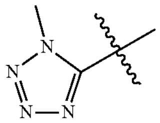 [SMILES: *c1nnnn1C] | H | Me | $SO_2Me$ | 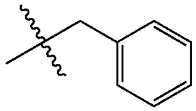 [SMILES: *Cc1ccccc1] |
| 531 | 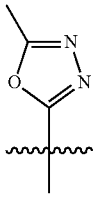 | H | OMe | $CF_3$ | 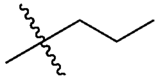 [SMILES: *CCC] |

TABLE 1-continued
Structures of compounds I
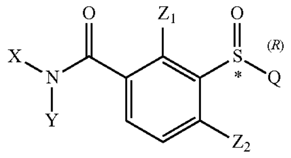
I
| Compound No. | X | Y | $Z_1$ | $Z_2$ | Q |
|---|---|---|---|---|---|
| 532 | 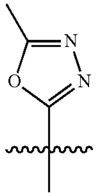 | H | OEt | $CF_3$ | 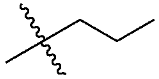 [SMILES: *CCC] |
| 533 | 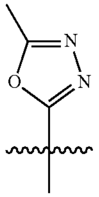 [SMILES: *c1nnc(C)o1] | H | 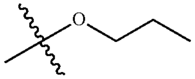 [SMILES: *OCCC] | $CF_3$ | 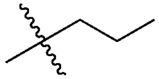 [SMILES: *CCC] |
| 534 | 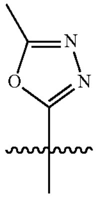 | H | 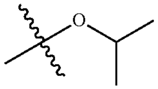 | $CF_3$ | 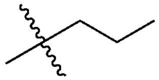 [SMILES: *CCC] |

TABLE 1-continued
Structures of compounds I
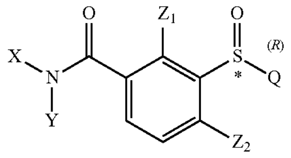
I
| Compound No. | X | Y | $Z_1$ | $Z_2$ | Q |
|---|---|---|---|---|---|
| 535 | 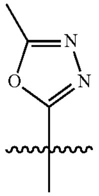 | H | 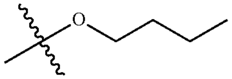 [SMILES: *OCCCC] | $CF_3$ | 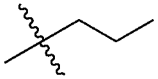 [SMILES: *CCC] |
| 536 | 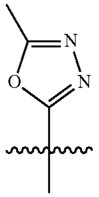 [SMILES: *c1nnc(C)o1] | H | 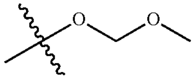 [SMILES: *OCOC] | $CF_3$ | 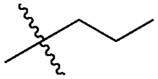 [SMILES: *CCC] |
| 537 | 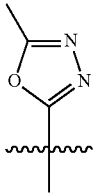 | H | Me | $CF_3$ | 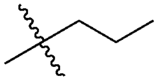 [SMILES: *CCC] |

TABLE 1-continued
Structures of compounds I
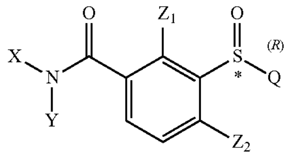
I
| Compound No. | X | Y | $Z_1$ | $Z_2$ | Q |
|---|---|---|---|---|---|
| 538 | 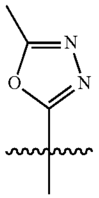 | H | Et | $CF_3$ | 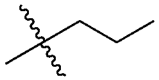 [SMILES: *CCC] |
| 539 | 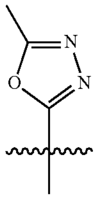 [SMILES: *c1nnc(C)o1] | H | 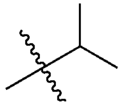 [SMILES: *C(C)C] | $CF_3$ | 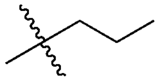 [SMILES: *CCC] |
| 540 | 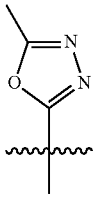 | H | 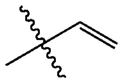 | $CF_3$ | 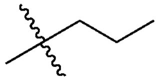 [SMILES: *CCC] |

TABLE 1-continued
Structures of compounds I
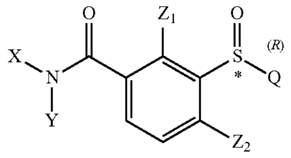
I
| Compound No. | X | Y | $Z_1$ | $Z_2$ | Q |
|---|---|---|---|---|---|
| 541 | 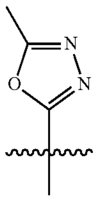 | H | 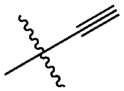 [SMILES: *C#C] | $CF_3$ | 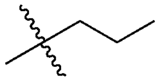 [SMILES: *CCC] |
| 542 | 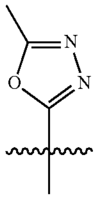 [SMILES: *c1nnc(C)o1] | H | 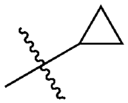 | $CF_3$ | 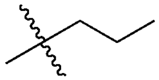 [SMILES: *CCC] |
| 543 | 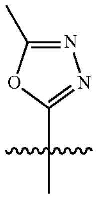 | H | Cl | $CF_3$ | 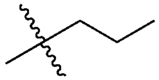 [SMILES: *CCC] |

TABLE 1-continued
Structures of compounds I
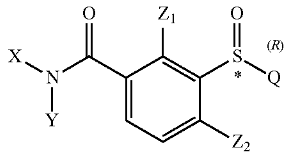
I
| Compound No. | X | Y | $Z_1$ | $Z_2$ | Q |
|---|---|---|---|---|---|
| 544 | 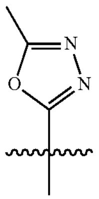 | H | Br | $CF_3$ | 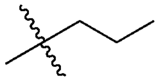 [SMILES: *CCC] |
| 545 | 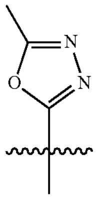 [SMILES: *c1nnc(C)o1] | H | I | $CF_3$ | 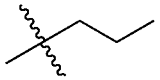 [SMILES: *CCC] |
| 546 | 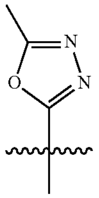 | H | CN | $CF_3$ | 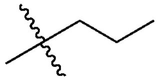 [SMILES: *CCC] |

TABLE 1-continued
Structures of compounds I
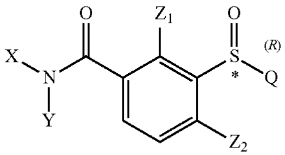
I
| Compound No. | X | Y | $Z_1$ | $Z_2$ | Q |
|---|---|---|---|---|---|
| 547 | 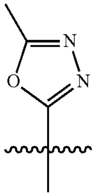 | H | SMe | $CF_3$ | Me |
| 548 | 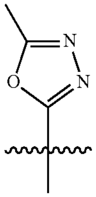 [SMILES: *c1nnc(C)o1] | H | SMe | $CF_3$ | Et |
| 549 | 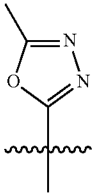 | H | SMe | $CF_3$ | 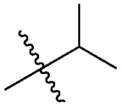 [SMILES: *C(C)C] |

TABLE 1-continued
Structures of compounds I
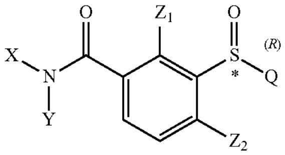
I
| Compound No. | X | Y | $Z_1$ | $Z_2$ | Q |
| --- | --- | --- | --- | --- | --- |
| 550 | 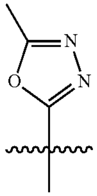 | H | SMe | $CF_3$ | 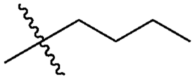 [SMILES: *CCCC] |
| 551 | 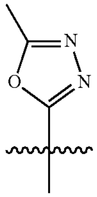 [SMILES: *c1nnc(C)o1] | H | SMe | $CF_3$ | 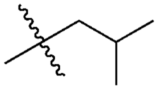 [SMILES: *CC(C)C] |
| 552 | 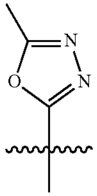 | H | SMe | $CF_3$ | 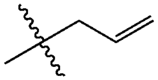 [SMILES: *CC=C] |

TABLE 1-continued
Structures of compounds I
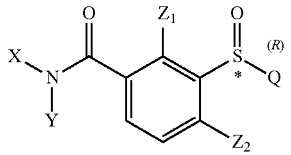
I
| Compound No. | X | Y | $Z_1$ | $Z_2$ | Q |
| --- | --- | --- | --- | --- | --- |
| 553 | 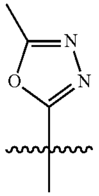 | H | SMe | $CF_3$ | 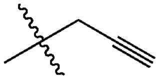 [SMILES: *CC#C] |
| 554 | 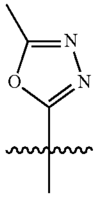 [SMILES: *c1nnc(C)o1] | H | SMe | $CF_3$ | 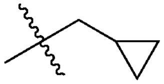 [SMILES: *CC1CC1] |
| 555 | 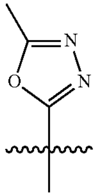 | H | SMe | $CF_3$ | 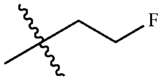 |

TABLE 1-continued
Structures of compounds I
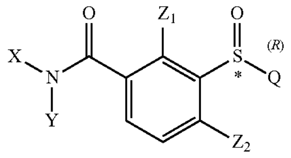
I
| Compound No. | X | Y | $Z_1$ | $Z_2$ | Q |
|---|---|---|---|---|---|
| 556 | 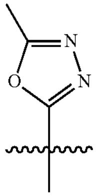 | H | SMe | $CF_3$ | 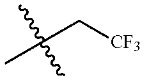 [SMILES: *CC(F)(F)F] |
| 557 | 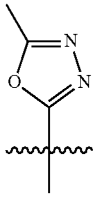 [SMILES: *c1nnc(C)o1] | H | SMe | $CF_3$ | 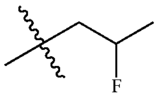 |
| 558 | 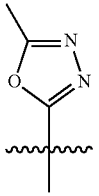 | H | SMe | $CF_3$ | 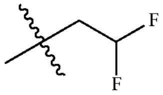 |

TABLE 1-continued
Structures of compounds I
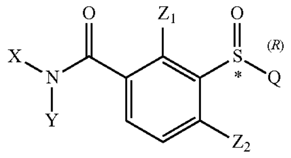
I
| Compound No. | X | Y | $Z_1$ | $Z_2$ | Q |
|---|---|---|---|---|---|
| 559 | 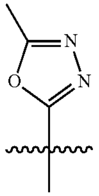 | H | SMe | $CF_3$ | 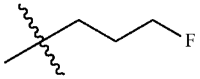 [SMILES: *CCCF] |
| 560 | 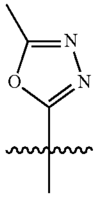 [SMILES: *c1nnc(C)o1] | H | SMe | $CF_3$ | 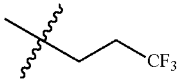 [SMILES: *CCC(F)(F)F] |
| 561 | 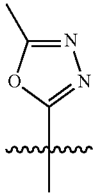 | H | SMe | $CF_3$ | 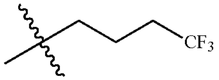 [SMILES: *CCCC(F)(F)F] |

TABLE 1-continued
Structures of compounds I
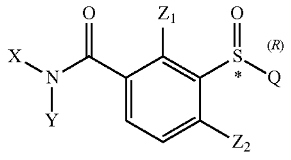
I
| Compound No. | X | Y | $Z_1$ | $Z_2$ | Q |
|---|---|---|---|---|---|
| 562 | 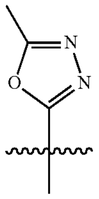 | H | SMe | $CF_3$ | 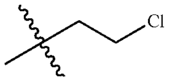 [SMILES: *CCCl] |
| 563 | 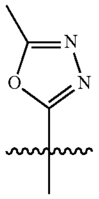 [SMILES: *c1nnc(C)o1] | H | SMe | $CF_3$ | 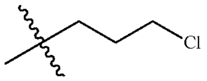 [SMILES: *CCCCl] |
| 564 | 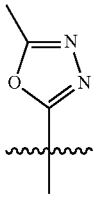 | H | SMe | $CF_3$ | 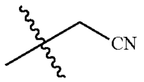 |

TABLE 1-continued
Structures of compounds I
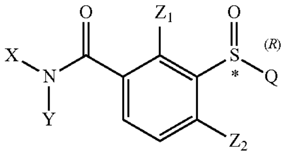
I
| Compound No. | X | Y | $Z_1$ | $Z_2$ | Q |
|---|---|---|---|---|---|
| 565 | 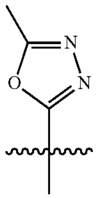 | H | SMe | $CF_3$ | 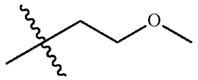 [SMILES: *CCOC] |
| 566 | 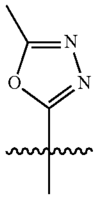 [SMILES: *c1nnc(C)o1] | H | SMe | $CF_3$ | 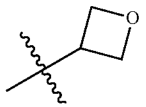 [SMILES: *C1COC1] |
| 567 | 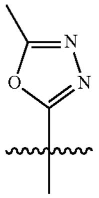 | H | SMe | $CF_3$ | 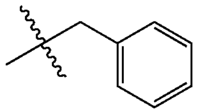 [SMILES: *Cc1ccccc1] |

TABLE 1-continued
Structures of compounds I
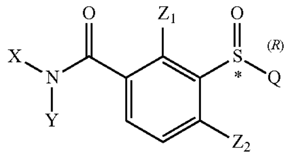
I
| Compound No. | X | Y | $Z_1$ | $Z_2$ | Q |
|---|---|---|---|---|---|
| 568 | 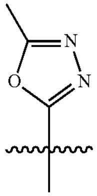 | H | SMe | $CF_3$ | 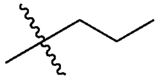 [SMILES: *CCC] |
| 569 | 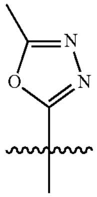 [SMILES: *c1nnc(C)o1] | H | SEt | $CF_3$ | 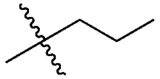 [SMILES: *CCC] |
| 570 | 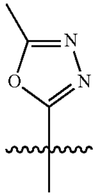 | H | 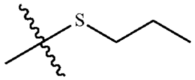 [SMILES: *SCCC] | $CF_3$ | 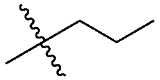 [SMILES: *CCC] |

TABLE 1-continued
Structures of compounds I
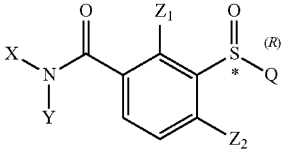
I
| Compound No. | X | Y | $Z_1$ | $Z_2$ | Q |
| --- | --- | --- | --- | --- | --- |
| 571 | 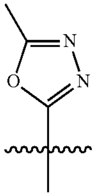 | H | 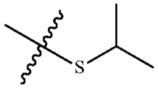 [SMILES: *SC(C)C] | $CF_3$ | 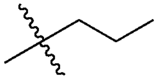 [SMILES: *CCC] |
| 572 | 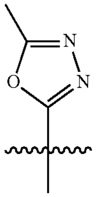 [SMILES: *c1nnc(C)o1] | H | 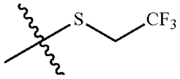 [SMILES: *SCC(F)(F)F] | $CF_3$ | 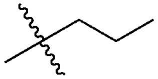 [SMILES: *CCC] |
| 573 | 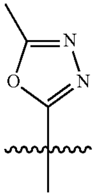 | H | 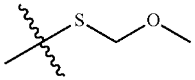 [SMILES: *SCOC] | $CF_3$ | 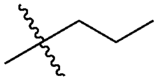 [SMILES: *CCC] |
| 574 | 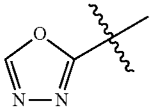 [SMILES: *c1nnco1] | H | F | $CF_3$ | Et |

TABLE 1-continued
Structures of compounds I
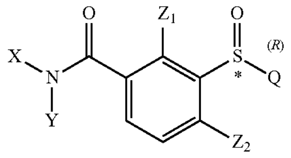
I
| Compound No. | X | Y | $Z_1$ | $Z_2$ | Q |
|---|---|---|---|---|---|
| 575 | 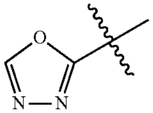 [SMILES: *c1nnco1] | H | F | $CF_3$ | 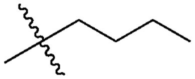 [SMILES: *CCCC] |
| 576 | 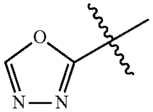 [SMILES: *c1nnco1] | H | F | $CF_3$ | 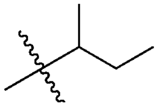 [SMILES: *C(C)CC] |
| 577 | 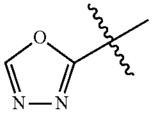 [SMILES: *c1nnco1] | H | F | $CF_3$ | 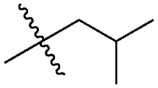 [SMILES: *CC(C)C] |
| 578 | 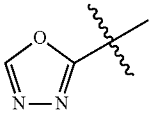 [SMILES: *c1nnco1] | H | F | $CF_3$ | 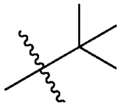 [SMILES: *C(C)(C)C] |
| 579 | 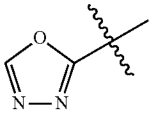 [SMILES: *c1nnco1] | H | F | $CF_3$ | 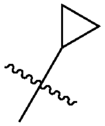 [SMILES: *C1CC1] |
| 580 | 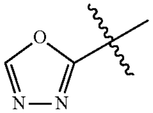 [SMILES: *c1nnco1] | H | F | $CF_3$ | 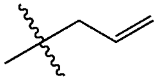 |

TABLE 1-continued
Structures of compounds I
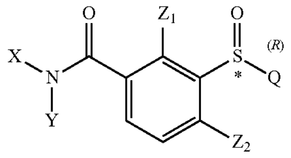
I
| Compound No. | X | Y | $Z_1$ | $Z_2$ | Q |
|---|---|---|---|---|---|
| 581 | 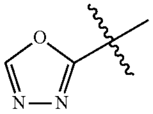 [SMILES: *c1nnco1] | H | F | $CF_3$ | 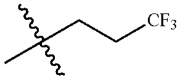 [SMILES: *CCC(F)(F)F] |
| 582 | 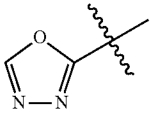 [SMILES: *c1nnco1] | H | F | $CF_3$ | 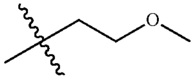 [SMILES: *CCOC] |
| 583 | 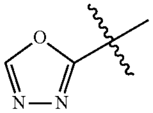 [SMILES: *c1nnco1] | H | F | $CF_3$ | 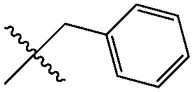 [SMILES: *Cc1ccccc1] |
| 584 | 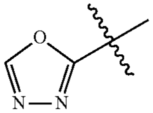 [SMILES: *c1nnco1] | H | SMe | $CF_3$ | Et |
| 585 | 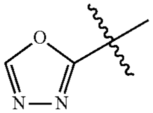 [SMILES: *c1nnco1] | H | SMe | $CF_3$ | 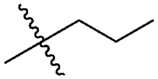 [SMILES: *CCC] |
| 586 | 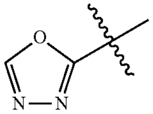 [SMILES: *c1nnco1] | H | SMe | $CF_3$ | 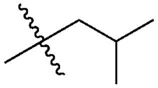 [SMILES: *CC(C)C] |

TABLE 1-continued
Structures of compounds I
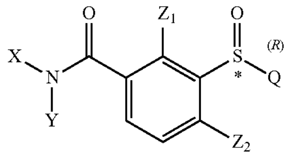
I
| Compound No. | X | Y | $Z_1$ | $Z_2$ | Q |
|---|---|---|---|---|---|
| 587 | 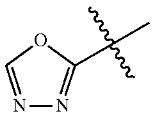 [SMILES: *c1nnco1] | H | SMe | $CF_3$ | 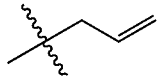 [SMILES: *CC=C] |
| 588 | 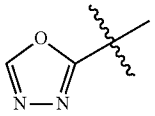 [SMILES: *c1nnco1] | H | SMe | $CF_3$ | 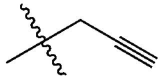 [SMILES: *CC#C] |
| 589 | 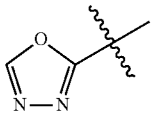 [SMILES: *c1nnco1] | H | SMe | $CF_3$ | 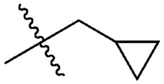 |
| 590 | 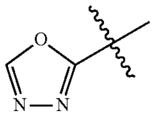 [SMILES: *c1nnco1] | H | SMe | $CF_3$ | 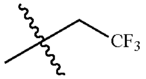 |
| 591 | 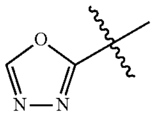 [SMILES: *c1nnco1] | H | SMe | $CF_3$ | 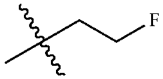 [SMILES: *CCF] |
| 592 | 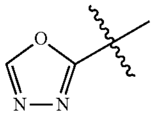 [SMILES: *c1nnco1] | H | SMe | $CF_3$ | 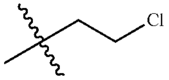 [SMILES: *CCCl] |

TABLE 1-continued
Structures of compounds I
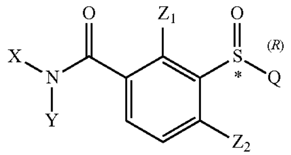
I
| Compound No. | X | Y | $Z_1$ | $Z_2$ | Q |
|---|---|---|---|---|---|
| 593 | 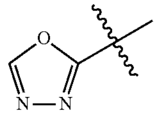 [SMILES: *c1nnco1] | H | SMe | $CF_3$ | 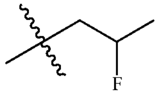 [SMILES: *CC(C)F] |
| 594 | 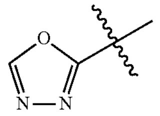 [SMILES: *c1nnco1] | H | SMe | $CF_3$ | 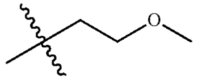 [SMILES: *CCOC] |
| 595 | 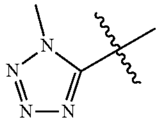 [SMILES: *c1nnnn1C] | H | SMe | $CF_3$ | 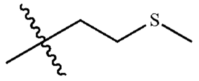 |
| 596 | 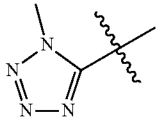 [SMILES: *c1nnnn1C] | H | SMe | $CF_3$ | 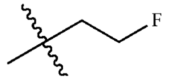 [SMILES: *CCF] |
| 597 | 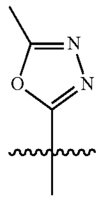 | H | F | $CF_3$ | 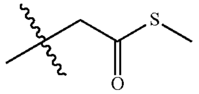 [SMILES: *CC(=O)SC] |

TABLE 1-continued
Structures of compounds I
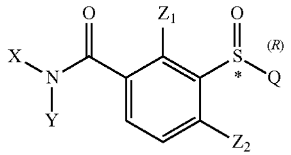
I
| Compound No. | X | Y | $Z_1$ | $Z_2$ | Q |
|---|---|---|---|---|---|
| 598 | 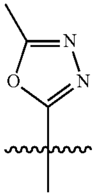 | H | F | $CF_3$ | 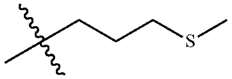 [SMILES: *CCCSC] |
| 599 | 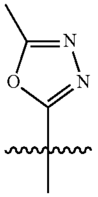 [SMILES: *c1nnc(C)o1] | H | SMe | $CF_3$ | 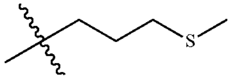 [SMILES: *CCCSC] |
| 600 | 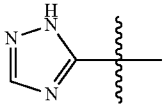 [SMILES: *c1ncn[nH]1] | H | F | $CF_3$ | 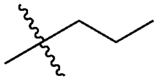 [SMILES: *CCC] |
| 601 | 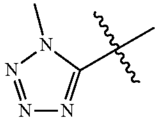 [SMILES: *c1nnnn1C] | H | Me | $SO_2Me$ | 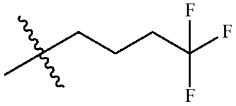 [SMILES: *CCCC(F)(F)F] |

TABLE 1-continued
Structures of compounds I
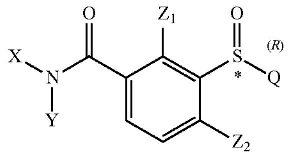
I
| Compound No. | X | Y | $Z_1$ | $Z_2$ | Q |
|---|---|---|---|---|---|
| 602 | 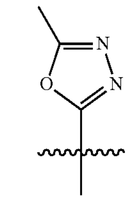 | H | Me | $SO_2Me$ | 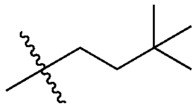 [SMILES: *CCC(C)(C)C] |
| 603 | 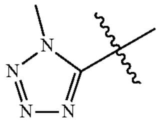 [SMILES: *c1nnnn1C] | H | Me | $SO_2Me$ | 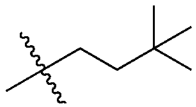 [SMILES: *CCC(C)(C)C] |
| 604 | 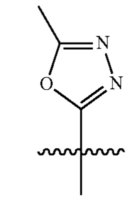 | H | Me | $SO_2Me$ | 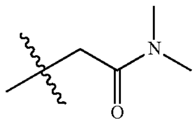 [SMILES: *CC(=O)N(C)C] |
| 605 | 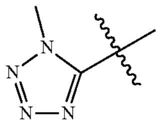 [SMILES: *c1nnnn1C] | H | Me | $SO_2Me$ | 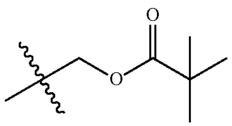 [SMILES: *COC(=O)C(C)(C)C] |

TABLE 1-continued
Structures of compounds I
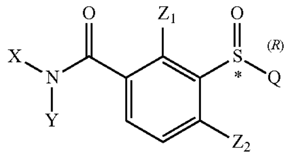
I
| Compound No. | X | Y | $Z_1$ | $Z_2$ | Q |
|---|---|---|---|---|---|
| 606 | 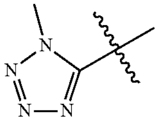 [SMILES: *c1nnnn1C] | H | Me | $SO_2Me$ | 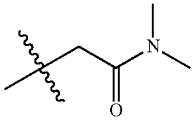 [SMILES: *CC(=O)N(C)C] |
| 607 | 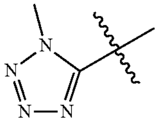 [SMILES: *c1nnnn1C] | H | Me | $SO_2Me$ | 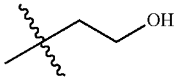 [SMILES: *CCO] |
| 608 | 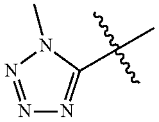 [SMILES: *c1nnnn1C] | H | Me | $SO_2Me$ | 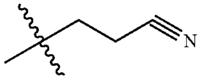 [SMILES: *CCC#N] |
| 609 | 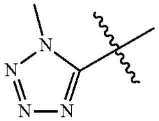 [SMILES: *c1nnnn1C] | H | Me | $SO_2Me$ | 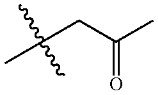 |
| 610 | 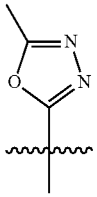 | H | Me | $SO_2Me$ | 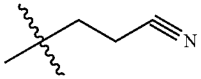 [SMILES: *CCC#N] |

TABLE 1-continued
Structures of compounds I
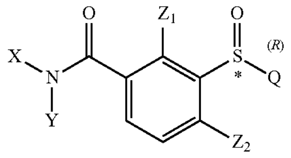
I
| Compound No. | X | Y | $Z_1$ | $Z_2$ | Q |
|---|---|---|---|---|---|
| 611 | 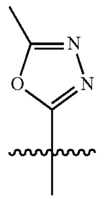 | H | Me | $SO_2Me$ | 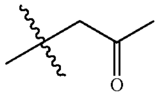 [SMILES: *CC(C)=O] |
| 612 | 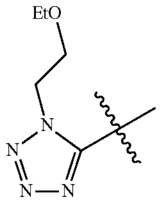 [SMILES: *c1nnnn1CCOCC] | H | Me | $SO_2Me$ | Et |
| 613 | 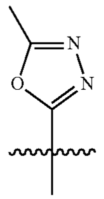 [SMILES: *c1nnc(C)o1] | H | Me | $SO_2Me$ | 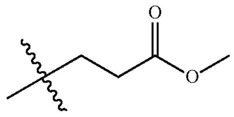 [SMILES: *CCC(=O)OC] |

TABLE 1-continued
Structures of compounds I
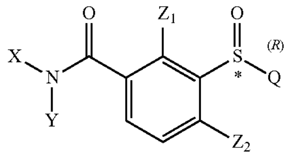
I
| Compound No. | X | Y | $Z_1$ | $Z_2$ | Q |
| --- | --- | --- | --- | --- | --- |
| 614 | 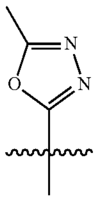 | H | Me | $SO_2Me$ | 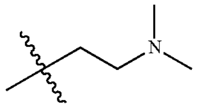 [SMILES: *CCN(C)C] |
| 615 | 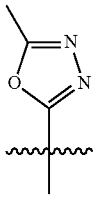 [SMILES: *c1nnc(C)o1] | H | SMe | $CF_3$ | 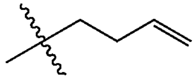 [SMILES: *CCC=C] |
| 616 | 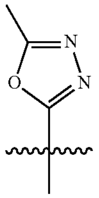 | H | F | $CF_3$ | 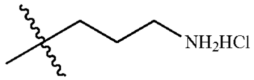 |

TABLE 1-continued
Structures of compounds I
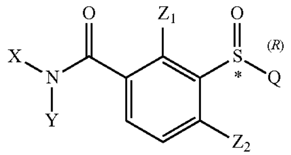
I
| Compound No. | X | Y | $Z_1$ | $Z_2$ | Q |
|---|---|---|---|---|---|
| 617 | 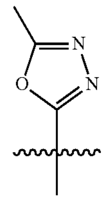 | H | Cl | $CHF_2$ | 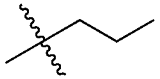 [SMILES: *CCC] |
| 618 | 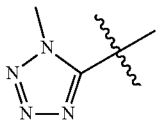 [SMILES: *c1nnnn1C] | H | Cl | $CHF_2$ | 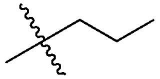 [SMILES: *CCC] |
| 619 | 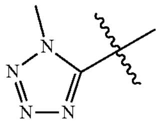 [SMILES: *c1nnnn1C] | H | Me | $SO_2Me$ | 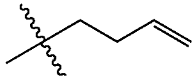 |
| 620 | 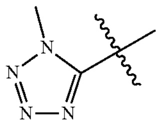 [SMILES: *c1nnnn1C] | H | Me | $SO_2Me$ | 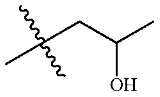 [SMILES: *CC(C)O] |

TABLE 1-continued
Structures of compounds I
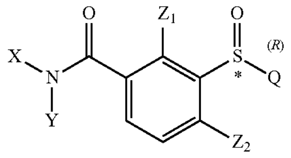
I
| Compound No. | X | Y | $Z_1$ | $Z_2$ | Q |
|---|---|---|---|---|---|
| 621 | 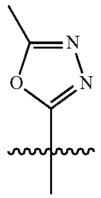 | H | Cl | Cl | Me |
| 622 | 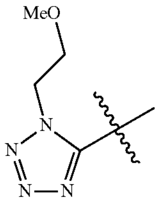 [SMILES: *c1nnnn1CCOC] | H | Me | $SO_2Me$ | Et |
| 623 | 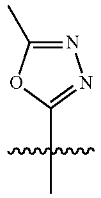 [SMILES: *c1nnc(C)o1] | H | F | F | Me |

TABLE 1-continued
Structures of compounds I
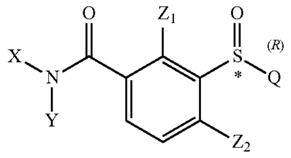
I
| Compound No. | X | Y | $Z_1$ | $Z_2$ | Q |
|---|---|---|---|---|---|
| 624 | 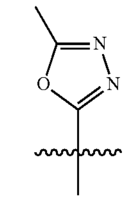 | H | Me | $SO_2Me$ | 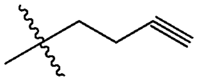 [SMILES: *CCC#C] |
| 625 | 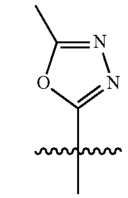 [SMILES: *c1nnc(C)o1] | H | Me | $SO_2Me$ | 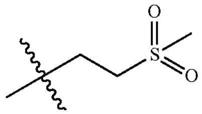 [SMILES: *CCS(C)(=O)=O] |
| 626 | 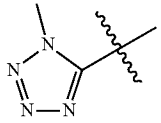 [SMILES: *c1nnnn1C] | H | Me | $SO_2Me$ | 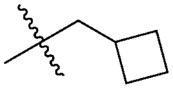 [SMILES: *CC1CCC1] |
| 627 | 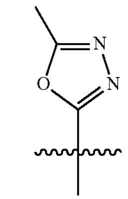 | H | Me | $SO_2Me$ | 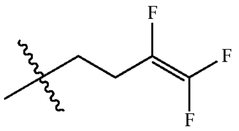 [SMILES: *CCC(F)=C(F)F] |

TABLE 1-continued
Structures of compounds I
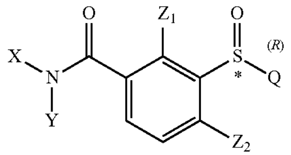
I
| Compound No. | X | Y | $Z_1$ | $Z_2$ | Q |
|---|---|---|---|---|---|
| 628 | 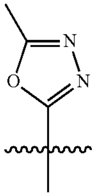 | H | Me | $SO_2Me$ | 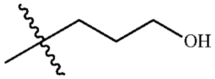 [SMILES: *CCCO] |
| 629 | 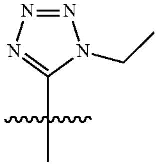 | H | Me | $SO_2Me$ | Et |
| 630 | 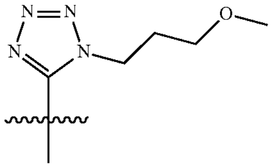 [SMILES: *c1nnnn1CCCOC] | H | Me | $SO_2Me$ | Et |
| 631 | 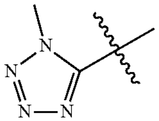 [SMILES: *c1nnnn1C] | H | Me | $SO_2Me$ | 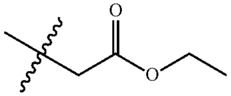 [SMILES: *CC(=O)OCC] |

TABLE 1-continued
Structures of compounds I
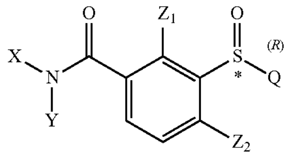
I
| Compound No. | X | Y | $Z_1$ | $Z_2$ | Q |
|---|---|---|---|---|---|
| 632 | 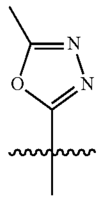 | H | Me | $SO_2Me$ | 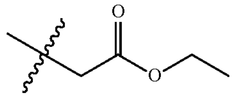 [SMILES: *CC(=O)OCC] |
| 633 | 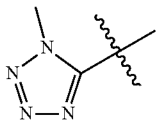 [SMILES: *c1nnnn1C] | H | Me | $SO_2Me$ | 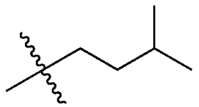 [SMILES: *CCC(C)C] |
| 634 | 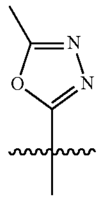 | H | Me | $SO_2Me$ | 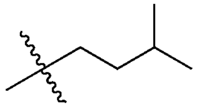 [SMILES: *CCC(C)C] |
| 635 | 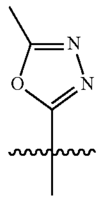 | H | F | $CHF_2$ | Me |

TABLE 1-continued
Structures of compounds I
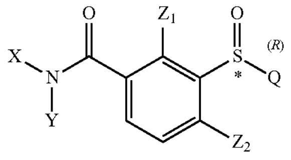
I
| Compound No. | X | Y | $Z_1$ | $Z_2$ | Q |
|---|---|---|---|---|---|
| 636 | 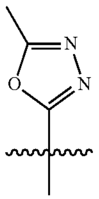 | H | F | $CHF_2$ | Et |
| 637 | 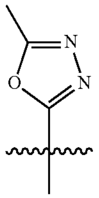 [SMILES: *c1nnc(C)o1] | H | F | $CHF_2$ | 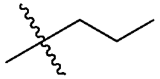 [SMILES: *CCC] |
| 638 | 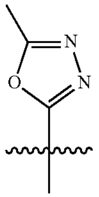 | H | F | $CHF_2$ | 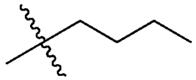 [SMILES: *CCCC] |

TABLE 1-continued
Structures of compounds I
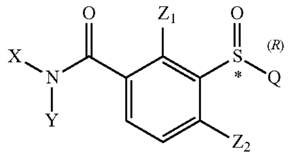
I
| Compound No. | X | Y | $Z_1$ | $Z_2$ | Q |
|---|---|---|---|---|---|
| 639 | 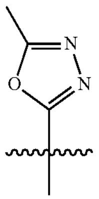 | H | F | $CHF_2$ | 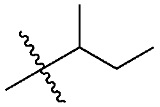 [SMILES: *C(C)CC] |
| 640 | 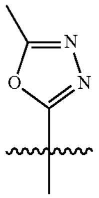 [SMILES: *c1nnc(C)o1] | H | F | $CHF_2$ | 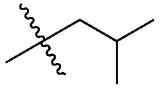 [SMILES: *CC(C)C] |
| 641 | 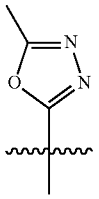 | H | F | $CHF_2$ | 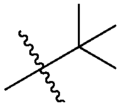 [SMILES: *C(C)(C)C] |

TABLE 1-continued
Structures of compounds I
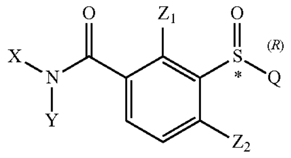
I
| Compound No. | X | Y | Z1 | Z2 | Q |
| --- | --- | --- | --- | --- | --- |
| 642 | 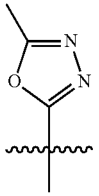 | H | F | $CHF_2$ | 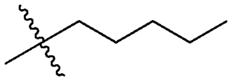 [SMILES: *CCCCC] |
| 643 | 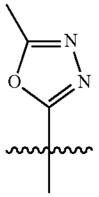 [SMILES: *c1nnc(C)o1] | H | F | $CHF_2$ | 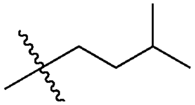 [SMILES: *CCC(C)C] |
| 644 | 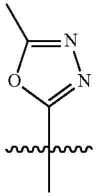 | H | F | $CHF_2$ | 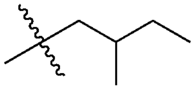 [SMILES: *CC(C)CC] |

TABLE 1-continued
Structures of compounds I
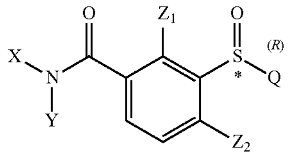
I
| Compound No. | X | Y | $Z_1$ | $Z_2$ | Q |
|---|---|---|---|---|---|
| 645 | 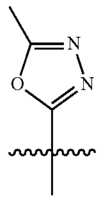 | H | F | $CHF_2$ | 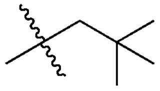 [SMILES: *CC(C)(C)C] |
| 646 | 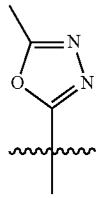 [SMILES: *c1nnc(C)o1] | H | F | $CHF_2$ | 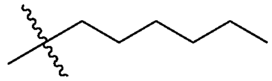 [SMILES: *CCCCCC] |
| 647 | 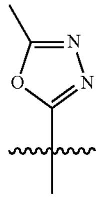 | H | F | $CHF_2$ | 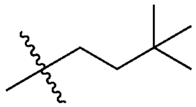 [SMILES: *CCC(C)(C)C] |

TABLE 1-continued
Structures of compounds I
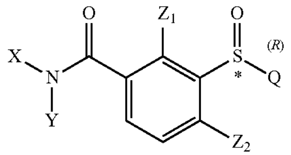
I
| Compound No. | X | Y | $Z_1$ | $Z_2$ | Q |
|---|---|---|---|---|---|
| 648 | 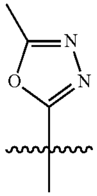 | H | F | $CHF_2$ | 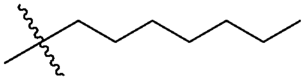 [SMILES: *CCCCCCC] |
| 649 | 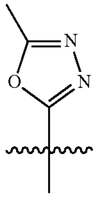 [SMILES: *c1nnc(C)o1] | H | F | $CHF_2$ | 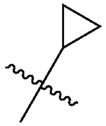 [SMILES: *C1CC1] |
| 650 | 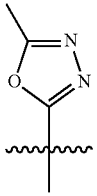 | H | F | $CHF_2$ | 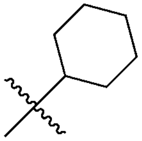 [SMILES: *C1CCCCC1] |

TABLE 1-continued
Structures of compounds I
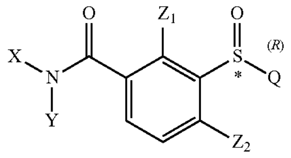
I
| Compound No. | X | Y | $Z_1$ | $Z_2$ | Q |
|---|---|---|---|---|---|
| 651 | 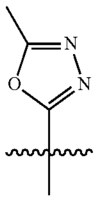 | H | F | $CHF_2$ | 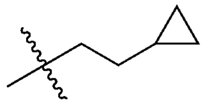 [SMILES: *CCC1CC1] |
| 652 | 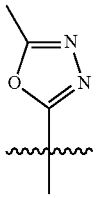 [SMILES: *c1nnc(C)o1] | H | F | $CHF_2$ | 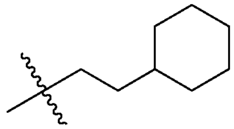 [SMILES: *CCC1CCCCC1] |
| 653 | 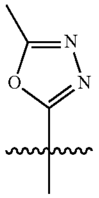 | H | F | $CHF_2$ | 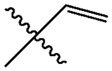 |

TABLE 1-continued
Structures of compounds I
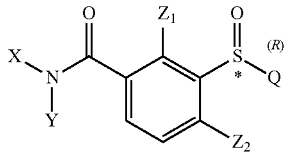
I
| Compound No. | X | Y | $Z_1$ | $Z_2$ | Q |
|---|---|---|---|---|---|
| 654 | 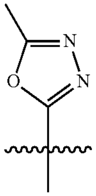 | H | F | $CHF_2$ | 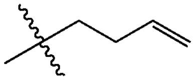 [SMILES: *CCC=C] |
| 655 | 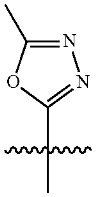 [SMILES: *c1nnc(C)o1] | H | F | $CHF_2$ | 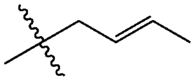 [SMILES: *C/C=C/C] |
| 656 | 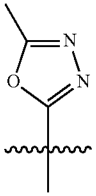 | H | F | $CHF_2$ | 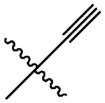 [SMILES: *C#C] |

TABLE 1-continued
Structures of compounds I
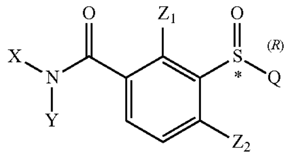
I
| Compound No. | X | Y | $Z_1$ | $Z_2$ | Q |
|---|---|---|---|---|---|
| 657 | 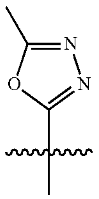 | H | F | $CHF_2$ | 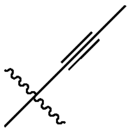 [SMILES: *C#CC] |
| 658 | 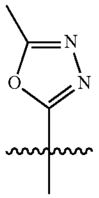 [SMILES: *c1nnc(C)o1] | H | F | $CHF_2$ | 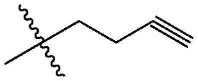 [SMILES: *CCC#C] |
| 659 | 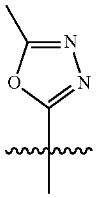 | H | F | $CHF_2$ | 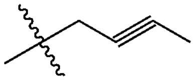 [SMILES: *CC#CC] |

TABLE 1-continued
Structures of compounds I
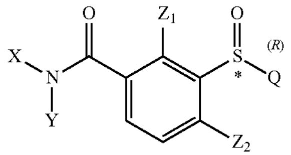
I
| Compound No. | X | Y | $Z_1$ | $Z_2$ | Q |
|---|---|---|---|---|---|
| 660 | 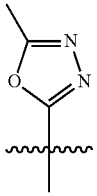 | H | F | $CHF_2$ | 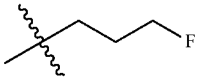 [SMILES: *CCCF] |
| 661 | 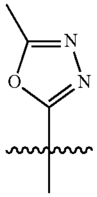 [SMILES: *c1nnc(C)o1] | H | F | $CHF_2$ | 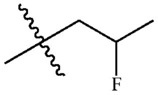 |
| 662 | 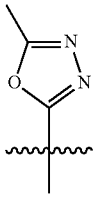 | H | F | $CHF_2$ | 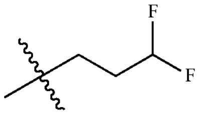 [SMILES: *CCC(F)F] |

TABLE 1-continued
Structures of compounds I
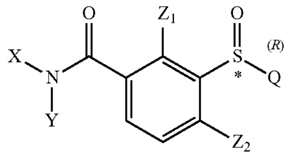
I
| Compound No. | X | Y | $Z_1$ | $Z_2$ | Q |
|---|---|---|---|---|---|
| 663 | 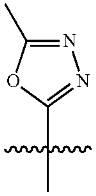 | H | F | $CHF_2$ | 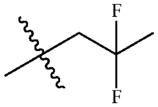 [SMILES: *CC(C)(F)F] |
| 664 | 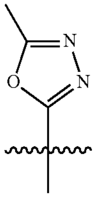 [SMILES: *c1nnc(C)o1] | H | F | $CHF_2$ | 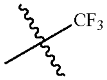 |
| 665 | 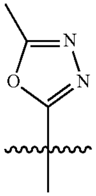 | H | F | $CHF_2$ | 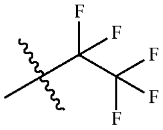 [SMILES: *C(F)(F)C(F)(F)F] |

TABLE 1-continued
Structures of compounds I
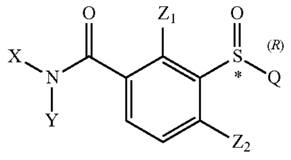
I
| Compound No. | X | Y | $Z_1$ | $Z_2$ | Q |
|---|---|---|---|---|---|
| 666 | 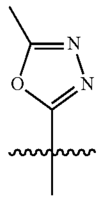 | H | F | $CHF_2$ | 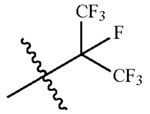 [SMILES: *C(F)(C(F)(F)F)C(F)(F)F] |
| 667 | 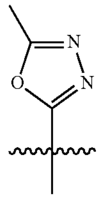 [SMILES: *c1nnc(C)o1] | H | F | $CHF_2$ | 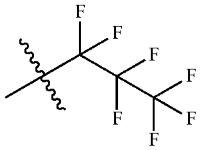 |
| 668 | 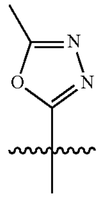 | H | F | $CHF_2$ | 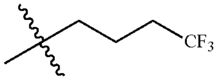 [SMILES: *CCCC(F)(F)F] |

TABLE 1-continued
Structures of compounds I
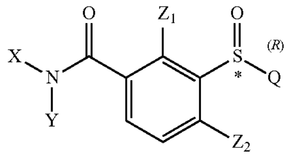
I
| Compound No. | X | Y | $Z_1$ | $Z_2$ | Q |
|---|---|---|---|---|---|
| 669 | 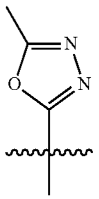 | H | F | $CHF_2$ | 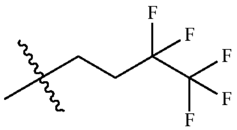 [SMILES: *CCC(F)(F)C(F)(F)F] |
| 670 | 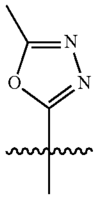 [SMILES: *c1nnc(C)o1] | H | F | $CHF_2$ | 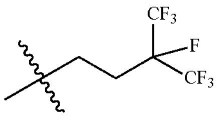 [SMILES: *CCC(F)(C(F)(F)F)C(F)(F)F] |
| 671 | 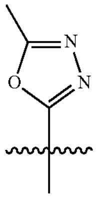 | H | F | $CHF_2$ | 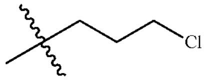 [SMILES: *CCCCl] |

TABLE 1-continued
Structures of compounds I
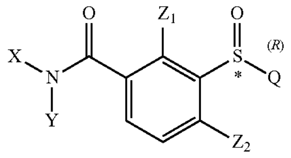
I
| Compound No. | X | Y | $Z_1$ | $Z_2$ | Q |
|---|---|---|---|---|---|
| 672 | 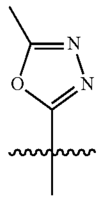 | H | F | $CHF_2$ | 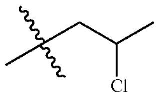 |
| 673 | 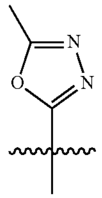 [SMILES: *c1nnc(C)o1] | H | F | $CHF_2$ | 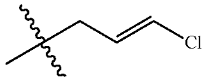 [SMILES: *C/C=C/Cl] |
| 674 | 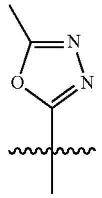 | H | F | $CHF_2$ | 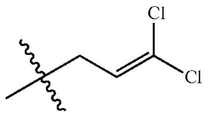 [SMILES: *CC=C(Cl)Cl] |

TABLE 1-continued
Structures of compounds I
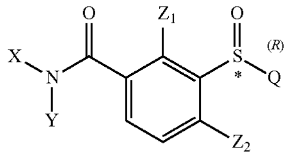
I
| Compound No. | X | Y | $Z_1$ | $Z_2$ | Q |
|---|---|---|---|---|---|
| 675 | 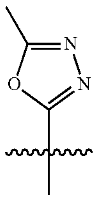 | H | F | $CHF_2$ | 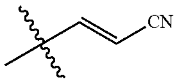 [SMILES: */C=C/C#N] |
| 676 | 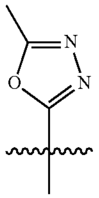 [SMILES: *c1nnc(C)o1] | H | F | $CHF_2$ | 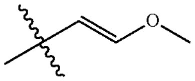 [SMILES: */C=C/OC] |
| 677 | 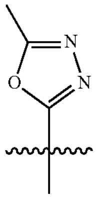 | H | F | $CHF_2$ | 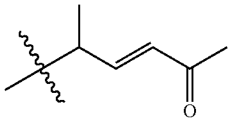 [SMILES: *C(C)/C=C/C(C)=O] |

TABLE 1-continued
Structures of compounds I
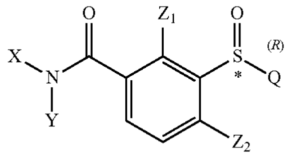
I
| Compound No. | X | Y | $Z_1$ | $Z_2$ | Q |
|---|---|---|---|---|---|
| 678 | 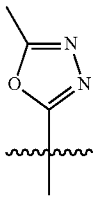 | H | F | $CHF_2$ | 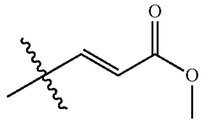 [SMILES: */C=C/C(=O)OC] |
| 679 | 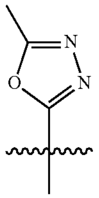 [SMILES: *c1nnc(C)o1] | H | F | $CHF_2$ | 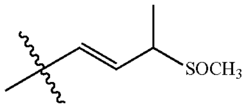 |
| 680 | 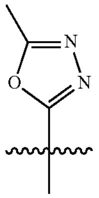 | H | F | $CHF_2$ | 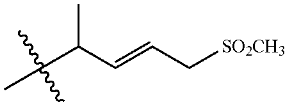 [SMILES: *C(C)/C=C/CS(C)(=O)=O] |

TABLE 1-continued
Structures of compounds I
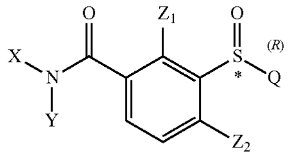
I
| Compound No. | X | Y | $Z_1$ | $Z_2$ | Q |
| --- | --- | --- | --- | --- | --- |
| 681 | 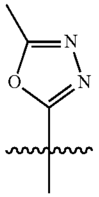 | H | F | $CHF_2$ | 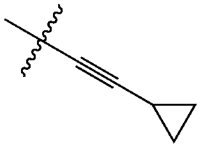 [SMILES: *C#CC1CC1] |
| 682 | 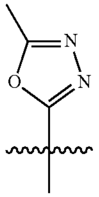 [SMILES: *c1nnc(C)o1] | H | F | $CHF_2$ | 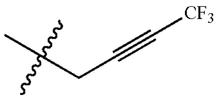 [SMILES: *CC#CC(F)(F)F] |
| 683 | 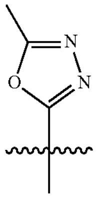 | H | F | $CHF_2$ | 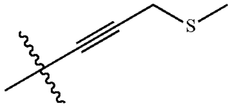 [SMILES: *C#CCSC] |

TABLE 1-continued
Structures of compounds I
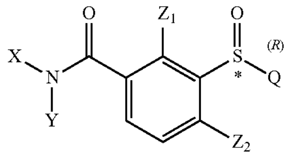
I
| Compound No. | X | Y | $Z_1$ | $Z_2$ | Q |
|---|---|---|---|---|---|
| 684 | 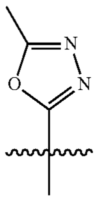 | H | F | $CHF_2$ | 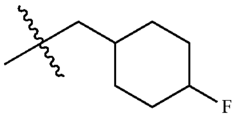 [SMILES: *CC1CCC(F)CC1] |
| 685 | 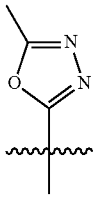 [SMILES: *c1nnc(C)o1] | H | F | $CHF_2$ | 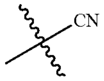 [SMILES: *C#N] |
| 686 | 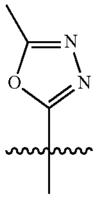 | H | F | $CHF_2$ | 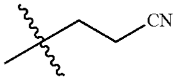 [SMILES: *CCC#N] |

TABLE 1-continued
Structures of compounds I
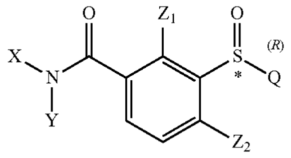
I
| Compound No. | X | Y | $Z_1$ | $Z_2$ | Q |
|---|---|---|---|---|---|
| 687 | 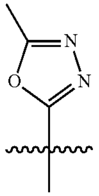 | H | F | $CHF_2$ | 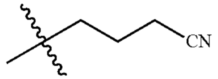 |
| 688 | 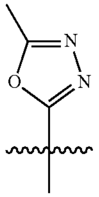 [SMILES: *c1nnc(C)o1] | H | F | $CHF_2$ | 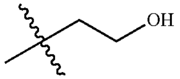 [SMILES: *CCO] |
| 689 | 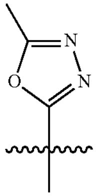 | H | F | $CHF_2$ | 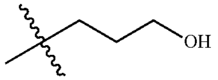 [SMILES: *CCCO] |

TABLE 1-continued
Structures of compounds I
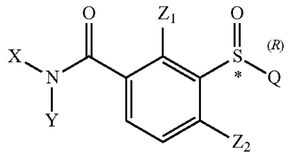
I
| Compound No. | X | Y | $Z_1$ | $Z_2$ | Q |
|---|---|---|---|---|---|
| 690 | 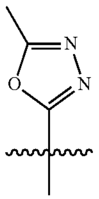 | H | F | $CHF_2$ | 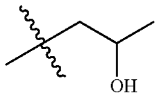 [SMILES: *CC(C)O] |
| 691 | 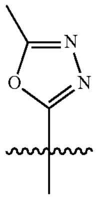 [SMILES: *c1nnc(C)o1] | H | F | $CHF_2$ | 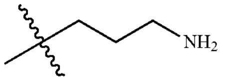 [SMILES: *CCCN] |
| 692 | 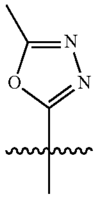 | H | F | $CHF_2$ | 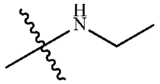 [SMILES: *NCC] |

TABLE 1-continued
Structures of compounds I
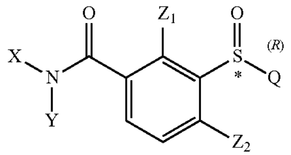
I
| Compound No. | X | Y | $Z_1$ | $Z_2$ | Q |
|---|---|---|---|---|---|
| 693 | 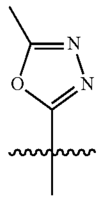 | H | F | $CHF_2$ | 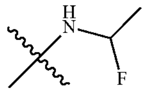 |
| 694 | 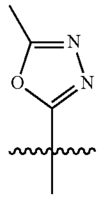 [SMILES: *c1nnc(C)o1] | H | F | $CHF_2$ | 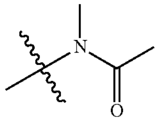 [SMILES: *N(C)C(C)=O] |
| 695 | 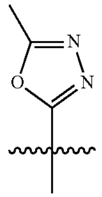 | H | F | $CHF_2$ | 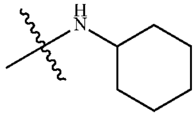 [SMILES: *NC1CCCCC1] |

TABLE 1-continued
Structures of compounds I
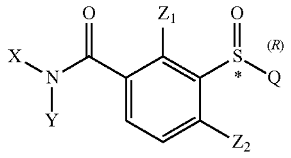
I
| Compound No. | X | Y | $Z_1$ | $Z_2$ | Q |
|---|---|---|---|---|---|
| 696 | 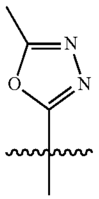 | H | F | $CHF_2$ | 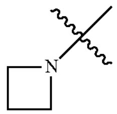 [SMILES: *N1CCC1] |
| 697 | 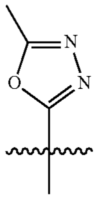 [SMILES: *c1nnc(C)o1] | H | F | $CHF_2$ | 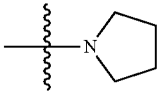 [SMILES: *N1CCCC1] |
| 698 | 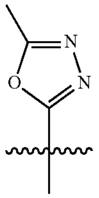 | H | F | $CHF_2$ | 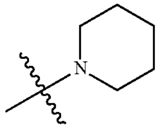 [SMILES: *N1CCCCC1] |

TABLE 1-continued
Structures of compounds I
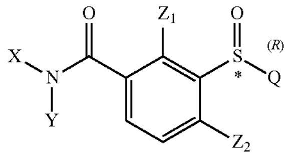
I
| Compound No. | X | Y | $Z_1$ | $Z_2$ | Q |
|---|---|---|---|---|---|
| 699 | 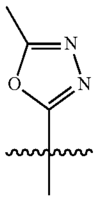 | H | F | $CHF_2$ | 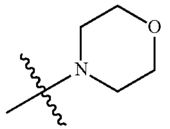 [SMILES: *N1CCOCC1] |
| 700 | 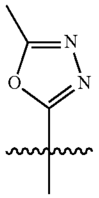 [SMILES: *c1nnc(C)o1] | H | F | $CHF_2$ | 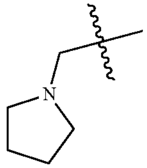 [SMILES: *CN1CCCC1] |
| 701 | 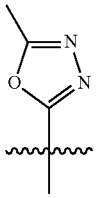 | H | F | $CHF_2$ | 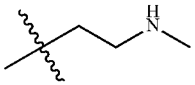 [SMILES: *CCNC] |

TABLE 1-continued
Structures of compounds I
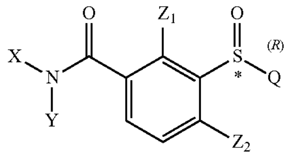
I
| Compound No. | X | Y | $Z_1$ | $Z_2$ | Q |
|---|---|---|---|---|---|
| 702 | 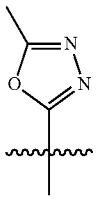 | H | F | $CHF_2$ | 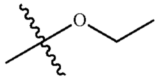 [SMILES: *OCC] |
| 703 | 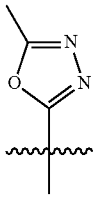 [SMILES: *c1nnc(C)o1] | H | F | $CHF_2$ | 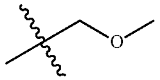 [SMILES: *COC] |
| 704 | 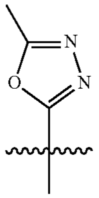 | H | F | $CHF_2$ | 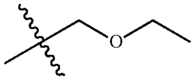 [SMILES: *COCC] |

TABLE 1-continued
Structures of compounds I
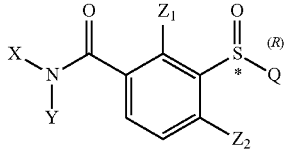
I
| Compound No. | X | Y | $Z_1$ | $Z_2$ | Q |
|---|---|---|---|---|---|
| 705 | 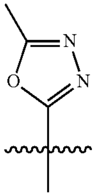 | H | F | $CHF_2$ | 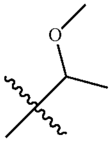 [SMILES: *C(C)OC] |
| 706 | 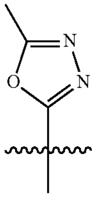 [SMILES: *c1nnc(C)o1] | H | F | $CHF_2$ | 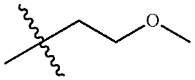 [SMILES: *CCOC] |
| 707 | 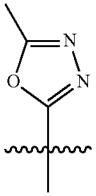 | H | F | $CHF_2$ | 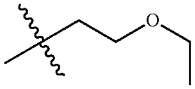 [SMILES: *CCOCC] |

TABLE 1-continued
Structures of compounds I
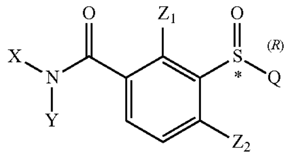
I
| Compound No. | X | Y | $Z_1$ | $Z_2$ | Q |
|---|---|---|---|---|---|
| 708 | 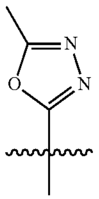 | H | F | $CHF_2$ | 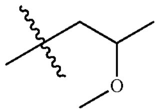 [SMILES: *CC(C)OC] |
| 709 | 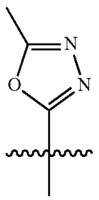 [SMILES: *c1nnc(C)o1] | H | F | $CHF_2$ | 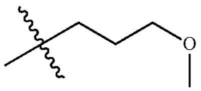 [SMILES: *CCCOC] |
| 710 | 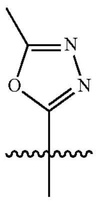 | H | F | $CHF_2$ | 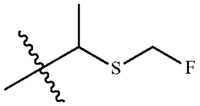 [SMILES: *C(C)SCF] |

TABLE 1-continued
Structures of compounds I
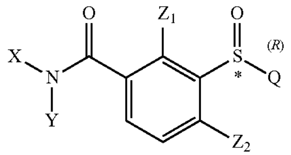
I
| Compound No. | X | Y | $Z_1$ | $Z_2$ | Q |
|---|---|---|---|---|---|
| 711 | 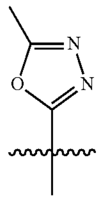 | H | F | $CHF_2$ | 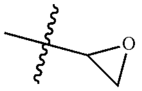 [SMILES: *C1CO1] |
| 712 | 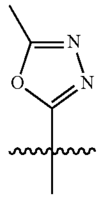 [SMILES: *c1nnc(C)o1] | H | F | $CHF_2$ | 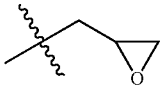 [SMILES: *CC1CO1] |
| 713 | 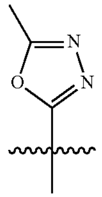 | H | F | $CHF_2$ | 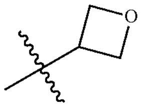 [SMILES: *C1COC1] |

TABLE 1-continued
Structures of compounds I
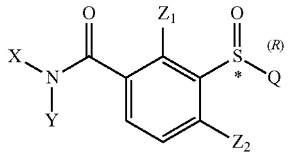
I
| Compound No. | X | Y | $Z_1$ | $Z_2$ | Q |
|---|---|---|---|---|---|
| 714 | 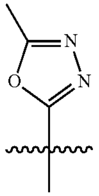 | H | F | $CHF_2$ | 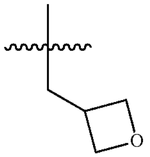 [SMILES: *CC1COC1] |
| 715 | 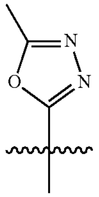 [SMILES: *c1nnc(C)o1] | H | F | $CHF_2$ | 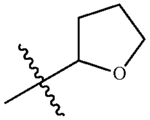 [SMILES: *C1CCCO1] |
| 716 | 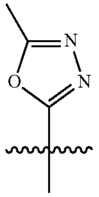 | H | F | $CHF_2$ | 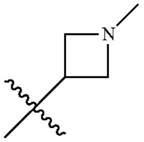 [SMILES: *C1CN(C)C1] |

TABLE 1-continued
Structures of compounds I
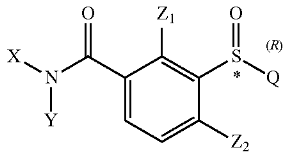
I
| Compound No. | X | Y | $Z_1$ | $Z_2$ | Q |
|---|---|---|---|---|---|
| 717 | 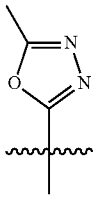 | H | F | $CHF_2$ | 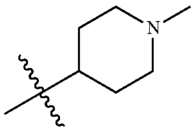 [SMILES: *C1CCN(C)CC1] |
| 718 | 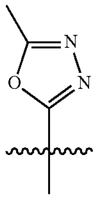 [SMILES: *c1nnc(C)o1] | H | F | $CHF_2$ | 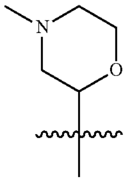 [SMILES: *C1CN(C)CCO1] |
| 719 | 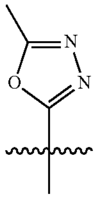 | H | F | $CHF_2$ | 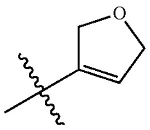 [SMILES: *C1=CCOC1] |

TABLE 1-continued
Structures of compounds I
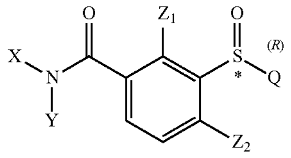
I
| Compound No. | X | Y | $Z_1$ | $Z_2$ | Q |
|---|---|---|---|---|---|
| 720 | 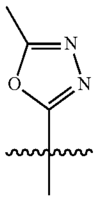 | H | F | $CHF_2$ | 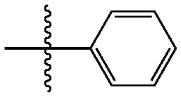 [SMILES: *c1ccccc1] |
| 721 | 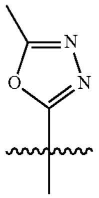 [SMILES: *c1nnc(C)o1] | H | F | $CHF_2$ | 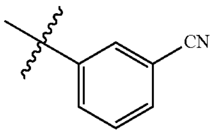 [SMILES: *c1cccc(C#N)c1] |
| 722 | 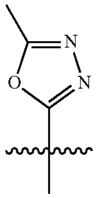 | H | F | $CHF_2$ | 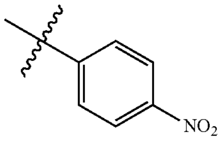 [SMILES: *c1ccc([N+](=O)[O-])cc1] |

TABLE 1-continued
Structures of compounds I
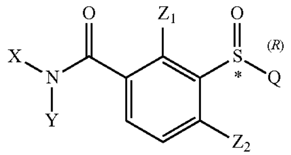
I
| Compound No. | X | Y | $Z_1$ | $Z_2$ | Q |
|---|---|---|---|---|---|
| 723 | 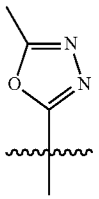 | H | F | $CHF_2$ | 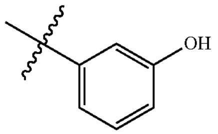 [SMILES: *c1cccc(O)c1] |
| 724 | 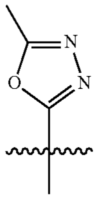 [SMILES: *c1nnc(C)o1] | H | F | $CHF_2$ | 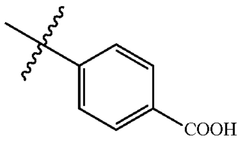 [SMILES: *c1ccc(C(=O)O)cc1] |
| 725 | 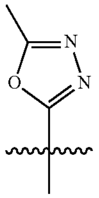 | H | F | $CHF_2$ | 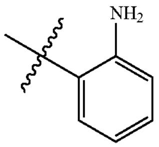 [SMILES: *c1ccccc1N] |

TABLE 1-continued
Structures of compounds I
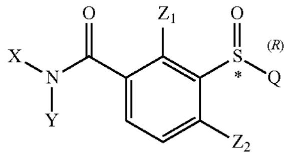
I
| Compound No. | X | Y | $Z_1$ | $Z_2$ | Q |
|---|---|---|---|---|---|
| 726 | 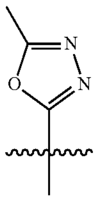 | H | F | $CHF_2$ | 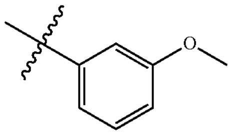 [SMILES: *c1cccc(OC)c1] |
| 727 | 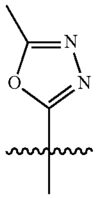 [SMILES: *c1nnc(C)o1] | H | F | $CHF_2$ | 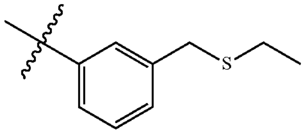 [SMILES: *c1cccc(CSCC)c1] |
| 728 | 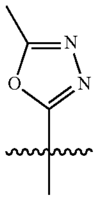 | H | F | $CHF_2$ | 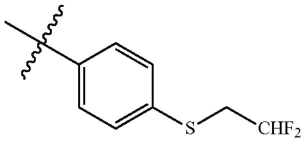 |

TABLE 1-continued
Structures of compounds I
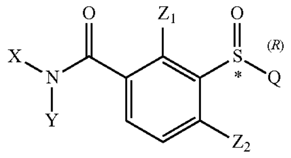
I
| Compound No. | X | Y | $Z_1$ | $Z_2$ | Q |
|---|---|---|---|---|---|
| 729 | 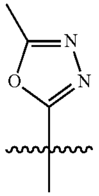 | H | F | $CHF_2$ | 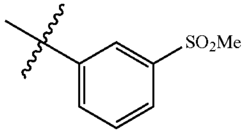 [SMILES: *c1cccc(S(C)(=O)=O)c1] |
| 730 | 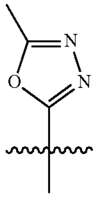 [SMILES: *c1nnc(C)o1] | H | F | $CHF_2$ | 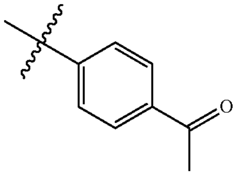 [SMILES: *c1ccc(C(C)=O)cc1] |
| 731 | 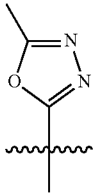 | H | F | $CHF_2$ | 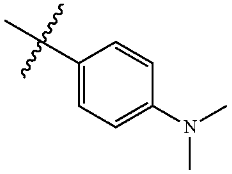 [SMILES: *c1ccc(N(C)C)cc1] |

TABLE 1-continued
Structures of compounds I
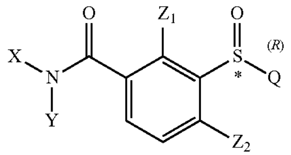
I
| Compound No. | X | Y | $Z_1$ | $Z_2$ | Q |
|---|---|---|---|---|---|
| 732 | 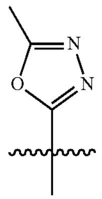 | H | F | $CHF_2$ | 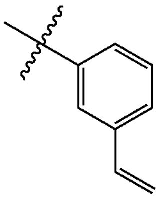 [SMILES: *c1cccc(C=C)c1] |
| 733 | 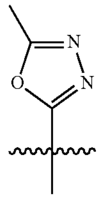 [SMILES: *c1nnc(C)o1] | H | F | $CHF_2$ | 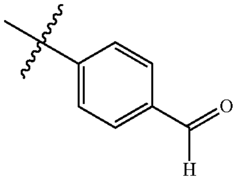 [SMILES: *c1ccc(C=O)cc1] |
| 734 | 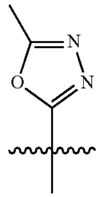 | H | F | $CHF_2$ | 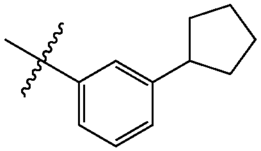 [SMILES: *c1cccc(C2CCCC2)c1] |

TABLE 1-continued
Structures of compounds I
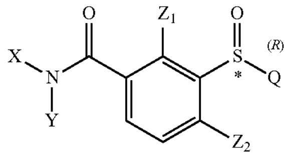
I
| Compound No. | X | Y | $Z_1$ | $Z_2$ | Q |
|---|---|---|---|---|---|
| 735 | 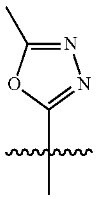 | H | F | $CHF_2$ | 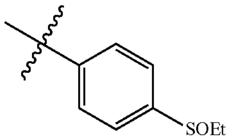 |
| 736 | 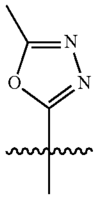 [SMILES: *c1nnc(C)o1] | H | F | $CHF_2$ | 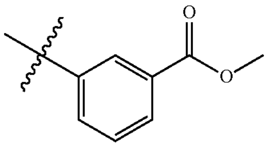 [SMILES: *c1cccc(C(=O)OC)c1] |
| 737 | 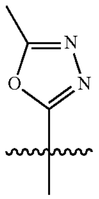 | H | F | $CHF_2$ | 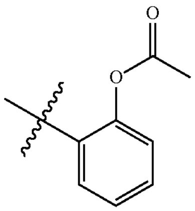 [SMILES: *c1ccccc1OC(C)=O] |

TABLE 1-continued
Structures of compounds I
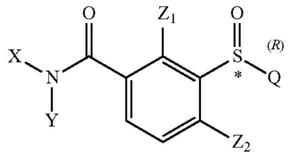
I
| Compound No. | X | Y | $Z_1$ | $Z_2$ | Q |
| --- | --- | --- | --- | --- | --- |
| 738 | 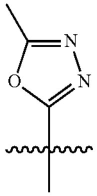 | H | F | $CHF_2$ | 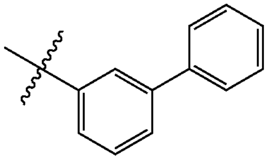 [SMILES: *c1cccc(-c2ccccc2)c1] |
| 739 | 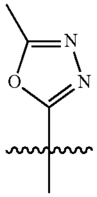 [SMILES: *c1nnc(C)o1] | H | F | $CHF_2$ | 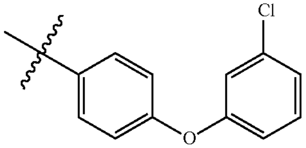 [SMILES: *c1ccc(Oc2cccc(Cl)c2)cc1] |
| 740 | 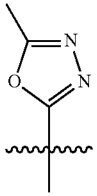 | H | F | $CHF_2$ | 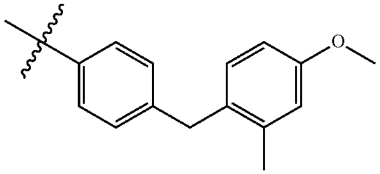 [SMILES: *c1ccc(Cc2ccc(OC)cc2C)cc1] |

TABLE 1-continued
Structures of compounds I
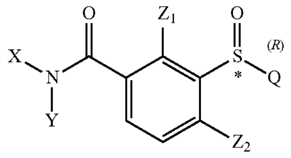
I
| Compound No. | X | Y | $Z_1$ | $Z_2$ | Q |
|---|---|---|---|---|---|
| 741 | 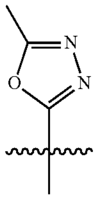 | H | F | $CHF_2$ | 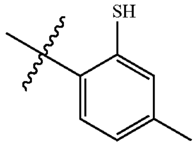 [SMILES: *c1ccc(C)cc1S] |
| 742 | 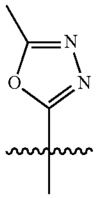 [SMILES: *c1nnc(C)o1] | H | F | $CHF_2$ | 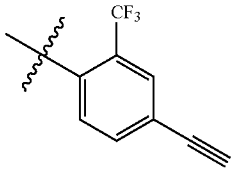 [SMILES: *c1ccc(C#C)cc1C(F)(F)F] |
| 743 | 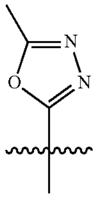 | H | F | $CHF_2$ | 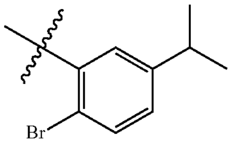 [SMILES: *c1cc(C(C)C)ccc1Br] |

TABLE 1-continued
Structures of compounds I
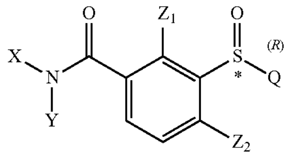
I
| Compound No. | X | Y | $Z_1$ | $Z_2$ | Q |
|---|---|---|---|---|---|
| 744 | 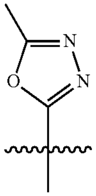 | H | F | $CHF_2$ | 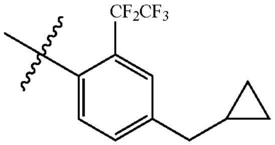 |
| 745 | 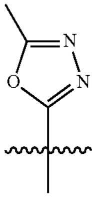 [SMILES: *c1nnc(C)o1] | H | F | $CHF_2$ | 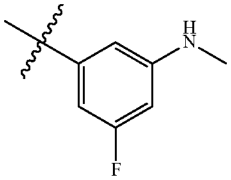 [SMILES: *c1cc(F)cc(NC)c1] |
| 746 | 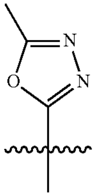 | H | F | $CHF_2$ | 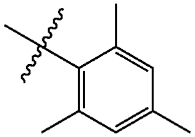 [SMILES: *c1c(C)cc(C)cc1C] |

TABLE 1-continued
Structures of compounds I
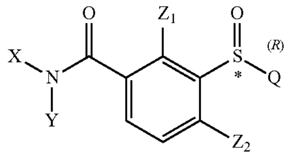
I
| Compound No. | X | Y | $Z_1$ | $Z_2$ | Q |
|---|---|---|---|---|---|
| 747 | 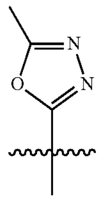 | H | F | $CHF_2$ | 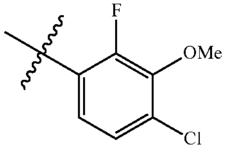 [SMILES: *c1ccc(Cl)c(OC)c1F] |
| 748 | 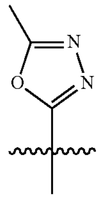 [SMILES: *c1nnc(C)o1] | H | F | $CHF_2$ | 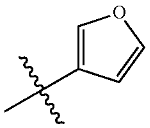 [SMILES: *c1ccoc1] |
| 749 | 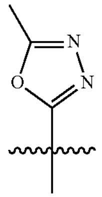 | H | F | $CHF_2$ | 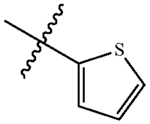 [SMILES: *c1cccs1] |

TABLE 1-continued
Structures of compounds I
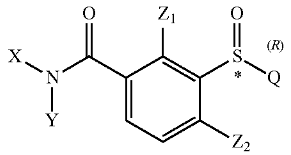
I
| Compound No. | X | Y | $Z_1$ | $Z_2$ | Q |
|---|---|---|---|---|---|
| 750 | 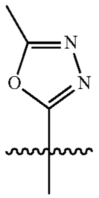 | H | F | $CHF_2$ | 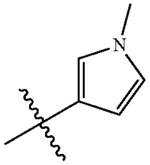 [SMILES: *c1ccn(C)c1] |
| 751 | 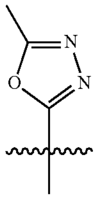 [SMILES: *c1nnc(C)o1] | H | F | $CHF_2$ | 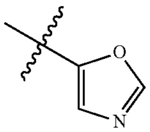 [SMILES: *c1cnco1] |
| 752 | 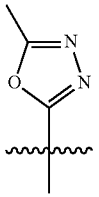 | H | F | $CHF_2$ | 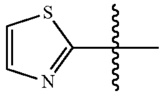 |

TABLE 1-continued
Structures of compounds I
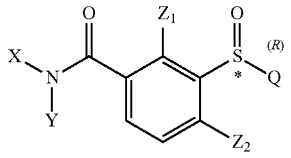
I
| Compound No. | X | Y | $Z_1$ | $Z_2$ | Q |
|---|---|---|---|---|---|
| 753 | 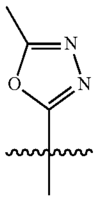 | H | F | $CHF_2$ | 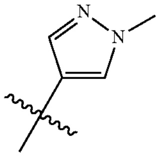 [SMILES: *c1cnn(C)c1] |
| 754 | 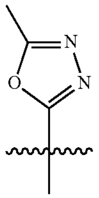 [SMILES: *c1nnc(C)o1] | H | F | $CHF_2$ | 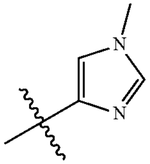 [SMILES: *c1cn(C)cn1] |
| 755 | 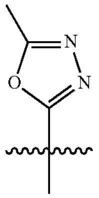 | H | F | $CHF_2$ | 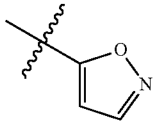 [SMILES: *c1ccno1] |

TABLE 1-continued
Structures of compounds I
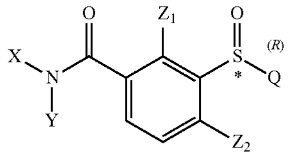
I
| Compound No. | X | Y | $Z_1$ | $Z_2$ | Q |
|---|---|---|---|---|---|
| 756 | 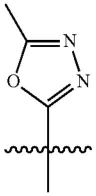 | H | F | $CHF_2$ | 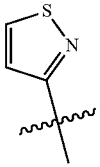 [SMILES: *c1ccsn1] |
| 757 | 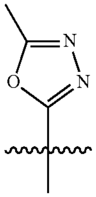 [SMILES: *c1nnc(C)o1] | H | F | $CHF_2$ | 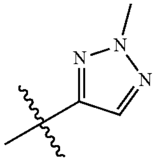 |
| 758 | 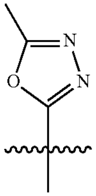 | H | F | $CHF_2$ | 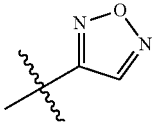 [SMILES: *c1cnon1] |

TABLE 1-continued
Structures of compounds I
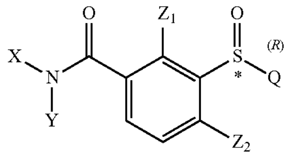
I
| Compound No. | X | Y | $Z_1$ | $Z_2$ | Q |
| --- | --- | --- | --- | --- | --- |
| 759 | 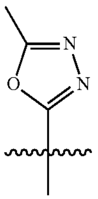 | H | F | $CHF_2$ | 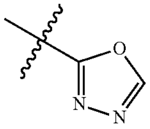 [SMILES: *c1nnco1] |
| 760 | 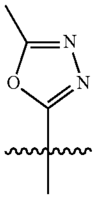 [SMILES: *c1nnc(C)o1] | H | F | $CHF_2$ | 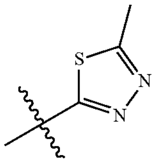 [SMILES: *c1nnc(C)s1] |
| 761 | 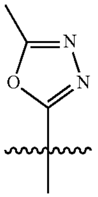 | H | F | $CHF_2$ | 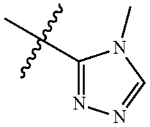 [SMILES: *c1nncn1C] |

TABLE 1-continued
Structures of compounds I
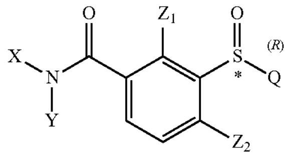
I
| Compound No. | X | Y | $Z_1$ | $Z_2$ | Q |
|---|---|---|---|---|---|
| 762 | 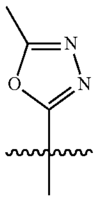 | H | F | $CHF_2$ | 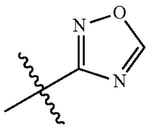 [SMILES: *c1ncon1] |
| 763 | 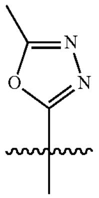 | H | F | $CHF_2$ | 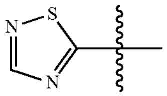 |
| 764 | 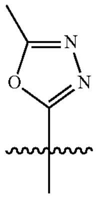 | H | F | $CHF_2$ | 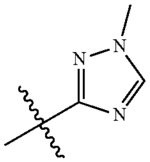 [SMILES: *c1ncn(C)n1] |

TABLE 1-continued
Structures of compounds I
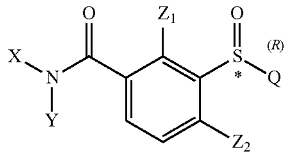
I
| Compound No. | X | Y | $Z_1$ | $Z_2$ | Q |
|---|---|---|---|---|---|
| 765 | 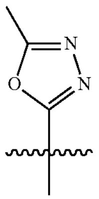 | H | F | $CHF_2$ | 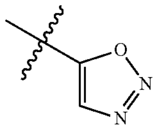 [SMILES: *c1cnno1] |
| 766 | 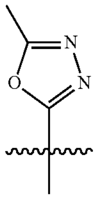 | H | F | $CHF_2$ | 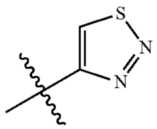 [SMILES: *c1csnn1] |
| 767 | 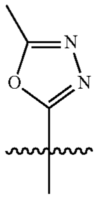 | H | F | $CHF_2$ | 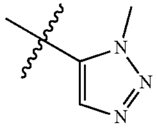 [SMILES: *c1cnnn1C] |

TABLE 1-continued
Structures of compounds I
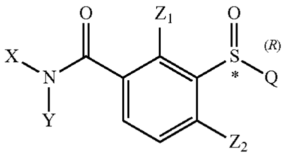
I
| Compound No. | X | Y | $Z_1$ | $Z_2$ | Q |
|---|---|---|---|---|---|
| 768 | 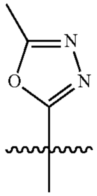 | H | F | $CHF_2$ | 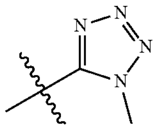 [SMILES: *c1nnnn1C] |
| 769 | 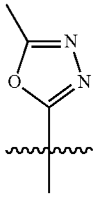 | H | F | $CHF_2$ | 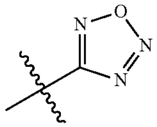 [SMILES: *c1nnon1] |
| 770 | 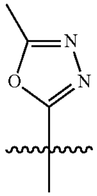 | H | F | $CHF_2$ | 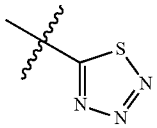 [SMILES: *c1nnns1] |

TABLE 1-continued
Structures of compounds I
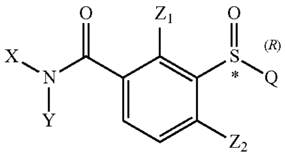
I
| Compound No. | X | Y | $Z_1$ | $Z_2$ | Q |
|---|---|---|---|---|---|
| 771 | 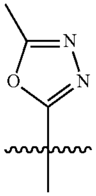 | H | F | $CHF_2$ | 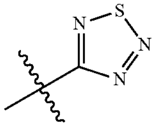 [SMILES: *c1nnsn1] |
| 772 | 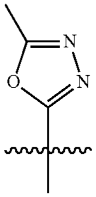 | H | F | $CHF_2$ | 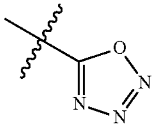 [SMILES: *c1nnno1] |
| 773 | 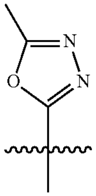 | H | F | $CHF_2$ | 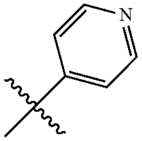 [SMILES: *c1ccncc1] |

TABLE 1-continued
Structures of compounds I
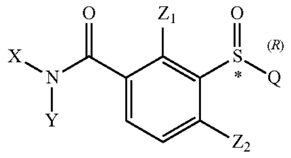
I
| Compound No. | X | Y | $Z_1$ | $Z_2$ | Q |
|---|---|---|---|---|---|
| 774 | 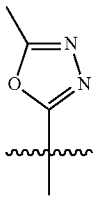 | H | F | $CHF_2$ | 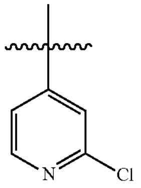 [SMILES: *c1ccnc(Cl)c1] |
| 775 | 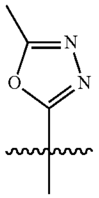 | H | F | $CHF_2$ | 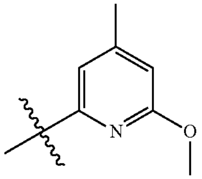 [SMILES: *c1cc(C)cc(OC)n1] |
| 776 | 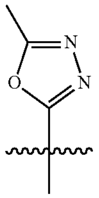 | H | F | $CHF_2$ | 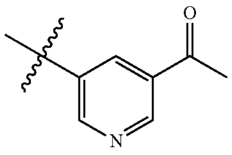 [SMILES: *c1cncc(C(C)=O)c1] |

TABLE 1-continued
Structures of compounds I
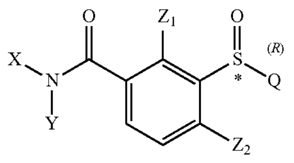
I
| Compound No. | X | Y | $Z_1$ | $Z_2$ | Q |
|---|---|---|---|---|---|
| 777 | 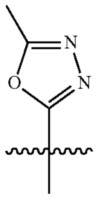 | H | F | $CHF_2$ | 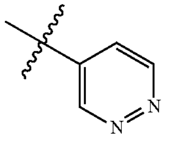 |
| 778 | 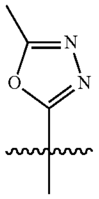 | H | F | $CHF_2$ | 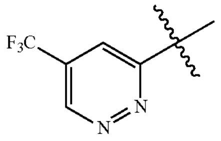 |
| 779 | 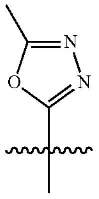 | H | F | $CHF_2$ | 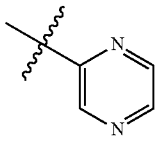 [SMILES: *c1cnccn1] |

TABLE 1-continued
Structures of compounds I
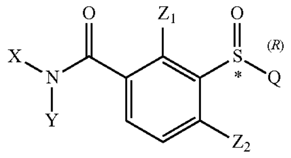
I
| Compound No. | X | Y | $Z_1$ | $Z_2$ | Q |
|---|---|---|---|---|---|
| 780 | 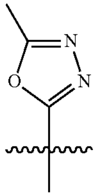 | H | F | $CHF_2$ | 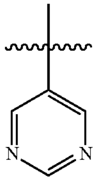 [SMILES: *c1cncnc1] |
| 781 | 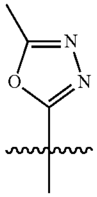 | H | F | $CHF_2$ | 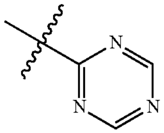 [SMILES: *c1ncncn1] |
| 782 | 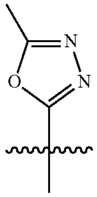 | H | F | $CHF_2$ | 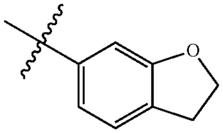 |

TABLE 1-continued
Structures of compounds I
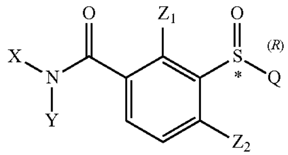
I
| Compound No. | X | Y | $Z_1$ | $Z_2$ | Q |
|---|---|---|---|---|---|
| 783 | 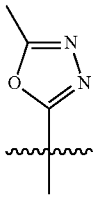 | H | F | $CHF_2$ | 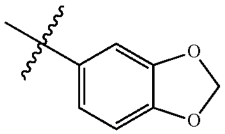 |
| 784 | 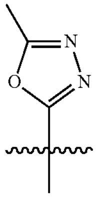 | H | F | $CHF_2$ | 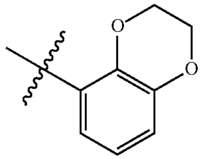 [SMILES: *c1cccc2c1OCCO2] |
| 785 | 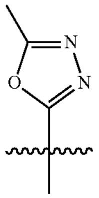 | H | F | $CHF_2$ | 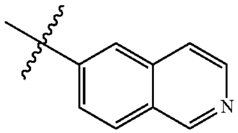 [SMILES: *c1ccc2cnccc2c1] |

TABLE 1-continued
Structures of compounds I
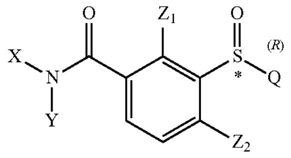
I
| Compound No. | X | Y | $Z_1$ | $Z_2$ | Q |
|---|---|---|---|---|---|
| 786 | 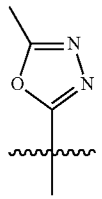 | H | F | $CHF_2$ | 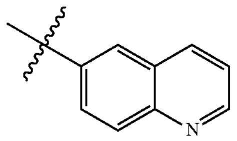 [SMILES: *c1ccc2ncccc2c1] |
| 787 | 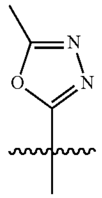 | H | F | $CHF_2$ | 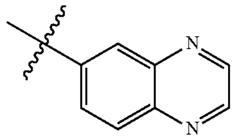 [SMILES: *c1ccc2nccnc2c1] |
| 788 | 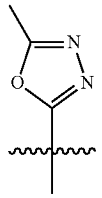 | H | F | $CHF_2$ | 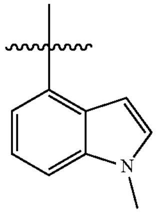 [SMILES: *c1cccc2c1ccn2C] |

TABLE 1-continued
Structures of compounds I
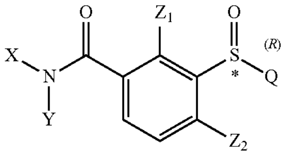
I
| Compound No. | X | Y | $Z_1$ | $Z_2$ | Q |
|---|---|---|---|---|---|
| 789 | 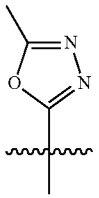 | H | F | $CHF_2$ | 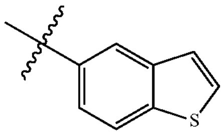 [SMILES: *c1ccc2sccc2c1] |
| 790 | 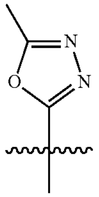 | H | F | $CHF_2$ | 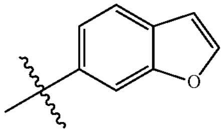 [SMILES: *c1ccc2ccoc2c1] |
| 791 | 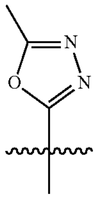 | H | F | $CHF_2$ | 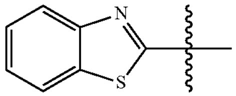 [SMILES: *c1nc2ccccc2s1] |

TABLE 1-continued
Structures of compounds I
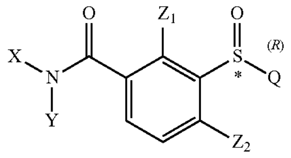
I
| Compound No. | X | Y | $Z_1$ | $Z_2$ | Q |
|---|---|---|---|---|---|
| 792 | 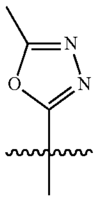 | H | F | $CHF_2$ | 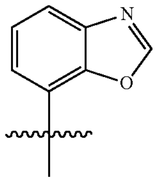 [SMILES: *c1cccc2ncoc12] |
| 793 | 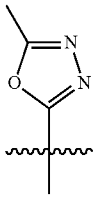 | H | F | $CHF_2$ | 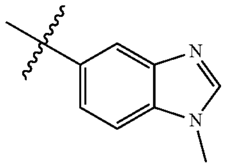 [SMILES: *c1ccc2c(c1)ncn2C] |
| 794 | 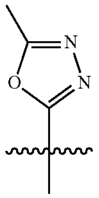 | H | F | $CHF_2$ | 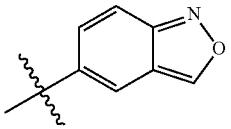 [SMILES: *c1ccc2nocc2c1] |

TABLE 1-continued
Structures of compounds I
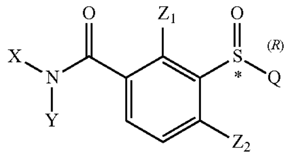
I
| Compound No. | X | Y | $Z_1$ | $Z_2$ | Q |
|---|---|---|---|---|---|
| 795 | 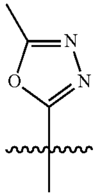 | H | F | $CHF_2$ | 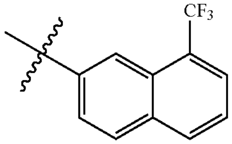 [SMILES: *c1ccc2cccc(C(F)(F)F)c2c1] |
| 796 | 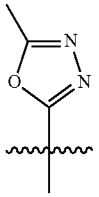 [SMILES: *c1nnc(C)o1] | H | F | $CHF_2$ | 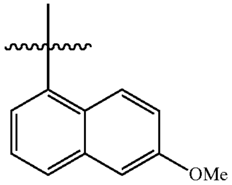 [SMILES: *c1cccc2cc(OC)ccc12] |
| 797 | 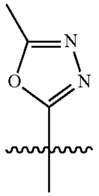 | H | F | $CHF_2$ | 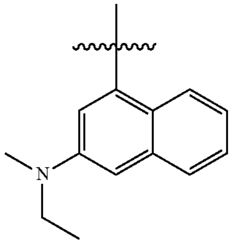 [SMILES: *c1cc(N(C)CC)cc2ccccc12] |

TABLE 1-continued
Structures of compounds I
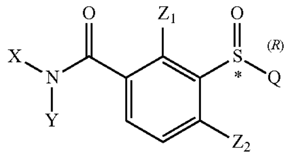
I
| Compound No. | X | Y | $Z_1$ | $Z_2$ | Q |
|---|---|---|---|---|---|
| 798 | 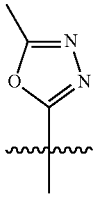 | H | F | $CHF_2$ | 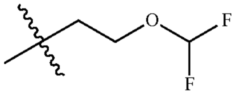 |
| 799 | 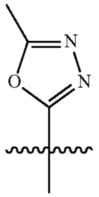 | H | F | $CHF_2$ | 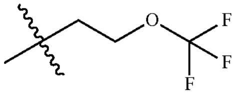 |
| 800 | 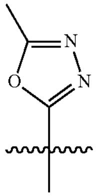 | H | F | $CHF_2$ | 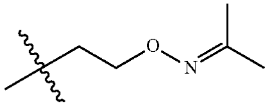 [SMILES: *CCON=C(C)C] |

TABLE 1-continued
Structures of compounds I
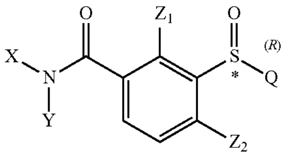
I
| Compound No. | X | Y | $Z_1$ | $Z_2$ | Q |
|---|---|---|---|---|---|
| 801 | 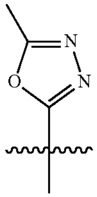 | H | F | $CHF_2$ | 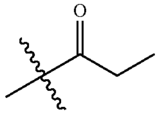 [SMILES: *C(=O)CC] |
| 802 | 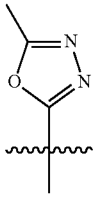 | H | F | $CHF_2$ | 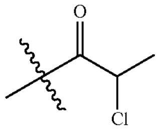 |
| 803 | 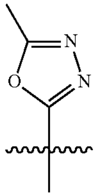 | H | F | $CHF_2$ | 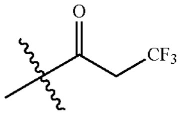 [SMILES: *C(=O)CC(F)(F)F] |

TABLE 1-continued
Structures of compounds I
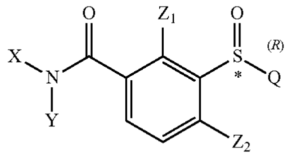
I
| Compound No. | X | Y | $Z_1$ | $Z_2$ | Q |
|---|---|---|---|---|---|
| 804 | 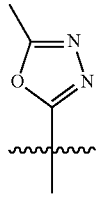 | H | F | $CHF_2$ | 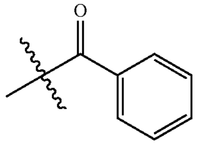 [SMILES: *C(=O)c1ccccc1] |
| 805 | 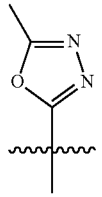 | H | F | $CHF_2$ | 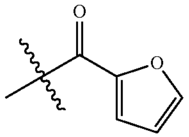 [SMILES: *C(=O)c1ccco1] |
| 806 | 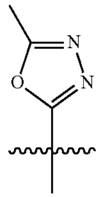 | H | F | $CHF_2$ | 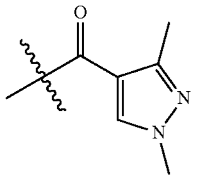 [SMILES: *C(=O)c1cn(C)nc1C] |

TABLE 1-continued
Structures of compounds I
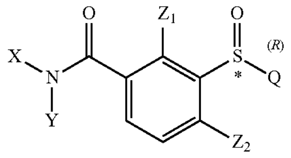
I
| Compound No. | X | Y | $Z_1$ | $Z_2$ | Q |
|---|---|---|---|---|---|
| 807 | 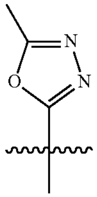 | H | F | $CHF_2$ | 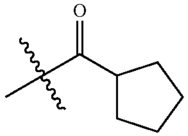 [SMILES: *C(=O)C1CCCC1] |
| 808 | 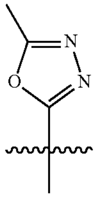 | H | F | $CHF_2$ | 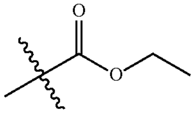 [SMILES: *C(=O)OCC] |
| 809 | 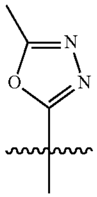 | H | F | $CHF_2$ | 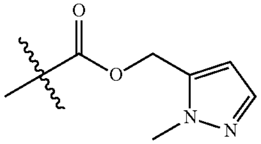 [SMILES: *C(=O)OCc1ccnn1C] |

TABLE 1-continued
Structures of compounds I
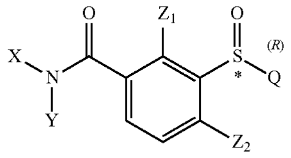
I
| Compound No. | X | Y | $Z_1$ | $Z_2$ | Q |
|---|---|---|---|---|---|
| 810 | 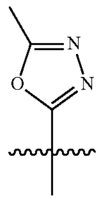 | H | F | $CHF_2$ | 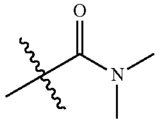 [SMILES: *C(=O)N(C)C] |
| 811 | 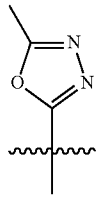 | H | F | $CHF_2$ | 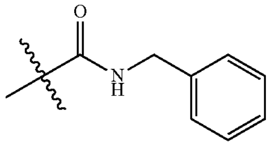 [SMILES: *C(=O)NCc1ccccc1] |
| 812 | 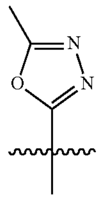 | H | F | $CHF_2$ | 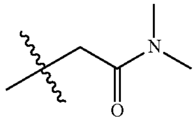 [SMILES: *CC(=O)N(C)C] |

TABLE 1-continued
Structures of compounds I
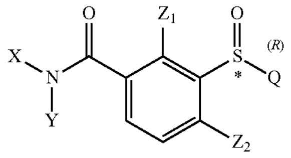
I
| Compound No. | X | Y | $Z_1$ | $Z_2$ | Q |
|---|---|---|---|---|---|
| 813 | 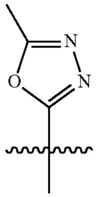 | H | F | $CHF_2$ | 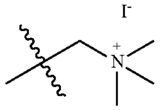 |
| 814 | 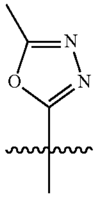 | H | F | $CHF_2$ | 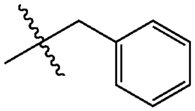 [SMILES: *Cc1ccccc1] |
| 815 | 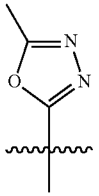 | H | F | $CHF_2$ | 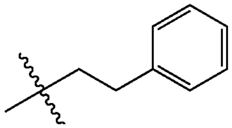 [SMILES: *CCc1ccccc1] |

TABLE 1-continued
Structures of compounds I
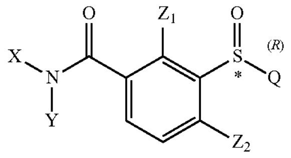
I
| Compound No. | X | Y | $Z_1$ | $Z_2$ | Q |
|---|---|---|---|---|---|
| 816 | 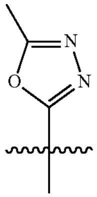 | H | F | $CHF_2$ | 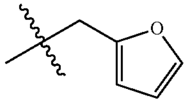 [SMILES: *Cc1ccco1] |
| 817 | 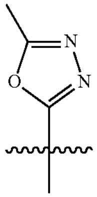 | H | F | $CHF_2$ | 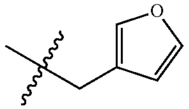 [SMILES: *Cc1ccoc1] |
| 818 | 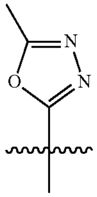 | H | F | $CHF_2$ | 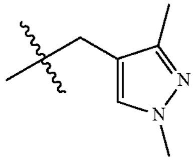 [SMILES: *Cc1cn(C)nc1C] |

TABLE 1-continued
Structures of compounds I
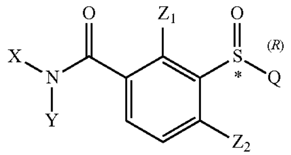
I
| Compound No. | X | Y | $Z_1$ | $Z_2$ | Q |
|---|---|---|---|---|---|
| 819 | 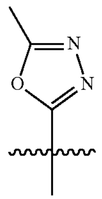 | H | F | $CHF_2$ | 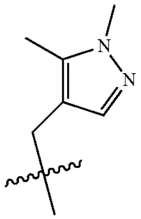 [SMILES: *Cc1cnn(C)c1C] |
| 820 | 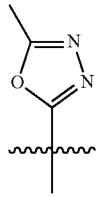 | H | F | $CHF_2$ | 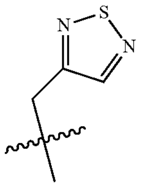 [SMILES: *Cc1cnsn1] |
| 821 | 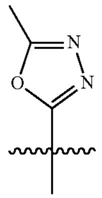 | H | F | $CHF_2$ | 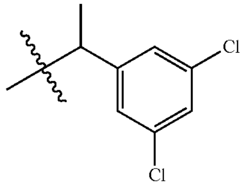 [SMILES: *C(C)c1cc(Cl)cc(Cl)c1] |

TABLE 1-continued
Structures of compounds I
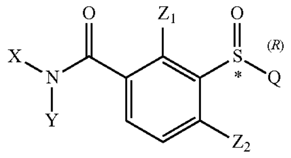
I
| Compound No. | X | Y | $Z_1$ | $Z_2$ | Q |
|---|---|---|---|---|---|
| 822 | 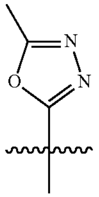 | H | F | $CHF_2$ | 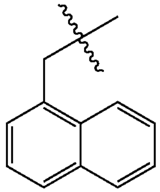 [SMILES: *Cc1cccc2ccccc12] |
| 823 | 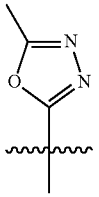 | H | F | $CHF_2$ | 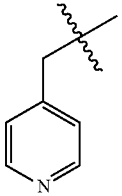 [SMILES: *Cc1ccncc1] |
| 824 | 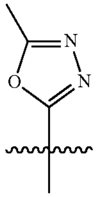 | H | F | $CHF_2$ | 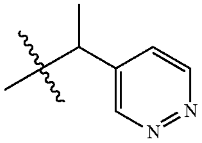 [SMILES: *C(C)c1ccnnc1] |

TABLE 1-continued
Structures of compounds I
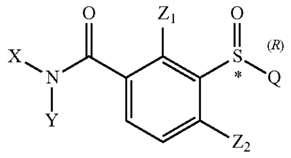
I
| Compound No. | X | Y | $Z_1$ | $Z_2$ | Q |
|---|---|---|---|---|---|
| 825 | 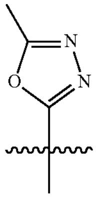 | H | F | $CHF_2$ | 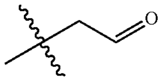 [SMILES: *CC=O] |
| 826 | 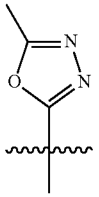 | H | F | $CHF_2$ | 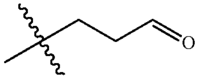 [SMILES: *CCC=O] |
| 827 | 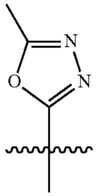 | H | F | $CHF_2$ | 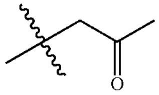 |

TABLE 1-continued
Structures of compounds I
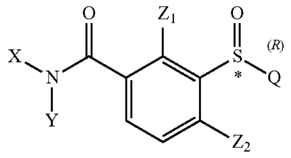
I
| Compound No. | X | Y | $Z_1$ | $Z_2$ | Q |
|---|---|---|---|---|---|
| 828 | 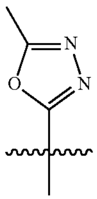 | H | F | $CHF_2$ | 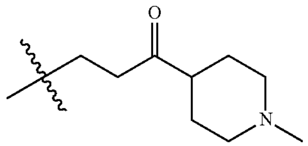 [SMILES: *CCC(=O)C1CCN(C)CC1] |
| 829 | 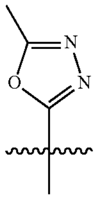 | H | F | $CHF_2$ | 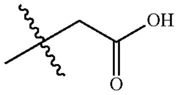 [SMILES: *CC(=O)O] |
| 830 | 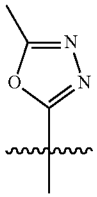 | H | F | $CHF_2$ | 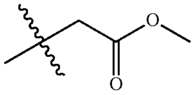 |

TABLE 1-continued
Structures of compounds I
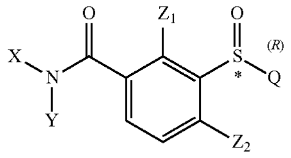
I
| Compound No. | X | Y | $Z_1$ | $Z_2$ | Q |
|---|---|---|---|---|---|
| 831 | 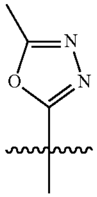 | H | F | $CHF_2$ | 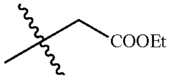 [SMILES: *CC(=O)OCC] |
| 832 | 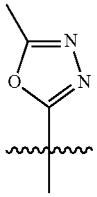 [SMILES: *c1nnc(C)o1] | H | F | $CHF_2$ | 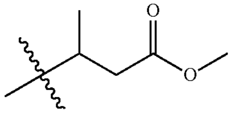 [SMILES: *C(C)CC(=O)OC] |
| 833 | 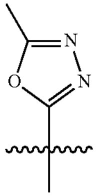 | H | F | $CHF_2$ | 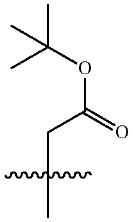 [SMILES: *CC(=O)OC(C)(C)C] |

TABLE 1-continued
Structures of compounds I
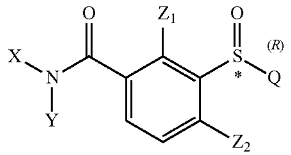
I
| Compound No. | X | Y | $Z_1$ | $Z_2$ | Q |
|---|---|---|---|---|---|
| 834 | 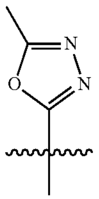 | H | F | $CHF_2$ | 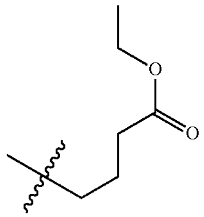 [SMILES: *CCCC(=O)OCC] |
| 835 | 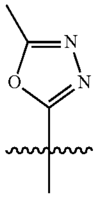 | H | F | $CHF_2$ | 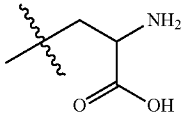 |
| 836 | 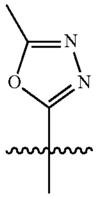 [SMILES: *c1nnc(C)o1] | H | F | $CHF_2$ | 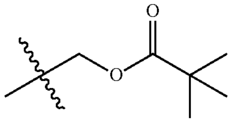 [SMILES: *COC(=O)C(C)(C)C] |

TABLE 1-continued
Structures of compounds I
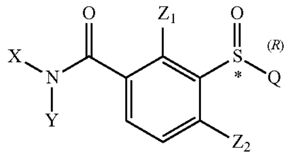
I
| Compound No. | X | Y | Z1 | Z2 | Q |
|---|---|---|---|---|---|
| 837 | 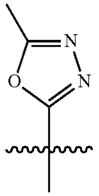 | H | F | $CHF_2$ | 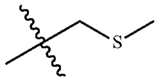 [SMILES: *CSC] |
| 838 | 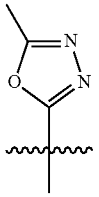 [SMILES: *c1nnc(C)o1] | H | F | $CHF_2$ | 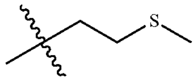 [SMILES: *CCSC] |
| 839 | 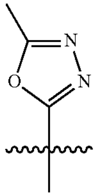 | H | F | $CHF_2$ | 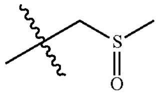 [SMILES: *CS(C)=O] |

TABLE 1-continued
Structures of compounds I
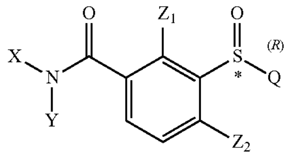
I
| Compound No. | X | Y | $Z_1$ | $Z_2$ | Q |
|---|---|---|---|---|---|
| 840 | 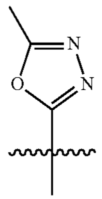 | H | F | $CHF_2$ | 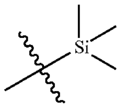 [SMILES: *[Si](C)(C)C] |
| 841 | 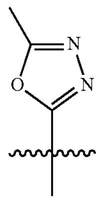 [SMILES: *c1nnc(C)o1] | H | F | $CHF_2$ | 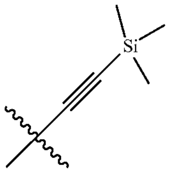 [SMILES: *C#C[Si](C)(C)C] |
| 842 | 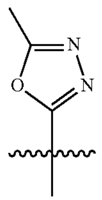 | H | F | $CHF_2$ | 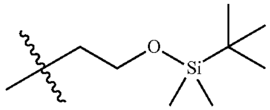 |

TABLE 1-continued
Structures of compounds I
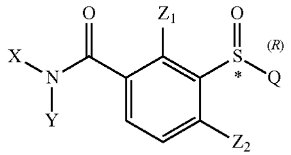
I
| Compound No. | X | Y | $Z_1$ | $Z_2$ | Q |
|---|---|---|---|---|---|
| 843 | 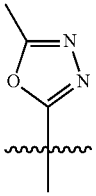 | H | F | $CHF_2$ | 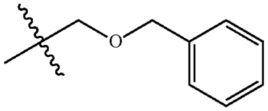 [SMILES: *COCc1ccccc1] |
| 844 | 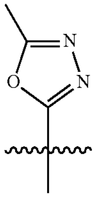 [SMILES: *c1nnc(C)o1] | Me | F | $CHF_2$ | 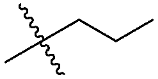 [SMILES: *CCC] |
| 845 | 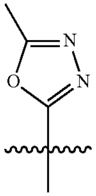 | 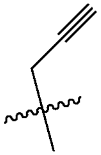 [SMILES: *CC#C] | F | $CHF_2$ | 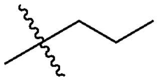 [SMILES: *CCC] |

TABLE 1-continued
Structures of compounds I
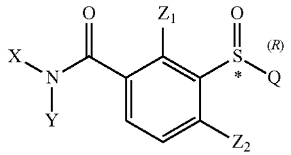
I
| Compound No. | X | Y | $Z_1$ | $Z_2$ | Q |
|---|---|---|---|---|---|
| 846 | 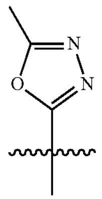 | 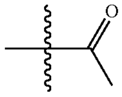 [SMILES: *C(C)=O] | F | $CHF_2$ | 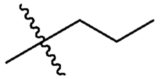 [SMILES: *CCC] |
| 847 | 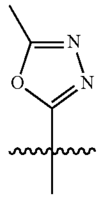 [SMILES: *c1nnc(C)o1] | 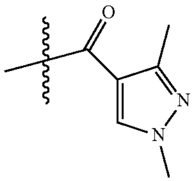 [SMILES: *C(=O)c1cn(C)nc1C] | F | $CHF_2$ | 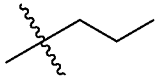 [SMILES: *CCC] |
| 848 | 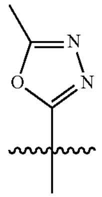 | 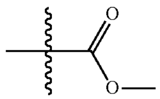 [SMILES: *C(=O)OC] | F | $CHF_2$ | 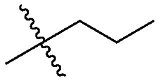 [SMILES: *CCC] |

TABLE 1-continued
Structures of compounds I
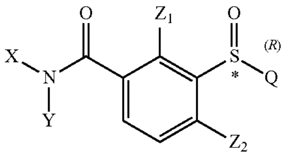
I
| Compound No. | X | Y | $Z_1$ | $Z_2$ | Q |
|---|---|---|---|---|---|
| 849 | 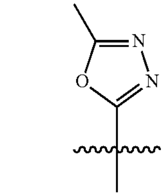 | 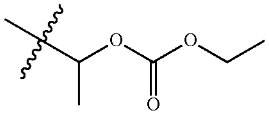 [SMILES: *C(C)OC(=O)OCC] | F | $CHF_2$ | 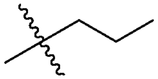 [SMILES: *CCC] |
| 850 | 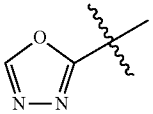 [SMILES: *c1nnco1] | H | F | $CHF_2$ | 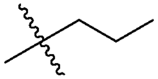 [SMILES: *CCC] |
| 851 | 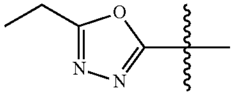 [SMILES: *c1nnc(CC)o1] | H | F | $CHF_2$ | 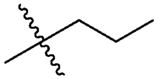 [SMILES: *CCC] |
| 852 | 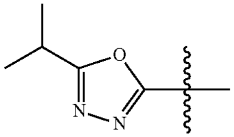 [SMILES: *c1nnc(C(C)C)o1] | H | F | $CHF_2$ | 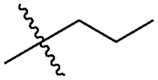 [SMILES: *CCC] |
| 853 | 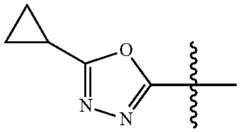 [SMILES: *c1nnc(C2CC2)o1] | H | F | $CHF_2$ | 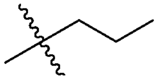 [SMILES: *CCC] |

TABLE 1-continued
Structures of compounds I
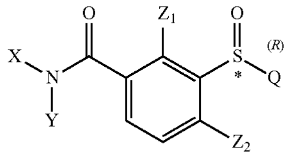
I
| Compound No. | X | Y | $Z_1$ | $Z_2$ | Q |
| --- | --- | --- | --- | --- | --- |
| 854 | 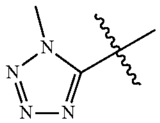 [SMILES: *c1nnnn1C] | H | F | $CHF_2$ | Me |
| 855 | 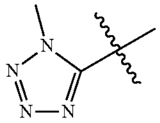 [SMILES: *c1nnnn1C] | H | F | $CHF_2$ | Et |
| 856 | 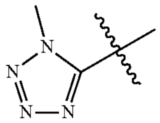 [SMILES: *c1nnnn1C] | H | F | $CHF_2$ | 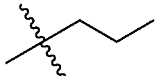 [SMILES: *CCC] |
| 857 | 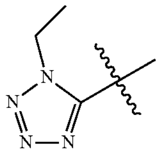 [SMILES: *c1nnnn1CC] | H | F | $CHF_2$ | 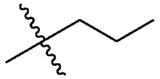 [SMILES: *CCC] |
| 858 | 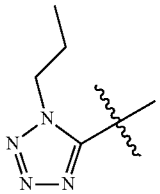 [SMILES: *c1nnnn1CCC] | H | F | $CHF_2$ | 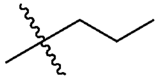 [SMILES: *CCC] |

TABLE 1-continued
Structures of compounds I
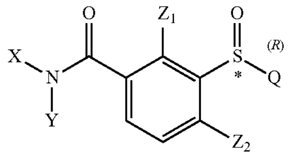
I
| Compound No. | X | Y | $Z_1$ | $Z_2$ | Q |
|---|---|---|---|---|---|
| 859 | 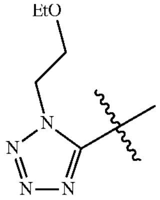 [SMILES: *c1nnnn1CCOCC] | H | F | $CHF_2$ | 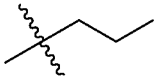 [SMILES: *CCC] |
| 860 | 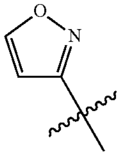 | H | F | $CHF_2$ | 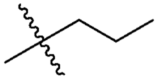 [SMILES: *CCC] |
| 861 | 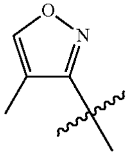 [SMILES: *c1nocc1C] | H | F | $CHF_2$ | 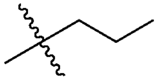 [SMILES: *CCC] |
| 862 | 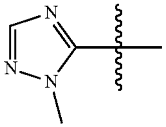 [SMILES: *c1ncnn1C] | H | F | $CHF_2$ | 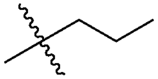 [SMILES: *CCC] |

TABLE 1-continued
Structures of compounds I
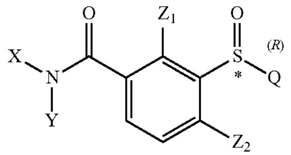
I
| Compound No. | X | Y | $Z_1$ | $Z_2$ | Q |
|---|---|---|---|---|---|
| 863 | 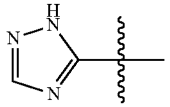 [SMILES: *c1ncn[nH]1] | H | F | $CHF_2$ | 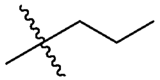 [SMILES: *CCC] |
| 864 | 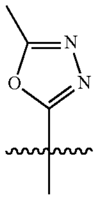 | H | OMe | $CHF_2$ | 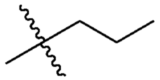 [SMILES: *CCC] |
| 865 | 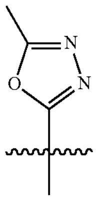 | H | SMe | $CHF_2$ | 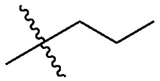 [SMILES: *CCC] |

TABLE 1-continued
Structures of compounds I
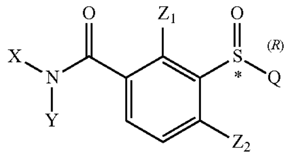
I
| Compound No. | X | Y | $Z_1$ | $Z_2$ | Q |
|---|---|---|---|---|---|
| 866 | 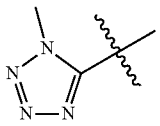 [SMILES: *c1nnnn1C] | H | OMe | $CHF_2$ | 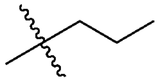 [SMILES: *CCC] |
| 867 | 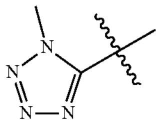 [SMILES: *c1nnnn1C] | H | SMe | $CHF_2$ | 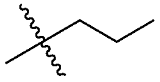 [SMILES: *CCC] |

TABLE 2

| Compound No. | $^1$HNMR |
|---|---|
| 1 | 1H NMR (500 MHz, DMSO-d6) 12.37 (s, 1H), 8.04 (dd, J = 8.0, 7.0 Hz, 1H), 7.78 (d, J = 8.0 Hz, 1H), 3.35 (s, 3H), 2.50 (s, 3H). |
| 2 | 1H NMR (500 MHz, DMSO-d6) 12.37 (s, 1H), 8.04 (dd, J = 8.0, 7.0 Hz, 1H), 7.78 (d, J = 8.0 Hz, 1H), 3.47 (q, J = 7.5 Hz, 2H), 2.50 (s, 3H), 1.12 (t, J = 7.5 Hz, 3H). |
| 3 | 1H NMR (500 MHz, DMSO-d6) 12.57 (s, 1H), 8.07 (dd, J = 8.0, 7.0 Hz, 1H), 7.82 (d, J = 8.0 Hz, 1H), 3.57-3.47 (m, 2H), 2.48 (s, 3H), 1.70-1.52 (m, 2H), 1.08-0.93 (m, 3H). |
| 4 | 1H NMR (500 MHz, DMSO-d6) 12.27 (s, 1H), 8.06 (dd, J = 8.0, 7.0 Hz, 1H), 7.88 (d, J = 8.0 Hz, 1H), 3.57 (t, J = 7.5 Hz, 2H), 2.48 (s, 3H), 1.72-1.46 (m, 4H), 0.93 (t, J = 7.5 Hz, 3H). |
| 5 | 1H NMR (500 MHz, DMSO-d6) 12.41 (s, 1H), 8.12 (dd, J = 8.0, 7.0 Hz, 1H), 7.83 (d, J = 8.0 Hz, 1H), 3.88-3.80 (m, 1H), 2.50 (s, 3H), 1.85-1.73 (m, 2H), 1.23 (d, J = 7.0 Hz, 3H), 1.10 (t, J = 7.5 Hz, 3H). |
| 6 | 1H NMR (500 MHz, DMSO-d6) 12.41 (s, 1H), 8.05 (dd, J = 8.0, 7.0 Hz, 1H), 7.79 (d, J = 8.0 Hz, 1H), 3.55 (d, J = 7.0 Hz, 2H), 2.50 (s, 3H), 1.92-1.86 (m, 1H), 1.20 (d, J = 7.5 Hz, 6H). |
| 7 | 1H NMR (500 MHz, DMSO-d6) 12.37 (s, 1H), 8.08 (dd, J = 8.0, 7.0 Hz, 1H), 7.72 (d, J = 8.0 Hz, 1H), 2.50 (s, 3H), 1.36 (s, 9H). |
| 8 | 1H NMR (500 MHz, DMSO-d6) 12.37 (s, 1H), 8.05 (dd, J = 8.0, 7.0 Hz, 1H), 7.75 (d, J = 8.0 Hz, 1H), 3.45 (t, J = 7.5 Hz, 2H), 2.50 (s, 3H), 1.82-1.56 (m, 6H), 1.12 (t, J = 7.5 Hz, 3H). |
| 9 | 1H NMR (500 MHz, DMSO-d6) 12.37 (s, 1H), 8.04 (dd, J = 8.0, 7.0 Hz, 1H), 7.78 (d, J = 8.0 Hz, 1H), 3.49 (t, J = 7.5 Hz, 2H), 2.50 (s, 3H), 1.82-1.76 (m, 3H), 1.22 (d, J = 7.5 Hz, 6H). |
| 10 | 1H NMR (500 MHz, DMSO-d6) 12.41 (s, 1H), 8.05 (dd, J = 8.0, 7.0 Hz, 1H), 7.79 (d, J = 8.0 Hz, 1H), 3.55 (d, J = 7.0 Hz, 2H), 2.50 (s, 3H), 1.92-1.66 (m, 3H), 1.29 (d, J = 7.5 Hz, 3H), 1.10 (t, J = 7.5 Hz, 3H). |
| 11 | 1H NMR (500 MHz, DMSO-d6) δ 12.38 (s, 1H), 8.03 (dd, J = 8.0, 7.0 Hz, 1H), 7.59 (d, J = 8.0 Hz, 1H), 2.64 (s, 2H), 2.46 (s, 3H), 0.94 (s, 9H). |
| 12 | 1H NMR (500 MHz, DMSO-d6) 12.38 (s, 1H), 8.05 (dd, J = 8.0, 7.0 Hz, 1H), 7.81 (d, J = 8.0 Hz, 1H), 3.47 (t, J = 7.5 Hz, 2H), 2.51 (s, 3H), 1.85-1.55 (m, 8H), 1.10 (t, J = 7.5 Hz, 3H). |
| 13 | 1H NMR (500 MHz, DMSO-d6) δ 12.38 (s, 1H), 8.04 (dd, J = 7.5,6.0 Hz, 1H), 7.61 (d, J = 7.5 Hz, 1H), 2.76 (t, J = 8.0 Hz, 2H), 2.46 (s, 3H), 1.49 (t, J = 8.0 Hz, 2H), 0.86 (s, 9H). |
| 14 | 1H NMR (500 MHz, DMSO-d6) 12.38 (s, 1H), 8.07 (dd, J = 8.0, 7.0 Hz, 1H), 7.79 (d, J = 8.0 Hz, 1H), 3.48 (t, J = 7.5 Hz, 2H), 2.50 (s, 3H), 1.85-1.53 (m, 10H), 1.10 (t, J = 7.5 Hz, 3H). |
| 17 | 1H NMR (500 MHz, DMSO-d6) δ 12.38 (s, 1H),8.04 (dd, J = 7.5, 6.0 Hz, 1H), 7.59 (d J = 7.5Hz, 1H), 2.76 (t, J = 8.1 Hz, 2H), 2.46 (s, 3H), 1.55-1.46 (m, 2H), 0.98-0.87 (m, 1H), 0.42-0.31 (m, 2H), 0.24-0.18 (m, 2H). |
| 18 | 1H NMR (500 MHz, DMSO-d6) δ 12.38 (s, 1H), 8.03 (dd, J = 7.5, 6.0 Hz, 1H), 7.59 (d, J = 7.5, 1H), 2.76 (t, J = 5.2 Hz, 2H), 2.46 (s, 3H), 1.72-1.43 (m, 7H), 1.40-1.29 (m, 3H), 1.29-1.20 (m, 2H), 1.20-1.15 (m, 1H). |
| 20 | 1H NMR (500 MHz, DMSO-d6) δ 12.38 (s, 1H), 8.03 (dd, J = 7.5, 6.0 Hz, 1H), 7.59 (d, J = 7.5 Hz, 1H), 5.87-5.76 (m, 1H), 5.08-4.93 (m, 2H), 2.82 (t, J = 8.0 Hz, 2H), 2.46 (s, 3H), 2.34-2.26 (m, 2H). |
| 21 | 1H NMR (500 MHz, DMSO-d6) δ 12.38 (s, 1H), 8.08 (dd, J = 7.5, 6.0 Hz, 1H), 7.60 (d, J = 7.5 Hz, 1H), 5.55-5.43 (m, 2H), 3.45-3.34 (m, 2H), 2.46 (s, 3H), 1.65-1.60 (m, 3H). |
| 24 | 1H NMR (500 MHz, DMSO-d6) δ 12.38 (s, 1H), 8.04 (dd, J = 7.5, 6.0 Hz, 1H), 7.59 (d, J = 7.5 Hz, 1H), 3.05 (t, J = 3.0 Hz, 1H), 2.95 (t, J = 8.0 Hz, 2H), 2.46 (s, 3H), 2.37-2.26 (m, 2H). |
| 25 | 1H NMR (500 MHz, DMSO-d6) δ 12.38 (s, 1H), 8.02 (dd, J = 7.5, 6.0 Hz, 1H), 7.59 (d, J = 7.5 Hz, 1H), 3.47 (q, J = 2.0 Hz, 2H), 2.46 (s, 3H), 1.77 (t, J = 2.0 Hz, 3H). |

TABLE 2-continued

| Compound No. | $^1$HNMR |
|---|---|
| 26 | 1H NMR (500 MHz, DMSO-d6) δ 12.38 (s, 1H),8.03 (dd, J = 7.5, 6.0 Hz, 1H), 7.59 (d, J = 7.5 Hz, 1H), 4.35 (t, J = 7.5 Hz, 1H), 4.25 (t, J = 7.5 Hz, 1H), 2.76 (t, J = 5.5 Hz, 2H), 2.46 (s, 3H), 1.90-1.76 (m, 2H). |
| 27 | 1H NMR (500 MHz, DMSO-d6) δ 12.38 (s, 1H), 8.08 (dd, J = 7.5, 6.0 Hz, 1H), 7.59 (d, J = 7.5 Hz, 1H), 5.20-5.11 (m, 1H), 3.04-2.93 (m, 1H), 2.79-2.68 (m, 1H), 2.40(s, 3H), 1.41 (dd, J = 25.0, 7.0 Hz, 3H). |
| 28 | 1H NMR (500 MHz, DMSO-d6) δ 12.38 (s, 1H), 8.04 (dd, J = 7.5, 6.0 Hz, 1H), 7.59 (d, J = 7.5 Hz, 1H), 5.37 (t, J = 7.0 Hz, 1H), 2.76 (t, J = 8.5 Hz, 2H), 2.46 (s, 3H), 1.99-1.88 (m, 2H). |
| 29 | 1H NMR (500 MHz, DMSO-d6) δ 12.38 (s, 1H), 8.03 (dd, J = 7.5, 6.0 Hz, 1H), 7.59 (d, J = 7.5 Hz, 1H),3.45-3.32 (m, 2H), 2.46 (s, 3H), 1.63-1.51 (m, 3H). |
| 30 | 1H NMR (500 MHz, DMSO-d6) δ 12.38 (s, 1H), 8.02 (dd, J = 7.5, 6.0 Hz, 1H), 7.57 (d, J = 7.5 Hz, 1H), 2.45 (s, 3H). |
| 31 | 1H NMR (500 MHz, DMSO-d6) δ 12.38 (s, 1H), 8.01 (dd, J = 7.5, 6.0 Hz, 1H), 7.59 (d, J = 7.5 Hz, 1H), 2.45 (s, 3H). |
| 32 | 1H NMR (500 MHz, DMSO-d6) δ 12.38 (s, 1H), 8.06 (dd, J = 7.5, 6.0 Hz, 1H), 7.61 (d, J = 7.5 Hz, 1H), 2.46 (s, 3H). |
| 33 | 1H NMR (500 MHz, DMSO-d6) δ 12.38 (s, 1H), 8.05 (dd, J = 7.5, 6.0 Hz, 1H), 7.59 (d, J = 7.5 Hz, 1H), 2.45 (s, 3H). |
| 34 | 1H NMR (500 MHz, DMSO-d6) δ 12.38 (s, 1H), 8.04 (dd, J = 7.5, 6.0 Hz, 1H), 7.61 (d, J = 7.5 Hz, 1H), 2.76 (t, J = 8.0 Hz, 2H), 2.52-2.40 (m, 5H), 1.38-1.27 (m, 2H). |
| 35 | 1H NMR (500 MHz, DMSO-d6) δ 12.38 (s, 1H), 8.02 (dd, J = 7.5, 6.0 Hz, 1H), 7.60 (d, J = 7.5 Hz, 1H), 2.76 (t, J = 8.5 Hz, 2H), 2.46 (s, 3H), 1.93-1.82 (m, 2H). |
| 36 | 1H NMR (500 MHz, DMSO-d6) δ 12.38 (s, 1H), 8.07 (dd, J = 7.5, 6.0 Hz, 1H), 7.59 (d, J = 7.5 Hz, 1H), 2.76 (t, J = 8.0 Hz, 2H), 2.46 (s, 3H), 1.71 (dt, J = 25.0, 8.0 Hz, 2H). |
| 37 | 1H NMR (500 MHz, DMSO-d6) δ 12.38 (s, 1H), 8.03 (dd, J = 7.5, 6.0 Hz, 1H), 7.59 (d, J = 7.5 Hz, 1H), 3.57 (t, J = 7.5 Hz, 2H), 2.76 (t, J = 5.5 Hz, 2H), 2.46 (s, 3H), 1.91-1.80 (m, 2H). |
| 38 | 1H NMR (500 MHz, DMSO-d6) δ 12.38 (s, 1H), 8.03 (dd, J = 7.5, 6.0 Hz, 1H), 7.59 (d, J = 7.5 Hz, 1H), 4.76-4.64(m, 1H), 3.13 (dd, J = 12.5, 7.0 Hz, 1H), 2.88 (dd, J = 12.5, 7.0 Hz, 1H), 2.46 (s, 3H), 1.55 (d, J = 7.0 Hz, 3H). |
| 40 | 1H NMR (500 MHz, DMSO-d6) δ 12.38 (s, 1H), 8.03 (dd, J = 7.5, 6.0 Hz, 1H), 7.56 (d, J = 7.5 Hz, 1H), 6.01 (t, J = 6.0 Hz, 1H), 3.45 (d, J = 6.0 Hz, 2H), 2.46 (s, 3H). |
| 51 | 1H NMR (500 MHz, DMSO-d6) δ 12.38 (s, 1H), 8.03 (dd, J = 7.5, 6.0 Hz, 1H), 7.62 (d, J = 7.5 Hz, 1H), 2.43 (s, 3H). |
| 52 | 1H NMR (500 MHz, DMSO-d6) δ 12.38 (s, 1H), 8.05 (dd, J = 7.5, 6.0 Hz, 1H), 7.60 (d, J = 7.5 Hz, 1H), 3.15 (t, J = 8.0 Hz, 2H), 2.55 (t, J = 8.0 Hz, 2H), 2.46 (s, 3H). |
| 53 | 1H NMR (500 MHz, DMSO-d6) δ 12.38 (s, 1H), 8.04 (dd, J = 7.5, 6.0 Hz, 1H), 7.59 (d, J = 7.5 Hz, 1H), 2.76 (t, J = 5.0 Hz, 2H), 2.46 (s, 3H), 2.14 (t, J = 5.5 Hz, 2H), 2.00 (p, J = 5.5 Hz, 2H). |
| 54 | 1H NMR (500 MHz, DMSO-d6) δ 12.38 (s, 1H), 8.03 (dd, J = 7.5, 6.0 Hz, 1H), 7.60 (d, J = 7.5 Hz, 1H), 4.27 (t, J = 5.0 Hz, 1H), 3.87-3.72 (m, 2H), 2.97 (t, J = 4.0 Hz, 2H), 2.46 (s, 3H). |
| 55 | 1H NMR (500 MHz, DMSO-d6) δ 12.38 (s, 1H), 8.04 (dd, J = 7.5, 6.0 Hz, 1H), 7.59 (d, J = 7.5 Hz, 1H), 4.34 (t, J = 5.0 Hz, 1H), 3.50 (q, J = 5.0 Hz, 2H), 2.76 (t, J = 8.0 Hz, 2H), 2.46 (s, 3H), 1.82-1.71 (m, 2H). |
| 56 | 1H NMR (500 MHz, DMSO-d6) δ 12.38 (s, 1H),8.04 (dd, J = 7.5, 6.0 Hz, 1H), 7.60 (d, J = 7.5 Hz, 1H), 5.24-5.15 (m, 1H), 4.34 (d, J = 5.0 Hz, 1H), 4.41 (d, J = 5.0 Hz, 2H), 3.12 (d, J = 7.0 Hz, 2H), 2.46 (s, 3H). |
| 57 | 1H NMR (500 MHz, DMSO-d6) δ 12.38 (s, 1H), 8.03 (dd, J = 7.5, 6.0 Hz, 1H), 7.61 (d, J = 7.5 Hz, 1H), 3.08-2.93 (m, 4H), 3.01-2.95 (m, 2H), 2.60 (s, 2H), 2.46 (s, 3H). |
| 58 | 1H NMR (500 MHz, DMSO-d6) δ 12.38 (s, 1H), 8.05 (dd, J = 7.5, 6.0 Hz, 1H), 7.61 (d, J = 7.5 Hz, 1H), 4.96 (s, |

TABLE 2-continued

| Compound No. | $^1$HNMR |
|---|---|
| | 1H), 2.81 (q, J = 8.0 Hz, 2H), 2.46 (s, 3H), 0.87 (t, J = 8.0 Hz, 3H). |
| 67 | 1H NMR (500 MHz, DMSO-d6) δ 12.38 (s, 1H), 8.04 (dd, J = 7.5, 6.0 Hz, 1H), 7.59 (d, J = 7.5 Hz, 1H), 4.04-3.92 (m, 2H), 3.85-3.72 (m, 2H), 2.46 (s, 3H), 2.32 (s, 3H), 1.97 (s, 1H). |
| 68 | 1H NMR (500 MHz, DMSO-d6) δ 12.38 (s, 1H), 8.04 (dd, J = 7.5, 6.0 Hz, 1H), 7.60 (d, J = 7.5 Hz, 1H), 3.57 (q, J = 8.0 Hz, 2H), 2.46 (s, 3H), 1.15 (t, J = 8.0 Hz, 3H). |
| 69 | 1H NMR (500 MHz, DMSO-d6) δ 12.38 (s, 1H), 8.02 (dd, J = 7.5, 6.0 Hz, 1H), 7.61-7.55 (m, 1H), 4.86-4.73 (m, 2H), 3.21 (s, 3H), 2.46 (s, 3H). |
| 70 | 1H NMR (500 MHz, DMSO-d6) δ 12.38 (s, 1H), 8.04 (dd, J = 7.5, 6.0 Hz, 1H), 7.61 (d, J = 7.5 Hz, 1H), 3.71 (t, J = 7.5 Hz, 1H), 3.43 (q, J = 8.0 Hz, 2H), 2.95 (t, J = 7.5 Hz, 1H), 2.45 (s, 3H), 1.08 (t, J = 8.0 Hz, 3H). |
| 71 | 1H NMR (500 MHz, DMSO-d6) 12.41 (s, 1H), 8.12 (dd, J = 8.0, 7.0 Hz, 1H), 7.83 (d, J = 8.0 Hz, 1H), 4.35-4.24 (m, 1H), 3.32 (s, 3H),2.50 (s, 3H), 1.45 (d, J = 7.5 Hz, 3H) |
| 72 | 1H NMR (500 MHz, DMSO-d6) 12.42 (s, 1H), 8.13 (dd, J = 8.0, 7.0 Hz, 1H), 8.01 (d, J = 8.0 Hz, 1H), 3.98 (t, J = 8.0 Hz, 2H), 3.39 (t, J = 8.0 Hz, 2H), 3.31 (s, 3H), 2.50 (s, 3H) |
| 73 | 1H NMR (500 MHz, DMSO-d6) δ 12.38 (s, 1H),8.02 (dd, J = 7.5, 6.0 Hz, 1H), 7.58 (d, J = 7.5 Hz, 1H), 4.86-4.73 (m, 2H), 4.56-4.43 (m, 2H), 3.46 (q, J = 8.0 Hz, 2H), 2.46 (s, 3H), 1.03 (t, J = 8.0 Hz, 3H). |
| 74 | 1H NMR (500 MHz, DMSO-d6) δ 12.38(s, 1H), 8.04 (dd, J = 7.5, 6.0 Hz, 1H), 7.64-7.58 (m, 1H), 3.70-3.61 (m, 1H), 3.22 (s, 3H), 3.02 (dd, J = 12.0, 7.0 Hz, 1H), 2.77 (dd, J = 12.0, 7.0 Hz, 1H), 2.46 (s, 3H), 1.18 (d, J = 7.0 Hz, 3H). |
| 75 | 1H NMR (500 MHz, DMSO-d6) δ 12.38 (s, 1H), 8.03 (dd, J = 7.5, 6.0 Hz, 1H), 7.59 (d, J = 7.5 Hz, 1H), 3.34 (t, J = 7.5 Hz, 2H), 3.18 (s, 3H), 2.76(t, J = 5.5 Hz, 2H), 2.46 (s, 3H), 1.80-1.71 (m, 2H). |
| 79 | 1H NMR (500 MHz, DMSO-d6) 12.41 (s, 1H), 8.13 (dd, J = 8.0, 7.0 Hz, 1H), 8.01 (d, J = 8.0 Hz, 1H), 5.11-.5.01 (m, 4H), 4.25-4.16 (m, 1H), 2.50 (s, 3H) |
| 80 | 1H NMR (500 MHz, DMSO-d6) δ 12.38 (s, 1H), 7.78 (dd, J = 7.5, 6.0 Hz, 1H), 7.60 (d, J = 7.5 Hz, 1H), 4.75 (dd, J = 7.0, 6.0 Hz, 2H), 4.51 (dd, J = 7.0, 6.0 Hz, 2H), 3.28-3.17 (m, 1H), 2.70 (d, J = 7.0 Hz, 2H), 2.45 (s, 3H). |
| 164 | 1H NMR (500 MHz, DMSO-d6) δ 12.38 (s, 1H), 8.07 (dd, J = 7.5, 6.0 Hz, 1H), 7.58 (d, J = 7.5 Hz, 1H), 7.15 (t, J = 50.0 Hz, 1H), 3.71 (t, J = 8.0 Hz, 2H), 2.95 (t, J = 8.0 Hz, 2H), 2.40 (s, 3H). |
| 165 | 1H NMR (500 MHz, DMSO-d6) δ 12.38 (s, 1H), 8.04 (dd, J = 7.5, 6.0 Hz, 1H), 7.59 (d, J = 7.5 Hz, 1H), 3.71.-3.62 (m, 2H), 2.95 (t, J = 8.0 Hz, 2H), 2.46 (s, 3H). |
| 166 | 1H NMR (500 MHz, DMSO-d6) δ 12.38 (s, 1H), 8.03 (dd, J = 7.5, 6.0 Hz, 1H), 7.59 (d, J = 7.5 Hz, 1H), 3.87-3.75 (m, 2H), 2.97 (t, J = 4.5 Hz, 2H), 2.46 (s, 3H), 2.42 (s, 6H). |
| 167 | 1H NMR (500 MHz, DMSO-d6) δ 12.38 (s, 1H), 8.04 (dd, J = 7.5, 6.0 Hz, 1H), 7.59 (d, J = 7.5 Hz, 1H), 2.48-2.40 (m, 2H), 1.26 (t, J = 8.0 Hz, 3H). |
| 169 | 1H NMR (500 MHz, DMSO-d6) δ 12.38 (s, 1H), 8.04 (dd, J = 7.5, 6.0 Hz, 1H), 7.59 (d, J = 7.5 Hz, 1H), 2.92 (q, J = 45.0 Hz, 2H), 2.45 (s, 3H). |
| 170 | 1H NMR (500 MHz, DMSO-d6) δ 12.38 (s, 1H), 8.10-8.03 (m, 2H), 7.79 (dd, J = 7.5, 6.0 Hz, 1H), 7.67-7.54 (m, 1H), 7.61 -7.51 (m, 3H), 2.45 (s, 3H). |
| 171 | 1H NMR (500 MHz, DMSO-d6) δ 12.38 (s, 1H), 8.05 (dd, J = 7.5, 6.0 Hz, 1H), 7.84 (d, J = 7.5 Hz, 1H), 7.60 (dd, J = 7.5 Hz, 1H), 7.52 (dd, J = 7.5, 1.5 Hz, 1H), 6.74 (t, J = 7.5 Hz, 1H), 2.46 (s, 3H). |
| 172 | 1H NMR (500 MHz, DMSO-d6) δ 12.38 (s, 1H), 8.25 (dd, J = 7.5, 6.0 Hz, 1H), 8.04 (s, 1H), 7.60 (d, J = 7.5 Hz, 1H), 3.81 (s, 3H), 2.60 (s, 3H), 2.46 (s, 3H). |
| 176 | 1H NMR (500 MHz, DMSO-d6) δ 12.38 (s, 1H), 8.04 (dd, J = 7.5, 6.0 Hz, 1H), 7.59 (d, J = 7.5 Hz, 1H), 3.06 (s, 6H), 2.45 (s, 3H). |
| 178 | 1H NMR (500 MHz, DMSO-d6) δ 12.38 (s, 1H), 8.06 (dd, J = 7.5, 6.0 Hz, 1H), 7.59 (d, J = 7.5 Hz, 1H), 3.67 (s, 2H), 2.91 (s, 6H), 2.46 (s, 3H). |
| 179 | 1H NMR (500 MHz, DMSO-d6) δ 12.38 (s, 1H), 7.77 (dd, J = 7.5, 6.0 Hz, 1H), 7.60-7.55 (m, 1H), 4.73 (s, 2H), 3.06 (s, 9H), 2.45 (s, 3H). |
| 184 | 1H NMR (500 MHz, DMSO-d6) δ 12.38 (s, 1H), 8.04 (dd, J = 7.5, 6.0 Hz, 1H), 7.60 (d, J = 7.5 Hz, 1H), 6.88 (s, 1H), 4.70 (s, 2H), 3.72 (s, 3H), 2.46 (s, 3H), 2.29 (s, 3H). |
| 191 | 1H NMR (500 MHz, DMSO-d6) δ 12.38 (s, 1H), 9.72 (t, J = 6.0 Hz, 1H), 8.09 (dd, J = 7.5, 6.0 Hz, 1H), 7.60 (d, J = 7.5 Hz, 1H), 3.89-3.78 (m, 2H), 2.46 (s, 3H). |
| 192 | 1H NMR (500 MHz, DMSO-d6) δ 12.38 (s, 1H), 9.90 (t, J = 6.0 Hz, 1H), 8.04 (dd, J = 7.5, 6.0 Hz, 1H), 7.61 (d, J = 7.5 Hz, 1H), 3.11-3.01 (m, 2H), 2.74-2.61 (m, 2H), 2.46 (s, 3H). |
| 193 | 1H NMR (500 MHz, DMSO-d6) δ 12.38 (s, 1H), 8.04 (dd, J = 7.5, 6.0 Hz, 1H), 7.57 (d, J = 7.5 Hz, 1H), 3.94-3.83 (m, 2H), 2.45 (s, 3H), 2.16 (s, 3H). |
| 195 | 1H NMR (500 MHz, DMSO-d6) δ 12.41 (s, 1H), 12.38 (s, 1H), 8.18 (dd, J = 7.5, 6.0 Hz, 1H), 7.61 (d, J = 7.5 Hz, 1H), 3.72-3.63 (m, 2H), 2.46 (s, 3H). |
| 196 | 1H NMR (500 MHz, DMSO-d6) δ 12.38 (s, 1H), 8.03 (dd, J = 7.5, 6.0 Hz, 1H), 7.61 (d, J = 7.5 Hz, 1H), 4.31-4.23 (m, 2H), 3.73 (s, 3H), 2.47 (s, 3H). |
| 199 | 1H NMR (500 MHz, DMSO-d6) δ 12.38 (s, 1H), 8.05 (dd, J = 7.5, 6.0 Hz, 1H), 7.60 (d, J = 7.5 Hz, 1H), 4.31-4.22 (m, 2H), 2.46 (s, 3H), 1.39 (s, 9H). |
| 200 | 1H NMR (500 MHz, DMSO-d6) δ 12.38 (s, 1H), 8.03 (dd, J = 7.5, 6.0 Hz, 1H), 7.63-7.57 (m, 1H), 4.31-4.22 (m, 2H), 4.02-3.86 (m, 4H), 4.17 (q, J = 8.0 Hz, 2H), 2.46 (s, 3H), 1.12 (t, J = 8.0 Hz, 3H). |
| 202 | 1H NMR (500 MHz, DMSO-d6) δ 12.38 (s, 1H), 8.05 (dd, J = 7.5, 6.0 Hz, 1H), 7.60 (d, J = 7.5 Hz, 1H), 4.31-4.22 (m, 2H), 2.46 (s, 3H), 1.39 (s, 9H). |
| 203 | 1H NMR (500 MHz, DMSO-d6) δ 12.38 (s, 1H), 8.09 (dd, J = 7.5, 6.0 Hz, 1H), 7.59 (d, J = 7.5 Hz, 1H), 3.93-3.82 (m, 2H), 2.45 (s, 3H), 2.21 (s, 3H). |
| 204 | 1H NMR (500 MHz, DMSO-d6) δ 12.38(s, 1H), 8.04 (dd, J = 7.5, 6.0 Hz, 1H), 7.60 (d, J = 7.5 Hz, 1H), 3.15 (t, J = 8.0 Hz, 2H), 2.67 (t, J = 8.0 Hz, 2H), 2.46 (s, 3H), 2.07 (s, 3H) |
| 205 | 1H NMR (500 MHz, DMSO-d6) δ 12.38 (s, 1H), 8.04 (dd, J = 7.5, 6.0 Hz, 1H), 7.56 (d, J = 7.5 Hz, 1H), 4.06-3.91 (m, 2H), 2.53 (s, 3H), 2.45 (s, 3H). |
| 206 | 1H NMR (500 MHz, DMSO-d6) δ 12.38 (s, 1H), 8.03 (dd, J = 7.5, 6.0 Hz, 1H), 7.62 (d, J = 7.5 Hz, 1H), 2.63 (s, 3H), 0.08 (s, 9H). |
| 208 | 1H NMR (500 MHz, DMSO-d6) δ 12.38 (s, 1H), 8.02 (dd, J = 7.5, 6.0 Hz, 1H), 7.59 (d, J = 7.5 Hz, 1H), 4.13-4.01 (m, 2H), 3.02 (t, J = 3.5 Hz, 2H), 2.46 (s, 3H), 1.03 (s, 9H), 0.21 (s, 6H). |
| 209 | 1H NMR (500 MHz, DMSO-d6) δ 12.38 (s, 1H), 8.03 (dd, J = 7.5, 6.0 Hz, 1H), 7.59 (dd, J = 7.5 Hz, 1H), 7.36-7.25 (m, 5H), 4.86 (s, 2H), 4.68 (s, 2H), 2.48 (s, 3H). |
| 210 | 1H NMR (500 MHz, DMSO-d6) δ 7.96 (dd, J = 7.5, 6.0 Hz, 1H), 7.57 (d, J = 7.5 Hz, 1H), 3.25 (s, 3H), 2.82 (q, J = 8.0 Hz, 2H), 2.45 (s, 3H), 1.33 (t, J = 8.0 Hz, 3H). |
| 213 | 1H NMR (500 MHz, DMSO-d6) δ 7.79 (dd, J = 7.5, 6.0 Hz, 1H), 7.54 (d, J = 7.5 Hz, 1H), 5.93-5.85 (m, 1H), 5.10-5.01 (m, 1H), 4.89- 4.79 (m, 1H), 4.47-4.43 (m, 2H), 2.85 (q, J = 8.0 Hz, 2H), 2.46 (s, 3H), 1.31 (t, J = 8.0 Hz, 3H). |
| 214 | 1H NMR (500 MHz, DMSO-d6) δ 7.81 (dd, J = 7.5, 6.0 Hz, 1H), 7.57 (d, J = 7.5 Hz, 1H), 3.94 (d, J = 3.0 Hz, 2H), 3.29 (t, J = 3.0 Hz, 1H), 2.84 (q, J = 8.0 Hz, 2H), 2.46 (s, 3H), 1.32 (t, J = 8.0 Hz, 3H). |
| 216 | 1H NMR (500 MHz, DMSO-d6) δ 7.66 (dd, J = 7.5, 6.0 Hz, 1H), 7.55-7.49 (m, 1H), 2.88 (q, J = 8.0 Hz, 2H), 2.46 (s, 3H), 2.22 (s, 3H), 1.34 (t, J = 8.0 Hz, 3H). |
| 217 | 1H NMR (500 MHz, DMSO-d6) δ 8.10 (dd, J = 7.5, 6.0 Hz, 1H), 7.91-7.84 (m, 2H), 7.63-7.56 (m, 2H), 7.52 (t, J = 7.5 Hz, 2H), 2.81 (q, J = 8.0 Hz, 2H), 2.33 (s, 3H), 1.32 (t, J = 8.0 Hz, 3H). |
| 223 | 1H NMR (500 MHz, DMSO-d6) δ 8.03 (dd, J = 7.5, 6.0 Hz, 1H), 7.62 (d, J = 7.5 Hz, 1H), 7.50 (s, 1H), 3.64 (s, 3H), 2.83 (q, J = 8.0 Hz, 2H), 2.63 (s, 3H), 2.46 (s, 3H), 1.17 (t, J = 8.0 Hz, 3H). |

TABLE 2-continued $^{1}$H NMR data of compounds I

| Compound No. | $^{1}$HNMR |
|---|---|
| 231 | 1H NMR (500 MHz, DMSO-d6) δ 8.11 (dd, J = 7.5, 6.0 Hz, 1H), 7.61 (d, J = 7.5 Hz, 1H), 3.71 (s, 3H), 2.84 (q, J = 8.0 Hz, 2H), 2.46 (s, 3H), 1.33 (t, J = 8.0 Hz, 3H). |
| 240 | 1H NMR (500 MHz, DMSO-d6) δ 8.11 (dd, J = 7.5, 6.0 Hz, 1H), 7.62 (d, J = 7.5 Hz, 1H), 3.52 (t, J = 4.5 Hz, 4H), 3.12 (t, J = 4.5 Hz, 4H), 2.85 (q, J = 8.0 Hz, 2H), 2.44 (s, 3H), 1.30 (t, J = 8.0 Hz, 3H). |
| 241 | 1H NMR (500 MHz, DMSO-d6) δ 7.94 (dd, J = 7.5, 6.0 Hz, 1H), 7.57 (d, J = 7.5 Hz, 1H), 3.72 (q, J = 9.0 Hz, 2H), 2.82 (q, J = 8.0 Hz, 2H), 2.46 (s, 3H), 1.31 (t, J = 8.0 Hz, 3H). |
| 242 | 1H NMR (500 MHz, DMSO-d6) δ 7.90 (dd, J = 7.5, 6.0 Hz, 1H), 7.61 (d, J = 7.5 Hz, 1H), 4.32 (s, 2H), 2.83 (q, J = 8.0 Hz, 2H), 2.47 (s, 3H), 1.31 (t, J = 8.0 Hz, 3H). |
| 243 | 1H NMR (500 MHz, DMSO-d6) δ 7.87 (dd, J = 7.5, 6.0 Hz, 1H), 7.60 (d, J = 7.5 Hz, 1H), 7.28-7.19 (m, 5H), 5.03 (s, 2H), 2.85 (q, J = 8.0 Hz, 2H), 2.47 (s, 3H), 1.27 (t, J = 8.0 Hz, 3H). |
| 248 | 1H NMR (500 MHz, DMSO-d6) δ 7.87 (dd, J = 7.5, 6.0 Hz, 1H), 7.66 (d, J = 7.5 Hz, 1H), 6.28 (q, J = 7.0 Hz, 1H), 3.81 (s, 3H), 2.83 (q, J = 8.0 Hz, 2H), 2.46 (s, 3H), 1.64 (d, J = 7.0 Hz, 3H), 1.31 (t, J = 8.0 Hz, 3H). |
| 261 | 1H NMR (500 MHz, DMSO-d6) δ 7.82 (dd, J = 7.5, 6.0 Hz, 1H), 7.56 (d, J = 7.5 Hz, 1H), 6.31 (q, J = 7.0 Hz, 1H), 4.70-4.53 (m, 2H), 3.50 (td, J = 12.5, 3.0 Hz, 1H), 3.24 (td, J = 12.5, 3.0 Hz, 1H), 2.56-2.42 (m, 1H), 2.36 (s, 3H), 1.67- 1.52 (m, 4H), 1.32 (t, J = 8.0 Hz, 3H), 0.88 (t, J = 8.0 Hz, 3H). |
| 306 | 1H NMR (500 MHz, DMSO-d6) δ 12.38 (s, 1H), 8.04 (d, J = 7.5 Hz, 1H), 7.67 (d, J = 7.5 Hz, 1H), 3.70 (s, 3H), 2.82 (q, J = 8.0 Hz, 2H), 2.46 (s, 3H), 1.32 (t, J = 8.0 Hz, 3H). |
| 307 | 1H NMR (500 MHz, DMSO-d6) δ 12.38 (s, 1H), 8.08 (d, J = 7.5 Hz, 1H), 7.64 (d, J = 7.5 Hz, 1H), 3.66 (s, 3H), 2.75-2.71 (m, 1H), 2.45 (s, 3H), 1.36 (d, J = 7.0 Hz, 6H). |
| 308 | 1H NMR (500 MHz, DMSO-d6) δ 12.38 (s, 1H), 8.01 (d, J = 7.5 Hz, 1H), 7.68 (d, J = 7.5 Hz, 1H), 3.75 (s, 3H), 2.76 (t, J = 8.0 Hz, 2H), 2.46 (s, 3H), 1.34-1.26 (m, 4H), 0.84 (t, J = 8.0 Hz, 3H). |
| 309 | 1H NMR (500 MHz, DMSO-d6) δ 12.38 (s, 1H), 8.01 (d, J = 7.5 Hz, 1H), 7.68 (d, J = 7.5 Hz, 1H), 3.75 (s, 3H), 2.76 (t, J = 8.0 Hz, 2H), 2.45 (s, 3H), 1.49 (t, J = 8.0 Hz, 2H), 0.86 (s, 9H). |
| 310 | 1H NMR (500 MHz, DMSO-d6) δ 12.38 (s, 1H), 8.01 (d, J = 7.5 Hz, 1H), 7.68 (d, J = 7.5 Hz, 1H), 3.75 (s, 3H), 2.70 (d, J = 7.0 Hz, 2H), 2.45 (s, 3H), 1.42-1.38 (m, 1H), 0.48-0.39 (m, 2H), 0.25-0.16 (m, 2H). |
| 311 | 1H NMR (500 MHz, DMSO-d6) δ 12.38 (s, 1H), 8.01 (d, J = 7.5 Hz, 1H), 7.69 (d, J = 7.5 Hz, 1H), 5.84-5.78 (m, 1H), 5.36-5.27 (m, 1H), 5.11 -5.00 (m, 1H), 3.76 (s, 3H), 3.45-3.40 (m, 2H), 2.46 (s, 3H). |
| 312 | 1H NMR (500 MHz, DMSO-d6) δ 12.38 (s, 1H), 8.03 (d, J = 7.5 Hz, 1H), 7.69 (d, J = 7.5 Hz, 1H), 5.96-5.90 (m, 1H), 5.10-4.99 (m, 2H), 3.74 (s, 3H), 2.82 (t, J = 5.5 Hz, 2H), 2.46 (s, 3H), 2.34-2.26 (m, 2H). |
| 313 | 1H NMR (500 MHz, DMSO-d6) δ 12.38 (s, 1H), 8.02 (d, J = 7.5Hz, 1H), 7.69 (d, J = 7.5 Hz, 1H), 5.61-5.52 (m, 1H), 5.52-5.48 (m, 1H), 3.76 (s, 3H), 3.45 (dd, J = 3.0, 1.0 Hz, 2H), 2.45 (s, 3H), 1.61 (dd, J = 6.0, 1.0 Hz, 3H). |
| 314 | 1H NMR (500 MHz, DMSO-d6) δ 12.38 (s, 1H), 8.02 (d, J = 7.5 Hz, 1H), 7.65 (d, J = 7.5 Hz, 1H), 3.71 (s, 3H), 3.52 (d, J = 3.0 Hz, 2H), 3.15 (t, J = 3.0 Hz, 1H), 2.45 (s, 3H). |
| 315 | 1H NMR (500 MHz, DMSO-d6) δ 12.38 (s, 1H), 8.01 (d, J = 7.5 Hz, 1H), 7.68 (d, J = 7.5 Hz, 1H), 3.74 (s, 3H), 3.04 (t, J = 3.0 Hz, 1H), 2.95 (t, J = 8.0 Hz, 2H), 2.45 (s, 3H), 2.37 (td, J = 8.0, 3.0 Hz, 2H). |
| 316 | 1H NMR (500 MHz, DMSO-d6) δ 12.38 (s, 1H), 8.01 (d, J = 7.5 Hz, 1H), 7.69 (d, J = 7.5 Hz, 1H), 3.76 (s, 3H), 3.47 (q, J = 2.0 Hz, 2H), 2.45 (s, 3H), 1.73 (t, J = 2.0 Hz, 3H). |
| 317 | 1H NMR (500 MHz, DMSO-d6) δ 12.38 (s, 1H), 8.04 (d, J = 7.5 Hz, 1H), 7.61 (d, J = 7.5 Hz, 1H), 7.50-7.39 (m, 4H), 7.32-7.28 (m, 1H), 3.78 (s, 3H), 2.46 (s, 3H). |
| 318 | 1H NMR (500 MHz, DMSO-d6) δ 12.38 (s, 1H), 8.01 (d, J = 7.5 Hz, 1H), 7.65 (d, J = 7.5 Hz, 1H), 7.26-7.15 (m, 5H), 3.73 (s, 3H), 3.11 (t, J = 5.5 Hz, 2H), 2.71 (t, J = 5.5 Hz, 2H), 2.46 (s, 3H). |

TABLE 2-continued $^{1}$H NMR data of compounds I

| Compound No. | $^{1}$HNMR |
|---|---|
| 319 | 1H NMR (500 MHz, DMSO-d6) δ 12.38 (s, 1H),7.96 (d, J = 7.5 Hz, 1H), 7.66 (d, J = 7.5 Hz, 1H), 4.48 (t, J = 8.0 Hz, 1H), 4.38 (t, J = 8.0 Hz, 1H), 3.73 (s, 3H), 2.98 (dt, J = 25.0, 8.0 Hz, 2H), 2.44 (s, 3H). |
| 320 | 1H NMR (500 MHz, DMSO-d6) δ 12.38 (s, 1H), 8.03 (d, J = 7.5 Hz, 1H), 7.65 (d, J = 7.5 Hz, 1H), 4.35 (t, J = 7.5 Hz, 1H), 4.25 (t, J = 7.5 Hz, 1H), 3.68 (s, 3H), 2.76 (t, J = 8.0 Hz, 2H), 2.45 (s, 3H), 1.83-1.74 (m, 2H). |
| 321 | 1H NMR (500 MHz, DMSO-d6) δ 12.38 (s, 1H), 8.03 (d, J = 7.5 Hz, 1H), 7.66 (d, J = 7.5 Hz, 1H), 5.41-5.32 (m, 1H), 3.71 (s, 3H), 3.04-2.92 (m, 1H), 2.79-2.68 (m, 1H), 2.46 (s, 3H), 1.40 (dd, J = 25.0, 7.0 Hz, 3H). |
| 322 | 1H NMR (500 MHz, DMSO-d6) δ 12.38 (s, 1H), 8.07 (d, J = 7.5 Hz, 1H), 7.65 (d, J = 7.5 Hz, 1H), 6.21 (s, 1H), 3.71 (s, 3H), 2.45 (s, 3H). |
| 323 | 1H NMR (500 MHz, DMSO-d6) δ 12.38 (s, 1H), 8.03 (d, J = 7.5 Hz, 1H), 7.68 (d, J = 7.5 Hz, 1H), 6.60 (t, J = 7.0 Hz, 1H), 3.75 (s, 3H), 3.14-3.04 (m, 2H), 2.45 (s, 3H). |
| 324 | 1H NMR (500 MHz, DMSO-d6) δ 12.38 (s, 1H), 8.09 (d, J = 7.5 Hz, 1H), 7.68 (d, J = 7.5 Hz, 1H), 3.73 (s, 3H), 3.30 (q, J = 9.0 Hz, 2H), 2.46 (s, 3H). |
| 325 | 1H NMR (500 MHz, DMSO-d6) δ 12.38 (s, 1H), 8.09 (d, J = 7.5 Hz, 1H), 7.68 (d, J = 7.5 Hz, 1H), 3.74 (s, 3H), 2.76 (t, J = 9.0 Hz, 2H), 2.45 (s, 3H), 2.15-2.06 (m, 2H). |
| 326 | 1H NMR (500 MHz, DMSO-d6) δ 12.38 (s, 1H), 8.03 (d, J = 7.5 Hz, 1H), 7.65 (d, J = 7.5Hz, 1H), 3.68 (s, 3H), 2.76 (t, J = 8.0 Hz, 2H), 2.46 (d, J = 8.5 Hz, 5H), 1.38 (p, J = 8.0 Hz, 2H). |
| 327 | 1H NMR (500 MHz, DMSO-d6) δ 12.38 (s, 1H), 8.09 (d, J = 7.5 Hz, 1H), 7.66 (d, J = 7.5 Hz, 1H), 3.73 (s, 3H), 2.46 (s, 3H). |
| 328 | 1H NMR (500 MHz, DMSO-d6) δ 12.38 (s, 1H), 7.92 (d, J = 7.5 Hz, 1H), 7.65 (d, J = 7.5 Hz, 1H), 3.76 (s, 3H), 2.45 (s, 3H). |
| 329 | 1H NMR (500 MHz, DMSO-d6) δ 12.38 (s, 1H), 8.01 (d, J = 7.5 Hz, 1H), 7.67 (d, J = 7.5Hz, 1H), 3.68 (s, 3H), 2.76 (t, J = 8.5 Hz, 2H), 2.46 (s, 3H), 1.93-1.84 (m, 2H). |
| 330 | 1H NMR (500 MHz, DMSO-d6) δ 12.38 (s, 1H), 8.03 (d, J = 7.5 Hz, 1H), 7.65 (d, J = 7.5Hz, 1H), 3.72 (s, 3H), 2.45 (s, 3H). |
| 331 | 1H NMR (500 MHz, DMSO-d6) δ 12.38 (s, 1H), 8.01 (d, J = 7.5 Hz, 1H), 7.69 (d, J = 7.5 Hz, 1H), 3.75 (s, 3H), 2.76 (t, J = 8.0 Hz, 2H), 2.45 (s, 3H), 1.74-1.69 (m, 2H). |
| 332 | 1H NMR (500 MHz, DMSO-d6) δ 12.38 (s, 1H), 7.95 (d, J = 7.5 Hz, 1H), 7.66 (d, J = 7.5 Hz, 1H), 3.76-3.68 (m, 5H), 3.06 (t, J = 8.0 Hz, 2H), 2.44 (s, 3H). |
| 333 | 1H NMR (500 MHz, DMSO-d6) δ 12.38 (s, 1H), 8.03 (d, J = 7.5 Hz, 1H), 7.65 (d, J = 7.5 Hz, 1H), 3.68 (s, 3H), 3.57 (t, J = 4.9 Hz, 2H), 2.76 (t, J = 8.0 Hz, 2H), 2.45 (s, 3H), 1.91-1.82 (m, 2H). |
| 334 | 1H NMR (500 MHz, DMSO-d6) δ 12.38 (s, 1H), 8.03 (d, J = 7.5 Hz, 1H), 7.65 (d, J = 7.5 Hz, 1H), 4.27 (t, J = 5.0 Hz, 1H), 3.87 (td, J = 8.0, 5.0 Hz, 2H), 3.68 (s, 3H), 2.97 (t, J = 8.0 Hz, 2H), 2.45 (s, 3H). |
| 335 | 1H NMR (500 MHz, DMSO-d6) δ 12.38 (s, 1H),8.03 (d, J = 7.5 Hz, 1H), 7.65 (d, J = 7.5 Hz, 1H), 4.31 (t, J = 5.0 Hz, 1H), 3.68 (s, 3H), 3.50 (td, J = 7.5, 5.0 Hz, 2H), 2.76 (t, J = 8.0 Hz, 2H), 2.45 (s, 3H), 1.82 (p, J = 8.0 Hz, 2H). |
| 336 | 1H NMR (500 MHz, DMSO-d6) δ 12.38 (s, 1H),8.09 (d, J = 7.5 Hz, 1H), 7.68 (d, J = 7.5 Hz, 1H), 4.50 (d, J = 5.0 Hz, 1H), 3.96-3.84 (m, 1H), 3.74(s, 3H), 3.04-2.92 (m, 1H), 2.79 (dd, J = 12.5, 7.0 Hz, 1H), 2.45 (s, 3H), 1.09(d, J = 6.8 Hz, 3H). |
| 337 | 1H NMR (500 MHz, DMSO-d6) δ 12.38 (s, 1H), 7.91 (d, J = 7.5 Hz, 1H), 7.66 (d, J = 7.5 Hz, 1H), 3.90 (s, 2H), 3.66 (s, 3H), 2.45 (s, 3H). |
| 338 | 1H NMR (500 MHz, DMSO-d6) δ 12.38 (s, 1H), 8.03 (d, J = 7.5 Hz, 1H), 7.69 (d, J = 7.5 Hz, 1H), 3.76 (s, 3H), 3.15 (t, J = 5.0 Hz, 2H), 2.55 (t, J = 5.0 Hz, 2H), 2.45 (s, 3H). |
| 339 | 1H NMR (500 MHz, DMSO-d6) δ 12.38 (s, 1H), 8.08 (d, J = 7.5 Hz, 1H), 7.67 (d, J = 7.5 Hz, 1H), 3.68 (s, 3H), 2.75-2.70 (m, 4H), 2.45 (s, 3H), 1.89 (p, J = 8.0 Hz, 2H), 1.45 (s, 2H). |

TABLE 2-continued

| Compound No. | ¹HNMR |
|---|---|
| 340 | 1H NMR (500 MHz, DMSO-d6) δ 12.38 (s, 1H), 8.03 (d, J = 7.5 Hz, 1H), 7.66 (d, J = 7.5 Hz, 1H), 3.70 (s, 3H), 2.88 (t, J = 5.0 Hz, 2H), 2.51 (t, J = 5.0 Hz, 2H), 2.46 (s, 3H), 2.22 (s, 6H). |
| 341 | 1H NMR (500 MHz, DMSO-d6) δ 13.48 (s, 1H), 12.38 (s, 1H), 8.07 (d, J = 7.5 Hz, 1H), 7.66 (d, J = 7.5 Hz, 1H), 3.72 (s, 2H), 3.67 (s, 3H), 2.45 (s, 3H). |
| 342 | 1H NMR (500 MHz, DMSO-d6) δ 12.38 (s, 1H), 8.05 (d, J = 7.5 Hz, 1H), 7.68 (d, J = 7.5 Hz, 1H), 4.86 (s, 2H), 3.71 (s, 3H), 3.30 (s, 3H), 2.46 (s, 3H). |
| 343 | 1H NMR (500 MHz, DMSO-d6) δ 12.38 (s, 1H), 8.09 (d, J = 7.5 Hz, 1H), 7.65 (d, J = 7.5 Hz, 1H), 4.86 (s, 2H), 3.71 (s, 3H), 3.46 (q, J = 8.0 Hz, 2H), 2.46 (s, 3H), 0.97 (t, J = 8.0 Hz, 3H). |
| 344 | 1H NMR (500 MHz, DMSO-d6) δ 12.38 (s, 1H), 8.03 (d, J = 7.5 Hz, 1H), 7.68 (d, J = 7.5 Hz, 1H), 3.76-3.67 (m, 5H), 3.21 (s, 3H), 2.95 (t, J = 8.0 Hz, 2H), 2.46 (s, 3H). |
| 345 | 1H NMR (500 MHz, DMSO-d6) δ 12.38 (s, 1H), 8.08 (d, J = 7.5 Hz, 1H), 7.66 (d, J = 7.5 Hz, 1H), 3.68 (s, 3H), 3.34 (t, J = 7.5 Hz, 2H), 3.70 (s, 3H), 2.76 (t, J = 8.0 Hz, 2H), 2.45 (s, 3H), 1.80-1.75 (m, 2H). |
| 346 | 1H NMR (500 MHz, DMSO-d6) δ 12.38 (s, 1H), 8.05 (d, J = 7.5 Hz, 1H), 7.66 (d, J = 7.5 Hz, 1H), 5.40 (dd, J = 7.0, 6.0 Hz, 2H), 4.71 (dd, J = 7.0, 6.0 Hz, 2H), 3.76 (d, J = 8.5 Hz, 4H), 2.46 (s, 3H). |
| 347 | 1H NMR (500 MHz, DMSO-d6) δ 12.38 (s, 1H), 8.03 (d, J = 7.5 Hz, 1H), 7.67 (d, J = 7.5 Hz, 1H), 7.36-7.25 (m, 5H), 4.86 (s, 2H), 4.68 (d, J = 1.0 Hz, 2H), 3.76 (s, 3H), 2.45 (s, 3H). |
| 348 | 1H NMR (500 MHz, DMSO-d6) δ 12.38 (s, 1H), 8.04 (d, J = 7.5 Hz, 1H), 7.65 (d, J = 7.5 Hz, 1H), 3.87 (t, J = 4.5 Hz, 2H), 3.68 (s, 3H), 2.97 (t, J = 4.5 Hz, 2H), 2.44 (s, 3H), 2.39 (s, 6H). |
| 349 | 1H NMR (500 MHz, DMSO-d6) δ 12.38 (s, 1H), 8.04 (d, J = 7.5 Hz, 1H), 7.68 (d, J = 7.5 Hz, 1H), 4.13 (t, J = 8.0 Hz, 2H), 3.75 (s, 3H), 3.02 (t, J = 8.0 Hz, 2H), 2.45 (s, 3H), 1.00 (s, 9H), 0.21 (s, 6H). |
| 350 | 1H NMR (500 MHz, DMSO-d6) δ 12.38 (s, 1H), 8.04 (d, J = 7.5 Hz, 1H), 7.63 (d, J = 7.5 Hz, 1H), 3.81 (s, 3H), 2.46 (s, 3H), 2.20 (s, 3H). |
| 351 | 1H NMR (500 MHz, DMSO-d6) δ 12.38 (s, 1H), 8.02 (d, J = 7.5 Hz, 1H), 7.70 (d, J = 7.5 Hz, 1H), 3.94 (s, 2H), 3.74 (s, 3H), 2.45 (s, 3H), 2.17 (s, 3H). |
| 352 | 1H NMR (500 MHz, DMSO-d6) δ 12.38 (s, 1H), 7.82 (d, J = 7.5 Hz, 1H), 7.65 (d, J = 7.5 Hz, 1H), 3.67 (s, 2H), 3.62 (s, 3H), 2.90 (s, 6H), 2.45 (s, 3H). |
| 353 | 1H NMR (500 MHz, DMSO-d6) δ 12.38 (s, 1H), 7.82 (d, J = 7.5 Hz, 1H), 7.66 (d, J = 7.5 Hz, 1H), 4.31 (s, 2H), 3.73 (s, 3H), 3.63 (s, 3H), 2.45 (s, 3H). |
| 354 | 1H NMR (500 MHz, DMSO-d6) δ 12.38 (s, 1H), 8.01 (d, J = 7.5 Hz, 1H), 7.68 (d, J = 7.5 Hz, 1H), 3.76 (s, 3H), 3.55 (s, 3H), 3.17 (t, J = 5.5 Hz, 2H), 2.46 (s, 3H), 2.41 (t, J = 5.5 Hz, 2H). |
| 355 | 1H NMR (500 MHz, DMSO-d6) δ 12.38 (s, 1H), 8.06 (d, J = 7.5 Hz, 1H), 7.66 (d, J = 7.5 Hz, 1H), 5.57 (s, 2H), 3.75 (s, 3H), 2.45 (s, 3H), 1.18 (s, 9H). |
| 356 | 1H NMR (500 MHz, DMSO-d6) δ 12.38 (s, 1H), 8.11 (d, J = 7.5 Hz, 1H), 7.53 (d, J = 7.5 Hz, 1H), 7.29 (s, 1H), 4.70 (s, 2H), 3.80 (s, 3H), 3.55 (s, 3H), 2.63 (s, 3H), 2.08 (s, 3H). |
| 357 | 1H NMR (500 MHz, DMSO-d6) δ 12.38 (s, 1H), 8.04 (dd, J = 7.5, 6.0 Hz, 1H), 7.71 (s, 1H), 7.65 (d, J = 7.5 Hz, 1H), 2.76 (t, J = 5.0 Hz, 2H), 1.47-1.44 (m, 2H), 0.95 (t, J = 8.0 Hz, 3H). |
| 358 | 1H NMR (500 MHz, DMSO-d6) δ 12.38 (s, 1H), 8.04 (dd, J = 7.5, 6.0 Hz, 1H), 7.65 (d, J = 7.5 Hz, 1H), 2.76 (t, J = 5.0 Hz, 2H), 2.59 (q, J = 8.0 Hz, 2H), 1.47-1.38 (m, 2H), 1.13 (t, J = 8.0 Hz, 3H), 0.94 (t, J = 8.0 Hz, 3H). |
| 359 | 1H NMR (500 MHz, DMSO-d6) δ 12.38 (s, 1H), 8.05 (dd, J = 7.5, 6.0 Hz, 1H), 7.68 (d, J = 7.5 Hz, 1H), 3.08 (p, J = 6.8 Hz, 1H), 2.76 (t, J = 8.1 Hz, 2H), 1.47--1.33(m, 2H), 1.26 (d, J = 6.8 Hz, 6H), 0.89 (t, J = 8.0 Hz, 3H). |
| 360 | 1H NMR (500 MHz, DMSO-d6) δ 12.38 (s, 1H), 8.02 (dd, J = 7.5, 6.0 Hz, 1H), 7.67 (d, J = 7.5 Hz, 1H), 2.76 (t, J = 8.0 Hz, 2H), 2.53 (t, J = 8.0 Hz, 2H), 1.61-1.55 (m, 2H), 1.47-1.33 (m, 2H), 0.87-0.83 (m, 6H). |
| 361 | 1H NMR (500 MHz, DMSO-d6) δ 12.38 (s, 1H), 8.04 (dd, J = 7.5, 6.0 Hz, 1H), 7.65 (d, J = 7.5 Hz, 1H), 2.76 (t, J = 5.0 Hz, 2H), 1.47-1.43 (m, 2H), 1.25 (s, 9H), 0.94 (t, J = 8.0 Hz, 3H). |
| 362 | 1H NMR (500 MHz, DMSO-d6) δ 12.38(s, 1H), 8.11 (dd, J = 7.5, 6.0 Hz, 1H), 7.53 (d, J = 7.5 Hz, 1H), 2.76(t, J = 7.0 Hz, 2H), 1.55-1.41 (m, 3H), 0.97 (t, J = 8.0 Hz, 3H), 0.89-0.78 (m, 2H), 0.71-0.61 (m, 2H) |
| 363 | 1H NMR (500 MHz, DMSO-d6) δ 12.38(s, 1H), 8.11 (dd, J = 7.5, 6.0 Hz, 1H), 7.53 (d, J = 7.5, 1.0 Hz, 1H), 2.76 (t, J = 7.0 Hz, 2H), 1.56- 1.41 (m, 4H), 0.97 (t, J = 8.0 Hz, 3H), 0.87 (d, J = 6.6 Hz, 3H), 0.63-0.54 (m, 1H), 0.38-0.29 (m, 1H). |
| 364 | 1H NMR (500 MHz, DMSO-d6) δ 12.38 (s, 1H), 8.11 (dd, J = 7.5, 6.0 Hz, 1H), 7.53 (dd, J = 7.5, 1.0 Hz, 1H), 3.24 (p, J = 7.0 Hz, 1H), 2.76 (t, J = 7.0 Hz, 2H), 2.38-2.29 (m, 2H), 2.18-2.08 (m, 2H), 2.04-1.86 (m, 2H), 1.47-1.38 (m, 2H), 0.97 (t, J = 8.0 Hz, 3H). |
| 365 | 1H NMR (500 MHz, DMSO-d6) δ 12.38 (s, 1H), 8.02 (dd, J = 7.5, 6.0 Hz, 1H), 7.66 (d, J = 7.5 Hz, 1H), 3.02 (p, J = 7.0 Hz, 1H), 2.76 (t, J = 8.0 Hz, 2H), 1.87-1.76 (m, 2H), 1.72-1.61 (m, 2H), 1.59-1.36 (m, 6H), 0.90 (t, J = 8.0 Hz, 3H). |
| 366 | 1H NMR (500 MHz, DMSO-d6) δ 12.38 (s, 1H), 7.84 (dd, J = 7.5, 6.0 Hz, 1H), 7.64 (d, J = 7.5 Hz, 1H), 6.37 (dd, J = 16.5, 10.0 Hz, 1H), 5.73 (dd, J = 14.0, 10.0 Hz, 1H), 5.48 (dd, J = 16.5, 14.0 Hz, 1H), 2.76 (t, J = 5.5 Hz, 2H), 1.47-1.38 (m, 2H), 0.94 (t, J = 8.0 Hz, 3H). |
| 367 | 1H NMR (500 MHz, DMSO-d6) δ 12.38 (s, 1H), 7.82 (dd, J = 7.5, 6.0 Hz, 1H), 7.66 (dd, J = 7.5, 1.0 Hz, 1H), 4.28 (s, 1H), 2.76 (t, J = 5.5 Hz, 2H), 1.47-1.42 (m, 2H), 0.94 (t, J = 8.0 Hz, 3H). |
| 368 | 1H NMR (500 MHz, DMSO-d6) δ 12.38 (s, 1H), 7.84 (dd, J = 7.5, 6.0 Hz, 1H), 7.64 (d, J = 7.5 Hz, 1H), 6.61 (s, 1H), 2.76 (t, J = 5.5 Hz, 2H), 1.47-1.38 (m, 2H), 0.94 (t, J = 8.0 Hz, 6H). |
| 369 | 1H NMR (500 MHz, DMSO-d6) δ 12.38 (s, 1H), 8.03 (dd, J = 7.5, 6.0 Hz, 1H), 7.68-7.63 (m, 1H), 2.76 (t, J = 5.5 Hz, 2H), 1.47-1.38 (m, 2H), 0.95 (t, J = 8.0 Hz, 3H). |
| 370 | 1H NMR (500 MHz, Chloroform-d) S 8.23 (s, 1H), 7.80 (dd, J = 7.5, 6.0 Hz, 1H), 7.68 (d, J = 7.5 Hz, 1H), 2.76 (t, J = 8.0 Hz, 2H), 2.53 (t, J = 8.5 Hz, 2H), 2.14-2.05 (m, 2H), 1.67-1.55 (m, 2H), 0.92 (t, J = 8.0 Hz, 3H). |
| 371 | 1H NMR (500 MHz, Chloroform-d)S 8.23 (s, 1H), 8.08 (dd, J = 7.5, 6.0 Hz, 1H), 7.52 (d, J = 7.5 Hz, 1H), 6.60 (q, J = 7.0 Hz, 1H), 6.50 (q, J = 7.0 Hz, 1H), 2.76 (t, J = 7.0 Hz, 2H), 2.05-1.91 (m, 1H), 1.73-1.61 (m, 1H), 1.08-0.92 (m, 1H), 0.95 (t, J = 8.0 Hz, 3H), 0.82-0.73 (m, 1H). |
| 372 | 1H NMR (500 MHz, Chloroform-d) S 8.23 (s, 1H), 8.08 (dd, J = 7.5, 6.0 Hz, 1H), 7.52 (d, J = 7.5 Hz, 1H), 2.76 (t, J = 7.0 Hz, 2H), 2.60-2.51(m, 1H), 1.73-1.61 (m, 2H), 1.51-1.40 (m, 1H), 1.26-1.13 (m, 1H), 0.95 (t, J = 8.0 Hz, 3H). |
| 373 | 1H NMR (500 MHz, Chloroform-d) S 8.23 (s, 1H), 8.08 (dd, J = 7.5, 6.0 Hz, 1H), 7.52 (d, J = 7.5 Hz, 1H), 7.37-7.32 (m, 2H), 7.25-7.14 (m, 3H), 3.51 (t, J = 7.0 Hz, 1H), 2.76 (t, J = 7.0 Hz, 2H), 2.45 (q, J = 7.0 Hz, 1H), 1.73-1.61 (m, 2H), 1.50-1.41 (m, 1H), 1.25-1.16 (m, 1H), 0.95 (t, J = 8.0 Hz, 3H). |
| 374 | 1H NMR (500 MHz, Chloroform-d) S 8.23 (s, 1H), 8.19 (dd, J = 7.5, 6.0 Hz, 1H), 7.42 (d, J = 7.5 Hz, 1H), 2.76 (t, J = 5.0 Hz, 2H), 1.67 (qt, J = 8.0, 5.0 Hz, 2H), 0.95 (t, J = 8.0 Hz, 3H) |
| 375 | 1H NMR (500 MHz, Chloroform-d) S 8.77 (s, 1H), 8.02 (dd, J = 7.5, 6.0 Hz, 1H), 7.68 (d, J = 7.5 Hz, 1H), 2.76 (t, J = 5.0 Hz, 2H), 1.67 (qt, J = 8.0, 5.0 Hz, 2H), 0.97 (t, J = 8.0 Hz, 3H) |

TABLE 2-continued $^1$H NMR data of compounds I

| Compound No. | $^1$HNMR |
|---|---|
| 376 | 1H NMR (500 MHz, Chloroform-d) S 8.09 (s, 1H), 7.79 (dd, J = 7.5, 6.0 Hz, 1H), 7.68 (d, J = 7.5 Hz, 1H), 3.77 (s, 3H), 2.76 (t, J = 8.0 Hz, 2H), 1.67-1.58 (m, 2H), 0.91 (t, J = 8.0 Hz, 3H). |
| 377 | 1H NMR (500 MHz, Chloroform-d) S 8.02 (s, 1H), 7.79 (dd, J = 7.5, 6.0 Hz, 1H), 7.67 (d, J = 7.5 Hz, 1H), 4.63 (s, 2H), 3.35 (s, 3H), 2.76 (t, J = 5.0 Hz, 2H), 1.67 (qt, J = 8.0, 5.0 Hz, 2H), 0.93 (t, J = 8.0 Hz, 3H). |
| 378 | 1H NMR (500 MHz, Chloroform-d) S 8.01 (s, 1H), 7.80 (dd, J = 7.5, 6.0 Hz, 1H), 7.67 (d, J = 7.5 Hz, 1H), 3.55 (t, J = 8.0 Hz, 2H), 3.25 (s, 3H), 2.74-2.65 (m, 4H), 1.67-1.58 (m, 2H), 0.91 (t, J = 8.0 Hz, 3H). |
| 379 | 1H NMR (500 MHz, Chloroform-d) S 8.02 (s, 1H), 7.85 (dd, J = 7.5, 6.0 Hz, 1H), 7.69 (d, J = 7.5 Hz, 1H), 4.36 (s, 3H), 2.76 (t, J = 8.0 Hz, 2H), 1.67-1.62 (m, 2H), 0.93 (t, J = 8.0 Hz, 3H). |
| 380 | 1H NMR (500 MHz, Chloroform-d) S 8.07 (s, 1H), 7.88 (dd, J = 7.5, 6.0 Hz, 1H), 7.61 (d, J = 7.5 Hz, 1H), 4.35 (s, 3H), 2.70 (d, J = 7.0 Hz, 2H), 1.82-1.74 (m, 1H), 0.87 (d, J = 7.0 Hz, 6H). |
| 381 | 1H NMR (500 MHz, Chloroform-d) S 8.07 (s, 1H), 7.70 (dd, J = 7.5, 6.0 Hz, 1H), 7.56 (d, J = 7.5 Hz, 1H), 7.36-7.27 (m, 2H), 7.29 -7.20 (m, 3H), 4.34 (s, 3H), 4.04 (s, 2H). |
| 382 | 1H NMR (500 MHz, DMSO-d6) δ 8.07 (d, J = 8.0 Hz, 1H), 7.88 (d, J = 8.0 Hz, 1H), 3.58-3.45 (m, 2H), 1.53 (t, J = 7.5 Hz, 2H), 1.37 (t, J = 7.5 Hz, 2H), 1.06-0.99 (m, 6H) |
| 383 | 1H NMR (500 MHz, DMSO-d6) δ 11.91 (s, 1H), 8.18 (d, J = 8.0 Hz, 1H), 7.94 (d, J = 8.0 Hz, 1H), 4.31 (t, J = 7.0 Hz, 2H), 3.60-3.50 (m, 1H), 3.20- 3.10 (m, 1H), 1.94-1.86 (m, 2H), 1.78- 1.75 (m, 1H), 1.68- 1.61 (m, 1H), 1.05 (t, J = 7.5 Hz, 3H), 0.89 (t, J = 7.5 Hz, 3H). |
| 384 | 1H NMR (500 MHz, Chloroform-d) S 8.03 (s, 1H), 7.83 (dd, J = 7.5, 6.0 Hz, 1H), 7.30 (d, J = 7.5 Hz, 1H), 4.30 (t, J = 8.0 Hz, 2H), 2.76 (t, J = 8.0 Hz, 2H), 1.90-1.85 (m, 2H), 1.67-1.58 (m, 2H), 1.38-1.32 (m, 2H), 0.95-0.90 (m, 6H). |
| 385 | 1H NMR (500 MHz, Chloroform-d) S 8.42 (s, 1H), 8.08 (dd, J = 7.5, 6.0 Hz, 1H), 7.52 (d, J = 7.5 Hz, 1H), 2.76 (t, J = 7.0 Hz, 2H), 2.42 (p, J = 7.0 Hz, 1H), 1.73-1.61 (m, 2H), 0.95 (t, J = 8.0 Hz, 3H), 0.84-0.74 (m, 2H), 0.54-0.46 (m, 2H). |
| 386 | 1H NMR (500 MHz, Chloroform-d) S 8.67 (s, 1H), 8.04 (dd, J = 7.5, 6.0 Hz, 1H), 7.59 (t, J = 7.5 Hz, 2H), 7.52-7.44 (m, 1H), 7.39-7.33 (m, 2H), 7.31 (d, J = 7.5 Hz, 1H), 2.76 (t, J = 8.0 Hz, 2H), 1.67-1.58 (m, 2H), 0.93 (t, J = 8.0 Hz, 3H). |
| 387 | 1H NMR (500 MHz, DMSO-d6) δ 11.76 (s, 1H), 7.88 (d, J = 7.5, 1H), 7.56 (d, J = 7.5 Hz, 1H), 4.49 (t, J = 7.0 Hz, 2H), 3.69 (t, J = 7.0 Hz, 2H), 3.20 (s, 3H), 2.76 (t, J = 5.5 Hz, 2H), 1.50-1.43 (m, 2H), 0.93 (t, J = 8.0 Hz, 3H). |
| 388 | 1H NMR (500 MHz, DMSO-d6) δ 11.76 (s, 1H), 8.17-8.13 (m, 1H), 7.95 (d, J = 8.0 Hz, 1H), 4.57 (t, J = 5.5 Hz, 2H), 3.82 (t, J = 5.5 Hz, 2H), 3.44 (q, J = 7.0 Hz, 2H), 3.26-3.12 (m, 2H), 1.81-1.63 (m, 2H), 1.08-1.03 (m, 6H). |
| 389 | 1H NMR (500 MHz, DMSO-d6) δ 12.05 (s, 1H), 8.10 (d, J = 7.5 Hz, 1H), 7.60-7.58 (m, 1H), 7.35-7.27 (m, 5H), 4.51 (s, 2H), 4.49 (t, J = 4.0 Hz, 2H), 3.77 (t, J = 4.0 Hz, 2H), 2.76 (t, J = 8.0 Hz, 2H), 1.51-1.43 (m, 2H), 0.90 (t, J = 8.0 Hz, 3H). |
| 390 | 1H NMR (500 MHz, Chloroform-d) S 8.96 (s, 1H), 8.09 (dd, J = 7.5, 6.0 Hz, 1H), 7.61 (d, J = 7.5 Hz, 1H), 3.78 (s, 2H), 3.34 (s, 3H), 2.76 (t, J = 8.0 Hz, 2H), 1.67-1.58 (m, 2H), 1.42 (s, 6H), 0.92 (t, J = 8.0 Hz, 3H). |
| 391 | 1H NMR (500 MHz, Chloroform-d)S 8.65 (s, 1H), 8.09 (dd, J = 7.5,6.0 Hz, 1H), 7.69 (d, J = 7.5 Hz, 1H), 4.30 (t, J = 8.0 Hz, 2H), 3.41 (t, J = 5.0 Hz, 2H), 3.30 (s, 3H), 2.76 (t, J = 8.0 Hz, 2H), 1.99-1.89 (m, 2H), 1.67-1.59 (m, 2H), 0.92 (t, J = 8.0 Hz, 3H). |
| 392 | 1H NMR (500 MHz, Chloroform-d) S 8.32 (s, 1H), 7.84 (dd, J = 7.5, 6.0 Hz, 1H), 7.70 (d, J = 7.5 Hz, 1H), 4.80 (dd, J = 12.0, 7.0 Hz, 1H), 4.26 (dd, J = 12.0, 7.0 Hz, 1H), 4.03-3.91 (m, 1H), 3.41 (s, 3H), 3.24-3.12 (m, 2H), 2.26-2.11 (m, 1H), 1.92-1.77 (m, 1H), 1.27 (d, J = 7.0 Hz, 3H), 0.92 (t, J = 8.0 Hz, 3H). |
| 393 | 1H NMR (500 MHz, Chloroform-d)S 9.41 (s, 1H), 8.06 (d, J = 7.5 Hz, 1H), 7.78 (dd, J = 7.5, 6.0 Hz, 1H), 7.31 (d, J = 7.5 Hz, 1H), 6.77 (d, J = 7.5 Hz, 1H), 2.76 (t, J = 8.0 Hz, 2H), 1.67-1.58 (m, 2H), 0.93 (t, J = 8.0 Hz, 3H). |
| 394 | 1H NMR (500 MHz, Chloroform-d) S 9.47 (s, 1H), 8.08 (dd, J = 7.5, 6.0 Hz, 1H), 7.79 (s, 1H), 7.69 (d, J = 7.5 Hz, 1H), 2.76 (t, J = 5.0 Hz, 2H), 2.37 (s, 3H), 1.67-1.58 (m, 2H), 0.96 (t, J = 8.0 Hz, 3H). |
| 395 | 1H NMR (500 MHz, Chloroform-d) S 8.66 (s, 1H), 7.88 (dd, J = 7.5, 6.0 Hz, 1H), 7.80 (s, 1H), 7.68 (d, J = 7.5 Hz, 1H), 3.31-2.24 (m, 1H), 2.76 (t, J = 8.0 Hz, 2H), 1.67-1.58 (m, 2H), 1.39 (d, J = 7.0 Hz, 6H), 0.92 (t, J = 8.0 Hz, 3H). |
| 396 | 1H NMR (500 MHz, Chloroform-d)S 8.67 (s, 1H), 7.82 (dd, J = 7.5, 6.0 Hz, 1H), 7.76-7.67 (m, 2H), 2.92 (t, J = 8.0 Hz, 2H), 2.75-2.70 (m, 4H), 1.67-1.58 (m, 2H), 0.92 (t, J = 8.1 Hz, 3H). |
| 397 | 1H NMR (500 MHz, Chloroform-d) S 8.71 (s, 1H), 8.06 (dd, J = 7.5, 6.0 Hz, 1H), 7.64 (d, J = 7.5 Hz, 1H), 2.76 (t, J = 5.0 Hz, 2H), 2.41 (s, 3H), 1.67 (qt, J = 8.0, 5.0 Hz, 2H), 0.96 (t, J = 8.0 Hz, 3H). |
| 398 | 1H NMR (500 MHz, Chloroform-d)S 8.88 (s, 1H), 8.06 (dd, J = 7.5, 6.0 Hz, 1H), 7.67 (d, J = 7.5 Hz, 1H), 2.93 (q, J = 8.0 Hz, 2H), 2.76 (t, J = 8.0Hz, 2H), 1.67-1.58 (m, 2H), 1.22 (t, J = 8.0 Hz, 3H), 0.91 (t, J = 8.0 Hz, 3H). |
| 399 | 1H NMR (500 MHz, Chloroform-d) S 8.23 (s, 1H), 7.89 (dd, J = 7.5, 6.0 Hz, 1H), 7.67 (d, J = 7.5 Hz, 1H), 2.85-2.72 (m, 3H), 1.67-1.58 (m, 2H), 1.23 (d, J = 7.0 Hz, 6H), 0.92 (t, J = 8.0 Hz, 3H). |
| 400 | 1H NMR (500 MHz, Chloroform-d) S 8.84 (s, 1H), 8.06 (dd, J = 7.5, 6.0 Hz, 1H), 7.68 (d, J = 7.5 Hz, 1H), 2.94 (t, J = 5.5 Hz, 2H), 2.76 (t, J = 5.0 Hz, 2H), 1.86-1.81(m, 2H), 1.67-1.62 (m, 2H), 0.99-0.94 (m, 6H). |
| 401 | 1H NMR (500 MHz, Chloroform-d) S 8.13 (s, 1H), 7.78 (dd, J = 7.5, 6.0 Hz, 1H), 7.67 (d, J = 7.5 Hz, 1H), 2.76 (t, J = 8.0 Hz, 2H), 1.67-1.58 (m, 2H), 1.28 (s, 9H), 0.93 (t, J = 8.0 Hz, 3H). |
| 402 | 1H NMR (500 MHz, Chloroform-d) S 8.33 (s, 1H), 8.08 (dd, J = 7.5, 6.0 Hz, 1H), 7.52 (d, J = 7.5 Hz, 1H), 2.76 (t, J = 7.0 Hz, 2H), 1.73-1.61 (m, 2H), 1.58 (q, J = 7.0 Hz, 1H), 0.95 (t, J = 8.0 Hz, 3H), 0.88-0.75 (m, 4H). |
| 403 | 1H NMR (500 MHz, Chloroform-d) S 8.81 (s, 1H), 7.89 (dd, J = 7.5, 6.0 Hz, 1H), 7.67 (d, J = 7.5 Hz, 1H), 2.76 (t, J = 8.0 Hz, 2H), 1.67-1.58 (m, 2H), 0.92 (t, J = 8.0 Hz, 3H). |
| 404 | 1H NMR (500 MHz, Chloroform-d) S 9.07 (s, 1H), 8.06 (dd, J = 7.5, 6.0 Hz, 1H), 7.68 (d, J = 7.5 Hz, 1H), 3.90 (s, 3H), 2.76 (t, J = 5.0 Hz, 2H), 1.67 (qt, J = 8.0, 5.0 Hz, 2H), 0.97 (t, J = 8.0 Hz, 3H). |
| 405 | 1H NMR (500 MHz, Chloroform-d) S 8.67 (s, 1H), 8.06 (dd, J = 7.5, 6.0 Hz, 1H), 7.71 (s, 1H), 7.29 (d, J = 7.5 Hz, 1H), 2.76 (t, J = 5.0 Hz, 2H), 2.15 (s, 3H), 1.67-1.62 (m, 2H), 0.95 (t, J = 8.0 Hz, 3H). |
| 406 | 1H NMR (500 MHz, Chloroform-d) S 8.81 (s, 1H), 7.98 (dd, J = 7.5, 6.0 Hz, 1H), 7.65 (d, J = 7.5 Hz, 1H), 5.80 (s, 2H), 2.76(t, J = 5.0 Hz, 2H), 1.67 (qt, J = 8.0, 5.0 Hz, 2H), 0.96 (t, J = 8.0 Hz, 3H). |
| 407 | 1H NMR (500 MHz, DMSO) S 9.05 (s, 1H), 8.15 (s, 1H), 7.89-7.79 (m, 2H), 3.70 (s, 3H), 2.62-2.41 (m, 2H), 1.80-1.50 (m, 2H), 1.02 (t, J = 7.0 Hz, 3H). |
| 408 | 1H NMR (500 MHz, Chloroform-d) S 8.63 (s, 1H), 8.06 (s, 1H), 7.87 (dd, J = 7.5, 6.0 Hz, 1H), 7.70 (d, J = 7.5 Hz, 1H), 4.40 (q, J = 8.0 Hz, 2H), 2.76 (t, J = 5.0 Hz, 2H), 1.67-1.63 (m, 2H), 1.52 (t, J = 8.0 Hz, 3H), 0.96 (t, J = 8.0 Hz, 3H). |
| 409 | 1H NMR (500 MHz, Chloroform-d) S 8.08 (dd, J = 7.5, 6.0 Hz, 1H), 7.84 (s, 1H), 7.52 (d, J = 7.5 Hz, 1H), 2.76 (t, J = 7.0 Hz, 2H), 2.42-2.38 (m, 1H), 1.73-1.61 (m, 2H), 0.95 (t, J = 8.0 Hz, 3H), 0.84-0.74 (m, 2H), 0.54-0.79 (m, 2H). |
| 410 | 1H NMR (500 MHz, Chloroform-d)S 7.93 (d, J = 7.5 Hz, 1H), 7.73 (d, J = 7.5 Hz, 1H), 3.79 (s, 3H), 3.46 (q, J = 8.0 Hz, 2H), 3.26 (s, 3H), 2.39 (s, 3H), 1.41 (t, J = 8.0 Hz, 3H). |
| 411 | 1H NMR (500 MHz, Chloroform-d)S 7.98 (d, J = 7.5 Hz, 1H), 7.75 (d, J = 7.5 Hz, 1H), 6.00-5.95 (m, 1H), 5.47- |

TABLE 2-continued

| $^1$H NMR data of compounds I | |
|---|---|
| Compound No. | $^1$HNMR |
| | 5.37 (m, 1H), 5.22-5.12 (m, 1H), 4.95 (dd, J = 6.0, 1.0 Hz, 2H), 3.74 (s, 3H), 3.46 (q, J = 8.0 Hz, 2H), 2.39 (s, 3H), 1.41 (t, J = 8.0 Hz, 3H). |
| 412 | 1H NMR (500 MHz, Chloroform-d) S 7.95 (d, J = 7.5 Hz, 1H), 7.76 (d, J = 7.5 Hz, 1H), 3.94 (d, J = 3.0 Hz, 2H), 3.80 (s, 3H), 3.46 (q, J = 8.0 Hz, 2H), 2.56 (t, J = 3.0 Hz, 1H), 2.40 (s, 3H), 1.42 (t, J = 8.0 Hz, 3H). |
| 413 | 1H NMR (500 MHz, Chloroform-d) S 7.87 (d, J = 7.5 Hz, 1H), 7.70 (d, J = 7.5 Hz, 1H), 7.34-7.22 (m, 5H), 5.13 (s, 2H), 3.82 (s, 3H), 3.46 (q, J = 8.0 Hz, 2H), 2.38 (s, 3H), 1.40 (t, J = 8.0 Hz, 3H). |
| 414 | 1H NMR (500 MHz, Chloroform-d) S 7.81 (d, J = 7.5 Hz, 1H), 7.72 (d, J = 7.5 Hz, 1H), 3.77-3.67 (m, 5H), 3.46 (q, J = 8.0 Hz, 2H), 2.38 (s, 3H), 1.41 (t, J = 8.0 Hz, 3H). |
| 415 | 1H NMR (500 MHz, Chloroform-d) S 7.89 (d, J = 7.5 Hz, 1H), 7.75 (d, J = 7.5 Hz, 1H), 4.32 (s, 2H), 3.82 (s, 3H), 3.46 (q, J = 8.0 Hz, 2H), 2.41 (s, 3H), 1.42 (t, J = 8.0 Hz, 3H). |
| 416 | 1H NMR (500 MHz, Chloroform-d)S 8.10 (d, J = 7.5 Hz, 1H), 7.74 (d, J = 7.5 Hz, 1H), 3.79 (s, 3H), 3.46 (q, J = 8.0 Hz, 2H), 2.40 (s, 3H), 2.34 (s, 3H), 1.41 (t, J = 8.0 Hz, 3H). |
| 417 | 1H NMR (500 MHz, Chloroform-d) S 8.08 (d, J = 7.5 Hz, 1H), 7.75 (d, J = 7.5 Hz, 1H), 7.64-7.57 (m, 2H), 7.35-7.23 (m, 3H), 3.84 (s, 3H), 3.46 (q, J = 8.0 Hz, 2H), 2.39 (s, 3H), 1.40 (t, J = 8.0 Hz, 3H). |
| 418 | 1H NMR (500 MHz, Chloroform-d) S 8.10 (d, J = 7.5 Hz, 1H), 7.77 (d, J = 7.5 Hz, 1H), 3.78 (s, 3H), 3.52 (t, J = 5.0 Hz, 4H), 3.46 (q, J = 8.0 Hz, 2H), 3.12 (t, J = 5.0 Hz, 4H), 2.38 (s, 3H), 1.41 (t, J = 8.0 Hz, 3H). |
| 419 | 1H NMR (500 MHz, Chloroform-d) S 8.00 (d, J = 7.5 Hz, 1H), 7.74 (d, J = 7.5 Hz, 1H), 7.61 (s, 1H), 3.92 (s, 3H), 3.84 (s, 3H), 3.46 (q, J = 8.0 Hz, 2H), 2.49 (s, 3H), 2.39 (s, 3H), 1.42 (t, J = 8.0 Hz, 3H). |
| 420 | 1H NMR (500 MHz, Chloroform-d) S 8.02 (d, J = 7.5 Hz, 1H), 7.75 (d, J = 7.5 Hz, 1H), 3.81 (s, 3H), 3.75 (s, 3H), 3.46 (q, J = 8.0 Hz, 2H), 2.42 (s, 3H), 1.41 (t, J = 8.0 Hz, 3H). |
| 421 | 1H NMR (500 MHz, Chloroform-d)S 8.01 (d, J = 7.5 Hz, 1H), 7.57 (d, J = 7.5 Hz, 1H), 6.80-6.76 (m, 1H), 4.17 (s, 3H), 3.82 (s, 3H), 3.64-3.61 (m, 1H), 3.08-2.96 (m, 1H), 2.46 (s, 3H), 1.70 (d, J = 4.0 Hz, 3H),1.11 (t, J = 7.5 Hz, 3H). |
| 422 | 1H NMR (500 MHz, Chloroform-d)S 8.08 (d, J = 7.5 Hz, 1H), 7.58 (d, J = 7.5 Hz, 1H), 6.80-6.75 (m, 1H), 4.29-4.17 (m, 2H), 3.82 (s, 3H), 3.64-3.61 (m, 1H), 3.08-2.96 (m, 1H), 2.46 (s, 3H), 1.70 (d, J = 4.0 Hz, 3H),1.33-1.28 (m, 3H), 1.11 (t, J = 7.5 Hz, 3H). |
| 423 | 1H NMR (500 MHz, Chloroform-d)S 8.71 (s, 1H), 8.10 (d, J = 7.5 Hz, 1H), 7.77-7.69 (m, 2H), 3.82 (s, 3H), 3.46 (q, J = 8.0 Hz, 2H), 1.41 (t, J = 8.0 Hz, 3H). |
| 424 | 1H NMR (500 MHz, Chloroform-d) S 8.73 (s, 1H), 8.06 (d, J = 7.5 Hz, 1H), 7.75 (d, J = 7.5 Hz, 1H), 3.82 (s, 3H), 3.46 (q, J = 8.0 Hz, 2H), 2.59 (q, J = 8.0 Hz, 2H), 1.41 (t, J = 8.0 Hz, 3H), 1.20 (t, J = 8.0 Hz, 3H). |
| 425 | 1H NMR (500 MHz, Chloroform-d) S 8.68 (s, 1H), 8.07 (d, J = 7.5 Hz, 1H), 7.75 (d, J = 7.5 Hz, 1H), 3.82 (s, 3H), 3.46 (q, J = 8.0 Hz, 2H), 2.94 (p, J = 7.0 Hz, 1H), 1.42 (t, J = 8.0 Hz, 3H), 1.22 (d, J = 7.0 Hz, 6H). |
| 426 | 1H NMR (500 MHz, Chloroform-d) S 8.75 (s, 1H), 8.04 (d, J = 7.5 Hz, 1H), 7.74 (d, J = 7.5 Hz, 1H), 3.82 (s, 3H), 2.53 (t, J = 5.5 Hz, 2H), 1.86 (qt, J = 8.0, 5.5 Hz, 2H), 1.40 (q, J = 8.0 Hz, 2H), 0.96-0.89 (m, 6H). |
| 427 | 1H NMR (500 MHz, Chloroform-d) S 8.73 (s, 1H), 8.08 (d, J = 7.5 Hz, 1H), 7.75 (d, J = 7.5 Hz, 1H), 3.82 (s, 3H), 3.46 (q, J = 8.0 Hz, 2H), 1.41 (t, J = 8.0 Hz, 3H), 1.37 (s, 9H). |
| 428 | 1H NMR (500 MHz, Chloroform-d) S 8.78 (s, 1H),8.10 (d, J = 7.5 Hz, 1H), 7.73 (d, J = 7.5 Hz, 1H), 3.85 (s, 3H), 3.46 (q, J = 8.0 Hz, 2H), 1.50 (p, J = 7.1 Hz, 1H), 1.31 (t, J = 8.0 Hz, 3H), 1.08-1.00 (m, 2H), 1.00-0.88 (m, 2H). |
| 429 | 1H NMR (500 MHz, Chloroform-d) S 8.78 (s, 1H),8.10 (d, J = 7.5 Hz, 1H), 7.73 (d, J = 7.5 Hz, 1H), 3.85 (s, 3H), 3.46 (q, J = 8.0 Hz, 2H), 1.47-1.38 (m, 2H), 1.31 (t, J = 8.0 Hz, 3H), 0.90 (d, J = 6.5 Hz, 3H), 0.63-0.52 (m, 1H), 0.38-0.29 (m, 1H). |
| 430 | 1H NMR (500 MHz, Chloroform-d) S 8.78 (s, 1H),8.10 (d, J = 7.5 Hz, 1H), 7.68 (d, J = 7.5 Hz, 1H), 3.85 (s, 3H), 3.46 (q, J = 8.0 Hz, 2H), 3.24 (p, J = 7.0 Hz, 1H), 2.38-2.34 (m, 2H), 2.18-2.08 (m, 2H), 2.07-1.97 (m, 1H), 1.91-1.85 (m, 1H), 1.31 (t, J = 8.0 Hz, 3H). |
| 431 | 1H NMR (500 MHz, Chloroform-d) S 8.70 (s, 1H), 7.82 (d, J = 7.5 Hz, 1H), 7.74 (d, J = 7.5 Hz, 1H), 3.69 (s, 3H), 3.46 (q, J = 8.0 Hz, 2H), 3.01 (p, J = 7.0 Hz, 1H), 1.94-1.83 (m, 2H), 1.74-1.68 (m, 2H), 1.63-1.52 (m, 2H), 1.51-1.38 (m, 5H). |
| 432 | 1H NMR (500 MHz, Chloroform-d)S 8.78 (s, 1H), 8.09 (d, J = 7.5 Hz, 1H), 7.75 (d, J = 7.5 Hz, 1H), 6.44 (dd, J = 16.5, 10.0 Hz, 1H), 5.65 (dd, J = 14.0, 10.0 Hz, 1H), 5.40 (dd, J = 16.5, 14.0 Hz, 1H), 3.82 (s, 3H), 3.46 (q, J = 8.0 Hz, 2H), 1.41 (t, J = 8.0 Hz, 3H). |
| 433 | 1H NMR (500 MHz, Chloroform-d) S 8.70 (s, 1H), 8.08 (d, J = 7.5 Hz, 1H), 7.74 (d, J = 7.5 Hz, 1H), 3.81 (s, 3H), 3.46 (q, J = 8.0 Hz, 2H), 3.22 (s, 1H), 1.41 (t, J = 8.0 Hz, 3H). |
| 434 | 1H NMR (500 MHz, Chloroform-d) S 8.74 (s, 1H), 8.01 (d, J = 7.5 Hz, 1H), 7.75 (d, J = 7.5 Hz, 1H), 6.53 (s, 1H), 3.82 (s, 3H), 3.46 (q, J = 8.0 Hz, 2H), 1.41 (t, J = 8.0 Hz, 3H). |
| 435 | 1H NMR (500 MHz, Chloroform-d) S 8.77 (s, 1H), 8.01 (d, J = 7.5 Hz, 1H), 7.75 (d, J = 7.5 Hz, 1H), 3.82 (s, 3H), 3.46 (q, J = 8.0 Hz, 2H), 1.41 (t, J = 8.0 Hz, 3H). |
| 436 | 1H NMR (500 MHz, Chloroform-d) S 8.73 (s, 1H), 8.09 (d, J = 7.5 Hz, 1H), 7.75 (d, J = 7.5 Hz, 1H), 3.82 (s, 3H), 3.46 (q, J = 8.0 Hz, 2H), 2.53 (t, J = 8.6 Hz, 2H), 2.14-2.09 (m, 2H), 1.41 (t, J = 8.0 Hz, 3H) |
| 437 | 1H NMR (500 MHz, Chloroform-d) S 8.86 (s, 1H), 8.06 (d, J = 7.5 Hz, 1H), 7.73 (d, J = 7.5 Hz, 1H), 3.85 (s, 3H), 3.46 (q, J = 8.0 Hz, 2H), 2.60-2.51 (m, 2H), 1.51-1.42 (m, 1H), 1.35-1.19 (m, 4H). |
| 438 | 1H NMR (500 MHz, Chloroform-d) S 8.86 (s, 1H), 8.10 (d, J = 7.5 Hz, 1H), 7.73 (d, J = 7.5 Hz, 1H), 3.85 (s, 3H), 3.46 (q, J = 8.0 Hz, 2H), 2.60-2.54 (m, 1H), 1.51-1.46 (m, 1H), 1.35-1.19 (m, 4H). |
| 439 | 1H NMR (500 MHz, Chloroform-d) S 8.86 (s, 1H), 8.10 (d, J = 7.5 Hz, 1H), 7.73 (d, J = 7.5 Hz, 1H), 7.37-7.29 (m, 2H), 7.25-7.14 (m, 3H), 3.85 (s, 3H), 3.55-3.45 (m, 2H), 2.45 (q, J = 7.0 Hz, 2H), 1.50-1.45 (m, 1H), 1.31 (t, J = 8.0 Hz, 3H), 1.25-1.19 (m, 1H). |
| 440 | 1H NMR (500 MHz, Chloroform-d) S 8.75 (s, 1H), 8.06 (d, J = 7.5 Hz, 1H), 7.75 (d, J = 7.5 Hz, 1H), 3.82 (s, 3H), 3.46 (q, J = 8.0 Hz, 2H), 1.41 (t, J = 8.0 Hz, 3H). |
| 441 | 1H NMR (500 MHz, Chloroform-d) S 8.86 (s, 1H), 8.01 (d, J = 7.5 Hz, 1H), 7.75 (d, J = 7.5 Hz, 1H), 3.82 (s, 3H), 3.46 (q, J = 8.0 Hz, 2H), 1.41 (t, J = 8.0 Hz, 3H). |
| 442 | 1H NMR (500 MHz, Chloroform-d) S 8.72 (s, 1H), 8.10 (d, J = 7.5 Hz, 1H), 7.74 (d, J = 7.5 Hz, 1H), 3.82 (s, 3H), 3.77 (s, 3H), 3.46 (q, J = 8.0 Hz, 2H), 1.41 (t, J = 8.0 Hz, 3H). |
| 443 | 1H NMR (500 MHz, Chloroform-d) S 8.72 (s, 1H), 8.10 (d, J = 7.5 Hz, 1H), 7.74 (d, J = 7.5 Hz, 1H), 4.63 (s, 2H), 3.82 (s, 3H), 3.46 (q, J = 8.0 Hz, 2H), 3.36 (s, 3H), 1.41 (t, J = 8.0 Hz, 3H). |
| 444 | 1H NMR (500 MHz, Chloroform-d) S 8.73 (s, 1H), 8.10 (d, J = 7.5 Hz, 1H), 7.75 (d, J = 7.5 Hz, 1H), 3.82 (s, 3H), 3.55 (t, J = 7.5 Hz, 2H), 3.46 (q, J = 8.0 Hz, 2H), 3.25 (s, 3H), 2.72 (t, J = 7.5 Hz, 2H), 1.41 (t, J = 8.0 Hz, 3H). |
| 445 | 1H NMR (500 MHz, Chloroform-d) S 9.01 (s, 1H), 8.11 (d, J = 7.5 Hz, 1H), 7.76 (d, J = 7.5 Hz, 1H), 4.34 (s, 3H), 3.85 (s, 3H), 3.46 (q, J = 8.0 Hz, 2H), 1.42 (t, J = 8.0 Hz, 3H). |
| 446 | 1H NMR (500 MHz, Chloroform-d)S 8.95 (s, 1H), 8.05 (d, J = 7.5 Hz, 1H), 7.76 (d, J = 7.5 Hz, 1H), 4.40 (q, J = 8.0 Hz, 2H), 3.86 (s, 3H), 3.46 (q, J = 8.0 Hz, 2H), 1.49 (t, J = 8.0 Hz, 3H), 1.42 (t, J = 8.0 Hz, 3H). |
| 447 | 1H NMR (500 MHz, Chloroform-d) S 8.92 (s, 1H), 8.06 (d, J = 7.5 Hz, 1H), 7.76 (d, J = 7.5 Hz, 1H), 4.30 (t, J = 8.0 Hz, 2H), 3.87 (s, 3H), 3.46 (q, J = 8.0 Hz, 2H), 1.97-1.88 (m, 2H), 1.42 (t, J = 8.0 Hz, 3H), 0.94 (t, J = 8.0 Hz, 3H). |
| 448 | 1H NMR (500 MHz, Chloroform-d) S 8.91 (s, 1H), 8.06 (d, J = 7.5 Hz, 1H), 7.76 (d, J = 7.5 Hz, 1H), 4.30 (t, J = 8.0 Hz, 2H), 3.86 (s, 3H), 3.46 (q, J = 8.0 Hz, 2H), 1.90-1.84 (m, 2H), 1.39-1.33 (m, 5H), 0.98 (t, J = 8.0 Hz, 3H). |

TABLE 2-continued $^1$H NMR data of compounds I

| Compound No. | $^1$HNMR |
|---|---|
| 449 | 1H NMR (500 MHz, Chloroform-d) S 8.91 (s, 1H), 8.10 (d, J = 7.5 Hz, 1H), 7.73 (d, J = 7.5 Hz, 1H), 3.85 (s, 3H), 3.46 (q, J = 8.0 Hz, 2H), 2.42 (p, J = 7.0 Hz, 1H), 1.31 (t, J = 8.0 Hz, 3H), 0.84-0.74 (m, 2H), 0.54-0.48 (m, 2H). |
| 450 | 1H NMR (500 MHz, Chloroform-d) S 8.64 (s, 1H), 8.08 (d, J = 7.5 Hz, 1H), 7.75 (d, J = 7.5 Hz, 1H), 7.59 (t, J = 7.5 Hz, 2H), 7.52-7.48 (m, 1H), 7.38-7.32 (m, 2H), 3.92 (s, 3H), 3.46 (q, J = 8.0 Hz, 2H), 1.41 (t, J = 8.0 Hz, 3H). |
| 451 | 1H NMR (500 MHz, Chloroform-d) S 8.78 (s, 1H), 8.07 (d, J = 7.5 Hz, 1H), 7.76 (d, J = 7.5 Hz, 1H), 4.30 (t, J = 7.5 Hz, 2H), 3.87 (s, 3H), 3.78 (t, J = 7.5 Hz, 2H), 3.46 (q, J = 8.0 Hz, 2H), 3.31 (s, 3H), 1.42 (t, J = 8.0 Hz, 3H). |
| 452 | 1H NMR (500 MHz, Chloroform-d) S 8.84 (s, 1H), 8.09 (d, J = 7.5 Hz, 1H), 7.76 (d, J = 7.5 Hz, 1H), 4.30 (t, J = 7.5 Hz, 2H), 3.94 (t, J = 7.5 Hz, 2H), 3.85 (s, 3H), 3.63 (q, J = 8.0 Hz, 2H), 3.46 (q, J = 8.0 Hz, 2H), 1.42 (t, J = 8.0 Hz, 3H), 1.18 (t, J = 8.0 Hz, 3H). |
| 453 | 1H NMR (500 MHz, Chloroform-d) S 8.81 (s, 1H), 8.06 (d, J = 7.5 Hz, 1H), 7.74 (d, J = 7.5 Hz, 1H), 7.30 (s, 5H), 4.47 (s, 2H), 4.30 (t, J = 7.5 Hz, 2H), 3.81 (d, J = 4.0 Hz, 5H), 3.46 (q, J = 8.0 Hz, 2H), 1.40 (t, J = 8.0 Hz, 3H). |
| 454 | 1H NMR (500 MHz, Chloroform-d) S 9.50 (s, 1H), 8.08 (d, J = 7.5 Hz, 1H), 7.65 (d, J = 7.5 Hz, 1H), 3.84 (s, 3H), 3.78 (s, 2H), 3.46 (q, J = 8.0 Hz, 2H), 3.24 (s, 3H), 1.43-1.32 (m, 9H). |
| 455 | 1H NMR (500 MHz, Chloroform-d) S 8.93 (s, 1H), 8.08 (d, J = 7.5 Hz, 1H), 7.76 (d, J = 7.5 Hz, 1H), 4.30 (t, J = 8.0 Hz, 2H), 3.85 (s, 3H), 3.50-3.37 (m, 4H), 3.30 (s, 3H), 1.99 (p, J = 8.0 Hz, 2H), 1.42 (t, J = 8.0 Hz, 3H). |
| 456 | 1H NMR (500 MHz, Chloroform-d)S 8.93 (s, 1H), 7.87 (d, J = 7.5 Hz, 1H), 7.76 (d, J = 7.5 Hz, 1H), 4.75 (dd, J = 12.5, 7.0 Hz, 1H), 4.27 (dd, J = 12.5, 7.0 Hz, 1H), 4.00-3.91 (m, 1H), 3.75 (s, 3H), 3.40 (s, 3H), 3.27-3.12 (m, 2H), 1.42 (t, J = 8.0 Hz, 3H), 1.26 (d, J = 7.0 Hz, 3H). |
| 457 | 1H NMR (500 MHz, Chloroform-d)S 9.38 (s, 1H), 8.76 (d, J = 7.5 Hz, 1H), 8.35 (d, J = 7.5 Hz, 1H), 7.75 (d, J = 7.5 Hz, 1H), 6.77 (d, J = 7.5 Hz, 1H), 3.86 (s, 3H), 3.46 (q, J = 8.0 Hz, 2H), 1.41 (t, J = 8.0 Hz, 3H). |
| 458 | 1H NMR (500 MHz, Chloroform-d)S 9.35 (s, 1H), 8.05 (d, J = 7.5 Hz, 1H), 7.81-7.73 (m, 2H), 3.86 (s, 3H), 3.46 (q, J = 8.0 Hz, 2H), 2.34 (s, 3H), 1.42 (t, J = 8.0 Hz, 3H). |
| 459 | 1H NMR (500 MHz, Chloroform-d)S 9.25 (s, 1H), 8.35 (d, J = 7.5 Hz, 1H), 7.82-7.73 (m, 2H), 3.87 (s, 3H), 3.50-3.45 (m, 2H), 3.42 (dd, J = 13.5, 7.0 Hz, 1H), 1.42 (t, J = 8.0 Hz, 9H). |
| 460 | 1H NMR (500 MHz, Chloroform-d)S 9.30 (s, 1H), 8.06 (d, J = 7.5 Hz, 1H), 7.79-7.72 (m, 2H), 3.87 (s, 3H), 3.46 (q, J = 8.0 Hz, 2H), 2.92 (t, J = 7.8 Hz, 2H), 2.78-2.70 (m, 2H), 1.42 (t, J = 8.0 Hz, 3H). |
| 461 | 1H NMR (500 MHz, Chloroform-d) S 8.96 (s, 1H), 8.06 (d, J = 7.5 Hz, 1H), 7.75 (d, J = 7.5 Hz, 1H), 3.82 (s, 3H), 3.46 (q, J = 8.0 Hz, 2H), 2.43 (s, 3H), 1.41 (t, J = 8.0 Hz, 3H). |
| 462 | 1H NMR (500 MHz, Chloroform-d) S 8.91 (s, 1H), 8.01 (d, J = 7.5 Hz, 1H), 7.74 (d, J = 7.5 Hz, 1H), 3.82 (s, 3H), 3.46 (q, J = 8.0 Hz, 2H), 2.93 (q, J = 8.0 Hz, 2H), 1.41 (t, J = 8.0 Hz, 3H), 1.20 (t, J = 8.0 Hz, 3H). |
| 463 | 1H NMR (500 MHz, Chloroform-d) S 8.91 (s, 1H), 8.08 (d, J = 7.5 Hz, 1H), 7.75 (d, J = 7.5 Hz, 1H), 3.82 (s, 3H), 3.54-3.47 (m, 1H), 3.46 (q, J = 8.0 Hz, 2H), 1.42 (t, J = 8.0 Hz, 3H), 1.22 (d, J = 7.0 Hz, 6H) |
| 464 | 1H NMR (500 MHz, Chloroform-d) S 8.92 (s, 1H), 8.02 (d, J = 7.5 Hz, 1H), 7.74 (d, J = 7.5 Hz, 1H), 3.82 (s, 3H), 3.46 (q, J = 8.0 Hz, 2H), 2.94 (t, J = 8.0 Hz, 2H), 1.86-1.80 (m, 2H), 1.41 (t, J = 8.0 Hz, 3H), 1.01 (t, J = 8.0 Hz, 3H). |
| 465 | 1H NMR (500 MHz, Chloroform-d) S 8.66 (s, 1H), 8.08 (d, J = 7.5 Hz, 1H), 7.74 (d, J = 7.5 Hz, 1H), 3.83 (s, 3H), 3.46 (q, J = 8.0 Hz, 2H), 1.41 (t, J = 8.0 Hz, 3H), 1.31 (s, 9H). |
| 466 | 1H NMR (500 MHz, Chloroform-d)S 8.10 (d, J = 7.5 Hz, 1H), 7.43 (d, J = 7.5 Hz, 1H), 3.85 (s, 3H), 3.46 (q, J = 8.0 Hz, 2H), 1.59 (p, J = 7.0 Hz, 1H), 1.31 (t, J = 8.0 Hz, 3H), 0.88-0.75 (m, 4H). |

TABLE 2-continued $^1$H NMR data of compounds I

| Compound No. | $^1$HNMR |
|---|---|
| 467 | 1H NMR (500 MHz, Chloroform-d) S 9.40 (s, 1H), 8.01 (d, J = 7.5 Hz, 1H), 7.75 (d, J = 7.5 Hz, 1H), 3.82 (s, 3H), 3.46 (q, J = 8.0 Hz, 2H), 1.41 (t, J = 8.0 Hz, 3H). |
| 468 | 1H NMR (500 MHz, Chloroform-d) S 9.09 (s, 1H), 8.01 (d, J = 7.5 Hz, 1H), 7.74 (d, J = 7.5 Hz, 1H), 3.89 (s, 3H), 3.82 (s, 3H), 3.46 (q, J = 8.0 Hz, 2H), 1.41 (t, J = 8.0 Hz, 3H). |
| 469 | 1H NMR (500 MHz, Chloroform-d)S 9.09 (s, 1H), 8.02 (d, J = 7.5 Hz, 1H), 7.76-7.69 (m, 2H), 3.74 (s, 3H), 3.46 (q, J = 8.0 Hz, 2H), 2.15 (s, 3H), 1.43 (t, J = 8.0 Hz, 3H). |
| 470 | 1H NMR (500 MHz, Chloroform-d) S 9.19 (s, 1H), 8.04 (d, J = 7.5 Hz, 1H), 7.75 (d, J = 7.5 Hz, 1H), 5.80 (s, 2H), 3.83 (s, 3H), 3.46 (q, J = 8.0 Hz, 2H), 1.41 (t, J = 8.0 Hz, 3H). |
| 471 | 1H NMR (500 MHz, Chloroform-d) S 9.10 (s, 1H), 8.12 (d, J = 7.5 Hz, 1H), 8.02 (s, 1H), 7.76 (d, J = 7.5 Hz, 1H), 3.95 (s, 3H), 3.86 (s, 3H), 3.46 (q, J = 8.0 Hz, 2H), 1.42 (t, J = 8.0 Hz, 3H). |
| 472 | 1H NMR (500 MHz, Chloroform-d) S 8.82 (s, 1H), 8.13 (s, 1H), 7.95 (d, J = 7.5 Hz, 1H), 7.75 (d, J = 7.5 Hz, 1H), 4.40 (q, J = 8.0 Hz, 2H), 3.83 (s, 3H), 3.46 (q, J = 8.0 Hz, 2H), 1.49 (t, J = 8.0 Hz, 3H), 1.42 (t, J = 8.0 Hz, 3H). |
| 473 | 1H NMR (500 MHz, Chloroform-d) S 8.10 (d, J = 7.5 Hz, 1H), 7.84 (s, 1H), 7.43 (d, J = 7.5 Hz, 1H), 3.85 (s, 3H), 3.46 (q, J = 8.0 Hz, 2H), 2.42 (p, J = 7.0 Hz, 1H), 1.31 (t, J = 8.0 Hz, 3H), 0.84-0.74 (m, 2H), 0.54-0.48 (m, 2H). |
| 474 | 1H NMR (300 MHz, DMSO-d6) δ 12.35 (s, 1H), 7.82 (d, J = 7.5 Hz, 1H), 7.33 (d, J = 7.5 Hz, 1H), 4.33 (s, 3H), 3.82 (q, J = 8.0 Hz, 1H), 3.56(q, J = 8.0 Hz, 1H), 2.40 (s, 3H), 2.31 (s, 3H), 1.31 (t, J = 8.0 Hz, 3H). |
| 475 | 1H NMR (300 MHz, DMSO-d6) δ 12.33 (s, 1H), 7.74 (d, J = 7.5 Hz, 1H), 7.45 (d, J = 7.5 Hz, 1H), 4.33 (s, 3H),3.76 (t, J = 8.0 Hz, 1H), 3.56(q, J = 8.0 Hz, 1H), 2.37-2.29 (m, 6H), 1.47-1.42(m, 2H), 0.89 (t, J = 8.0 Hz, 3H). |
| 476 | 1H NMR (300 MHz, DMSO-d6) δ 12.36 (s, 1H), 7.83 (d, J = 7.5 Hz, 1H), 7.37-7.27 (m, 1H), 4.33 (s, 3H), 3.74-3.70 (m, 1H), 2.42 (s, 3H), 2.33 (s, 3H), 1.37 (d, J = 6.5 Hz, 6H). |
| 477 | 1H NMR (300 MHz, DMSO-d6) δ 12.36 (s, 1H), 7.84 (d, J = 7.5 Hz, 1H), 7.38-7.28 (m, 1H), 4.33 (s, 3H), 3.70 (d, J = 7.0 Hz, 1H), 3.55 (d, J = 7.0 Hz, 1H), 2.42 (s, 3H), 2.42-2.21 (m, 4H), 0.92 (d, J = 6.5Hz, 6H). |
| 478 | 1H NMR (300 MHz, DMSO-d6) 6.12.35(s, 1H), 7.75 (d, J = 7.5 Hz, 1H), 7.41-7.31 (m, 1H), 4.33 (s, 3H), 3.90 (s, 1H), 3.73 (s, 1H), 2.38-2.30 (m, 6H). |
| 479 | 1H NMR (300 MHz, DMSO-d6) δ 12.33(s, 1H), 7.87 (d, J = 7.5 Hz, 1H), 7.44 (d, J = 7.5Hz, 1H), 4.33 (s, 3H), 3.56-3.52(m, 1H), 2.77 (s, 3H), 2.47 (s, 3H), 1.19 (d, J = 6.5 Hz, 6H). |
| 480 | 1H NMR (300 MHz, DMSO-d6) δ 12.34 (s, 1H), 7.76 (d, J = 7.5 Hz, 1H), 7.28 (d, J = 7.5Hz, 1H), 4.33 (s, 3H), 3.64-3.60(m, 1H), 2.80(s, 3H), 2.34(s, 3H), 1.24-1.09 (m, 2H), 0.85 -0.70 (m, 2H) |
| 481 | 1H NMR (300 MHz, DMSO-d6) δ 12.57 (s, 1H), 7.83 (d, J = 7.5 Hz, 1H), 7.31 (d, J = 7.5Hz, 1H), 3.82 (q, J = 8.0 Hz, 1H), 3.51 (q, J = 8.0 Hz, 1H), 2.45 (s, 3H), 2.36(s, 3H), 2.29 (s, 3H), 1.31 (t, J = 8.0 Hz, 3H). |
| 482 | 1H NMR (300 MHz, DMSO-d6) δ 12.57 (s, 1H), 7.80 (d, J = 7.5 Hz, 1H), 7.31 (d, J = 7.5Hz, 1H), 3.76 (t, J = 8.0 Hz, 1H), 3.56 (t, J = 8.0 Hz, 1H), 2.45 (s, 3H), 2.36 (s, 3H), 2.29 (s, 3H), 1.47-1.42(m, 2H), 0.89 (t, J = 8.0 Hz, 3H). |
| 483 | 1H NMR (300 MHz, DMSO-d6) δ 12.63 (s, 1H), 7.75 (d, J = 7.5 Hz, 1H), 7.33 (d, J = 7.5Hz, 1H), 3.75-3.71(m, 1H), 2.33-2.12(m, 9H), 1.37 (d, J = 6.5 Hz, 6H). |
| 484 | 1H NMR (300 MHz, DMSO-d6) δ 12.57 (s, 1H), 7.84 (d, J = 7.5 Hz, 1H), 7.36-7.26 (m, 1H), 3.70 (d, J = 7.0 Hz, 1H), 3.52 (d, J = 7.0 Hz, 1H), 2.48-2.29 (m, 10H), 0.91 (d, J = 6.5 Hz, 6H). |
| 485 | 1H NMR (300 MHz, DMSO-d6) δ 12.63 (s, 1H), 7.74 (d, J = 7.5 Hz, 1H), 7.32 (d, J = 7.5Hz, = 1H), 3.90 (s, 1H), 3.75 (s, 1H), 2.40-2.28 (m, 9H). |
| 486 | 1H NMR (300 MHz, DMSO-d6) δ 12.62 (s, 1H), 7.70 (d, J = 7.5 Hz, 1H), 7.40 (d, J = 7.5Hz, 1H), 3.55-3.50 (m, 1H), 2.75 (s, 3H), 2.40-2.35(m, 6H), 1.19 (d, J = 6.5 Hz, 6H). |

TABLE 2-continued $^1$H NMR data of compounds I

| Compound No. | $^1$HNMR |
|---|---|
| 487 | 1H NMR (300 MHz, DMSO-d6) δ 12.61 (s, 1H), 7.68 (d, J = 7.5 Hz, 1H), 7.25 (d, J = 7.5Hz, 1H), 3.55-3.50 (m, 1H), 2.74 (s, 3H), 2.45 (s, 3H), 2.31 (s, 3H), 1.20-1.09(m, 2H), 0.84-0.72(m, 2H). |
| 488 | 1H NMR (500 MHz, DMSO-d6) δ 12.94 (s, 1H), 8.03 (dd, J = 7.5, 6.0 Hz, 1H), 7.63 (d, J = 7.5 Hz, 1H), 2.77 (s, 3H), 2.46 (s, 3H). |
| 489 | 1H NMR (500 MHz, DMSO-d6) δ 12.89 (s, 1H), 8.06 (d, J = 7.5 Hz, 1H), 7.76 (d, J = 7.5 Hz, 1H), 2.77 (s, 3H), 2.45 (s, 3H). |
| 490 | 1H NMR (500 MHz, DMSO-d6) δ 12.64 (s, 1H), 7.87 (d, J = 7.5 Hz, 1H), 7.69 (d, J = 7.5 Hz, 1H), 2.74 (s, 3H), 2.44 (s, 3H), 2.37 (s, 3H). |
| 491 | 1H NMR (500 MHz, DMSO-d6) δ 12.56 (s, 1H), 8.08-7.97 (m, 2H), 3.22 (s, 3H), 2.79 (s, 3H), 2.48 (s, 3H), 240 (s, 3H). |
| 492 | $^1$H NMR (500 MHz, DMSO-d6) δ 12.44(s, 1H), 8.08 (d, J = 7.5 Hz, 1H), 7.74 (d, J = 7.5 Hz, 1H), 3.46 (t, J = 7.0 Hz, 1H), 3.22 (s, 3H), 3.16(t, J = 7.0 Hz, 1H),2.50 (s, 3H), 2.31 (s, 3H), 1.47-1.42 (m, 2H), 0.97 (t, J = 8.0 Hz, 3H). |
| 493 | 1H NMR (500 MHz, DMSO-d6) δ 12.41 (s, 1H), 8.06 (d, J = 7.5Hz, 1H), 7.70 (d, J = 7.5 Hz, 1H), 3.75-3.71(m, 1H), 3.34(s, 3H), 2.50(s, 3H), 2.31 (s, 3H), 1.23 (d, J = 6.5Hz, 6H). |
| 494 | 1H NMR (500 MHz, DMSO-d6) δ 12.44 (s, 1H), 8.01 (d, J = 7.5 Hz, 1H), 7.80 (d, J = 7.5 Hz, 1H), 3.36 (t, J = 7.0Hz, 1H), 3.24 (s, 3H),3.10 (t, J = 7.0Hz, 1H), 2.58 (s, 3H), 2.31 (s, 3H), 1.43-1.25 (m, 4H), 0.88 (t, J = 7.5Hz, 3H). |
| 495 | 1H NMR (500 MHz, DMSO-d6) δ 12.44 (s, 1H), 8.05 (d, J = 7.5 Hz, 1H), 7.70 (d, J = 7.5 Hz, 1H), 3.70 (d, J = 7.0 Hz, 1H), 3.39(d, J = 7.0 Hz, 1H), 3.21 (s, 3H), 2.51 (s, 3H), 2.31 (s, 3H), 1.70-1.65 (m, 1H), 0.92 (d, J = 6.5 Hz, 6H). |
| 496 | 1H NMR (300 MHz, DMSO-d6) δ 12.60 (s, 1H), 8.08 (d, J = 7.5 Hz, 1H), 7.68 (d, J = 7.5 Hz, 1H), 5.84-5.80(m, 1H), 5.28-5.14 (m, 1H), 5.15 -4.97 (m, 1H), 3.45 (d, J = 6.5 Hz, 1H), 3.31 (d, J = 6.5 Hz, 1H),3.21 (s, 3H), 2.44 (s, 3H), 2.40 (s, 3H). |
| 497 | 1H NMR (300 MHz, DMSO-d6) δ 12.58 (s, 1H), 8.08-7.93 (m, 2H), 3.52 (s, 1H), 3.33 (s, 1H), 3.19 (s, 3H), 3.17 (s, 1H), 2.46 (s, 3H), 2.38 (s, 3H). |
| 498 | 1H NMR (300 MHz, DMSO-d6) δ 12.40(s, 1H), 8.08 (d, J = 7.5 Hz, 1H), 7.74 (d, J = 7.5 Hz, 1H), 3.76 (t, J = 8.0 Hz, 1H), 3.46 (t, J = 8.0 Hz, 1H), 3.19 (s, 3H), 2.46 (s, 3H), 2.31 (s, 3H), 1.12-0.90 (m, 1H), 0.51-0.27 (m, 4H). |
| 499 | 1H NMR (500 MHz, DMSO-d6) δ 12.40 (s, 1H), 8.05 (d, J = 7.5Hz, 1H), 7.73 (d, J = 7.5 Hz, 1H), 4.48-4.38 (m, 2H), 3.81 (t, J = 7.0 Hz, 1H), 3.51 (t, J = 7.0 Hz, 1H), 3.25 (s, 3H),2.55(s, 3H), 2.32(s, 3H). |
| 500 | 1H NMR (500 MHz, DMSO-d6) δ 12.43 (s, 1H), 8.04 (d, J = 7.5 Hz, 1H), 7.68 (d, J = 7.5 Hz, 1H), 3.30 (s, 1H), 3.18-3.13 (m, 4H), 2.59 (s, 3H), 2.31 (s, 3H). |
| 501 | 1H NMR (300 MHz, DMSO-d6) δ 12.44 (s, 1H), 8.08 (d, J = 7.5 Hz, 1H), 7.74 (d, J = 7.5 Hz, 1H), 3.95-3.90 (m, 1H), 3.82-3.78 (m, 1H), 3.60-3.55(m, 1H), 3.18(s, 3H), 2.56(s,3H ), 2.31 (s, 3H), 1.39-1.34 (m, 3H). |
| 502 | 1H NMR (500 MHz, DMSO-d6) δ 12.41 (s, 1H), 8.06 (d, J = 7.5 Hz, 1H), 7.75(d, J = 7.5Hz, 1H), 5.35-5.10 (m, 1H), 3.14-3.06(m, 2H), 3.10(s, 3H), 2.56(s, 3H), 2.32(s, 3H). |
| 503 | 1H NMR (500 MHz, DMSO-d6) δ 12.40 (s, 1H), 8.01 (d, J = 7.5 Hz, 1H), 7.78(d, J = 7.5Hz, 1H), 4.35-4.25 (m, 2H), 3.71 (t, J = 7.0Hz, 1H), 3.25 (t, J = 7.0Hz, 1H), 3.11(s, 3H), 2.56 (s, 3H), 2.31 (s, 3H), 1.83-1.78(m, 2H). |
| 504 | 1H NMR (300 MHz, DMSO-d6) δ 12.58 (s, 1H), 8.06 (d, J = 7.5 Hz, 1H), 7.97 (d, J = 7.5 Hz, 1H), 3.76 (t, J = 8.0 Hz, 1H), 3.46 (t, J = 8.0 Hz, 1H), 3.19(s, 3H), 2.46 (s, 3H), 2.39 (s, 3H), 2.15 (d, J = 8.0 Hz, 2H). |
| 505 | 1H NMR (500 MHz, DMSO-d6) δ 12.43 (s, 1H), 8.02(d, J = 7.5 Hz, 1H), 7.76 (d, J = 7.5Hz, 1H), 3.72 (t, J = 7.0 Hz, 2H), 3.36 (t, J = 7.0 Hz, 1H),3.22(s,3H), 3.15 (t, J = 7.0 Hz, 1H), 2.50 (s, 3H), 2.30 (s, 3H). |
| 506 | 1H NMR (300 MHz, DMSO-d6) δ12.48 (s, 1H), 8.10-7.94 (m, 2H), 3.86 (t, J = 8.0 Hz, 1H), 3.57 (t, J = 7.5 Hz, 2H), 3.50 (t, J = 8.0 Hz, 1H), 3.22 (s, 3H), 2.46 (s, 3H), 2.39 (s, 3H), 1.91-1.87 (m, 2H). |
| 507 | 1H NMR (300 MHz, DMSO-d6) δ 12.63 (s, 1H), 8.07 (d, J = 7.5 Hz, 1H), 7.94 (d, J = 7.5 Hz, 1H), 3.90 (s, 1H), 3.72 (s, 1H), 3.20 (s, 3H), 2.46 (s, 3H), 2.35 (s, 3H). |
| 508 | 1H NMR (500 MHz, DMSO-d6) δ 12.58 (s, 1H), 8.05 (d, J = 7.5 Hz, 1H), 7.97 (d, J = 7.5 Hz, 1H), 3.95 (t, J = 7.5Hz, 1H), 3.71 (t, J = 7.5 Hz, 2H), 3.63 (t, J = 7.5Hz, 1H), 3.19 (s, 3H), 3.10 (s, 3H), 2.46 (s, 3H), 2.40 (s, 3H). |
| 509 | 1H NMR (500 MHz, DMSO-d6) δ 12.42 (s, 1H), 8.03 (d, J = 7.5 Hz, 1H), 7.74 (d, J = 7.5 Hz, 1H), 5.16-5.12(m, 2H), 4.91-4.88(m, 2H), 3.77-3.71 (m, 1H), 3.34 (s, 3H),2.52(s, 3H), 2.31 (s, 3H). |
| 510 | 1H NMR (500 MHz, DMSO-d6) δ 12.44 (s, 1H), 8.01 (d, J = 7.5 Hz, 1H), 7.72 (d, J = 7.5Hz, 1H), 7.38-7.29 (m, 5H), 4.70 (s, 1H), 4.51 (s, 1H), 3.15 (s, 3H), 2.58 (s, 3H), 2.31 (s, 3H). |
| 511 | 1H NMR (500 MHz, DMSO-d6) δ 12.35 (s, 1H), 8.09 (d, J = 7.5Hz, 1H), 8.01 (d, J = 7.5 Hz, 1H), 4.33 (s, 3H), 3.20 (s, 3H), 2.76 (s, 3H), 2.49 (s, 3H). |
| 512 | 1H NMR (500 MHz, DMSO-d6) δ 12.35 (s, 1H), 8.08 (d, J = 7.5 Hz, 1H), 7.74 (d, J = 7.5 Hz, 1H), 4.33 (s, 3H), 3.45(t, J = 7.0 Hz, 1H), 3.40 (s, 3H), 3.16 (t, J = 7.0 Hz, 1H), 2.41 (s, 3H), 1.45-1.40 (m, 2H), 0.97 (t, J = 8.0 Hz, 3H). |
| 513 | 1H NMR (500 MHz, DMSO-d6) δ 12.34 (s, 1H), 8.07 (d, J = 7.5 Hz, 1H), 7.73(d, J = 7.5 Hz, 1H), 4.33 (s, 3H), 3.75-3.71 (m, 1H), 3.44 (s, 3H), 2.31 (s, 3H), 1.23 (d, J = 6.5 Hz, 6H). |
| 514 | 1H NMR (500 MHz, DMSO-d6) δ 12.34 (s, 1H), 8.05 (d, J = 7.5Hz, 1H), 7.72 (d, J = 7.5Hz, 1H), 4.33 (s, 3H), 3.82 (t, J = 7.0 Hz, 1H), 3.75 (t, J = 7.0 Hz, 1H),3.42 (s, 3H), 2.48 (s, 3H), 1.43-1.25 (m, 4H), 0.88 (t, J = 7.5Hz, 3H). |
| 515 | 1H NMR (500 MHz, DMSO-d6) δ 12.36 (s, 1H), 8.02 (d, J = 7.5 Hz, 1H), 7.74 (d, J = 7.5 Hz, 1H), 4.33 (s, 3H), 3.70 (d, J = 7.0 Hz, 1H), 3.35 (d, J = 7.0 Hz, 1H), 3.45(s, 3H), 2.31 (s, 3H), 1.70-1.65(m, 1H), 0.92 (d, J = 6.5Hz, 6H). |
| 516 | 1H NMR (500 MHz, DMSO-d6) δ 12.36 (s, 1H), 8.05 (d, J = 7.5 Hz, 1H), 8.02 (d, J = 7.5 Hz, 1H), 5.84-5.80 (m, 1H), 5.29-5.25 (m, 1H), 5.06-5.00 (m, 1H), 4.33 (s, 3H), 3.45 (d, J = 6.0 Hz, 1H), 3.25 (d, J = 6.0 Hz, 1H),3.20 (s, 3H), 2.48 (s, 3H). |
| 517 | 1H NMR (500 MHz, DMSO-d6) δ 12.36 (s, 1H), 8.08 (d, J = 7.5 Hz, 1H), 7.99 (d, J = 7.5Hz, 1H), 4.33 (s, 3H), 3.52 (s, 1H), 3.33(s, 1H), 3.18-3.15(m, 4H), 2.44 (s, 3H). |
| 518 | $^1$H NMR (500 MHz, DMSO-d6) δ 12.33 (s, 1H), 8.08 (d, J = 7.5 Hz, 1H), 7.74 (d, J = 7.5 Hz, 1H), 4.33 (s, 3H), 3.70 (d, J = 7.0 Hz, 1H), 3.34 (s, 3H), 3.25 (d, J = 6.0 Hz, 1H), 2.31 (s, 3H), 1.02-0.96(m, 1H), 0.47-0.31 (m, 4H). |
| 519 | $^1$H NMR (500 MHz, DMSO-d6) δ 12.35 (s, 1H), 8.08 (d, J = 7.5 Hz, 1H), 7.74 (d, J = 7.5Hz, 1H), 4.48 (t, J = 7.0 Hz, 1H), 4.38 (t, J = 7.0 Hz, 1H), 4.33 (s, 3H), 3.45 (s, 3H), 2.98-2.86 (m, 2H), 2.31 (s, 3H). |
| 520 | 1H NMR (500 MHz, DMSO-d6) M2.33 (s, 1H), 8.08 (d, J = 7.5 Hz, 1H), 7.74 (d, J = 7.5Hz, 1H), 4.33 (s, 3H), 3.50 (s, 1H), 3.34 (s, 3H), 3.22(s, 1H), 2.31 (s, 3H). |
| 521 | 1H NMR (500 MHz, DMSO-d6) M2.36 (s, 1H), 8.08 (d, J = 7.5 Hz, 1H), 7.74 (d, J = 7.5Hz, 1H), 4.33 (s, 3H), 3.82-3.75 (m, 1H), 3.54-3.50 (m, 1H), 3.25 (s, 3H), 3.15-3.10 (m, 1H), 2.31 (s, 3H), 1.39-1.35 (m, 3H). |
| 522 | $^1$H NMR (500 MHz, DMSO-d6) δ 12.35 (s, 1H), 8.05 (d, J = 7.5 Hz,1H), 7.82 (d, J = 7.5 Hz,1H), 5.35-5.05 (m, 1H), 4.33 (s, 3H), 3.64-3.60 (m, 1H), 3.42 (s, 3H), 3.30-3.25 (m, 1H), 2.31 (s, 3H). |
| 523 | 1H NMR (500 MHz, DMSO-d6) δ 12.34 (s, 1H), 8.01 (d, J = 7.5 Hz, 1H), 7.79 (d, J = 7.5 Hz, 1H), 4.35-4.30(m, 5H), 3.78 (t, J = 7.5 Hz,1H), 3.49 (t, J = 7.5 Hz,1H), 3.41 (s, 3H), 2.31 (s, 3H), 1.83-1.79 (m, 2H). |

TABLE 2-continued $^1$H NMR data of compounds I

| Compound No. | $^1$HNMR |
|---|---|
| 524 | 1H NMR (500 MHz, DMSO-d6) δ 12.33(s, 1H), 8.04 (d, J = 7.5 Hz, 1H), 7.98 (d, J = 7.5 Hz, 1H), 4.33 (s, 3H), 3.95(t, J = 8.5 Hz, 1H),3.54 (t, J = 8.5 Hz, 1H), 3.20 (s, 3H), 2.38 (s, 3H), 2.15 (d, J = 8.0Hz, 2H). |
| 525 | 1H NMR (500 MHz, DMSO-d6) δ 12.31(s, 1H), 8.06 (d, J = 7.5 Hz, 1H), 7.69 (d, J = 7.5 Hz, 1H), 4.33 (s, 3H), 3.72 (t, J = 7.0Hz, 2H), 3.56 (t, J = 7.0 Hz, 1H), 3.39(s, 3H), 3.29 (t, J = 7.0 Hz, 1H), 2.31 (s, 3H). |
| 526 | 1H NMR (500 MHz, DMSO-d6) δ 12.34(s, 1H), 8.01 (d, J = 7.5 Hz, 1H), 7.69 (d, J = 7.5 Hz, 1H), 4.33 (s, 3H), 3.79(t, J = 8.0 Hz, 1H), 3.57 (t, J = 7.5 Hz, 2H), 3.45 (t, J = 8.0 Hz, 1H), 3.22 (s, 3H), 2.44 (s, 3H), 1.91-1.85(m, 2H). |
| 527 | $^1$H NMR (500 MHz, DMSO-d6) δ 12.30(s, 1H), 8.10 (d, J = 7.5 Hz, 1H), 8.03 (d, J = 7.5 Hz, 1H), 4.33 (s, 3H), 3.90 (s, 1H), 3.54 (s, 1H), 3.21 (s, 3H), 2.45 (s, 3H). |
| 528 | 1H NMR (500 MHz, DMSO-d6) M2.36 (s, 1H), 8.06 (d, J = 7.5 Hz, 1H), 7.99 (d, J = 7.5 Hz, 1H), 4.33 (s, 3H), 3.71 (t, J = 7.5 Hz, 2H), 3.55 (t, J = 7.5 Hz, 1H), 3.20-3.15(m, 7H), 2.44 (s, 3H). |
| 529 | 1H NMR (500 MHz, DMSO-d6) δ 12.36 (s, 1H), 8.05 (d, J = 7.5 Hz, 1H), 7.70 (d, J = 7.5 Hz, 1H), 5.16-5.13 (m, 2H), 4.91-4.88 (m, 2H), 4.33 (s, 3H), 3.77-3.72 (m, 1H), 3.44 (s, 3H), 2.31 (s, 3H). |
| 530 | 1H NMR (500 MHz, DMSO-d6) δ 12.35 (s, 1H), 8.06 (d, J = 7.5 Hz, 1H), 7.70 (d, J = 7.5 Hz, 1H), 7.38-7.30 (m, 5H), 4.70 (s, 2H), 4.33 (s, 3H), 3.44 (s, 3H), 2.31 (s, 3H). |
| 531 | 1H NMR (500 MHz, DMSO-d6) δ 12.79 (s, 1H), 8.05 (d, J = 7.5 Hz, 1H), 7.67 (d, J = 7.5 Hz, 1H), 3.68 (s, 3H), 3.45(t, J = 8.0 Hz, 1H),3.13 (t, J = 8.0 Hz, 1H), 2.46 (s, 3H), 1.47-1.41(m, 2H), 0.89 (t, J = 8.0 Hz, 3H). |
| 532 | 1H NMR (500 MHz, DMSO-d6) δ 12.86 (s, 1H), 8.08 (d, J = 7.5 Hz, 1H), 7.68 (d, J = 7.5Hz, 1H), 4.10 (q, J = 8.0 Hz, 2H), 3.42 (t, J = 5.0 Hz, 1H), 3.15 (t, J = 5.0 Hz, 1H), 2.46 (s, 3H), 1.47-1.42 (m, 2H), 1.34 (t, J = 8.0 Hz, 3H), 0.95 (t, J = 8.0 Hz, 3H). |
| 533 | 1H NMR (500 MHz, DMSO-d6) δ 12.79 (s, 1H), 8.01 (d, J = 7.5 Hz, 1H), 7.67 (d, J = 7.5 Hz, 1H), 4.02 (t, J = 7.5 Hz, 2H), 3.45 (t, J = 8.0 Hz, 1H), 3.14(t, J = 8.0 Hz, 1H), 2.46 (s, 3H), 1.74-1.69 (m, 2H), 1.47-1.41 (m, 2H), 0.98 (t, J = 8.0 Hz, 3H), 0.90 (t, J = 8.0 Hz, 3H). |
| 534 | 1H NMR (500 MHz, DMSO-d6) δ 12.69 (s, 1H), 8.02 (d, J = 7.5 Hz, 1H), 7.64 (d, J = 7.5 Hz, 1H), 4.46-4.42(m, 1H), 3.44 (t, J = 8.0 Hz, 1H), 3.15 (t, J = 8.0 Hz, 1H), 2.46 (s, 3H), 1.47-1.41(m, 2H), 1.31 (d, J = 6.5 Hz, 6H), 0.90 (t, J = 8.0 Hz, 3H). |
| 535 | 1H NMR (500 MHz, DMSO-d6) δ 12.80 (s, 1H), 8.01 (d, J = 7.5Hz, 1H), 7.70 (d, J = 7.5Hz, 1H), 4.00 (t, J = 7.5 Hz, 2H), 3.45(t, J = 8.0 Hz, 1H), 3.15(t, J = 8.0 Hz, 1H) 2.46 (s, 3H), 1.76-1.72 (m, 2H), 1.48-1.41(m, 4H), 0.92-0.81(m, 6H). |
| 536 | 1H NMR (500 MHz, DMSO-d6) δ 12.85 (s, 1H), 8.04 (d, J = 7.5 Hz, 1H), 7.70 (d, J = 7.5 Hz, 1H), 6.02 (s, 2H), 3.42(t, J = 8.0 Hz, 1H), 3.22 (s, 3H), 3.12 (t, J = 8.0 Hz, 1H), 2.46 (s, 3H), 1.47-1.41(m, 2H), 0.89 (t, J = 8.0 Hz, 3H). |
| 537 | 1H NMR (500 MHz, DMSO-d6) δ 12.59 (s, 1H), 7.99 (d, J = 7.5 Hz, 1H), 7.68 (d, J = 7.5 Hz, 1H),3.46(t, J = 8.0 Hz, 1H), 3.15(t, J = 8.0 Hz,1H), 2.46 (s, 3H), 2.35 (s, 3H), 1.47-1.40 (m, 2H), 0.90 (t, J = 8.0 Hz, 3H). |
| 538 | 1H NMR (500 MHz, DMSO-d6) δ 12.60 (s, 1H), 7.80-7.69 (m, 2H), 3.42(t, J = 8.0 Hz, 1H), 3.19(t, J = 8.0 Hz,1H), 2.88(t, J = 8.0 Hz, 2H), 2.46 (s, 3H), 1.47-1.41 (m, 2H), 1.15 (t, J = 8.0 Hz, 3H), 0.92 (t, J = 8.0 Hz, 3H). |
| 539 | 1H NMR (500 MHz, DMSO-d6) δ 12.52 (s, 1H), 7.85 (d, J = 7.5 Hz, 1H), 7.72 (d, J = 7.5Hz, 1H),3.46 (t, J = 8.0 Hz, 1H), 3.13 (t, J = 8.0 Hz, 1H), 3.00-2.95(m, 1H), 2.46 (s, 3H), 1.47-1.41 (m, 2H), 1.20 (d, J = 6.5 Hz, 6H), 0.89 (t, J = 8.0 Hz, 3H). |
| 540 | 1H NMR (500 MHz, DMSO-d6) δ 12.64 (s, 1H), 7.93 (d, J = 7.5Hz, 1H), 7.79 (d, J = 7.5 Hz, 1H), 6.88-6.82 (m, 1H), 5.78-5.75(m, 1H), 5.45-5.41(m, 1H), 3.45 (t, J = 8.0 Hz, 1H), 3.13(t, J = 8.0 Hz, 1H), 2.46 (s, 3H), 1.47-1.41(m, 2H), 0.90 (t, J = 8.0 Hz, 3H). |

TABLE 2-continued $^1$H NMR data of compounds I

| Compound No. | $^1$HNMR |
|---|---|
| 541 | 1H NMR (500 MHz, DMSO-d6) δ 12.80 (s, 1H), 7.97 (d, J = 7.5 Hz, 1H), 7.82 (d, J = 7.5 Hz, 1H), 4.41 (s, 1H), 3.49(t, J = 8.0 Hz, 1H), 3.20 (t, J = 8.0 Hz, 1H), 2.47 (s, 3H), 1.47-1.41 (m, 2H), 0.91 (t, J = 8.0 Hz, 3H). |
| 542 | 1H NMR (500 MHz, DMSO-d6) δ 12.65 (s, 1H), 7.96 (d, J = 7.5 Hz, 1H), 7.72 (d, J = 7.5 Hz, 1H), 3.46 (t, J = 8.0 Hz, 1H), 3.16 (t, J = 8.0 Hz, 1H), 2.70-2.67(m, 1H), 2.46 (s, 3H), 1.47-1.42 (m, 2H), 1.13-1.09 (m, 2H), 0.91 (t, J = 8.0 Hz, 3H), 0.82-0.78 (m 2H). |
| 543 | 1H NMR (500 MHz, DMSO-d6) δ 12.82 (s, 1H), 7.99 (d, J = 7.5Hz, 1H), 7.71 (d, J = 7.5 Hz, 1H), 3.50 (t, J = 8.0 Hz, 1H), 3.21(t, J = 8.0 Hz, 1H), 2.46 (s, 3H), 1.47-1.42 (m, 2H), 0.89 (t, J = 7.5 Hz, 3H). |
| 544 | 1H NMR (500 MHz, DMSO-d6) δ 12.68 (s, 1H), 7.89 (d, J = 7.5 Hz, 1H), 7.78 (d, J = 7.5 Hz, 1H), 3.48 (t, J = 8.0 Hz, 1H), 3.20 (t, J = 8.0 Hz, 1H), 2.45 (s, 3H), 1.47-1.42 (m, 2H), 0.90 (t, J = 7.9 Hz, 3H). |
| 545 | 1H NMR (500 MHz, DMSO-d6) δ 12.65 (s, 1H), 7.96 (d, J = 7.5 Hz, 1H), 7.75 (d, J = 7.5 Hz, 1H), 3.53(t, J = 8.0 Hz, 1H), 3.21 (t, J = 8.0 Hz, 1H), 2.48(s, 3H), 1.46-1.40 (m, 2H), 0.90 (t, J = 8.0 Hz, 3H). |
| 546 | 1H NMR (500 MHz, DMSO-d6) δ 12.72 (s, 1H), 8.10 (d, J = 7.5 Hz, 1H), 7.71 (d, J = 7.5 Hz, 1H), 3.60 (t, J = 7.5 Hz, 1H), 3.29(t, J = 7.5 Hz, 1H), 2.44 (s, 3H), 1.47-1.41(m, 2H), 0.95 (t, J = 7.5 Hz, 3H). |
| 547 | $^1$H NMR (500 MHz, DMSO-d6) δ 12.80(s, 1H), 8.10 (d, J = 7.5 Hz, 1H), 7.71 (d, J = 7.5 Hz, 1H), 2.76(s, 3H), 2.46 (s, 3H), 2.36 (s, 3H). |
| 548 | 1H NMR (500 MHz, DMSO-d6) δ 12.77 (s, 1H), 8.06 (d, J = 7.5Hz, 1H), 7.71 (d, J = 7.5 Hz, 1H), 3.30 (q, J = 8.0 Hz, 1H), 3.12 (q, J = 8.0 Hz, 1H), 2.46 (s, 3H), 2.23 (s, 3H), 1.32 (t, J = 8.0 Hz, 3H). |
| 549 | 1H NMR (500 MHz, DMSO-d6) δ 12.73 (s, 1H), 8.02 (d, J = 7.5 Hz, 1H), 7.70 (d, J = 7.5Hz, 1H), 2.95-2.92 (m, 1H), 2.46 (s, 3H), 2.23 (s, 3H), 1.37 (d, J = 7.0 Hz, 6H). |
| 550 | 1H NMR (500 MHz, DMSO-d6) δ 12.76 (s, 1H), 8.04 (d, J = 7.5 Hz, 1H), 7.70 (d, J = 7.5Hz, 1H), 3.33 (t, J = 8.0Hz, 1H), 3.10 (t, J = 8.0Hz, 1H), 2.46 (s, 3H), 2.23 (s, 3H), 1.43-1.25 (m, 4H), 0.84 (t, J = 7.5 Hz, 3H). |
| 551 | 1H NMR (500 MHz, DMSO-d6) δ 12.77 (s, 1H), 8.06 (d, J = 7.5 Hz, 1H), 7.71 (d, J = 7.5Hz, 1H), 3.42(d, J = 7.0 Hz, 1H), 3.10 (d, J = 7.0 Hz, 1H), 2.46 (s, 3H), 2.23 (s, 3H), 1.96-1.91 (m, 1H), 0.92 (d, J = 7.5 Hz, 6H). |
| 552 | $^1$H NMR (500 MHz, DMSO-d6) δ 12.77 (s, 1H), 8.06 (d, J = 7.5 Hz, 1H), 7.74 (d, J = 7.5 Hz, 1H), 5.84-5.80 (m, 1H), 5.28-5.26 (m, 1H), 5.05-5.03 (m, 1H), 3.45 (d, J = 6.0 Hz, 1H), 3.38 (d, J = 6.0 Hz, 1H), 2.46(s, 3H), 2.26 (s, 3H). |
| 553 | 1H NMR (500 MHz, DMSO-d6) δ 12.77 (s, 1H), 8.06 (d, J = 7.5 Hz, 1H), 7.69 (d, J = 7.5 Hz, 1H), 3.92 (s, 1H), 3.76 (s, 1H), 3.44 (s, 1H), 2.46 (s, 3H), 2.32 (s, 3H). |
| 554 | 1H NMR (500 MHz, DMSO-d6) δ 12.80 (s, 1H), 8.11 (d, J = 7.5 Hz, 1H), 7.74 (d, J = 7.5 Hz, 1H), 3.70 (d, J = 7.0 Hz, 1H), 3.41 (d, J = 7.0 Hz, 1H), 2.46 (s, 3H), 2.27 (s, 3H), 1.44-1.40 (m, 1H), 0.43-0.39 (m, 2H), 0.26-0.17 (m, 2H). |
| 555 | 1H NMR (500 MHz, DMSO-d6) δ 12.77 (s, 1H), 8.07 (d, J = 7.5 Hz, 1H), 7.71 (d, J = 7.5 Hz, 1H), 4.48-4.38 (m, 2H), 3.98 (t, J = 3.0Hz, 1H), 3.76 (t, J = 3.0Hz, 1H), 2.46 (s, 3H), 2.24 (s, 3H). |
| 556 | 1H NMR (500 MHz, DMSO-d6) δ 12.75 (s, 1H), 8.06 (d, J = 7.5 Hz, 1H), 7.74 (d, J = 7.5 Hz, 1H), 3.98 (t, J = 8.0Hz, 1H), 3.56 (t, J = 8.0Hz, 1H), 2.46 (s, 3H), 2.24 (s, 3H). |
| 557 | 1H NMR (500 MHz, DMSO-d6) δ 12.77 (s, 1H), 8.06 (d, J = 7.5 Hz, 1H), 7.71 (d, J = 7.5 Hz, 1H), 5.88-5.79 (m, 1H), 4.04-4.00 (m, 1H), 3.79-3.75 (m, 1H), 2.46 (s, 3H), 2.24 (s, 3H), 1.38-1.33 (m, 3H) |
| 558 | 1H NMR (500 MHz, DMSO-d6) δ 12.77 (s, 1H), 8.06 (d, J = 7.5 Hz, 1H), 7.74 (d, J = 7.5 Hz, 1H), 6.97-6.52(m, 1H), 3.74-3.71 (m, 1H), 3.55-3.51 (m, 1H), 2.46 (s, 3H), 2.23 (s, 3H). |

TABLE 2-continued $^1$H NMR data of compounds I

| Compound No. | $^1$HNMR |
|---|---|
| 559 | 1H NMR (500 MHz, DMSO-d6) δ 12.81 (s, 1H), 8.02 (d, J = 7.5 Hz, 1H), 7.75 (d, J = 7.5 Hz, 1H), 4.35-4.31 (m, 2H), 3.56(t, J = 8.0 Hz, 1H), 3.21(t, J = 8.0 Hz, 1H), 2.46 (s, 3H), 2.27 (s, 3H), 1.83-1.78 (m, 2H). |
| 560 | 1H NMR (500 MHz, DMSO-d6) δ 12.86 (s, 1H), 8.01 (d, J = 7.5 Hz, 1H), 7.68 (d, J = 7.5Hz, 1H), 3.40 (t, J = 8.5 Hz, 1H), 3.26 (t, J = 8.5 Hz, 1H), 2.46 (s, 3H), 2.23 (s, 3H), 2.14-2.10 (m, 2H). |
| 561 | 1H NMR (500 MHz, DMSO-d6) δ 12.76 (s, 1H), 8.05 (d, J = 7.5 Hz, 1H), 7.74 (d, J = 7.5 Hz-1H), 3.46 (t, J = 8.0 Hz, 1H), 3.15 (t, J = 8.0 Hz, 1H), 2.46-2.42 (m, 5H), 2.23 (s, 3H), 1.38-1.35 (m, 2H). |
| 562 | 1H NMR (500 MHz, DMSO-d6) δ 12.77 (s, 1H), 8.07 (d, J = 7.5Hz, 1H), 7.71 (d, J = 7.5 Hz, 1H), 3.72 (t, J = 7.5 Hz, 2H), 3.65 (t, J = 7.5Hz, 1H), 3.36 (t, J = 7.5Hz, 1H), 2.46 (s, 3H), 2.24 (s, 3H). |
| 563 | 1H NMR (500 MHz, DMSO-d6) δ 12.76 (s, 1H), 8.05 (d, J = 7.5 Hz, 1H), 7.71 (d, J = 7.5 Hz, 1H), 3.57 (t, J = 7.5 Hz, 2H), 3.43 (t, J = 8.0 Hz, 1H), 3.21 (t, J = 8.0 Hz, 1H), 2.46 (s, 3H), 2.23 (s, 3H), 1.91-.185 (m, 2H). |
| 564 | 1H NMR (500 MHz, DMSO-d6) δ 12.75 (s, 1H), 8.07 (d, J = 7.5 Hz, 1H), 7.71 (d, J = 7.5 Hz, 1H), 3.90 (s, 1H), 3.72 (s, 1H), 2.46 (s, 3H), 2.25 (s, 3H). |
| 565 | 1H NMR (500 MHz, DMSO-d6) δ 12.62 (s, 1H), 7.96 (d, J = 7.5 Hz, 1H), 7.68 (d, J = 7.5 Hz, 1H), 3.71 (t, J = 7.5Hz, 2H), 3.65 (t, J = 7.5 Hz, 1H), 3.21 (s, 3H), 3.18(t, J = 7.5 Hz, 1H), 2.46 (s, 3H), 2.15 (s, 3H). |
| 566 | 1H NMR (500 MHz, DMSO-d6) δ 12.78 (s, 1H), 8.05 (d, J = 7.5 Hz, 1H), 7.69 (d, J = 7.5 Hz, 1H), 5.41-5.35 (m, 4H), 3.77-3.72 (m, 1H), 2.46 (s, 3H), 2.27 (s, 3H). |
| 567 | $^1$H NMR (500 MHz, DMSO-d6) δ 12.45 (s, 1H), 8.07 (d, J = 7.5 Hz, 1H), 7.76 (d, J = 7.5 Hz, 1H), 7.41-7.29 (m, 5H), 4.70 (s, 1H), 4.61 (s, 1H) 2.46 (s, 3H), 2.20 (s, 3H). |
| 569 | 1H NMR (500 MHz, DMSO-d6) δ 12.50 (s, 1H), 8.02 (d, J = 7.5 Hz, 1H), 7.69 (d, J = 7.5 Hz, 1H), 3.45 (t, J = 8.0 Hz, 1H), 3.16 (t, J = 8.0 Hz, 1H), 2.86 (q, J = 8.0 Hz, 2H), 2.50 (s, 3H), 1.47-1.42 (m, 2H), 1.25 (t, J = 8.0 Hz, 3H), 0.89 (t, J = 8.0 Hz, 3H). |
| 570 | 1H NMR (500 MHz, DMSO-d6) δ 12.30 (s, 1H), 8.07 (d, J = 8.0Hz, 1H), 7.87 (d, J = 8.0 Hz, 1H), 3.45 (t, J = 8.0 Hz, 1H), 3.16 (t, J = 8.0 Hz, 1H), 2.94-2.89 (m, 2H), 2.52 (s, 3H), 1.85-1.79 (m, 2H), 1.54-1.49 (m, 2H), 1.11 (t, J = 7.5Hz, 3H), 0.91 (t, J = 7.5 Hz, 3H). |
| 571 | 1H NMR (500 MHz, DMSO-d6) δ 12.27 (s, 1H), 8.08 (d, J = 8.0 Hz, 1H), 7.88 (d, J = 8.0 Hz, 1H), 3.48 (t, J = 8.0 Hz, 1H), 3.17 (t, J = 8.0 Hz, 1H), 2.91-2.85 (m, 2H), 2.52 (s, 3H), 1.85-1.80(m, 1H), 1.20 (t, J = 7.5 Hz, 6H), 1.11 (t, J = 7.5Hz, 3H). |
| 572 | 1H NMR (500 MHz, DMSO-d6) δ 12.75 (s, 1H), 8.01 (d, J = 7.5Hz, 1H), 7.69 (d, J = 7.5 Hz, 1H), 3.45 (t, J = 8.0 Hz, 1H), 3.31 (s, 2H), 3.16 (t, J = 8.0 Hz, 1H), 2.46 (s, 3H), 1.47-1.44 (m, 2H), 0.91 (t, J = 8.0 Hz, 3H). |
| 573 | 1H NMR (500 MHz, DMSO-d6) δ 12.58(s, 1H), 8.01 (d, J = 7.5 Hz, 1H), 7.70 (d, J = 7.5Hz, 1H), 4.87 (s, 2H), 3.45 (t, J = 8.0 Hz, 1H), 3.25 (s, 3H), 3.18 (t, J = 8.0 Hz, 1H), 2.46 (s, 3H), 1.47-1.43 (m, 2H), 0.93 (t, J = 8.0 Hz, 3H). |
| 574 | 1H NMR (500 MHz, DMSO-d6) δ 12.72 (s, 1H), 9.06 (s, 1H), 8.18-8.04 (m, 1H), 7.86 (d, J = 8.0 Hz, 1H), 3.51-3.44 (m, 1H), 3.29-3.22 (m, 1H), 1.17 (t, J = 7.5 Hz, 3H). |
| 575 | 1H NMR (500 MHz, DMSO-d6) δ 12.78 (s, 1H), 9.07 (s, 1H), 8.14-8.06 (m, 1H), 7.76 (d, J = 8.0 Hz, 1H), 3.58-3.47 (m, 1H), 3.20-3.10 (m, 1H), 1.73- 1.51 (m, 2H), 1.50-1.35(m, 2H), 0.88 (t, J = 7.5 Hz, 3H). |
| 576 | 1H NMR (500 MHz, DMSO-d6) δ 12.61 (s, 1H), 9.08 (s, 1H), 8.01-7.92 (m, 1H), 7.59 (d, J = 8.0 Hz, 1H), 2.75-2.68 (m, 1H), 1.78-1.69 (m, 2H), 1.40 (d, J = 7.0 Hz, 3H), 0.94 (t, J = 8.0 Hz, 3H). |
| 577 | 1H NMR (500 MHz, DMSO-d6) δ 12.77 (s, 1H), 9.02 (s, 1H), 8.13-8.03 (m, 1H), 7.86 (d, J = 8.0 Hz, 1H), 3.59-3.48 (m, 1H), 2.90-2.81 (m, 1H), 2.19-2.04 (m, 1H), 1.11-0.99 (m, 6H). |
| 581 | 1H NMR (500 MHz, DMSO-d6) δ 12.67 (s, 1H), 9.05 (s, 1H), 8.07-7.98 (m, 1H), 7.72 (d J = 8.0 Hz, 1H), 2.76-2.62 (m, 2H), 2.15-2.05 (m, 2H). |

TABLE 2-continued $^1$H NMR data of compounds I

| Compound No. | $^1$HNMR |
|---|---|
| 582 | 1H NMR (500 MHz, DMSO-d6) δ 8.67 (s, 1H), 8.08-7.97 (m, 1H), 7.74 (d, J = 8.0 Hz, 1H), 3.81-3.71 (m, 1H), 3.69 -3.60 (m, 2H), 3.42-3.35 (m, 1H), 3.23 (s, 3H). |
| 595 | 1H NMR (500 MHz, DMSO) S 12.37 (s, 1H), 7.84 (d, J = 7.5 Hz, 1H), 7.63 (d, J = 8.0 Hz, 1H), 3.71 (s, 3H), 3.40-3.35 (m, 2H), 3.02-2.92 (m, 1H), 2.90-2.86 (m, 1H), 2.49 (s, 3H), 2.12 (s, 3H). |
| 596 | 1H NMR (500 MHz, DMSO) S 12.37 (s, 1H), 8.06 (d, J = 7.0 Hz, 1H), 7.71 (d, J = 8.0 Hz, 1H), 4.95-4.83 (m, 1H), 4.83-4.71 (m, 1H), 3.85-3.80 (m, 1H), 3.69 (s, 3H), 3.66-3.56 (m, 1H). |
| 597 | 1H NMR (500 MHz, DMSO-d6) 12.37 (s, 1H), 8.04 (dd, J = 8.0, 7.0 Hz, 1H), 7.78 (d, J = 8.0 Hz, 1H), 4.25-4.23 (m, 2H), 3.55 (s, 3H), 2.50 (s, 3H). |
| 598 | 1H NMR (500 MHz, DMSO) S 12.37 (s, 1H), 8.02-7.97 (m, 1H), 7.66 (d, J = 8.0 Hz, 1H), 3.60-3.51 (m, 1H), 3.25-3.17 (m, 1H), 2.59 (t, J = 6.5 Hz, 2H), 2.27 (s, 3H), 2.00 (s, 3H), 1.96-1.91 (m, 1H), 1.84-1.77 (m, 1H). |
| 599 | 1H NMR (500 MHz, DMSO) S 12.37 (s, 1H), 7.98 (d, J = 7.5 Hz, 1H), 7.65 (d, J = 8.0 Hz, 1H), 3.41-3.26 (m, 2H), 2.70-2.60 (m, 2H), 2.46 (s, 3H), 2.26 (s, 3H), 2.07-2.04 (m, 1H), 2.02 (s, 3H), 2.00- 1.89 (m, 1H). |
| 600 | 1H NMR (500 MHz, DMSO) S 12.37 (s, 1H), 8.22 (s, 1H), 7.89-7.85 (m, 2H), 7.65 (d, J = 7.5 Hz, 1H), 3.59-3.51 (m, 1H), 3.24-3.10 (m, 1H), 1.80-1.70 (m, 1H), 1.70-1.55 (m, 1H), 1.04 (t, J = 7.0 Hz, 3H). |
| 601 | 1H NMR (500 MHz, DMSO-d6) δ 11.35 (s, 1H), 8.07 (d, J = 7.5 Hz, 1H), 7.89 (d, J = 7.5 Hz, 1H), 4.33 (s, 3H), 3.34 (s, 3H), 2.78 (t, J = 5.5 Hz, 2H), 2.51-2.45 (m, 2H), 2.44 (s, 3H), 1.31-1.26 (m, 2H). |
| 602 | 1H NMR (500 MHz, DMSO-d6) δ 12.50 (s, 1H), 7.97 (d, J = 8.0 Hz, 1H), 7.85 (d, J = 8.0 Hz, 1H), 3.47 (s, 3H), 3.33-3.30 (m, 1H), 3.06-3.00 (m, 1H), 2.77 (s, 3H), 2.47 (s, 3H), 1.79-1.75 (m, 1H), 1.66-1.60 (m, 1H), 0.93 (s, 9H). |
| 603 | 1H NMR (500 MHz, DMSO-d6) δ 12.50 (s, 1H); 7.95 (d, J = 6.5 Hz, 1H), 7.72 (d, J = 8.0 Hz, 1H), 3.74 (s, 3H), 3.42 (s, 3H), 3.27-3.23 (m, 1H), 3.05-2.98 (m, 1H), 2.82 (s, 3H), 1.76 (s, 1H), 1.64-1.58 (m, 1H), 0.93 (s, 9H). |
| 604 | 1H NMR (500 MHz, DMSO-d6) δ 11.84 (s, 1H), 7.86 (d, J = 8.0 Hz, 1H), 7.68 (d, J = 8.0 Hz, 1H), 4.67-4.62 (m, 1H), 4.08 (d, J = 15.0 Hz, 1H), 3.42 (s, 3H), 3.00 (s, 3H), 2.89 (s, 3H), 2.78 (s, 3H), 2.35 (s, 3H). |
| 605 | 1H NMR (500 MHz, DMSO-d6) δ 13.26 (s, 1H), 7.90 (d, J = 8.0 Hz, 1H), 7.71 (d, J = 8.0 Hz, 1H), 5.83-5.78 (m, 1H), 5.36-5.32 (m, 1H), 4.02 (s, 3H), 3.50 (s, 3H), 2.82 (s, 3H), 1.21 (s, 9H). |
| 606 | 1H NMR (500 MHz, DMSO-d6) δ 11.88 (s, 1H), 7.85 (d, J = 8.0 Hz, 1H), 7.70 (d, J = 8.0 Hz, 1H), 4.76-4.62 (m, 1H), 4.10 (d, J = 15.0 Hz, 1H), 3.71 (s, 3H), 3.43 (s, 3H), 3.03 (s, 3H), 2.92 (s, 3H), 2.85 (s, 3H). |
| 607 | 1H NMR (500 MHz, DMSO-d6) δ 11.88 (s, 1H), 8.02 (d, J = 8.0 Hz, 1H), 7.88 (d, J = 8.0 Hz, 1H), 4.01 (s, 3H), 3.97 -3.82 (m, 2H), 3.64-3.61 (m, 1H), 3.50 (s, 3H), 3.25-3.19 (m, 1H), 2.81 (s, 3H). |
| 608 | 1H NMR (500 MHz, DMSO-d6) δ 11.99 (s, 1H), 8.02 (d, J = 8.0 Hz, 1H), 7.84 (d, J = 8.0 Hz, 1H), 4.01 (s, 3H), 3.51 (s, 3H), 3.43-3.32 (m, 2H), 3.20-3.04 (m, 2H), 2.82 (s, 3H). |
| 609 | 1H NMR (500 MHz, DMSO-d6) δ 11.48 (s, 1H), 8.10 (d, J = 7.5 Hz, 1H), 7.88 (d, J = 7.5 Hz, 1H), 4.33 (s, 3H), 3.94 (s, 2H), 3.21 (s, 3H), 2.36 (s, 3H), 2.16 (s, 3H). |
| 610 | 1H NMR (500 MHz, DMSO-d6) S11.48 (s, 1H), 8.04(d, J = 7.5 Hz, 1H), 7.88 (d, J = 7.5 Hz, 1H)-3.60-3.56(m, 2H), 3.49 (s, 3H), 2.76 (s, 3H), 2.70-2.65 (m, 2H), 2.48 (s, 3H). |
| 611 | 1H NMR (500 MHz, DMSO-d6) δ 12.58 (s, 1H), 8.03 (d, J = 7.5 Hz, 1H), 7.81 (d, J = 7.5 Hz, 1H), 3.94 (s, 2H), 3.23 (s, 3H), 2.46 (s, 3H), 2.38 (s, 3H), 2.15 (s, 3H). |
| 612 | 1H NMR (500 MHz, DMSO-d6) δ 12.58 (s, 1H), 8.02 (d, J = 8.0 Hz, 1H), 7.91 (d, J = 8.0 Hz, 1H), 4.57 (t, J = 5.5 Hz, 2H), 3.79 (t, J = 5.5 Hz, 2H), 3.54-3.48 (m, 1H), 3.48 (s, 3H), 3.41 (q, J = 7.0 Hz, 2H), 3.15-3.07 (m, 1H), 2.82 (s, 3H), 1.36 (t, J = 7.5 Hz, 3H), 1.03 (t, J = 7.0 Hz, 3H). |

TABLE 2-continued $^1$H NMR data of compounds I

| Compound No. | $^1$HNMR |
|---|---|
| 613 | 1H NMR (500 MHz, DMSO-d6) δ 12.63 (s, 1H), 8.08 (d, J = 7.5 Hz, 1H), 7.91 (d, J = 7.5 Hz, 1H), 3.55 (s, 3H), 3.20-3.15 (m, 5H), 2.45 (s, 3H), 2.41 (t, J = 8.5 Hz, 2H), 2.31 (s, 3H). |
| 614 | 1H NMR (500 MHz, DMSO) S 12.58 (s, 1H), 8.08 (d, J = 7.5 Hz, 1H), 7.91 (d, J = 7.5 Hz, 1H), 3.53 (s, 3H), 3.29 (s, 3H), 3.14-3.12 (m, 2H), 2.79 (s, 6H), 2.65-2.63 (m, 2H), 2.49 (s, 3H). |
| 615 | 1H NMR (500 MHz, DMSO) S 12.29 (s, 1H), 8.09 (d, J = 8.0 Hz, 1H), 7.92 (d, J = 8.0 Hz, 1H), 5.94-5.93 (m, 1H), 5.24 (d, J = 17.0 Hz, 1H), 5.15 (d, J = 17.0 Hz, 1H), 3.27 (m, 1H), 2.61-2.60 (m, 1H), 2.49-2.47 (m, 2H), 2.47 (s, 3H), 2.37 (s, 3H). |
| 616 | 1H NMR (500 MHz, DMSO-d6) δ 12.61 (s, 1H), 7.72 (d, J = 7.5Hz, 1H), 7.64 (d, J = 7.5Hz, 1H), 2.78-2.71 (m, 4H), 2.44 (s, 3H), 1.92-1.86 (m, 2H), 1.42 (s, 2H). |
| 617 | $^1$H NMR (500 MHz, Chloroform-d) 8.25 -7.74 (m, 3H), 3.33-3.28 (m, 1H), 3.15-3.09 (m, 1H), 2.58 (s, 3H), 2.00 (d, J = 7.0 Hz, 2H), 1.18 (t, J = 7.0 Hz, 3H). |
| 618 | $^1$H NMR (500 MHz, Chloroform-d)S 8.19-7.80 (m, 3H), 4.17 (s, 3H), 3.36-3.32 (m, 1H), 3.22-3.07 (m, 1H), 2.02-1.99(m, 2H), 1.19 (t, J = 7.5 Hz, 3H). |
| 619 | 1H NMR (500 MHz, DMSO-d6) M1.22 (s, 1H), 8.09 (d, J = 8.0 Hz, 1H), 7.94 (d, J = 8.0 Hz, 1H), 5.96-5.88 (m, 1H), 5.25-5.12 (m, 2H), 4.01 (s, 3H), 3.60-5.57(m, 2H), 3.49 (s, 3H), 3.17-3.11 (m, 1H), 2.83 (s, 3H), 2.66-2.63 (m, 1H). |
| 620 | 1H NMR (500 MHz, DMSO-d6) δ 11.22 (s, 1H), 8.05 (d, J = 8.0 Hz, 1H), 7.92 (d, J = 8.0 Hz, 1H), 5.20 (s, 1H), 4.19-4.12 (m, 1H), 3.71 (s, 3H), 3.43 (s, 3H), 2.84 (s, 3H), 2.79-2.76 (m, 2H), 1.29 (d, J = 6.0 Hz, 3H). |
| 621 | 1H NMR (500 MHz, DMSO-d6) δ 11.22 (s, 1H), 7.54-7.47 (m, 2H), 3.06 (s, 3H), 2.29 (s, 3H). |
| 622 | 1H NMR (500 MHz, DMSO-d6) δ 11.89 (s, 1H), 7.99 (d, J = 8.0 Hz, 1H), 7.88 (d, J = 8.0 Hz, 1H), 4.54 (t, J = 5.0 Hz, 2H), 3.75 (t, J = 5.0 Hz, 2H), 3.47 (s, 3H), 3.23 (s, 3H), 3.21-3.20 (m, 1H), 3.13-3.06 (m, 1H), 2.81 (s, 3H), 1.36 (t, J = 7.5 Hz, 3H). |
| 623 | 1H NMR (500 MHz, DMSO-d6) δ 11.89 (s, 1H), 8.01-8.00 (m, 1H), 7.41-7.38 (m, 1H), 3.17 (s, 3H), 2.47 (s, 3H). |
| 624 | 1H NMR (500 MHz, DMSO-d6) δ 12.63 (s, 1H), 7.93 (d, J = 7.5 Hz, 1H), 7.68 (d, J = 7.5 Hz, 1H), 3.21 (s, 3H), 3.03 (s, 1H), 2.95 (t, J = 8.0 Hz, 2H), 2.42 (s, 3H), 2.38-2.35(m, 2H), 2.33 (s, 3H). |
| 625 | 1H NMR (500 MHz, DMSO-d6) δ 12.63 (s, 1H), 8.07 (d, J = 7.5 Hz, 1H), 7.96 (d, J = 7.5 Hz, 1H), 3.75 (t, J = 5.0 Hz, 2H), 3.34 (t, J = 5.0 Hz, 2H), 3.18 (s, 3H), 2.90 (s, 3H), 2.43 (s, 3H), 2.34 (s, 3H). |
| 626 | 1H NMR (500 MHz, DMSO-d6) δ 12.01 (s, 1H),7.84 (d, J = 8.0 Hz, 1H), 7.70 (d, J = 8.0 Hz, 1H), 3.78-3.69 (m, 4H), 3.67-3.63 (m, 1H), 3.41 (s, 3H), 3.13-3.08 (m, 1H), 2.82 (s, 3H), 2.23-2.10 (m, 4H), 1.98-1.84 (m, 2H). |
| 627 | 1H NMR (500 MHz, DMSO-d6) δ 12.44 (s, 1H), 8.12 (d, J = 8.0 Hz, 1H), 7.95 (d, J = 8.0 Hz, 1H), 3.65-3.55 (m, 4H), 3.10-3.00 (m, 1H), 2.63 (s, 3H), 2.31 (s, 3H), 2.30 (t, J = 7.0 Hz, 2H). |
| 628 | 1H NMR (500 MHz, DMSO-d6) δ 12.57(s, 1H), 8.03-7.96 (m, 2H), 4.31 (t, J = 5.0 Hz, 1H), 3.85-3.70 (m, 2H), 3.55-3.45 (m, 4H), 3.10-2.98 (m, 1H),2.45 (s, 3H), 2.37 (s, 3H), 2.03-1.76 (m, 2H). |
| 629 | 1H NMR (500 MHz, DMSO-d6) δ 12.04 (s, 1H),8.01 (d, J = 8.0 Hz, 1H), 7.96 (d, J = 8.0 Hz, 1H), 4.36 (q, J = 7.0 Hz, 2H), 3.51-3.47 (m, 4H), 3.15-3.04 (m, 1H), 2.82 (s, 3H), 1.47 (t, J = 7.0 Hz, 3H), 1.37 (t, J = 7.5 Hz, 3H). |
| 630 | 1H NMR (500 MHz, DMSO-d6) δ 11.93 (s, 1H), 8.02 (d, J = 8.0 Hz, 1H), 7.91 (d, J = 8.0 Hz, 1H), 4.38 (t, J = 7.0 Hz, 2H),3.55-3.48 (m, 4H), 3.22 (s, 3H), 3.15-3.08 (m, 1H), 2.82 (s, 3H), 2.12-2.08 (m, 4H), 1.37 (t, J = 7.5 Hz, 3H). |
| 631 | 1H NMR (500 MHz, DMSO-d6) δ 12.07 (s, 1H), 8.10-7.98 (m, 2H), 4.57-4.54 (m, 1H), 4.24-4.20 (m, 3H), 3.99 (s, 3H), 3.49 (s, 3H), 2.82 (s, 3H), 1.24 (t, J = 7.0 Hz, 3H). |
| 632 | 1H NMR (500 MHz, DMSO-d6) δ 12.40 (s, 1H), 7.97 (d, J = 8.0 Hz, 1H), 7.88 (d, J = 8.0 Hz, 1H), 4.55-4.52 (m, 1H), 4.27-4.15 (m, 3H), 3.48 (s, 3H), 2.75 (s, 3H), 2.47 (s, 3H), 1.23 (t, J = 7.0 Hz, 3H). |
| 633 | 1H NMR (500 MHz, DMSO-d6) δ 12.35 (s, 1H), 7.92 (d, J = 8.0 Hz, 1H), 7.84 (d, J = 8.0 Hz, 1H), 3.87 (s, 3H), 3.52 -3.45 (m, 4H), 3.09-2.98 (m, 1H), 2.82 (s, 3H), 1.82-1.62 (m, 3H), 0.94 (d, J = 6.5 Hz, 6H). |
| 634 | 1H NMR (500 MHz, DMSO-d6) M2.25 (s, 1H), 7.94 (d, J = 8.0 Hz, 1H), 7.80 (d, J = 8.0 Hz, 1H), 3.52-3.44 (m, 4H), 3.07-3.10 (m, 1H), 2.77 (s, 3H), 2.44 (s, 3H), 1.82-1.61 (m, 3H), 0.94 (d, J = 6.5 Hz, 6H) |
| 637 | $^1$H NMR (500 MHz, DMSO) S 8.10-8.02 (s, 1H), 7.92-7.68 (m 2H), 3.16-3.02 (m, 2H), 2.53 (s, 3H), 1.77-1.70 (m, 2H), 1.05 (t, J = 7.0 Hz, 3H). |
| 856 | $^1$H NMR (500 MHz, DMSO) δ 8.14-8.02 (m, 1H), 7.95-7.65 (m, 2H), 3.89 (s, 3H), 3.10-3.05 (m, 2H), 1.75-1.70 (m, 2H), 1.05 (t, J = 7.0 Hz, 3H). |
| 864 | $^1$H NMR (500 MHz, DMSO) δ 7.70 (d, J = 8.0 Hz, 1H), 7.54 (d, J = 8.0 Hz, 1H), 7.38 (t, J = 55.0 Hz, 1H), 3.90 (s, 3H), 2.90 (t, J = 7.0 Hz, 2H), 2.50 (s, 3H), 1.55-1.46 (m, 2H), 0.94 (t, J = 7.0 Hz, 3H). |
| 865 | $^1$H NMR (500 MHz, DMSO) δ 8.22 (t, J = 55.5 Hz, 1H), 7.95-7.90 (m, 1H), 7.75-7.68 (m, 1H), 3.25-3.16 (m, 2H), 2.46 (s, 3H), 2.34 (s, 3H), 1.94-1.74 (m, 2H), 1.08 (t, J = 7.0 Hz, 3H). |
| 866 | $^1$H NMR (500 MHz, DMSO) δ 8.21 -7.85 (m, 2H), 7.68-7.64 (m, 1H), 3.89 (s, 3H), 3.15-3.08 (m, 2H), 2.53 (s, 3H), 1.77-1.70 (m, 2H), 1.10 (t, J = 7.0 Hz, 3H). |
| 867 | $^1$H NMR (500 MHz, DMSO) δ 8.23 (t, J = 55.0 Hz, 1H), 8.02 (d, J = 8.0 Hz, 1H), 7.90 (d, J = 7.5 Hz, 1H), 3.99 (s, 3H), 3.23 (t, J = 7.0 Hz, 2H), 2.48 (s, 3H), 1.95-1.79 (m, 2H), 1.10 (t, J = 7.0 Hz, 3H). |

The method for preparing the compound of the invention will be explained in detail in the following program and embodiment. The material is commercial available or prepared through known method reported in the literature or shown in the route. Those skilled in the art should understand that the compound of the invention can also be synthesized by other synthetic route. Although the detailed material and reaction condition in the synthetic route have been explicated in the following text, it is still easy to be replaced by other similar material and condition. Isomer of the compound, for example, that produced with the variation of the preparation method of the present invention is included in the scope of the present invention. In addition, the following preparation method can be further modified according to the disclosures of the present invention by using common chemical method known to those skilled in the art, for example, protection of suitable group in the process of the reaction, etc.

The following method of application can be used to improve further understanding of the preparation method of the present invention. The specific material, class and condition have been determined to be further explication of the present invention, not to be any limit of the reasonable scope thereof. Reagents of the following synthetic compound showed in the table can either be purchased from the market or easily prepared by those skilled in the art.

Examples of representative compounds are as follows, the synthetic methods of other compounds are similar, and will not be described in detail here.

1. Synthesis of Compound 3

(1) Compound a(3 g, 16 mmol, 1.0 eq), NaOH (0.72 g, 18 mmol, 1.1 eq) were added sequentially into 30 ml of DMF, and then compound n-PrSH (1.28 g, 16.8 mmol, 1.05 eq) was added dropwise at 0° C., and the reaction solution was stirred at 0° C. for 1 hour. When LCMS test showed that the reaction of starting materials was basically completed, there was one major new peak. The reaction solution was poured into 30 ml of water, and the mixture was separated, and the aqueous phase was extracted once with 50 ml of ethyl acetate, and the resultant organic phase was washed three times with saturated saline solution (50 ml), dried, evaporated to dryness under reduced pressure and separated by column chromatography to obtain compound 3-1 (3.6 g, 91% yield) (colorless oil).

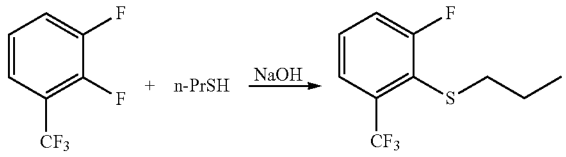

a 3-1

(2) Compound 3-1(3.1 g, 13 mmol, 1.0 eq) was added to 30 ml of THF, then n-BuLi (6.42 ml, 2.5 M, 16 mmol, 1.2 eq) was slowly added at −78° C., then the reaction solution was stirred at −78° C. for 0.5 hour, and slowly fed with C02 for 10 minutes, then the reaction solution was slowly warmed to room temperature. The product was detected by LCMS. 20 ml of water was poured into the reaction solution, the mixture was separated, the aqueous phase was extracted once with 30 ml of ethyl acetate, and the resultant aqueous phase was gradually adjusted to pH=4-5 with concentrated hydrochloric acid, filtered and dried to give compound 3-2 (3.2 g, 87% yield) (white solid).

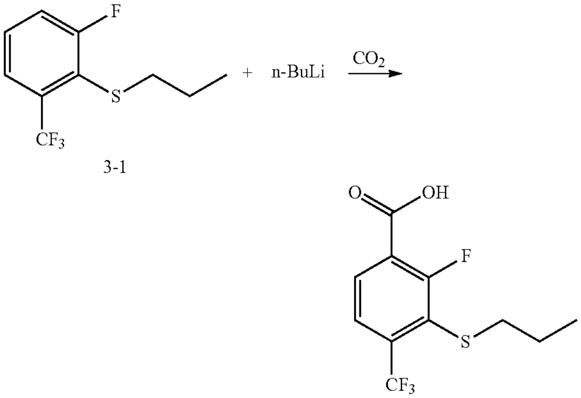

3-1 3-2

(3) Compound 3-2(3.1 g, 11 mmol, 1.0 eq), compound b (1.66 g, 16.8 mmol, 1.5 eq), DMAP (0.13 g, 1.1 mmol, 0.1 eq) were sequentially added to 30 ml of pyridine. Then, $SOCl_2$ (2.0 g, 16.8 mmol, 1.5 eq) was slowly added at 0° C., and the reaction solution was stirred at room temperature for 3 hours. The product was detected by LCMS. Pyridine was removed by concentration, then 30 ml of water was poured into the reaction solution, and the mixture was separated. The aqueous phase was extracted three times with 30 ml of ethyl acetate, and the resultant organic phase was washed three times with saturated saline solution (50 ml), dried, and evaporated to dryness under reduced pressure and separated by column chromatography to obtain Compound 3-3 (2.5 g, 63% yield) (white solid).

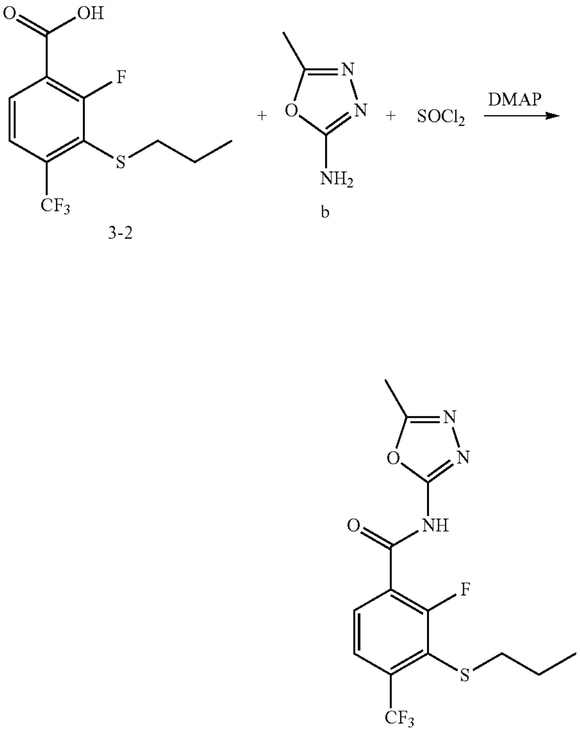

3-2 b 3-3

(4) Compound 3-3(1 g, 2.8 mmol, 1.0 eq) and compound c (0.54 g, 3.1 mmol, 1.1 eq) were added sequentially in 10 mL of dichloromethane. The reaction solution was then stirred at room temperature for 1 hour. The product was detected by LCMS, and the reaction of raw materials was basically completed. The reaction solution was poured into 10 ml of water, the reaction was quenched with sodium hydrogen sulfite, and the mixture was separated. The aqueous phase was extracted three times with 30 ml of dichloromethane, and the resultant organic phase was washed once with saturated saline solution (30 ml), dried, and evaporated to dryness under reduced pressure, and separated by column chromatography to give Compound 3-racemate (0.85 g, 82% yield) (greyish white solid).

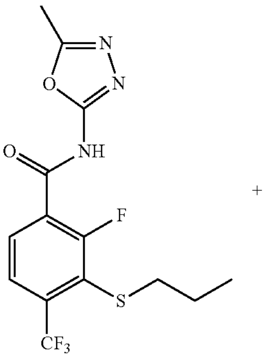

3-3

-continued

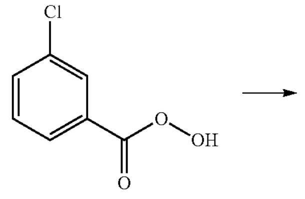

c

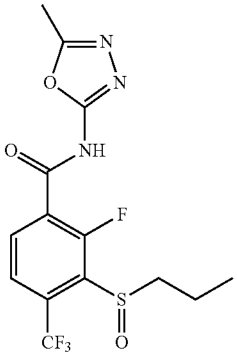

3-racemate (5) Compound 3-racemate (0.5 g, 98% purity) was resolved and separated by chiral HPLC (Column: CHIRALPAK IG; Column Size: 3 cm×25 cm, 5 μm; Injection: 3.0 ml; Mobile phase: Hex(0.2% FA): IPA=50:50; Flow rate: 28 ml/min; Wavelength: UV 254 nm; Temperature: 25° C.; Sample solution: 70 mg/ml in EtOH/DCM; Run time=60 mins), and then concentrated, white solids 3 (0.16 g, Rt=10.51 min, 100% ee, purity 98%)和 3-S(0.13 g, Rt=30.81 min, 99.8% ee, purity 96%) were determined by single crystal diffraction.

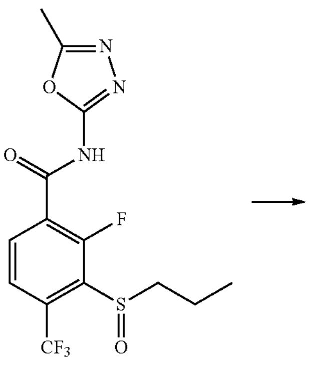

3-racemate

-continued

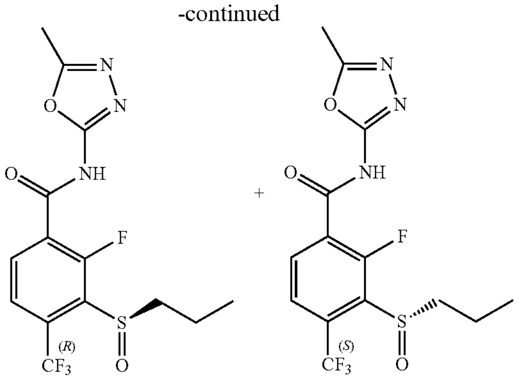

3 3-S

2. Synthesis of Compound 306

(1) Compound a was dissolved in 5 volumes of DMF solution, 1 equivalent of sodium hydroxide was added, the temperature was controlled at 5° C., and 1.05 equivalents of ethanethiol was added dropwise, the reaction continued for 2 hours. After the completion of In-Process Control, 20 volumes of water were added, 5 volumes of methyl tert-butyl ether were used to extract twice, the combined organic phases were dried under reduced pressure, and purified by column chromatography, the product 306-1 was obtained with a yield of 93%.

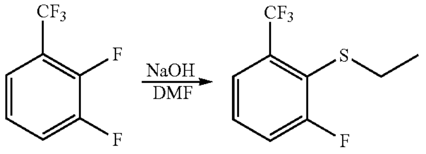

a 306-1

(2) Product 306-1 was dissolved in 10 volumes of tetrahydrofuran solution, the temperature was controlled at −65° C. in the protection of nitrogen, and 1.05 equivalents of n-butyl lithium solution was added dropwise, stirred for 30 minutes. In-Process Control was completed after 5 minutes of carbon dioxide gas injection, and 5 volumes of water were added to quench the reaction. Tetrahydrofuran solution was removed by vacuum, and ethyl acetate was used for extraction once. The pH value of the aqueous phase was adjusted to 2-3 with 1M hydrochloric acid, and solid was precipitated, filtered and dried to obtain product 306-2 with 88% yield.

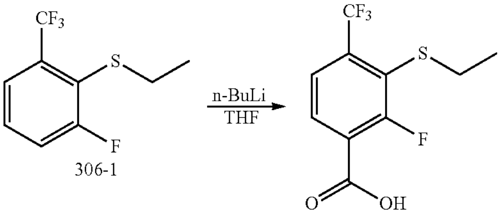

306-1 306-2

(3) Product 306-2 was dissolved in 10 volumes of dichloromethane solution, and 1.1 equivalents of CDI was added; after being stirring for 30 minutes, 1.05 equivalents of b and 1.05 equivalents of DBU were added, and stirred at room temperature for 5 hours. After the completion of In-Process Control, washed with 5 volumes of water to collect an organic phase, and then the organic phase was washed with 5 volumes of 1M hydrochloric acid aqueous solution, dried and concentrated under reduced pressure to obtain product 306-3 with 80% yield.

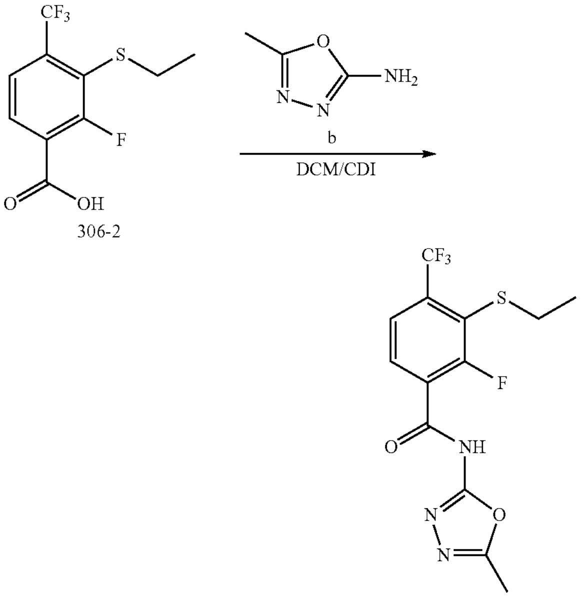

306-2 b 306-3

(4) Product 306-3 was dissolved in 5 volumes of DMF solution, 3 equivalents of sodium methanol solution was added, and the temperature was increased to 80° C. and the reaction continued for 1 hour. After the completion of In-Process Control, 20 volumes of water were added, 5 volumes of dichloromethane were used to extract twice, and the organic phase was dried under reduced pressure and purified by reverse phase chromatography to obtain product 306-4 with a yield of 75%.

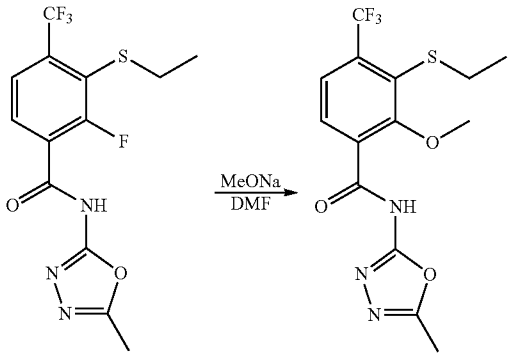

306-3 306-4

(5) Product 306-4 was dissolved in 10 volumes of dichloromethane, 1.0 equivalent of C was added, and stirred at room temperature for 30 minutes. After the completion of In-Process Control, sodium bisulfite solution was used to quench the reaction. After the removal of dichloromethane, the reaction product was purified by the reverse phase chromatography to obtain product 306-racemate with 85% yield.

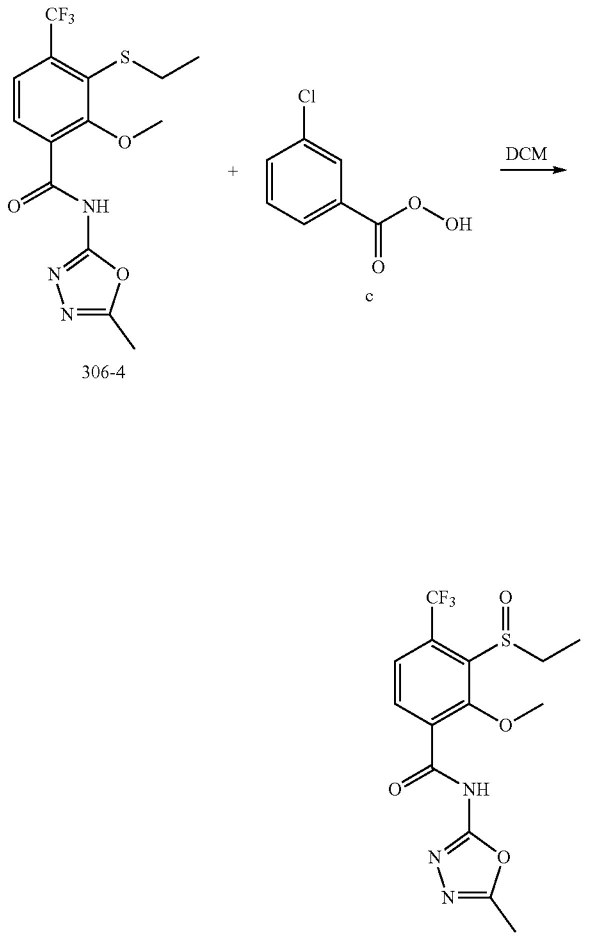

306-4 c 306-racemic (6) Compound 306-racemate (0.3 g, 95% purity) was resolved and separated by chiral HPLC (Column: CHIRALPAK IE; Column Size: 2 cm×25 cm, 5 μm; Injection: 1.5 ml; Mobile Phase: MtBE (0.2% FA): MeOH=90:10; The Flow rate: 20 ml/min; Wavelength: UV 254 nm; Temperature 25° C.; Sample Solution: 20 mg/ml in MeOH/DCM; Run time=12 mins), and then concentrated to obtain white solids 306-S(0.09 g, Rt=6.02 min, 98.9% ee, 95% purity) and 306 (0.08 g, Rt=8.87 min, 99.2% ee, 97% purity).

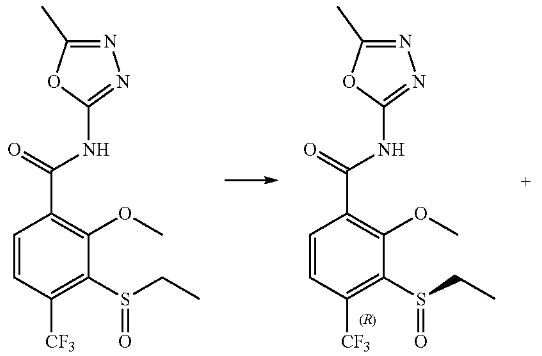
306-racemic 306

-continued

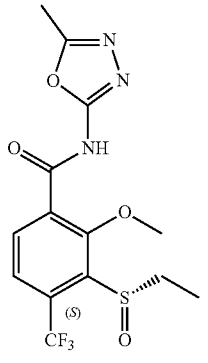

306-S

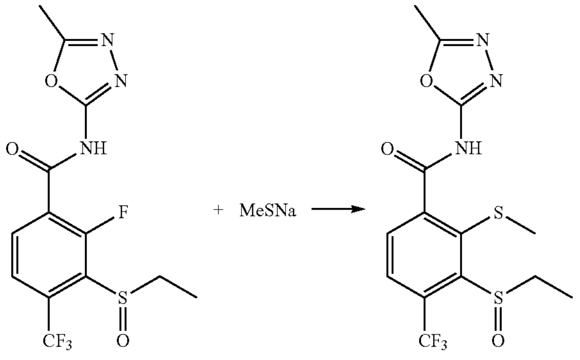

548-1 548-racemate

3. Synthesis of Compound 548

(1) Compound 306-3 was synthesized according to the Item 2 above, compound 306-3 (10 g, 29 mmol, 1.0 eq) and m-CPBA (6.4 g, 31 mmol, 85% purity, 1.1 eq) were added into 200 ml of DCM successively, and then the reaction continued at 0° C. for 0.5 h. Then through LCMS detection, it was found that the raw materials disappeared, and the main peak was the product. Saturated sodium bisulfite solution was added into the reaction solution to quench the excess oxide, then the reaction was concentrated and separated by column chromatography to obtain product 548-1 (9.0 g, 86% yield) (white solid).

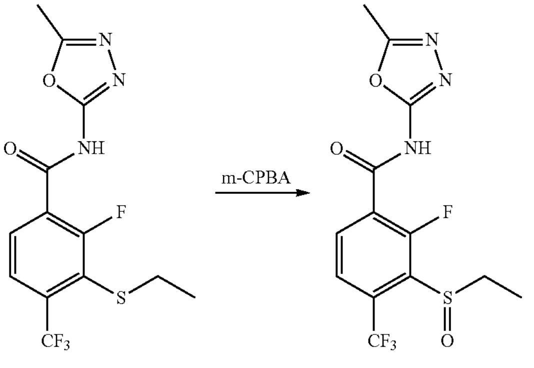

306-3 548-1

(2) Product 548-1 (2.5 g, 6.8 mmol, 1.0 eq) and MeSNa (2.4 g, 34 mmol, 5.0 eq) were added to 40 mL of DMF, and the reaction solution was heated at 60° C. for 2 hours. Through LCMS detection, it was found that the raw materials was substantially consumed and the main peak was the product. The product was filtered with a syringe, purified with the reverse phase column chromatography and concentrated to obtain a white solid product 548-racemate (1.2 g, 44.6% yield) (white solid).

(3) Product 548-racemate (0.5 g, 98% purity) was resolved and separated by chiral HPLC (Column: CHIRALPAK IG; Column Size: 3 cm×25 cm, 5 μm; Injection: 3.0 ml; Mobile Phase: Hex(0.2% FA): IPA=50:50; Flow rate: 28 ml/min; Wavelength: UV 254 nm; Temperature 25° C.; Sample Solution: 70 mg/ml in EtOH/DCM; Run time=60 mins), then concentrated to obtain white solid 548-5 (0.21 g, Rt=10.11 min, 100% ee, 98% purity) and 548 (0.18 g, Rt=31.12 min, 99% ee, 96% purity).

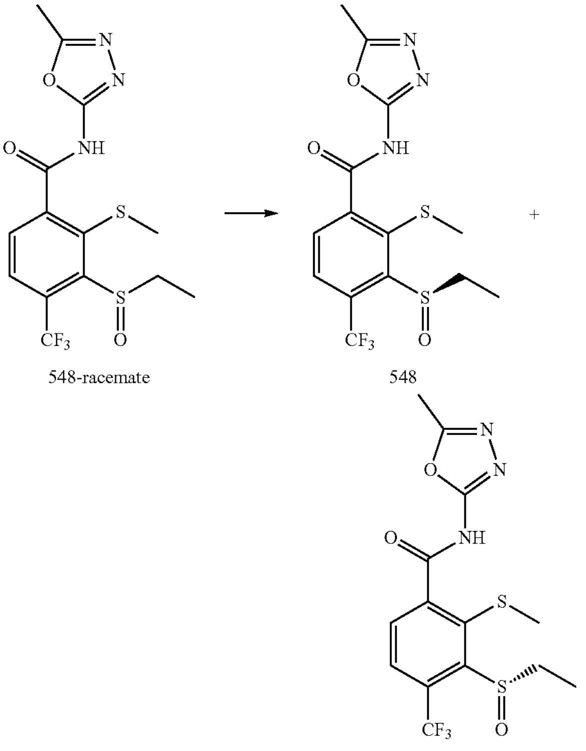

548-racemate 548 548-S

4. Synthesis of Compound 637

(1) 637-1 (10 g, 70.4 mmol, 1.0 eq) was added to 100 ml of DCM, and DAST (22.7 g, 140.8 mmol, 2 eq) was then added dropwise to the reaction solution at 0° C. The reaction solution was stirred at 20° C. for 16 hours after the completion of adding. Through LCMS detection, it was found that raw materials were almost consumed and a major new peak appeared. The reaction solution was poured into 100 ml of saturated $NaHCO_3$ aqueous solution, and the solution was extracted and separated. The organic phase was washed with 100 ml of saturated saline for 3 times, and dried under reduced pressure at low temperature. The crude product was purified by column chromatography with petroleum ether as eluant and concentrated to obtain 637-2 (5 g, 43% yield) (colorless liquid).

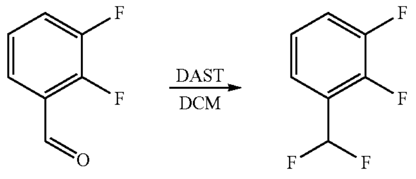

637-1 637-2

(2) 637-2 (5 g, 30.5 mmol, 1.0 eq) and NaOH (1.34 g, 33.55 mmol, 1.1 eq) were successively added into 50 ml of DMF, then 637-3(2.55 g, 33.55 mmol, 1.1 eq) was added dropwise to the reaction solution at 0° C. The reaction solution was stirred at 0° C. for 3 hours after the completion of adding. Through LCMS detection, it was found that raw materials were almost consumed and a major new peak appeared. The reaction solution was poured into 50 ml of water, then separated, and the aqueous phase was extracted once with 50 ml ethyl acetate. The organic phase was washed with saturated saline (50 ml) for 3 times and dried under reduced pressure. The crude product was purified by column chromatography with petroleum ether as eluant and concentrated to obtain 637-4 (4 g, 60% yield) (colorless liquid).

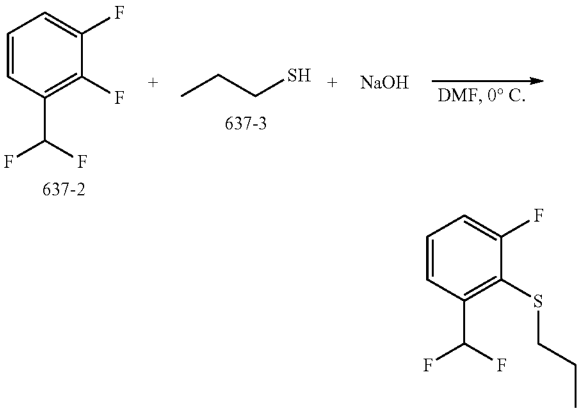

637-2 637-3 637-4

(3) 637-4 (4 g, 18.2 mmol, 1.0 eq) was added to 50 ml of THF, then n-BuLi (9.5 mL, 23.66 mmol, 1.3 eq) was added dropwise to the reaction solution at −78° C. After adding, the reaction solution was stirred for 0.5 hours at −78° C., and then solid dry ice was added gradually. After adding, the reaction solution was warmed gradually to room temperature. Through LCMS detection, it was found the product appeared. The reaction solution was poured into 50 ml of water for quenching, and concentrated to remove THF. Then the aqueous phase was extracted once with ethyl acetate (50 ml), adjusted to pH of 1-2 by concentrated hydrochloric acid, and solid was precipitated and filtered, and the filter cake was dried to obtain 637-5 (1.5 g, 31% yield) (yellow solid).

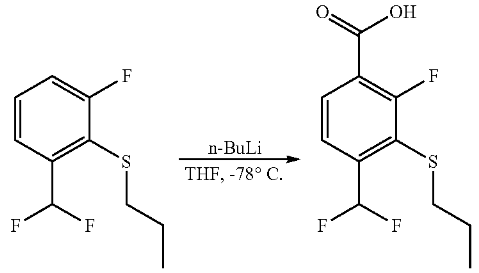

637-4 637-5

(4) 637-5 (1.5 g, 5.7 mmol, 1.0 eq) and CDI (1.1 g, 6.27 mmol, 1.1 eq) were added into 20 ml of DCM. The reaction continued at 0° C. for 1 hour, then DBU (0.95 g, 6.27 mmol, 1.1 eq) and b (0.627 g, 6.27 mmol, 1.1 eq) were added into the reaction solution successively. The reaction solution was warmed gradually to room temperature and then reacted for 8 hours. Through LCMS detection, it was found the product appeared. The reaction solution was poured into 50 ml of water and extracted three times with dichloromethane (50 mL). Then the organic phase was washed once with 4N hydrochloric acid (50 ml), dried with anhydrous sodium sulfate, concentrated, and purified by column chromatography to obtain 637-6 (1.2 g, 61% yield) (white solid).

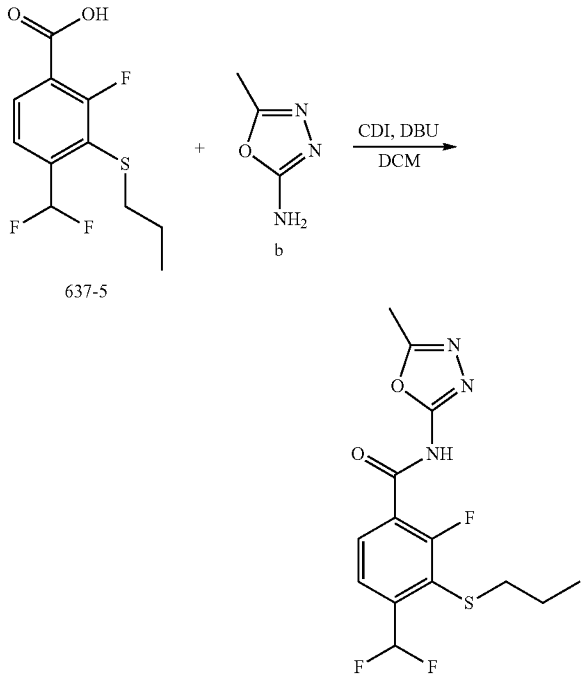

637-5 b 637-6

(5) 637-6 (1.2 g, 3.5 mmol, 1.0 eq) and m-CPBA (0.78 g, 3.85 mmol, 1.1 eq) were added to 20 ml of DCM successively. The reaction solution reacted at 0° C. for 0.5 h, then through LCMS detection, it was found that the raw materials disappeared, and the main peak was the product. Saturated sodium bisulfite solution was added to the reaction solution for quenching the excess oxide, then the reaction solution was concentrated. The crude product was purified by column chromatography to obtain 637-7 (0.7 g, 54% yield) (white solid).

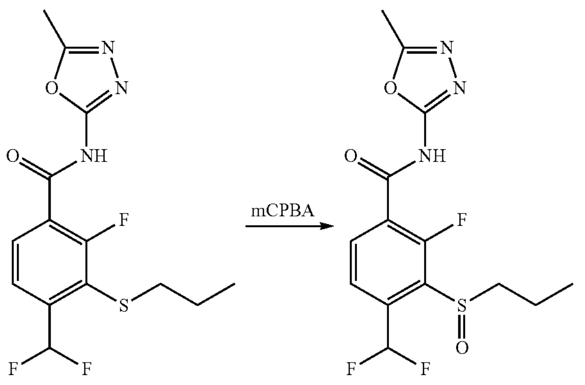

637-6 637-7

(6) 637-6 (0.6 g, 1.7 mmol, 1.0 eq), $H_2O_2$ (1.97 g, 17.4 mmol, 10 eq) and catalyst I (CAS: 135620-04-1, 35 mg) were added to 10 ml of isopropanol successively. The reaction solution reacted at 0° C. for 12 hours, then through LCMS detection, it was found the product peak appeared. Saturated sodium bisulfite solution was added to the reaction solution for quenching the excess oxide, then the reaction solution was concentrated. The crude product was purified by column chromatography and crystallized by ethyl acetate and ethanol to obtain 637 (0.15 g, 24% yield, ee=95%, purity 95%) (white solid).

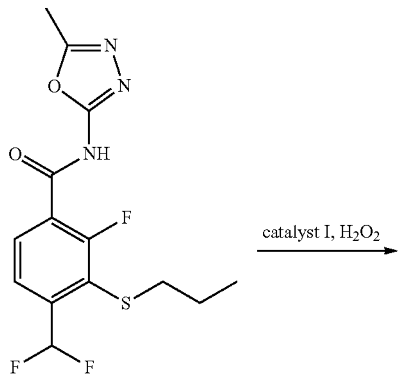

637-6

-continued

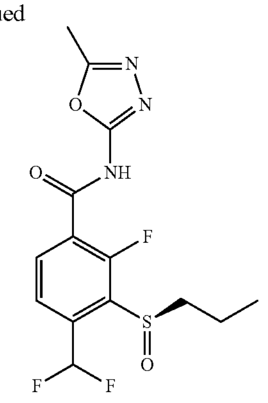

637

I

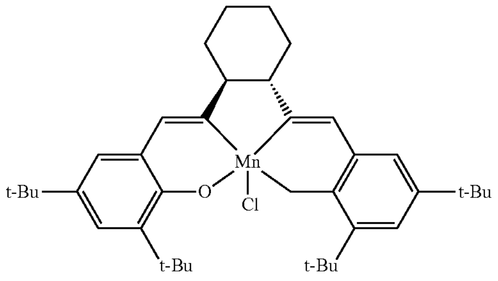

S,S

Biological Activity Evaluation:

The activity level criteria for harmful plant damage (i.e., growth control rate) are as follows:

Level 5: growth control rate is above 85%;

Level 4: growth control rate is greater than or equal to 60% and less than 85%;

Level 3: growth control rate is greater than or equal to 40% and less than 60%;

Level 2: growth control rate is greater than or equal to 20% and less than 40%;

Level 1: growth control rate is greater than or equal to 5% and less than 20%;

Level 0: growth control rate is less than 5%.

The above growth control rates are fresh weight control rates.

Experiment on weeding effect in post-emergence stage: monocotyledonous and dicotyledonous weed seeds (*Descurainia sophia, Capsella bursa-pastoris, Galium aparine, Stellaria media, Lithospermum arvense, Rorippa indica, Alopecurus aequalis, Beckmannia syzigachne, Sclerochloa dura, Phleum paniculatum, Bromus japonicus, Aegilops tauschii, Phalaris arundinacea, Amaranthus retroflexus*, Chenopodiaceae, *Commelina communis, Sonchus arvensis, convolvulus arvensis, Cirsium setosum, Solanum nigrum, Acalypha australis, Digitaria sanguinalis, Echinochloa crusgalli, Setaria viridis, Setaria glauca, Leptochloa chinensis, Monochoria vaginalis, Sagittaria trifolia, Scirpus juncoides, Cyperus rotundus, Cyperus iria, Cyperus difformis, Fimbristylis, Portulaca oleracea, Xanthium sibiricum, Pharbitis nil*) and major crop seeds (wheat, corn, rice, soybean, cotton, oilseed rape, millet, sorghum, potato, sesame, *ricinus*) were placed in plastic pots filled with soil, then covered with 0.5-2 cm of soil, allowed to grow in a good greenhouse environment. After 2 weeks of sowing, the test plants were treated in the 2 leaf stage. The tested compounds of the present invention were respectively dissolved in acetone, then added with Tween 80 and 1.5 liter/ha of emulsifiable concentrate of methyl oleate as synergist, diluted with a certain amount of water to obtain a solution with a certain concentration, and sprayed with a spray tower onto the plants. After the application, the plants were cultured for 15 days in the greenhouse, and then the experimental results of the weeding were counted. The doses of the used compounds were 500, 250, 125, 60, 30, 15 g/ha, and the averages were obtained by repeating for three times. Representative data are listed in Table 3.

TABLE 3

Results on weeding effect in post-emergence stage (250 g/ha)

| Compound No. | *Amaranthus retroflexus* | *Echinochloa crusgali* | *Digitaria sanguinalis* | *Abutilon theophrasti* | *Setaria viridis* |
|---|---|---|---|---|---|
| 1 | 5 | 5 | 3 | 5 | 3 |
| 2 | 5 | 5 | 4 | 5 | 4 |
| 3 | 5 | 5 | 5 | 5 | 5 |
| 4 | 5 | 5 | 5 | 5 | 5 |
| 5 | 5 | 5 | 5 | 5 | 5 |
| 6 | 5 | 5 | 5 | 5 | 5 |
| 7 | 5 | 5 | 4 | 5 | 4 |
| 8 | 5 | 5 | 4 | 5 | 4 |
| 9 | 5 | 5 | 5 | 5 | 5 |
| 10 | 5 | 5 | 5 | 5 | 5 |
| 11 | 5 | 5 | 5 | 5 | 5 |
| 12 | 5 | 5 | 3 | 5 | 3 |
| 13 | 5 | 5 | N | N | N |
| 14 | 5 | 5 | N | N | N |
| 17 | 5 | 5 | 5 | 5 | 5 |
| 18 | 5 | 5 | N | N | N |
| 20 | 5 | 5 | 5 | 5 | 5 |
| 21 | 5 | 5 | 5 | 5 | 5 |
| 24 | 5 | 5 | 5 | 5 | 5 |
| 25 | 5 | 5 | 5 | 5 | 5 |
| 26 | 5 | 5 | 5 | 5 | 5 |
| 27 | 5 | 5 | 5 | 5 | 5 |
| 28 | 5 | 5 | 5 | 5 | 5 |
| 29 | 5 | 5 | 5 | 5 | 5 |
| 30 | 5 | 5 | 5 | 5 | 5 |
| 31 | 5 | 5 | 5 | 5 | 5 |
| 32 | 5 | 5 | 5 | 5 | 5 |
| 33 | 5 | 5 | 5 | 5 | 5 |
| 34 | 5 | 5 | 5 | 5 | 5 |
| 35 | 5 | 5 | 5 | 5 | 5 |
| 36 | 5 | 5 | 5 | 5 | 5 |
| 37 | 5 | 5 | 5 | 5 | 5 |
| 38 | 5 | 5 | 5 | 5 | 5 |
| 40 | 5 | 5 | 5 | 5 | 5 |
| 51 | 5 | 5 | N | N | N |
| 52 | 5 | 5 | 5 | 5 | 5 |
| 53 | 5 | 5 | 5 | 5 | 5 |
| 54 | 5 | 5 | 5 | 5 | 5 |
| 55 | 5 | 5 | 5 | 5 | 5 |
| 56 | 5 | 5 | 5 | 5 | 5 |
| 57 | 5 | 5 | 5 | 5 | 5 |
| 67 | 5 | 5 | 5 | 5 | 5 |
| 69 | 5 | 5 | 5 | 5 | 5 |
| 70 | 5 | 5 | 5 | 5 | 5 |
| 71 | 5 | 5 | 5 | 5 | 5 |
| 72 | 5 | 5 | 5 | 5 | 5 |
| 73 | 5 | 5 | 5 | 5 | 5 |
| 74 | 5 | 5 | 5 | 5 | 5 |
| 75 | 5 | 5 | 5 | 5 | 5 |
| 79 | 5 | 5 | 5 | 5 | 5 |
| 80 | 5 | 5 | N | N | N |
| 164 | 5 | 5 | 5 | 5 | 5 |
| 165 | 5 | 5 | 5 | 5 | 5 |
| 166 | 5 | 5 | 5 | 5 | 5 |
| 167 | 5 | 5 | 5 | 5 | 5 |
| 169 | 5 | 5 | 5 | 5 | 5 |
| 171 | 5 | 5 | N | N | N |
| 176 | 5 | 5 | N | N | N |
| 178 | 5 | 5 | N | N | N |
| 184 | 5 | 5 | N | N | N |
| 191 | 5 | 5 | N | N | N |

TABLE 3-continued

Results on weeding effect in post-emergence stage (250 g/ha)

| Compound No. | *Amaranthus retroflexus* | *Echinochloa crusgali* | *Digitaria sanguinalis* | *Abutilon theophrasti* | *Setaria viridis* |
|---|---|---|---|---|---|
| 192 | 5 | 5 | N | N | N |
| 193 | 5 | 5 | N | N | N |
| 196 | 5 | 5 | N | N | N |
| 199 | 5 | 5 | N | N | N |
| 202 | 5 | 5 | N | N | N |
| 203 | 5 | 5 | 5 | 5 | 5 |
| 204 | 5 | 5 | 5 | 5 | 5 |
| 205 | 5 | 5 | 5 | 5 | 5 |
| 206 | 5 | 5 | N | N | N |
| 214 | 5 | 5 | N | N | N |
| 216 | 5 | 5 | N | N | N |
| 223 | 5 | 5 | N | N | N |
| 231 | 5 | 5 | N | N | N |
| 248 | 5 | 5 | N | N | N |
| 261 | 5 | 5 | 5 | 5 | 5 |
| 306 | 5 | 5 | 5 | 5 | 5 |
| 307 | 5 | 5 | 5 | 5 | 5 |
| 308 | 5 | 5 | 5 | 5 | 5 |
| 309 | 5 | 5 | 5 | 5 | 5 |
| 310 | 5 | 5 | 5 | 5 | 5 |
| 311 | 5 | 5 | 5 | 5 | 5 |
| 312 | 5 | 5 | 5 | 5 | 5 |
| 313 | 5 | 5 | 5 | 5 | 5 |
| 314 | 5 | 5 | 5 | 5 | 5 |
| 315 | 5 | 5 | 5 | 5 | 5 |
| 316 | 5 | 5 | 5 | 5 | 5 |
| 318 | 5 | 5 | N | N | N |
| 319 | 5 | 5 | 5 | 5 | 5 |
| 320 | 5 | 5 | 5 | 5 | 5 |
| 321 | 5 | 5 | 5 | 5 | 5 |
| 322 | 5 | 5 | 5 | 5 | 5 |
| 323 | 5 | 5 | 5 | 5 | 5 |
| 324 | 5 | 5 | 5 | 5 | 5 |
| 325 | 5 | 5 | 5 | 5 | 5 |
| 326 | 5 | 5 | 5 | 5 | 5 |
| 327 | 5 | 5 | 5 | 5 | 5 |
| 328 | 5 | 5 | 5 | 5 | 5 |
| 329 | 5 | 5 | 5 | 5 | 5 |
| 330 | 5 | 5 | 5 | 5 | 5 |
| 331 | 5 | 5 | 5 | 5 | 5 |
| 332 | 5 | 5 | 5 | 5 | 5 |
| 333 | 5 | 5 | 5 | 5 | 5 |
| 334 | 5 | 5 | 5 | 5 | 5 |
| 335 | 5 | 5 | 5 | 5 | 5 |
| 336 | 5 | 5 | 5 | 5 | 5 |
| 337 | 5 | 5 | 5 | 5 | 5 |
| 338 | 5 | 5 | 5 | 5 | 5 |
| 339 | 5 | 5 | 5 | 5 | 5 |
| 340 | 5 | 5 | 5 | 5 | 5 |
| 341 | 5 | 5 | 5 | 5 | 5 |
| 342 | 5 | 5 | 5 | 5 | 5 |
| 343 | 5 | 5 | 5 | 5 | 5 |
| 344 | 5 | 5 | 5 | 5 | 5 |
| 345 | 5 | 5 | 5 | 5 | 5 |
| 346 | 5 | 5 | 5 | 5 | 5 |
| 347 | 5 | 5 | 5 | 5 | 5 |
| 348 | 5 | 5 | 5 | 5 | 5 |
| 349 | 5 | 5 | N | N | N |
| 351 | 5 | 5 | N | N | N |
| 353 | 5 | 5 | N | N | N |
| 354 | 5 | 5 | N | N | N |
| 355 | 5 | 5 | N | N | N |
| 356 | 5 | 5 | N | N | N |
| 357 | 5 | 5 | 5 | 5 | 5 |
| 358 | 5 | 5 | 5 | 5 | 5 |
| 359 | 5 | 5 | 5 | 5 | 5 |
| 379 | 5 | 5 | 5 | 5 | 5 |
| 380 | 5 | 5 | 5 | 5 | 5 |
| 382 | 5 | 5 | N | N | N |
| 383 | 5 | 5 | N | N | N |
| 421 | 5 | 5 | 5 | 5 | 5 |
| 422 | 5 | 5 | 5 | 5 | 5 |
| 423 | 5 | 5 | 5 | 5 | 5 |
| 424 | 5 | 5 | 5 | 5 | 5 |
| 425 | 5 | 5 | N | N | N |

TABLE 3-continued

| Results on weeding effect in post-emergence stage (250 g/ha) | | | | | |
|---|---|---|---|---|---|
| Compound No. | *Amaranthus retroflexus* | *Echinochloa crusgali* | *Digitaria sanguinalis* | *Abutilon theophrasti* | *Setaria viridis* |
| 428 | 5 | 5 | N | N | N |
| 445 | 5 | 5 | 5 | 5 | 5 |
| 446 | 5 | 5 | 5 | 5 | 5 |
| 447 | 5 | 5 | 5 | 5 | 5 |
| 448 | 5 | 5 | N | N | N |
| 457 | 5 | 5 | N | N | N |
| 458 | 5 | 5 | N | N | N |
| 471 | 5 | 5 | N | N | N |
| 476 | 5 | 5 | N | N | N |
| 477 | 5 | 5 | N | N | N |
| 478 | 5 | 5 | N | N | N |
| 481 | 5 | 5 | N | N | N |
| 482 | 5 | 5 | N | N | N |
| 483 | 5 | 5 | N | N | N |
| 484 | 5 | 5 | N | N | N |
| 485 | 5 | 5 | N | N | N |
| 486 | 5 | 5 | N | N | N |
| 491 | 5 | 5 | N | N | N |
| 492 | 5 | 5 | N | N | N |
| 493 | 5 | 5 | N | N | N |
| 496 | 5 | 5 | N | N | N |
| 497 | 5 | 5 | N | N | N |
| 498 | 5 | 5 | N | N | N |
| 499 | 5 | 5 | N | N | N |
| 500 | 5 | 5 | N | N | N |
| 501 | 5 | 5 | N | N | N |
| 511 | 5 | 5 | N | N | N |
| 512 | 5 | 5 | N | N | N |
| 513 | 5 | 5 | N | N | N |
| 515 | 5 | 5 | N | N | N |
| 516 | 5 | 5 | N | N | N |
| 517 | 5 | 5 | N | N | N |
| 518 | 5 | 5 | 5 | 5 | N |
| 519 | 5 | 5 | 5 | 5 | N |
| 520 | 5 | 5 | 5 | 5 | N |
| 521 | 5 | 5 | 5 | 5 | N |
| 522 | 5 | 5 | 5 | 5 | N |
| 523 | 5 | 5 | 5 | 5 | N |
| 524 | 5 | 5 | 5 | 5 | N |
| 525 | 5 | 5 | 5 | 5 | N |
| 526 | 5 | 5 | 5 | 5 | N |
| 527 | 5 | 5 | 5 | 5 | N |
| 528 | 5 | 5 | 5 | 5 | N |
| 529 | 5 | 5 | 5 | 5 | N |
| 531 | 5 | 5 | 5 | 5 | 5 |
| 532 | 5 | 5 | 5 | 5 | 5 |
| 533 | 5 | 5 | 5 | 5 | 5 |
| 534 | 5 | 5 | 5 | 5 | 5 |
| 535 | 5 | 5 | 5 | 5 | 5 |
| 536 | 5 | 5 | 5 | 5 | N |
| 537 | 5 | 5 | 5 | 5 | N |
| 538 | 5 | 5 | 5 | 5 | N |
| 543 | 5 | 5 | 5 | 5 | 5 |
| 544 | 5 | 5 | 5 | 5 | N |
| 545 | 5 | 5 | 5 | 5 | N |
| 546 | 5 | 5 | 5 | 5 | N |
| 548 | 5 | 5 | 5 | 5 | 5 |
| 549 | 5 | 5 | 5 | 5 | N |
| 550 | 5 | 5 | 5 | 5 | 5 |
| 551 | 5 | 5 | 5 | 5 | 5 |
| 552 | 5 | 5 | 5 | 5 | 5 |
| 553 | 5 | 5 | 5 | 5 | 5 |
| 554 | 5 | 5 | 5 | 5 | 5 |
| 555 | 5 | 5 | 5 | 5 | 5 |
| 556 | 5 | 5 | 5 | 5 | 5 |
| 557 | 5 | 5 | 5 | 5 | 5 |
| 558 | 5 | 5 | 5 | 5 | 5 |
| 559 | 5 | 5 | 5 | 5 | 5 |
| 560 | 5 | 5 | 5 | 5 | 5 |
| 561 | 5 | 5 | 5 | 5 | 5 |
| 562 | 5 | 5 | 5 | 5 | 5 |
| 563 | 5 | 5 | 5 | 5 | 5 |
| 564 | 5 | 5 | 5 | 5 | 5 |
| 565 | 5 | 5 | 5 | 5 | 5 |
| 569 | 5 | 5 | 5 | 5 | 5 |
| 570 | 5 | 5 | 5 | 5 | 5 |
| 573 | 5 | 5 | 5 | 5 | N |
| 574 | 5 | 5 | 5 | 5 | 5 |
| 575 | 5 | 5 | 5 | 5 | 5 |
| 576 | 5 | 5 | 5 | 5 | 5 |
| 577 | 5 | 5 | 5 | 5 | 5 |
| 581 | 5 | 5 | 5 | 5 | 5 |
| 582 | 5 | 5 | 5 | 5 | 5 |
| 595 | 5 | 5 | 5 | N | N |
| 596 | 5 | 5 | 5 | N | N |
| 597 | 5 | 5 | 5 | N | N |
| 598 | 5 | 5 | 5 | N | N |
| 599 | 5 | 5 | 5 | N | N |
| 600 | 5 | 5 | 5 | N | N |
| 601 | 5 | 5 | 5 | N | N |
| 602 | 5 | 5 | 5 | N | N |
| 603 | 5 | 5 | 5 | N | N |
| 604 | 5 | 5 | 5 | N | N |
| 605 | 5 | 5 | 5 | N | N |
| 606 | 5 | 5 | 5 | N | N |
| 607 | 5 | 5 | 5 | N | N |
| 608 | 5 | 5 | 5 | N | N |
| 609 | 5 | 5 | 5 | N | N |
| 610 | 5 | 5 | 5 | N | N |
| 611 | 5 | 5 | 5 | N | N |
| 612 | 5 | 5 | 5 | N | N |
| 617 | 5 | 5 | 5 | 5 | 5 |
| 618 | 5 | 5 | 5 | N | N |
| 619 | 5 | 5 | 5 | N | N |
| 620 | 5 | 5 | 5 | N | N |
| 621 | 5 | 5 | 5 | N | N |
| 622 | 5 | 5 | 5 | N | N |
| 623 | 5 | 5 | 5 | N | N |
| 624 | 5 | 5 | 5 | N | N |
| 625 | 5 | 5 | 5 | N | N |
| 626 | 5 | 5 | 5 | N | N |
| 627 | 5 | 5 | 5 | N | N |
| 628 | 5 | 5 | 5 | N | N |
| 629 | 5 | 5 | 5 | N | N |
| 637 | 5 | 5 | 5 | 5 | 5 |
| 856 | 5 | 5 | 5 | 5 | 5 |
| 864 | 5 | 5 | 5 | 5 | 5 |
| 865 | 5 | 5 | 5 | 5 | 5 |
| 866 | 5 | 5 | 5 | 5 | 5 |
| 867 | 5 | 5 | 5 | N | N |

Note:
N represents untested.

Comparative Experiment:

If there is no clear marker, the post-seedling test conditions are the same as above, and the experimental results are shown in Tables 4-7.

TABLE 4
Results of comparison experiment (3-4 weeks after sowing, 4-5 leaf-stage of weed, 25DAA)
| Compound No. | *Digitaria sanguinalis* (30 g/ha) | Green *Setaria viridis* (60 g/ha) | *Leptochloa chinensis* (60 g/ha) | *Abutilon theophrasti* (30 g/ha) |
|---|---|---|---|---|
| 3 | 100% | 100% | 85% | 100% |
| Control Compound A | 0% | 15% | 0% | 0% |
| 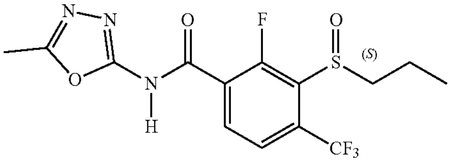 | | | | |
| Control Compound B | 80% | 90% | 30% | 90% |
| 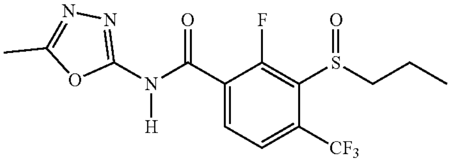 [SMILES: CCCS(=O)c1c(C(F)(F)F)ccc(C(=O)Nc2nnc(C)o2)c1F] | | | | |
| Control Compound C | 0% | 20% | 0% | 60% |
| 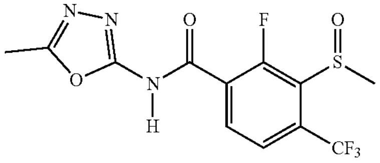 | | | | |
| 1 | 90% | 80% | 70% | 100% |
| Control Compound D | 0% | 10% | 0% | 50% |
| 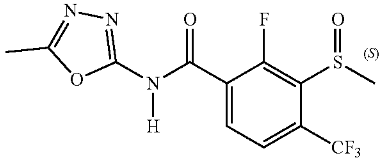 | | | | |
| 637 | 100% | 100% | 90% | 100% |
| Control Compound E | 5% | 25% | 10% | 60% |
| 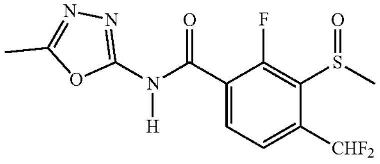 | | | | |

TABLE 5

| Results of comparison experiment (3-4 weeks after sowing, 1.5-2 leaf-stage of direct seeding rice variety Longyang 16, 4-5 leaf-stage of weed, 25 DAA) | | | | |
|---|---|---|---|---|
| Compound No. | Green *Setaria viridis* (30 g/ha) | *Leptochloa chinensis* (125 g/ha) | Rice(Long-yang 16) (250 g/ha) | Rice(Long-yang 16) (500 g/ha) |
| 3 | 75% | 100% | 0% | 0% |
| Control Compound A | 0% | 10% | 15% | 25% |
| Control Compound B | 10% | 80% | 5% | 15% |

Longyang 16 is an important cultivated variety representative of long-grain fragrant rice in northeast China. Long-grain fragrant rice is sensitive to herbicides and prone to drug damage, especially HPPD herbicides such as mesotrione and benzobicylon. Surprisingly, R configurational compound 3 shows higher safety to rice (Longyang 16) and better activity against key weeds such as *Leptochloa chinensis*. However, the control compound A (S configuration) is not safe for rice, (that is, the crop was badly damaged) but has lower activity for key weeds, or even has no activity at low dose. It was not consistent with the well-known structure-activity relationship that aryloxyphenoxypropionic acid herbicides and phenoxypropionic acid herbicides in effective form have high activity to weeds and heavy damage to crops, and in ineffective form have almost no activity.

In addition, the present invention, for example, compounds 2, 4, 8, 17, 20, 26, 40, 52, 54, 67, 69, 80, 166, 184, 205, 248, 261, 617, 637 have higher safety to rice and other crops and better activity to key weeds such as *Digitaria sanguinalis, Leptochloa chinensis* and so on at the dose of 125, 60, 30, 15 g/ha compared with the corresponding racemate or S configuration. Moreover, when X is replaced by other five membered rings, such as

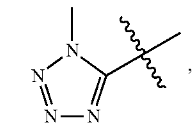 [SMILES: *c1nnnn1C]
, for example, compounds 379, 380, 382, 618, 856 have better herbicidal activity and/or crop safety at the doses of 125, 60, 30, 15 g/ha compared with the corresponding racemate or S configuration.

TABLE 6

| Results of comparison experiment | | | |
|---|---|---|---|
| Compound No. | *Digitaria sanguinalis* (30 g/ha) | Green *Setaria viridis* (30 g/ha) | *Alopecurus japonicas* (120 g/ha) |
| 548 | 100% | 100% | 50% |
| Control Compound A' 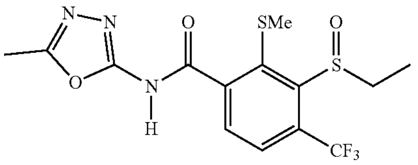 [SMILES: CCS(=O)c1c(C(F)(F)F)ccc(C(=O)Nc2nnc(C)o2)c1SC] | 50% | 90% | 20% |
| Control Compound B' 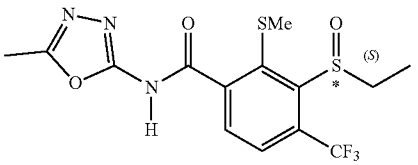 | 30% | 30% | 0% |
| Control Compound C' 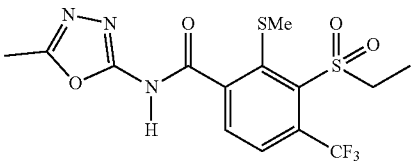 [SMILES: CCS(=O)(=O)c1c(C(F)(F)F)ccc(C(=O)Nc2nnc(C)o2)c1SC] | 10% | 80% | 20% |

TABLE 6-continued

Results of comparison experiment

| Compound No. | *Digitaria sanguinalis* (30 g/ha) | Green *Setaria viridis* (30 g/ha) | *Alopecurus japonicas* (120 g/ha) |
|---|---|---|---|
| Control Compound D' | 20% | 20% | 0% |
| 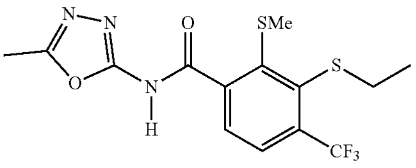 [SMILES: CCSc1c(C(F)(F)F)ccc(C(=O)Nc2nnc(C)o2)c1SC] | | | |
| 547 | 90% | 80% | 40% |
| Control Compound E' | 40% | 40% | 15% |
| 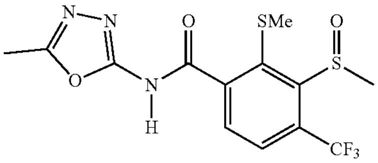 | | | |
| Control Compound F' | 0% | 5% | 0% |
| 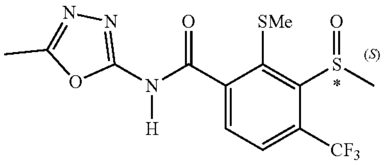 | | | |

TABLE 7

Results of comparison experiment (16DAA)

| Compound No. | | 548 | Control Compound A' |
|---|---|---|---|
| Corn-Zhengdan 958 (3.5 leaf) | 3 g/ha | 0% | 0% |
| | 6 g/ha | 0% | 0% |
| | 12 g/ha | 0% | 0% |
| | 24 g/ha | 0% | 0% |
| | 48 g/ha | 0% | 0% |
| *Setaria viridis* (4 leaf) | 3 g/ha | 20% | 0% |
| | 6 g/ha | 40% | 0% |
| | 12 g/ha | 80% | 10% |
| | 24 g/ha | 100% | 40% |
| | 48 g/ha | 100% | 50% |
| *Digitaria sanguinalis* (3.5 leaf) | 3 g/ha | 40% | 10% |
| | 6 g/ha | 40% | 10% |
| | 12 g/ha | 60% | 20% |
| | 24 g/ha | 80% | 30% |
| | 48 g/ha | 100% | 30% |
| *Abutilon theophrasti* (3.5 leaf) | 3 g/ha | 30% | 10% |
| | 6 g/ha | 40% | 20% |
| | 12 g/ha | 50% | 30% |
| | 24 g/ha | 70% | 40% |
| | 48 g/ha | 100% | 50% |
| *Amaranthus retroflexus* (6 leaf) | 3 g/ha | 30% | 10% |
| | 6 g/ha | 40% | 10% |
| | 12 g/ha | 60% | 40% |
| | 24 g/ha | 80% | 50% |
| | 48 g/ha | 100% | 50% |
| *Echinochloa crusgali* (3 leaf) | 3 g/ha | 50% | 10% |
| | 6 g/ha | 50% | 20% |
| | 12 g/ha | 70% | 30% |
| | 24 g/ha | 80% | 40% |
| | 48 g/ha | 100% | 50% |

TABLE 7-continued

Results of comparison experiment (16DAA)

| Compound No. | | 548 | Control Compound A' |
|---|---|---|---|
| *Leptochloa chinensis* (4.5 leaf) | 3 g/ha | 0% | 0% |
| | 6 g/ha | 20% | 0% |
| | 12 g/ha | 50% | 0% |
| | 24 g/ha | 70% | 10% |
| | 48 g/ha | 80% | 20% |
| *Capsella bursa-pastoris* (10-11 leaf) | 3 g/ha | 10% | 0% |
| | 6 g/ha | 30% | 10% |
| | 12 g/ha | 50% | 10% |
| | 24 g/ha | 70% | 20% |
| | 48 g/ha | 100% | 30% |
| *Descurainia sophia* (12 leaf) | 3 g/ha | 50% | 0% |
| | 6 g/ha | 70% | 10% |
| | 12 g/ha | 80% | 20% |
| | 24 g/ha | 100% | 30% |
| | 48 g/ha | 100% | 40% |
| *Galium aparine* (5 branches) | 3 g/ha | 10% | 0% |
| | 6 g/ha | 10% | 0% |
| | 12 g/ha | 20% | 0% |
| | 24 g/ha | 20% | 0% |
| | 48 g/ha | 30% | 10% |
| *Veronica didyma* (2 branches) | 3 g/ha | 10% | 10% |
| | 6 g/ha | 20% | 10% |
| | 12 g/ha | 20% | 20% |
| | 24 g/ha | 50% | 20% |
| | 48 g/ha | 70% | 20% |
| *Malachium aquaticum* (2 branches) | 3 g/ha | 30% | 10% |
| | 6 g/ha | 50% | 10% |
| | 12 g/ha | 70% | 20% |
| | 24 g/ha | 100% | 30% |
| | 48 g/ha | 100% | 50% |
| *Sinapis arvensis* | 3 g/ha | 30% | 0% |
| | 6 g/ha | 40% | 0% |

TABLE 7-continued

Results of comparison experiment (16DAA)

| Compound No. | | 548 | Control Compound A' |
|---|---|---|---|
| (3.5 leaf) | 12 g/ha | 50% | 20% |
| | 24 g/ha | 60% | 40% |
| | 48 g/ha | 80% | 50% |

In addition, in the present invention, for example, compounds 549, 550, 552, 554, 559, 569, 865 have also better herbicidal activity and/or crop safety at the dose of 120, 48, 30, 24 g/ha compared with the corresponding racemate or S configuration; for example, compounds 306, 308, 310, 311, 321, 348, 353, 864 have better herbicidal activity and/or crop safety compared with the corresponding racemate or S configuration; And when X is replaced by other five membered rings, such as

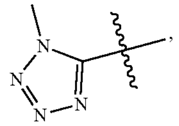 [SMILES: *c1nnnn1C]

$Z_1$ is replaced by methyl, and $Z_2$ is replaced by methyl sulfonyl or Y is replaced by

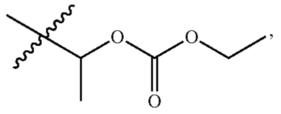 [SMILES: *C(C)OC(=O)OCC]

it has the same or similar technical effect.

In conclusion, the R-configuration compound in the present application obviously has better herbicidal activity than racemate and S-configuration compound, and can maintain good crop safety.

Experiment on Weed Effect in Pre-Emergence Stage:

Seeds of monocotyledonous and dicotyledonous weeds and main crops (e.g. wheat, corn, nice, soybean, cotton, oilseed rape, millet and sorghum) were put into a plastic pot loaded with soil and covered with 0.5-2 cm soil. The test compounds of the present invention was dissolved with acetone, then added with tween 80, diluted by a certain amount of water to reach a certain concentration, and sprayed immediately after sowing. The obtained seeds were incubated for 4 weeks in the greenhouse after spraying, then the test results were observed after 3 weeks. It was observed that the herbicide mostly had excellent effect at the application rate of 1000 g/ha, especially to weeds such as *Echinochloa crusgali, Digitaria sanguinalis* and *Abutilon theophrasti*, etc. And many compounds had good selectivity for corn, wheat, rice, soybean, oilseed rape, etc.

It is indicated from the experiment that the compound of the present invention generally have good weed control efficacy, especially for major grass weeds such as *Echinochloa crusgali, Digitaria sanguinalis* and *Setaria viridis*, etc. and major broad-leaved weeds such as *Abutilon theophrasti, Rorippa indica* and *Bidens pilosa*, which are widely occurred in corn, rice and wheat fields, and have excellent commercial value. Above all, it is noted that the compound of the invention have extremely high activity to broad-leaved weeds, which are resistant to ALS inhibitor, like *Rorippa indica, Descurainia sophia, Capsella bursa-pastoris, Lithospermum arvense, Galium aparine* and *Stellaria media*, etc.

Transplanted rice safety evaluation and weed control effect evaluation in rice field:

Rice field soil was loaded into a 1/1,000,000 ha pot. The seeds of *Echinochloa crusgali, Scirpus juncoides, Bidens tripartita, Sagittaria trifolia, Monochoria vaginalis* and *Leptochloa chinensis* were sowed and gently covered with soil, then left to stand still in greenhouse in the state of 0.5-1 cm of water storage. The tuber of *Sagittaria trifolia* was planted in the next day or 2 days later. It was kept at 3-4 cm of water storage thereafter. The weeds were treated by dripping the WP or SC water diluents prepared according to the common preparation method of the compounds of the present invention with pipette homogeneously to achieve specified effective amount when *Echinochloa crusgali, Scirpus juncoides, Bidens tripartita, Monochoria vaginalis* and *Leptochloa chinensis* reached 0.5 leaf stage and *Sagittaria trifolia* reached the time point of primary leaf stage.

In addition, the rice field soil that loaded into the 1/1,000,000 ha pot was leveled to keep water storage at 3-4 cm depth. The 3 leaf stage rice (*japonica* rice/*Indica* rice) was transplanted at 3 cm of transplanting depth the next day. The compound of the present invention was treated by the same way after 5 days of transplantation.

The fertility condition of *Echinochloa crusgali, Scirpus juncoides, Bidens tripartita, Leptochloa chinensis, Sagittaria trifolia* and *Monochoria vaginalis* 14 days after the treatment of the compound of the invention and the fertility condition of rice 21 days after the treatment of the compound of the invention respectively with the naked eye. Evaluate the weed control effect with 0-5 activity standard level. Many compounds show excellent activity and selectivity.

TABLE 8

Herbicidal effects of compounds (the dose of the compounds of the present invention: 60 g/ha)

| Compound No. | *Echinochloa crusgali* | *Leptochloa chinensis* | *Sagittaria trifolia* | *Monochoria vaginalis* | Rice |
|---|---|---|---|---|---|
| 3 | 5 | 5 | 5 | 5 | 0 |
| 4 | 5 | 5 | 5 | 5 | 0 |
| 6 | 5 | 5 | 5 | 5 | 0 |
| 26 | 5 | 5 | 5 | 5 | 0 |
| 37 | 5 | 5 | 5 | 5 | 0 |
| 79 | 5 | 5 | 5 | 5 | 0 |
| 548 | 5 | 5 | 5 | 5 | 0 |
| Penoxsulam (30 g/ha) | 0 | 1 | 0 | 1 | 1 |

Note:
The seeds of *Echinochloa crusgali*, *Scirpus juncoides*, *Bidens tripartita*, *Sagittaria trifolia* and *Monochoria vaginalis* were collected from Heilongjiang Province of China. The tests indicated that the weeds were resistant to the common doses of Pyrazosulfuron-ethyl and Penoxsulam.

It could be seen from the present experiment that the compound of the present invention had excellent activity against weeds having an anti-ALS inhibiting mechanism and being a serious challenge in production, and thus could solve the increasingly serious resistance problem.

At the same time, the compounds and compositions of the present invention have good selectivity to many gramineae grasses such as *Zoysia japonica, Bermuda* grass, tall fescue, bluegrass, ryegrass and seashore *paspalum* etc, and are able to control many important grass weeds and broad-leaved weeds. The compounds also show excellent selectivity and commercial value in the tests on wheat, corn, rice, sugarcane, soybean, cotton, oil sunflower, potato, orchards and vegetables in different herbicide application methods.

What is claimed is:

1. An aryl formamide compound containing chiral sulfur oxide or salt thereof, wherein the compound has the structural formula as follows:

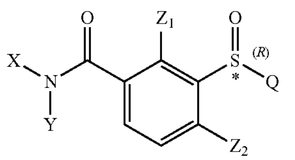

I wherein:

$Z_1$ is halogen or C1-C6 alkylsulfanyl;

$Z_2$ is halogenated C1-C6 alkyl;

X is

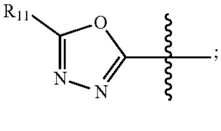

;

$R_{11}$ is C1-C6 alkyl;

Q is C1-C6 alkyl; and

Y is hydrogen.

2. An aryl formamide compound containing chiral sulfur oxide or salt thereof selected from the following compounds of formula I:

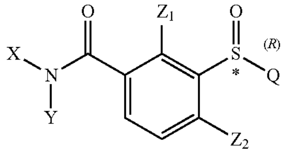

I

| NO. | X | Y | $Z_1$ | $Z_2$ | Q |
|---|---|---|---|---|---|
| 1 | 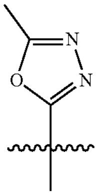 [SMILES: *c1nnc(C)o1] | H | F | $CF_3$ | Me |
| 3 | 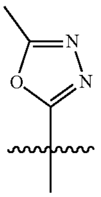 [SMILES: *c1nnc(C)o1] | H | F | $CF_3$ | 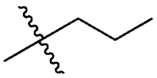 [SMILES: *CCC] |

-continued

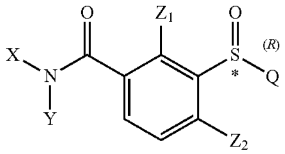

I

| NO. | X | Y | $Z_1$ | $Z_2$ | Q |
|---|---|---|---|---|---|
| 547 | 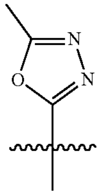 [SMILES: *c1nnc(C)o1] | H | SMe | $CF_3$ | Me |
| 548 | 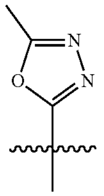 [SMILES: *c1nnc(C)o1] | H | SMe | $CF_3$ | Et |
| 637 | 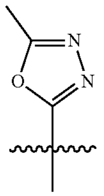 [SMILES: *c1nnc(C)o1] | H | F | $CHF_2$ | 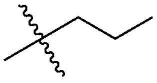 . |

3. A method for preparing the aryl formamide compound containing chiral sulfur oxide or salt thereof according to claim 1, which comprises the following step:

(1) the compound of formula I is obtained by liquid phase separation from a compound of formula I'

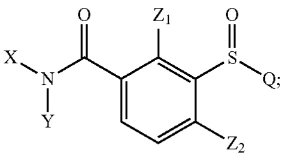

I' or (2) the compound of formula I is prepared by using a compound of formula I"

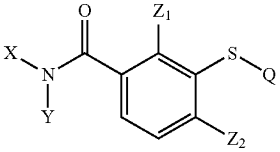

I"

in the presence of peroxide and Jacobsen catalyst.

4. The method for preparing the aryl formamide compound containing chiral sulfur oxide or salt thereof according to claim 3, wherein, the peroxide in the reaction (2) is $H_2O_2$; the reaction (2) is carried out in the presence of a solvent.

5. The method for preparing the aryl formamide compound containing chiral sulfur oxide or salt thereof according to claim 4, wherein, the reaction (2) is carried out in the presence of a solvent; and the solvent is at least one of methanol, ethanol, isopropanol, acetonitrile, dichloroethane, DMF, DMSO, dioxane, dichloromethane or ethyl acetate.

6. A herbicidal composition, characterized in comprising (i) the aryl formamide compound containing chiral sulfur oxide or salt thereof according to claim 1.

7. The herbicidal composition according to claim 6, which is characterized in that, the composition further comprises (ii) one or more additional herbicides and/or safeners.

8. The herbicidal composition according to claim 6, which is characterized in that, the composition further comprises (iii) an agrochemically acceptable formulation auxiliary.

9. A method for controlling a weed comprising: applying at least one of the aryl formamide compounds containing chiral sulfur oxide or salts thereof according to claim 1 in an herbicidally effective amount on a plant or in a weed area.

10. A method for controlling a weed comprising: applying at least one of the herbicidal composition according to claim 6 in an herbicidally effective amount on a plant or in a weed area.

11. A method for preventing and/or controlling a weed in a useful crop comprising: applying at least one of the aryl formamide compounds containing chiral sulfur oxide or salts thereof according to claim 1.

12. The method according to claim 11, wherein the useful crop is a transgenic crop or a crop treated by gene editing technique.

13. A method for preventing and/or controlling a weed in a useful crop comprising: applying at least one of the herbicidal composition according to claim 6.

14. The method according to claim 13, wherein the useful crop is a transgenic crop or a crop treated by gene editing technique.

* * * * *